US012703872B2

(12) United States Patent
Kudithipudi et al.

(10) Patent No.: US 12,703,872 B2
(45) Date of Patent: Aug. 11, 2026

(54) COMPOSITION AND METHODS FOR PRODUCING TOBACCO PLANTS AND PRODUCTS HAVING INCREASED PHENYLALANINE AND REDUCED TOBACCO-SPECIFIC NITROSAMINES (TSNAs)

(71) Applicant: Altria Client Services LLC, Richmond, VA (US)

(72) Inventors: Chengalrayan Kudithipudi, Midlothian, VA (US); Dongmei Xu, Glen Allen, VA (US); James Strickland, Richmond, VA (US); Yanxin Shen, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 280 days.

(21) Appl. No.: 18/651,995

(22) Filed: May 1, 2024

(65) Prior Publication Data

US 2024/0368614 A1 Nov. 7, 2024

Related U.S. Application Data

(60) Division of application No. 17/830,072, filed on Jun. 1, 2022, now Pat. No. 11,999,961, which is a continuation of application No. 16/372,833, filed on Apr. 2, 2019, now Pat. No. 11,377,665.

(60) Provisional application No. 62/652,092, filed on Apr. 3, 2018.

(51) Int. Cl.

| | |
|---|---|
| ***C12N 15/82*** | (2006.01) |
| ***A24B 15/10*** | (2006.01) |
| *A24B 13/00* | (2006.01) |

(52) U.S. Cl.

CPC .. *C12N 15/8243* (2013.01); *C12Y 402/01091* (2013.01); *A24B 13/00* (2013.01); *A24B 15/10* (2013.01)

(58) Field of Classification Search

None

See application file for complete search history.

(56) References Cited

U.S. PATENT DOCUMENTS

| | | | |
|---|---|---|---|
| 4,516,590 | A | 5/1985 | Teng |
| 4,528,993 | A | 7/1985 | Sensabaugh et al. |
| 4,660,577 | A | 4/1987 | Sensabaugh et al. |
| 4,732,856 | A | 3/1988 | Federoff |
| 4,762,785 | A | 8/1988 | Comai |
| 4,848,373 | A | 7/1989 | Lenkey |
| 4,945,050 | A | 7/1990 | Sanford et al. |
| 4,987,907 | A | 1/1991 | Townsend |
| 5,004,863 | A | 4/1991 | Umbeck |
| 5,013,658 | A | 5/1991 | Dooner et al. |
| 5,104,310 | A | 4/1992 | Saltin |
| 5,141,131 | A | 8/1992 | Miller, Jr. et al. |
| 5,149,645 | A | 9/1992 | Hoekema et al. |
| 5,159,135 | A | 10/1992 | Umbeck |
| 5,177,010 | A | 1/1993 | Goldman et al. |
| 5,231,019 | A | 7/1993 | Paszkowski et al. |
| 5,316,931 | A | 5/1994 | Donson et al. |
| 5,372,149 | A | 12/1994 | Roth et al. |
| 5,463,174 | A | 10/1995 | Moloney et al. |
| 5,464,763 | A | 11/1995 | Schilperoort et al. |
| 5,469,976 | A | 11/1995 | Burchell |
| 5,491,081 | A | 2/1996 | Webb |
| 5,563,055 | A | 10/1996 | Townsend et al. |
| 5,565,350 | A | 10/1996 | Kmiec |
| 5,589,367 | A | 12/1996 | Donson et al. |
| 5,659,026 | A | 8/1997 | Baszezynski et al. |
| 5,689,035 | A | 11/1997 | Webb |
| 5,731,181 | A | 3/1998 | Kmiec |
| 5,756,325 | A | 5/1998 | Kmiec |
| 5,760,012 | A | 6/1998 | Kmiec et al. |
| 5,789,156 | A | 8/1998 | Bujard et al. |
| 5,795,972 | A | 8/1998 | Kmiec |
| 5,814,618 | A | 9/1998 | Bujard et al. |
| 5,866,785 | A | 2/1999 | Donson et al. |
| 5,871,984 | A | 2/1999 | Kmiec |
| 5,879,918 | A | 3/1999 | Tomes et al. |
| 5,886,244 | A | 3/1999 | Tomes et al. |

(Continued)

FOREIGN PATENT DOCUMENTS

| | | |
|---|---|---|
| WO | WO 98/49350 | 11/1998 |
| WO | WO 99/07865 | 2/1999 |

(Continued)

OTHER PUBLICATIONS

Tzin et al. Expression of a bacterial bi-functional chorismate mutase / phrephenate dehydratase modulates primary and secondary metabolism associated with aromatic amino acids in *Arabidopsis*. (2009) The Plant Journal; vol. 60; pp. 156-167 (Year: 2009).*

Beetham et al., "A Tool for Functional Plant Genomics: Chimeric RNA/DNA Oligonucleotides Cause in Vivo Gene-Specific Mutations," *Proc. Natl. Acad. Sci. USA*, 96, pp. 8774-8778 (Jul. 1999) (electronic publication).

Benzie et al., "The Ferric Reducing Ability of Plasma (FRAP) as a Measure of "Antioxidant Power": The FRAP Assay," *Analytical Biochemistry*, 239(1), pp. 70-76, (Jul. 1996), available online: https://doi.org/10.1006/abio.1996.0292.

Bowman et al., "Revised North Carolina Grade Index for Flue-Cured Tobacco," *Tobacco Science*, 32, pp. 39-40 (1988) (electronic publication).

(Continued)

*Primary Examiner* — Cathy Kingdon

(74) *Attorney, Agent, or Firm* — Arnold & Porter Kaye Scholer LLP

(57) ABSTRACT

The present disclosure provides approaches for reducing tobacco-specific nitrosamines (TSNAs) in tobacco. Some of these approaches include genetically engineering tobacco plants to increase one or more antioxidants, increase oxygen radicle absorbance capacity (ORAC), increase phenylalanine, or reduce nitrite. Also provided are methods and compositions for producing modified tobacco plants and tobacco products therefrom comprising reduced TSNAs.

10 Claims, 30 Drawing Sheets

Specification includes a Sequence Listing.

(56) References Cited

U.S. PATENT DOCUMENTS

| | | | |
|---|---|---|---|
| 5,889,190 | A | 3/1999 | Donson et al. |
| 5,889,191 | A | 3/1999 | Turpen |
| 5,932,782 | A | 8/1999 | Bidney |
| 5,981,840 | A | 11/1999 | Zho et al. |
| 6,072,050 | A | 6/2000 | Bowen et al. |
| 8,124,851 | B2 | 2/2012 | Dewey et al. |
| 8,319,011 | B2 | 11/2012 | Xu et al. |
| 9,187,759 | B2 | 11/2015 | Dewey et al. |
| 9,228,194 | B2 | 1/2016 | Dewey et al. |
| 9,228,195 | B2 | 1/2016 | Dewey et al. |
| 9,247,706 | B2 | 2/2016 | Dewey et al. |
| 2004/0118422 | A1 | 6/2004 | Lundin et al. |
| 2005/0178398 | A1 | 8/2005 | Breslin et al. |
| 2006/0191548 | A1 | 8/2006 | Strickland et al. |
| 2006/0260014 | A1 | 11/2006 | Li et al. |
| 2017/0233756 | A1 | 8/2017 | Begemann et al. |

FOREIGN PATENT DOCUMENTS

| | | | |
|---|---|---|---|
| WO | WO 99/25921 | | 5/1999 |
| WO | WO 03/022081 | A1 | 3/2003 |
| WO | WO 2004/041006 | A1 | 5/2004 |
| WO | WO 2008/005474 | A2 | 1/2008 |
| WO | WO 2009/063312 | A2 | 5/2009 |
| WO | WO 2009/063460 | A2 | 5/2009 |
| WO | WO 2009/072118 | A1 | 6/2009 |
| WO | WO 2011/027315 | A1 | 3/2011 |
| WO | WO 2012/004795 | A1 | 1/2012 |
| WO | WO 2014/151504 | A1 | 9/2014 |
| WO | WO 2017/066845 | A1 | 4/2017 |
| WO | WO 2018/067985 | A1 | 4/2018 |

OTHER PUBLICATIONS

Canevascini et al., "Tissue-Specific Expression and Promoter Analysis of the Tobacco itp1 Gene," *Plant Physiol.*, 112(2), pp. 513-524 (Feb. 1996) (electronic publication).

Centers for Disease Control and Prevention's Protocol for Analysis of Nicotine, Total Moisture and pH in Smokeless Tobacco Products, as published in the Federal Register vol. 64, No. 55, pp. 13897-13912 (Mar. 1999)(and as amended in vol. 74, No. 4, Jan. 2009).

Cermak et al., "Efficient design and assembly of custom TALEN and other TAL effector-based constructs for DNA targeting," *Nucleic Acids Research*, 39(12):e82 (Jul. 2011) (Oxford, UK), available online: 10.1093/nar/gkr218.

Chang et al., "Regulation of polyphenols accumulation by combined overexpression/silencing of key enzymes of phenylpropanoid pathway," *Acta Biochim Biophys Sin*. 41, pp. 123-130 (Feb. 2009) (electronic publication).

Chapters 4B and 4C of Tobacco, Production, Chemistry and Technology, Davis & Nielsen, eds., Blackwell Publishing, pp. 70-103, (1999) (Oxford, UK).

Christensen et al., "Sequence analysis and transcriptional regulation by heat shock of polyubiquitin transcripts from maize," *Plant Molecular Biology*, 12, pp. 619-632 (Jun. 1989), available online: https://doi.org/10.1007/BF00044153.

Christensen et al., "Maize polyubiquitin genes: structure, thermal perturbation of expression and transcript splicing, and promoter activity following transfer to protoplasts by electroporation," *Plant Molecular Biology*, 18:675-689 (Feb. 1992) available online: https://doi.org/10.1007/BF00020010.

Christou et al., "Stable Transformation of Soybean Callus by DNA-Coated Gold Particles," *Plant Physiol.*, 87, pp. 671-674, (Jul. 1988), available online: https://doi.org/10.1104/pp.87.3.671.

Cho et al., "Phenylalanine Biosynthesis in *Arabidopsis thaliana* Identification and Characterization of Arogenate Dehydratases," *Journal of Biological Chemistry*, 282(42), p. 20827-20835 (Aug. 2007) (electronic publication).

Collins et al., "Determination of Nicotine Alkaloids in Tobacco Using the Autoanalyzer," *Tobacco Science* 13, pp. 79-81 (1969) (electronic publication).

"Coresta Recommended Method No. 7: Determination of Nicotine in the Mainstream Smoke of Cigarettes By Gas Chromatographic Analysis," pp. 1-5, (1987) (updated Aug. 1991) (Paris, France).

"Coresta Recommended Method No. 62: Determination of Nicotine in Tobacco and Tobacco Products By Gas Chromatographic Analysis," *Coresta Cooperation Centre for Scientific Research Relative to Tobacco* (Feb. 2005) (Version 2: Apr. 2020) (Paris, FR).

Crossway et al., "Micromanipulation Techniques in Plant Biotechnology," *Biotechniques*, 4, pp. 320-334 (1986) (electronic publication).

D'Halluin et al., "Transgenic Maize Plants by Tissue Electroporation," *Plant Cell*, 4(12), pp. 1495-1505 (Dec. 1992), available online: DOI: 10.1105/tpc.4.12.1495.

De Wet et al. "Exogenous Gene Transfer in Maize (*Zea mays*) Using DNA-Treated Pollen," in *The Experimental Manipulation of Ovule Tissues*, (ed. Chapman et al. Longman, N.Y.), pp. 197-209 (1985) (Longman, New York).

Doyle et al., "TAL Effector-Nucleotide Targeter (TALE-NT) 2.0: tools for TAL effector design and target prediction," *Nucleic Acids Research*, 40(W1): W117-W122 (Jul. 2012), available online: DOI: https://doi.org/10.1093/nar/gks608.

"Draft for Diplomatic Conference for the Revision of the International Convention for the Protection of New Varieties of Plants," (of Dec. 2, 1961, as revised at Geneva on Nov. 10, 1972; on Oct. 23, 1978; and on Mar. 19, 1991),54 pages, Mar. 4-19, 1991 (Geneva, Switzerland).

Elkind et al., "Abnormal Plant Development and Down-Regulation of Phenylpropanoid Biosynthesis in Transgenic Tobacco Containing a Heterologous Phenylalanine Ammonia-Lyase Gene," *Proceedings of the National Academy of Sciences of the United States of America, National Academy of Sciences* 87:9057-9061 (Nov. 1990) (Washington, DC).

Estruch et al., "Transgenic Plants: An Emerging Approach to Pest Control," *Nat. Biotechnol.*, 15, pp. 137 (Feb. 1997) (electronic publication).

Extended European Search Report dated Aug. 11, 2022 in EP22168036.6.

Fedoroff et al., "Cloning of the bronze locus in maize by a simple and generalizable procedure using the transposable controlling element Activator (Ac)," *Proc Natl Acad Sci USA*, 81 (12), pp. 3825-3829 (Jun. 1984), available online: DOI: 10.1073/pnas.81.12.3825.

Finer et al., "Transformation of Soybean VIA Particle Bombardment of Embryogenic Suspension Culture Tissue," *In Vitro Cell Dev. Biol.*, 27P, pp. 175-182 (Oct. 1991) (electronic publication).

Gatz et al., "Regulation of a Modified CaMV 35S Promoter by the Tn10-encoded Tet Represser in Transgenic Tobacco," *Mol. Gen. Genet.*, 227, pp. 229-237 (Jun. 1991), available online: https://doi.org/10.1007/BF00259675.

GenPept XP_016479687.1 Predicted: chorismate mutase 1, chlorplastic-like [Nicotiana tabacum] pp. 1-2 (2016).

Goldman et al., "Female Sterile Tobacco Plants are Produced by Stigma-Specific Cell Ablation," *EMBO Journal*, 13, pp. 2976-2984 (Apr. 1994) (electronic publication).

Guevara-Garcia et al., "Tissue-Specific and Would-Inducible Pattern of Expression of the Mannopine Synthase Promoter is Determined by the Interaction Between Positive and Negative cis-Regulatory Elements," *Plant J.*, 4(3), pp. 495-505 (Apr. 1993) (electronic publication).

Hansen et al., "Would-Inducible and Organ-Specific Expression of ORF13 from *Agrobacterium rhizogenes* 8196 T-DNA in Transgenic Tobacco Plants," *Mol. Gen. Genet.*, 254(3), pp. 337-343, (Apr. 1997), available online: DOI: 10.1007/s004380050424.

Hibi et al., "Putrescine N-Methyltransferase in Cultured Roots of *Hyoscyamus albus," Plant Physiology*, 100, pp. 826-835 (May 1992) (electronic publication).

Hildering et al., "Chimeric structure of tomato plants after seed treatment with EMS and X-rays." *The Use of Induced Mutations in Plant Breeding* (Supplement to Radiation Botany), vol. 5, Pergamon Press Ltd., pp. 317-320, with cover page (1965) (London, UK).

Hoekema et al., "A Binary Plant Vector Strategy Based on Separation of vir- and T-region of the *Agrobacterium tumefaciens*

(56) References Cited

OTHER PUBLICATIONS

Ti-plasmid," *Nature*, 303, pp. 179-180 (May 1983), available online: https://doi.org/10.1038/303179a0.

Horsch et al., "A Simple and General Method for Transferring Genes into Plants," *Science*, vol. 227, Issue 4691, pp. 1229-1231, with cover page and table of contents (Mar. 1985) (Washington, DC). Available online: DOI: 10.1126/science.227.4691.1229.

International Search Report dated Jun. 24, 2019 issued in Int'l. Application No. PCT/US2019/025319.

Kaeppler et al., "Silicon Carbide Fiber-Mediated DNA Delivery into Plant Cells," *Plant Cell Reports*, 9, pp. 415-418 (Oct. 1990) (electronic publication).

Kaeppler et al., "Silicon Carbide Fiber-Mediated Stable Transformation of Plant Cells," *Theor. Appl. Genet.*, 84, pp. 560-566 (1992) (electronic publication).

Kawamata et al., "Temporal and Spatial Pattern of Expression of the Pea Phenylalanine Ammonia-Lyase Genel Promoter in Transgenic Tobacco," (1997) *Plant Cell Physiol.*, 38(7), pp. 792-803, (Jan. 1997), available online: https://doi.org/10.1093/oxfordjournals.pcp.a029237.

Lam, "8 Analysis of Tissue-Specific Elements in the CaMV 35S Promoter," *Results Probl. Cell Differ.*, 20, pp. 181-196 (1994) (electronic publication).

Last et al., "pEmu: an improved promoter for gene expression in cereal cells," *Theoretical and Applied Genetics*, 81(5), pp. 581-588 (May 1991), available online: DOI: 10.1007/BF00226722. PMID: 24221371.

Li et al., "De novo Production of Resveratrol from Glucose or Ethanol by Engineered *Saccharomyces cerevisiae*," *Metabolic Engineering* 32, pp. 1-11 (Sep. 2015) (electronic publication).

Lu et al., "Expression of a constitutively active nitrate reductase variant in tobacco reduces tobacco-specific nitrosamine accumulation in cured leaves and cigarette smaoke," *Plant Biotechnology Journal* 14(7), pp. 1500-1510 (Jul. 2016) (electronic publication).

Matsuoka et al., "Tissue-Specific Light-Regulated Expression Directed by the Promoter of a $C_4$ Gene, Maize Pyruvate, orthophosphate Dikinase, in a $C_3$ Plant, Rice," *Proc Natl. Acad. Sci., USA*, 90(20), pp. 9586-9590 (Oct. 1993) (electronic publication).

Mayo et al., "Genetic transformation of tobacco NT1 cells with Agrobacterium tumefaciens." *Nature Protocols* vol. 1, No. 3, pp. 1105-1111 (Aug. 2006) (online publication). Available online: https://doi.org/10.1038/nprot.2006.176.

McCabe et al., "Stable Transformation of Soybean (*Glycine max*) by Particle Acceleration," *Biotechnology*, 6, pp. 923-926 (Aug. 1998) (electronic publication).

McCallum et al., "Targeting Induced Local Lesions In Genomes (Tilling) for Plant Functional Genomics," *Nat. Biotechnol.* 18, pp. 455-457 (Apr. 2000) (electronic publication).

McNellis et al., "Glucocordticoid-Inducible Expression of a Bacterial Avirulence Gene in Transgenic *Arabidopsis* Induces Hypersensitive Cell Death," *Plant J.*, 14(2), pp. 247-257 (Apr. 1998), available online: DOI: 10.1046/j.1365-313x.1998.00106.x.

Miller "Memorandum: Proposed Burley Tobacco Grade Index," Legacy Tobacco Document Library, The University of Tennessee Agricultural Experiment Station (Bates Document #523267826-523267833) (Jul. 1988) (Knoxville, USA).

Miller et al., "A Grade Index for Type 22 and 23 Fire-Cured Tobacco," *Tobacco Intern.*, 192, pp. 55-57 (Dec. 1990) (New York, New York).

Odell et al., "Identification of DNA sequences required for activity of the cauliflower mosaic virus 35S promoter," *Nature*, 313, pp. 810-812, (Feb. 1985), available online: DOI: https://doi.org/10.1038/313810a0.

Official Standard Grades for Burley Tobacco (U.S. Type 31 and Foreign Type 93), effective Nov. 5, 1990 (55 F.R. 40645).

Official Standard Grades for Flue-Cured Tobacco (U.S. Types 11, 12, 13, 14 and Foreign Type 92), effective Mar. 27, 1989 (54 F.R. 7925).

Official Standard Grades for Pennsylvania Seedleaf Tobacco (U.S. Type 41), effective Jan. 8, 1965 (29 F.R. 16854).

Official Standard Grades for Ohio Cigar-Leaf Tobacco (U.S. Types 42, 43, and 44), effective Dec. 8, 1963 (28 F.R. 11719 and 28 F.R. 11926).

Official Standard Grades for Wisconsin Cigar-Binder Tobacco (U.S. Types 54 and 55), effective Nov. 20, 1969 (34 F.R. 17061).

Official Standard Grades for Georgia and Florida Shade-Grown Cigar-Wrapper Tobacco (U.S. Type 62), Effective Apr. 1971. A USDA grade index value can be determined according to an industry accepted grade index.

Oliva et al., "Phenylpyruvate Contributes to the Synthesis of Fragrant Benzenoid-Phenylpropanoids in Petunia × hybrida Flowers," *Frontiers in Plant Science*, 8, p. 769 (May 2017) (electronic publication).

Orozco et al., "Localization of Light-Inducible and Tissue-Specific Regions of the Spinach Ribulose Bisphosphate Carboylase/Oxygenase (Rubisco) Activate Promoter in Transgenic Tobacco Plants," *Plant Mol. Biol.*, 23(6), pp. 1129-1138 (1993) (Belgium).

Paszkowski et al., "Direct Gene Transfer to Plants," *EMBO J.*, 3:2717-2722 (Dec. 1984), available online: https://doi.org/10.1002/j.1460-2075.1984.tb02201.x.

Porta et al., "Use of Viral Replicons for the Expression of Genes in Plants," *Molecular Biotechnology*, 5(3), pp. 209-221 (Jun. 1996), available online: DOI: 10.1007/BF02900359.

Qian et al., "Completion of the Cytosolic Post-Chorismate Phenylalanine Biosynthetic Pathway in Plants," *Nature Communications* 10:15 (Jan. 2019) (electronic publication).

Riggs et al., "Stable Transformation of Tobacco by Electroporation: Evidence for Plasmid Concatenation," *Proc. Natl. Acad. Sci. USA*, 83, pp. 5602-5606 (Aug. 1986) (electronic publication).

Rinehart et al., "Tissue-Specific and Developmental Regulation of Cotton Gene FbL2A," *Plant Physiology*, 112, pp. 1331-1341 (Nov. 1996), available online: https://doi.org/10.1104/pp.112.3.1331.

Rippert et al., "Engineering Plant Shikimate Pathway for Production of Tocotrienol and Improving Herbicide Resistance," *Plant Physiology*, 134, pp. 92-100 (Jan. 2004) (electronic publication).

Rommens et al., "Engineered Native Pathways for High Kaempferol and Caffeoylquinate Production in Potato," *Plant Biotechnology Journal*, 6(9), pp. 870-886 (Dec. 2008) (electronic publication).

Russell et al., "Tissue-Specific Expression in Transgenic Maize of Four Endosperm Promoters from Maize and Rice," *Transgenic Res.*, 6(2), pp. 157-168 (Mar. 1997), available online: DOI: 10.1023/a:1018429821858.

Schena et al., "A Steroid-Inducible Gene Expression System for Plant Cells," *Proc. Natl. Acad. Sci. USA*, 88, pp. 10421-10425 (Dec. 1991), available online: https://www.pnas.org/doi/pdf/10.1073/pnas.88.23.10421.

Shillito et al., "[19] Direct Transfer to Protoplasts of Dicotyledonous and Monocotyledonous Plants by a No. of Methods Including Electroporation," *Meth. Enzymol.*, 153, pp. 313-336 (1987) (electronic publication).

Singh et al., "Cytological Characterization of Transgenic Soybean," *Theor. Appl. Genet.*, 96(2), pp. 319-324 (Feb. 1998) (electronic publication).

Tanaka, "Studies on Biological Effects of Ion Beams on Lethality, Molecular Nature of Mutation, Mutation Rate, and Spectrum of Mutation Phenotype for Mutation Breeding in Higher Plants," *J. Radiat. Res.*, 51, pp. 223-233 (Mar. 2010) (electronic publication).

Tomes et al., "16 Direct DNA Transfer into Intact Plant Cells Via Microprojectile Bombardment," in *Plant Cell, Tissue, and Organ Culture Fundamental Methods*, pp. 197-198 (Aug. 1995) (electronic publication).

Tso "Seed to Smoke," Chapter 1 in Davis and Nielsen (ed.), *Tobacco: Production, Chemistry and Technology*, Blackwell Science Publishing, pp. 1-31 with cover page (Oxford, UK).

Tzin et al., "Expression of a Bacterial bi-functional Chorismate mutase/prephenate Dehydratase Modulates Primary and Secondary Metabolism Associated With Aromatic Amino Acids in *Arabidopsis*," *The Plant Journal*, 60(1), pp. 156-167 (Oct. 2009) (electronic publication).

Tzin et al., "New Insights into the Shikimate and Aromatic Amino Acids Biosynthesis Pathways in Plants," *Molecular Plant*, 3(6), pp. 956-972 (Nov. 2010) (electronic publication).

(56) References Cited

OTHER PUBLICATIONS

Tzin et al., "The Biosynthetic Pathways for Shikimate and Aromatic Amino Acids in *Arabidopsis thaliana." Arabidopsis Book*, 8:e0132, pp. 1-18, (May 2010), available online: DOI: 10.1199/tab.0132.

Van Camp et al., "Tissue-Specific Activity of Two Manganese Superoxide Dismutase Promoters in Transgenic Tobacco," *Plant Physiology*, 112(2), pp. 525-535 (Jun. 1996) (electronic publication).

Velten et al., "Isolation of a Dual Plant Promoter Fragment from the Ti Plasmid of *Agrobacterium tumefaciens," The EMBO Journal*, 3(12), pp. 2723-2730 (Dec. 1984), available online: DOI: 10.1002/j.1460-2075.1984.tb02202.x.

Verkerk, "Chimerism of the Tomato Plant After Seed Irradiation wit Fast Neutrons," *Neth. J. Agric. Sci.*, 19, pp. 197-203 (1971) (Wageningent, the Netherlands).

Wahlberg et al., "Effect of Air-Curing on the Chemical Composition of Tobacco," *Coresta Meeting, Agronomy/Phytopathology*, Oxford, 1995.

Weising et al., "Foreign Genes in Plants: Transfer, Structure, Expressions and Applications," *Annual Review of Genetics*, 22, pp. 421-477 (Dec. 1988), accessed on Feb. 23, 2016, available online: 10.1146/annurev.ge.22.120188.002225.

Wernsman et al., "Chapter Seventeen: Tobacco" in *Principles of Cultivar Development, Crop Species*, vol. 2 , W. H. Fehr (ed.), MacMillan Publishing Go., Inc., pp. 669-698 with cover page, (1987) (New York, NY).

Wiernik et al., "Effect of Air-Curing on the Chemical Composition of Tobacco" *Recent Adv. Tab. Sci*, vol. 21 (Impact of Plant Manipulation and Post Harvest Phenomena on Leaf Composition), pp. 39-80 *Symposium Proceedings 49th Meeting Tobacco Chemists' Research Conference*, Sep. 24-27, 1995, Lexington, Kentucky, USA, available online: https://www.industrydocuments.ucsf.edu/docs/#id=xkvw0008.

Yamamoto et al., "The Promoter of a Pine Photosynthetic Gene Allows Expression of a jS-Glucuronidase Reporter Gene in Transgenic Rice Plants in a Light-Independent but Tissue-Specific Manner," *Plant Cell Physiol.*, 35(5), pp. 773-778 (1994) (electronic publication).

Yamamoto et al., "Light-Responsive Elements of the Tobacco PSI-D Gene are Located Both Upstream and within the Transcribed Region," *The Plant Journal*, 12(2), pp. 255-265 (Mar. 1997), available online: https://www1.gifu-u.ac.jp/~yyy/pdf/97PlantJYampsaDb.pdf.

Yoo et al., "An Alternative Pathway Contributes to Phenylalanine Biosynthesis in Plants Via a Cytosolic Tyrosine: Phenylpyruvate Aminotransferase," *Nature Communications*, 4, p. 2833 (Nov. 2013) (electronic publication).

Zhang et al., "Genetic and Biochemical Basis for Alternative Routes of Tocotrienol Biosynthesis for Enhanced Vitamin E Antioxidant Production," *The Plant Journal*, 73, pp. 628-639 (Feb. 2013) (electronic publication).

* cited by examiner

Figure 2

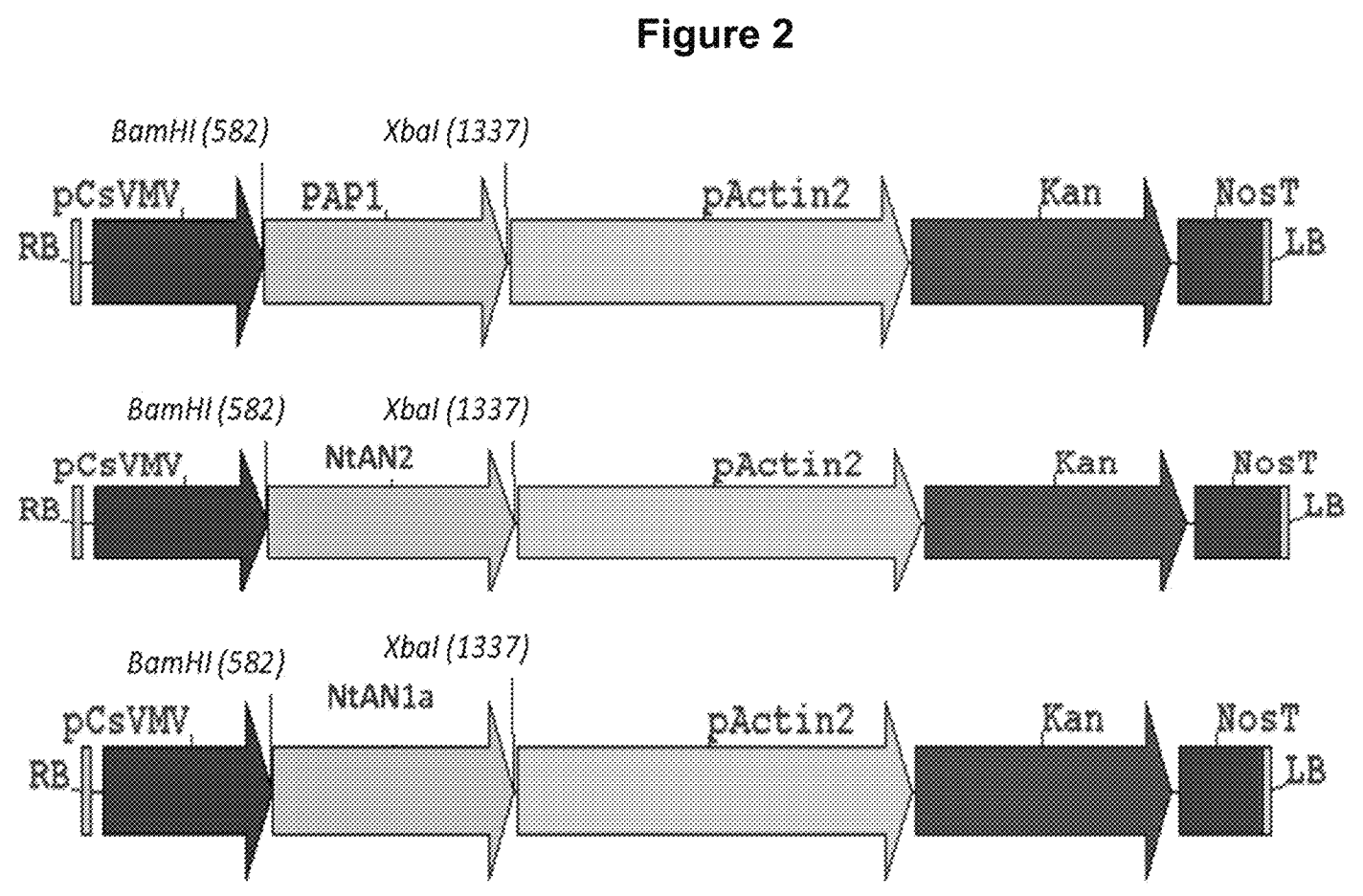

RB pCsVMV BamHI (582) PAP1 XbaI (1337) pActin2 Kan NosT LB

RB pCsVMV BamHI (582) NtAN2 XbaI (1337) pActin2 Kan NosT LB

RB pCsVMV BamHI (582) NtAN1a XbaI (1337) pActin2 Kan NosT LB

NNK (ppm)
1.4
1.2
1
0.8
0.6
0.4
0.2
0
12GH471
12GH472
12GH473
12GH474
12GH475
Control NNN (ppm)
1.6
1.4
1.2
1
0.8
0.6
0.4
0.2
0
12GH471
12GH472
12GH473
12GH474
12GH475
Control
NAB (ppm)
0.08
0.07
0.06
0.05
0.04
0.03
0.02
0.01
0
12GH471
12GH472
12GH473
12GH474
12GH475
Control
NAT (ppm)
2
1.5
1
0.5
0
12GH471
12GH472
12GH473
12GH474
12GH475
Control Nitrite (ppm)
7
6
5
4
3
2
1
0
12GH471
12GH472
12GH473
12GH474
12GH475
Control Nitrate (ppm)
12000
10000
8000
6000
4000
2000
0
12GH471
12GH472
12GH473
12GH473
12GH475
Control

Figure 10
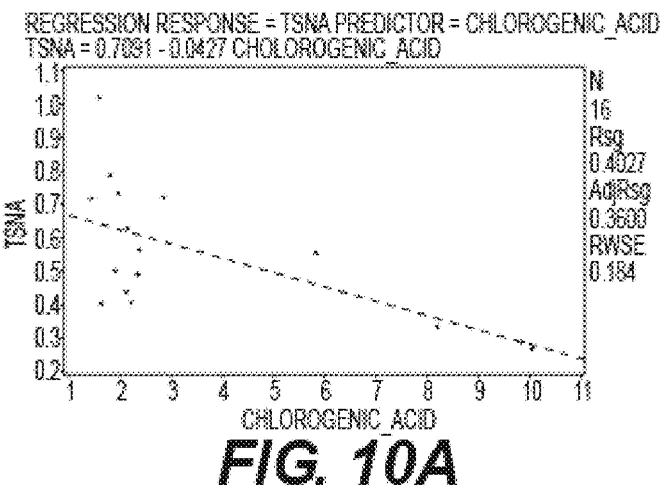
*FIG. 10A*
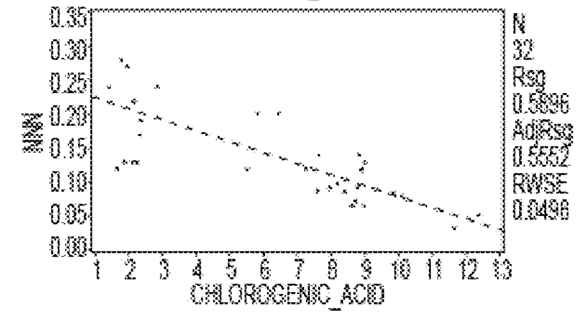
*FIG. 10B*
REGRESSION RESPONSE = NNK PREDICTOR = CHOLOROGENIC_ACID
NNK = 0.112 -0.0054 CHOLORGENIC_ACID
NNK
CHLOROGENIC_ACID
N 32 Rsq 0.3507 AdjRsq 0.3291 RWSE 0.0258
*FIG. 10C*

Figure 10
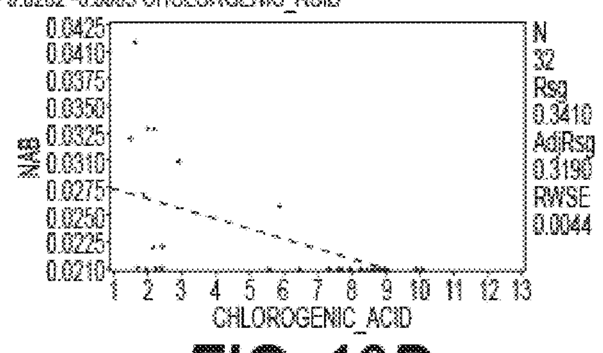
*FIG. 10D*
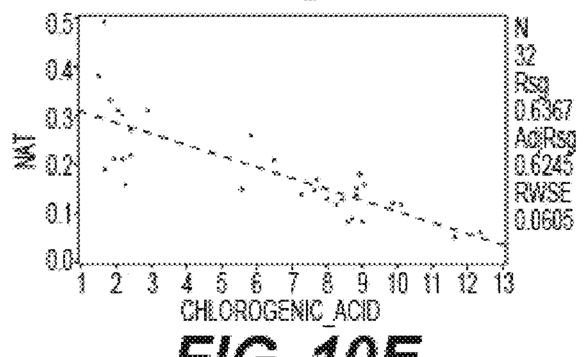
*FIG. 10E*

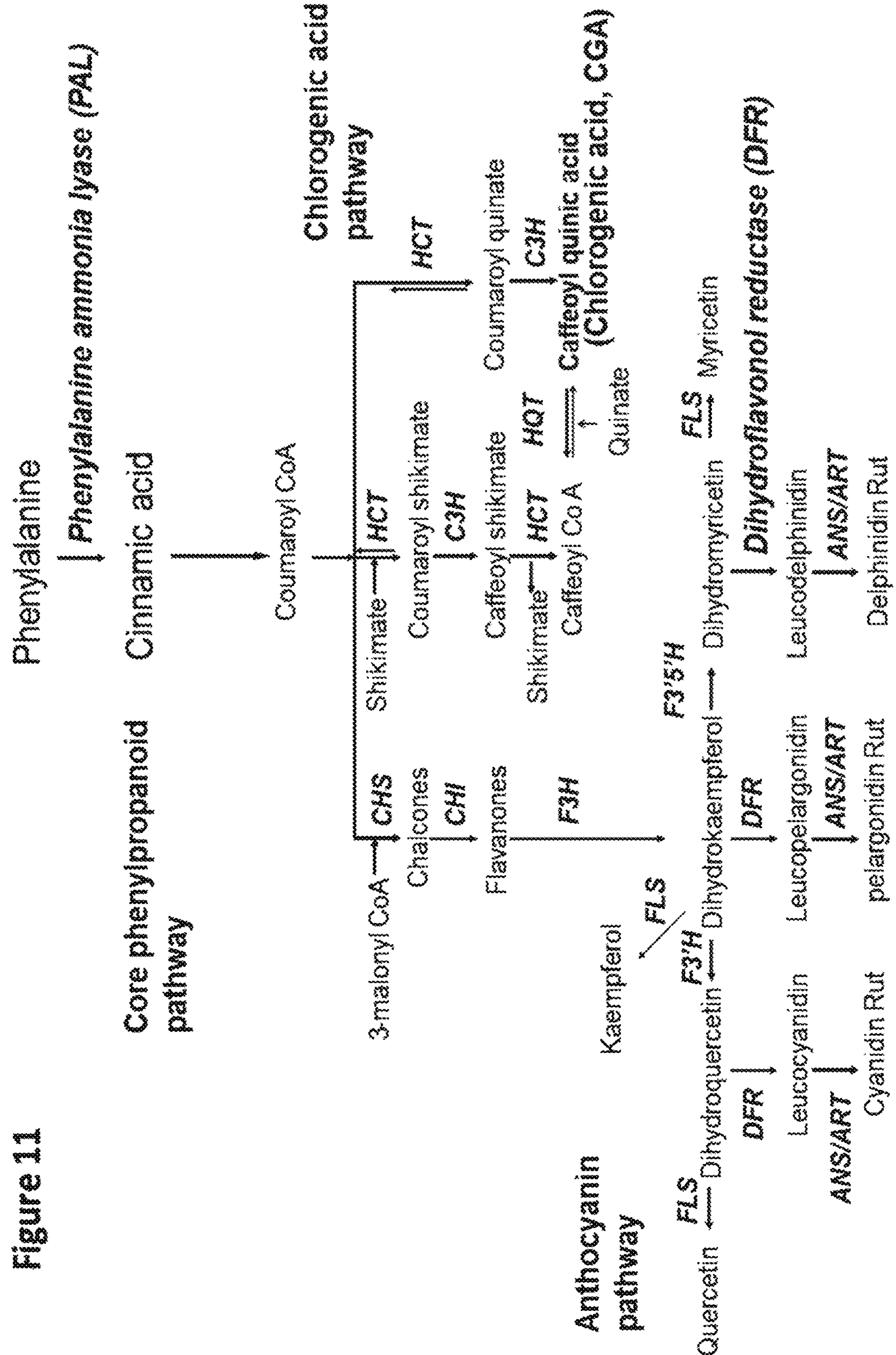
Figure 11
Phenylalanine
Phenylalanine ammonia lyase (PAL)
Core phenylpropanoid pathway
Cinnamic acid
Coumaroyl CoA
Chlorogenic acid pathway
3-malonyl CoA
CHS
Shikimate
HCT
Chalcones
Coumaroyl shikimate
HCT
CHI
C3H
Flavanones
Caffeoyl shikimate
Coumaroyl quinate
Shikimate
HCT
HQT
C3H
F3H
Caffeoyl Co A
Caffeoyl quinic acid
(Chlorogenic acid, CGA)
Anthocyanin pathway
Kaempferol
Quinate
FLS
F3'5'H
Quercetin
FLS
Dihydroquercetin
F3'H
Dihydrokaempferol
Dihydromyricetin
FLS
Myricetin
DFR
DFR
Dihydroflavonol reductase (DFR)
Leucocyanidin
Leucopelargonidin
Leucodelphinidin
ANS/ART
ANS/ART
ANS/ART
Cyanidin Rut
pelargonidin Rut
Delphinidin Rut A) Total TSNA: Dark Fire Cured
PPM
12.0
10.0
8.0
6.0
4.0
2.0
0.0
NLM LC Control 100%
NLM LC PAP1 23%
NLM LC MYB3 38%
NLM SRC 46%
NLM SRC PAP1 10%
NLM SRC MYB3 28%
B) Total TSNA: Dark Air Cured
PPM
15.0
10.0
5.0
0.0
NLM LC Control 100%
NLM LC PAP1 13%
NLM LC MYB3 38%
NLM SRC 42%
NLM SRC PAP1 5%
NLM SRC MYB3 26%

A) NNN: Dark Fire Cured
PPM
4.0
3.0
2.0
1.0
0.0
NLM LC Control 100%
NLM LC PAP1 19%
NLM LC MYB3 28%
NLM SRC 13%
NLM SRC PAP1 4%
NLM SRC MYB3 8%
B) NNK: Dark Fire Cured
PPM
0.8
0.6
0.4
0.2
0
NLM LC Control 100%
NLM LC PAP1 54%
NLM LC MYB3 64%
NLM SRC 59%
NLM SRC PAP1 32%
NLM SRC MYB3 46%

A) NAT: Dark Fire Cured
PPM
8.0
6.0
4.0
2.0
0.0
NLM LC Control 100%
NLM LC PAP1 23%
NLM LC MYB3 41%
NLM SRC 63%
NLM SRC PAP1 11%
NLM SRC MYB3 38%
B) NAB: Dark Fire Cured
PPM
0.50
0.40
0.30
0.20
0.10
0.00
NLM LC Control 100%
NLM LC PAP1 30%
NLM LC MYB3 48%
NLM SRC 61%
NLM SRC PAP1 13%
NLM SRC MYB3 39%

A) NNN: Dark Air Cured
PPM
8.0
6.0
4.0
2.0
0.0
NLM LC Control 100%
NLM LC PAP1 11%
NLM LC MYB3 28%
NLM SRC 18%
NLM SRC PAP1 4%
NLM SRC MYB3 12%
B) NNK: Dark Air Cured
PPM
1.6
1.2
0.8
0.4
0.0
NLM LC Control 100%
NLM LC PAP1 11%
NLM LC MYB3 91%
NLM SRC 80%
NLM SRC PAP1 21%
NLM SRC MYB3 80%

A) NAB: Dark Air Cured
PPM
0.4
0.3
0.2
0.1
0
NLM LC Control 100%
NLM LC PAP1 15%
NLM LC MYB3 47%
NLM SRC 58%
NLM SRC PAP1 7%
NLM SRC MYB3 41%
B) NAT: Dark Air Cured
PPM
8.0
6.0
4.0
2.0
0.0
NLM LC Control 100%
NLM LC PAP1 9%
NLM LC MYB3 36%
NLM SRC 57%
NLM SRC PAP1 3%
NLM SRC MYB3 29%

A) Nicotine in fire cured dark tobacco
Percent per gram
8.0
6.0
4.0
2.0
0.0
NLM LC Control
NLM LC PAP1
NLM LC MYB3
NLM SRC
NLM SRC PAP1
NLM SRC MYB3
B) Other Alkaloids in fire cured dark tobacco
Nornicotine
Anabasine
Anatabine
Percent per gram
0.20
0.15
0.10
0.05
0.00
NLM LC Control
NLM LC PAP1
NLM LC MYB3
NLM SRC
NLM SRC PAP1
NLM SRC MYB3

A) Nicotine in air cured dark tobacco
Percent per gram
8.0
6.0
4.0
2.0
0.0
NLM LC Control
NLM LC PAP1
NLM LC MYB3
NLM SRC
NLM SRC PAP1
NLM SRC MYB3
B) Other Alkaloids in air cured dark tobacco
Nornicotine
Anabasine
Anatabine
Percent per gram
0.20
0.15
0.10
0.05
0.00
NLM LC Control
NLM LC PAP1
NLM LC MYB3
NLM SRC
NLM SRC PAP1
NLM SRC MYB3

SEQUENCE LISTING

```
Sequence total quantity: 73
SEQ ID NO: 1            moltype = AA  length = 330
FEATURE                 Location/Qualifiers
source                  1..330
                        mol_type = protein
                        organism = Nicotiana sp.
SEQUENCE: 1
MESKSSGGGE GKVVCVTGAS GFIASWLVKM LLQRGYTVNA TVRNLKDASK VDHLLGLDGA  60
KERLHLFKAE LLGEHSFDPA VDGCEGVFHT ASPVSLTAKS KEELVDPAVS GTLNVLRSCT  120
KSTSVRRVVI TSSTASVICN KNMSTPGAVA DETWYSDAEL CEERKEWYQL SKTLAEEAAW  180
KFAKENGLDL VTLHPGLVIG PLLQPTLNFS CEAIVNFIKE GKEAWSGGIY RFVDVRDVAN  240
AHILAFEVPS ANGRYCLVGV NGYSSLVLKI VQKLYPSITL PENFEDGLPL IPTFQVSSER  300
AKSLGVNFTS LELSVKDTVE SLIEKNFLKI                                  330

SEQ ID NO: 2            moltype = AA  length = 416
FEATURE                 Location/Qualifiers
source                  1..416
                        mol_type = protein
                        organism = Nicotiana sp.
SEQUENCE: 2
MMCNIISLVS IINFFLLFYR VVVLPQHAAA SHSTVEFLPG FEGPLPFHLE TGYIGVGEYE  60
EVQLFYYFLK SESEPTKDPI LIWLSGGPGC SSFTALVYQI GPLYFEPNEY NGSLPKLTLN  120
PNSWTKVANI IFLDQPVNSG FSYATTSTTF KSTDLQACHH IYQFLRKWLI KHQEFIRNPM  180
YIGGDSYSGI TVPVITQLIS NGIEAGHKPS INLKGYILGN PSTFPLQYNY WVPYAHGMGL  240
ISDELYQATT LILYFKIYHI INAINLAYMV EVHRLSTYWA NDPRVQEALN VRKGAITRWT  300
RCRESIVNKT YTITFQDSIP YHVELSKKLY RSLIYSGDHD MGIPFQSTQF WIKSLNYSIV  360
DEWRPWSFDG QVAGYTRSYS NQMTFATVKG AGHVAPEYKP KECFTMFQRW LSHEPL      416

SEQ ID NO: 3            moltype = AA  length = 569
FEATURE                 Location/Qualifiers
source                  1..569
                        mol_type = protein
                        organism = Nicotiana sp.
SEQUENCE: 3
MLSVASVEAQ KAELSSSVIP PSDQSTEEIH VFRSRLPDIQ ISNNVPLHVY LFERLSEFQD  60
RTCLIAGSSG QSYTFAETHL ICQKIAAGLT NIGIKKGDVI MTFLQNCAEF VFTFLSASMI  120
GAVITTANPF YTKAEAFKQL KASNAKLIVT QSQYVDKFRD SGENDPKIGE DFSVITIDDP  180
PENCLHFSVL SEANEEEMPK GIVIQPDDPV ALPFSSGTTG LPKGVILTHK SLITGVAQLV  240
DGDNPNLYLK QDDVVLCVLP LFHIFALNSV LLVSLRAGAS VLLMQKFEIG ALLELIQNHR  300
VSVAAVVPPL VLALAKNPMV DSFDLSSIRL VLSGAAPLGK ELEEALHQRV PQAIFGQGYG  360
MTEAGPVVTM CPAFAKQPFS TKSGSCGSVV RNADLKVVDP ETGGSLGRNQ PGEICIRGSQ  420
IMKGYLNDDE ATARTIDVDG WLHTGDIGYV DDDDEIYIVD RVKELIKFKG FQVPPAELES  480
LLVSHPDIAD AAVVPQKDDA AGEVPVAFVV RSANGFEITE EAIKEFIAKQ VIFYKRLHKV  540
YFIHAIPKSP SGKILRKELR AKLAAPSTQ                                   569

SEQ ID NO: 4            moltype = AA  length = 551
FEATURE                 Location/Qualifiers
source                  1..551
                        mol_type = protein
                        organism = Nicotiana sp.
SEQUENCE: 4
MGTRAVESSQ QQECEHIFRS RYPPVQVPDN VTLPDFVLHN VELYTDKMAF VDATTGKGYT  60
YGQVARDIRR FAKALRSLGL RKGRVVVVVL PNVPEYAIVA LGIMAAGGVF SGANPAAHSS  120
```

```
EIVKQVESAD GKLIVSDLPT YHKVKDCGLP VIILGEEHVE GTIHWDELLE AAERAGSRTD  180
HITNHEDEMV QQNDLCALPF SSGTTGLSKG VMLTHRNLVA NLCSTLFSVS PEMVGQVTTL  240
GLIPFFHIYG ITGICCATIR NKGKVVVLRR YELRAFLNAL ITHEVTFAPI VPPIILALVK  300
NPIVDEFDLS KLKLRSIMTA AAPLAPEILN EFEKKFPDVQ VQEAYGMTEH SCITLSHSDQ  360
HTAKRNSVGF ILPNLEVKFV DPDTGRSLPK NKPGEICVKS QCVMKGYYKN EFETCLTIDK  420
DGWLQTGDIG YIDDDGDIFL VDRIKELIKY KGFQVAPAEL EGILLTHPSV EDAAVVGLPD  480
EEAGEIPVAW VVLNSKAKES EEDIINYIAS TVAQYKRVRV VQFVDSIPKS PSGKILRRLI  540
KDKMLERLKN A                                                       551

SEQ ID NO: 5            moltype = AA  length = 671
FEATURE                 Location/Qualifiers
source                  1..671
                        mol_type = protein
                        organism = Nicotiana sp.
SEQUENCE: 5
MTEIPPNSQM KTMLQKAVQS VQWTYTLFWQ LCPQQGALVW RDGYYNGAIK TRKTVQPMEV  60
SAEEASLHRS QQLRELYESL SAGESNQPAR RPSAALSPED LTESEWFYLM CVSFSFPPGI  120
GLPGKAYSKK HHIWIMGANE VDSKVFCRAI LAKSARIQTV VGIPLLDGVL ELGTTERVQE  180
EIGFINHVKS FFTEQQQPQL PKPALSEHST SNPTTFSEPH FYSGNTSPSA NVDIAHQDGG  240
AAGEEDEEEE EEEDDDEAEL DSDSIAIQSA ANPIAVEASE LMQLDVSEAI QLGSPDDDSD  300
NMDSDFHLVG AGNTAHDYQR QADSFKAETA ISWPHFQDLQ QLPGGSSYDE LSQEDTHYSQ  360
TVSTILEHRS SKFSSTTMGC ISHDSAQSAF TLCPSTTVCS PNPAHCRHDD SLVDGGGASQ  420
WLLKSILFTV PFLHTKYQSE ASPKSRDVAT VDSSSTASRF RKGCSITSQE EPSGNHVLAE  480
RRRREKLNER FIILRSLVPF VTKMDKASIL GDTIEYVKQL RKKVQDLEAR ARDTEHSRDA  540
DKKGGTATVK VLQGRGKRRM NTVDGSVGGG QATITASPPS TTENEEVVQV QVSIIESDAL  600
VELRCPYKEG LLLNVMQMLR ELKVEVVAIQ SALNNGVFLA ELRAKVKENI CGRKASILEV  660
KRSIHQIIPR D                                                       671

SEQ ID NO: 6            moltype = AA  length = 683
FEATURE                 Location/Qualifiers
source                  1..683
                        mol_type = protein
                        organism = Nicotiana sp.
SEQUENCE: 6
MTEIPPNSQM QTMLQKAVQS VQWTYTLFWQ LCSQQGVLVW RDGYYNGAIK TRKTVQPMEV  60
SAEEASLHRS QQLRELYESL SAGESNQPAR RPSAALSPED LTESEWFYLM CVSFSFPPGI  120
GLPGKAYSKK HHIWIMCANE VDSKVFCRAI LAKSARIQTV VCIPLLDGVL ELGTTERVQE  180
DIGFINHVKS FFTEQQQPQP PKPALSEHST SNSTTFSEPH FYSGNTPPSG NADIAQQDGG  240
AAGEEDEEEE EEEDDEAELD SDSIAIQSEV GGAANPIAAE ASELMQLDMS EAIRLGSPDD  300
GSNNMDSDFH LVGAGNTADY QRQPDSFKAE TAISWAHFQD LQHLPGGSSY EELSQEDTHY  360
SQTVSTILEH FSNRSSKFSS TTMGCISHDS AQSAFTLCPS TTVDCSPNPA HCRRRHDDSL  420
LDGGGASPSS QWLLKSILFT VPFLHTKYQS EASPKSVDVA TVDSSSTASR FRKGCSITSQ  480
EEPSGNHVLA ERRRREKLNE RFIILRSLVP FVTKMDKASI LGDTIEYVKQ LHKKVQDLEA  540
RARHTEQSKD ADQKSGTATV KVLQGRGKRR MNTVEAGNIG GGQAKMTAFP LSTTEDEEVV  600
QVEVSIIESD ALLELRCPYK EGLLLDVMQM LRELKVEVVA IQSSLNNGIF LAELRAKVKE  660
NIYGRKASIV EVKKSIHQII PRD                                          683

SEQ ID NO: 7            moltype = AA  length = 220
FEATURE                 Location/Qualifiers
source                  1..220
                        mol_type = protein
                        organism = Nicotiana sp.
SEQUENCE: 7
MNICTNKSSS GVKKGAWTEE EDVLLKKCIE KYGEGKWHQV PLRAGLNRCR KSCRLRWLNY  60
LRPHIKRGDF SFDEVDLILR LHKLLGNRWS LIAGRLPGRT ANDVKNYWNS HLRKKLIAPH  120
DQKESKQKAK KITIFRPRPR TFSKTNTCVK SNTNTVDKDI EGSSEIIRFN DNLKPTTEEL  180
TDDGIQWWAD LLANNYNNNG IEEADNSSPT LLHEEMPLLS                        220

SEQ ID NO: 8            moltype = AA  length = 419
FEATURE                 Location/Qualifiers
source                  1..419
                        mol_type = protein
                        organism = Nicotiana sp.
SEQUENCE: 8
MVVISAVVPT PSRVESLAKS GIQAIPKEYV RPQEELNGIG NIFEEEKKDE GPQVPTIDLK  60
EIDSEDKEIR EKCHKELKKA AMEWGVMYLV NHGISDQLID RVKVAGKTFF DQPVEEKEKY  120
ANDQPSGNVQ GYGSKLANSA CGQLEWEDYF FHCVFPEDKC DLSIWPKIPT DYIPATSEYA  180
KQIRNLATKI LAVLSIGLGL EEGRLEKEVG GKEDLLLQMK INYYPKCPQP ELALGVEAHT  240
DVSALTFILH NMVPGLQLFY EGQWVTAKCV PNSIIMHIGD TLEILSNGKY KSILHRGVVN  300
KEKVRISWAI FCEPPKEKII LKPLSETITE AEPPRFPPRT FAQHMAHKLF KKDDQDAAAE  360
HKVSKKDDPD SAAGHKPFKK DDQDAVVQQK VLKEDEQDAA AEHKVFKKDN QDAAAEESK   419

SEQ ID NO: 9            moltype = AA  length = 419
FEATURE                 Location/Qualifiers
source                  1..419
                        mol_type = protein
                        organism = Nicotiana sp.
SEQUENCE: 9
MVVISAVVPT PSRVESLAKS GIQAIPKEYV RPQEELNGIG NIFEEEKKDE GPQVPTIDLT  60
```

```
EIDSEDKEIR EKCHQELKKA AIEWGVMHLV NHGISDELID RVKVSGDTFF DQPVEEKEKY  120
ANDQPSGNVQ GYGSKLANSA CGQLEWEDYF FHCVFPEDKC NLSIWPKTPT DYIPATSEYA  180
KQIRNLATKI LAVLSIGLRL EEGRLEKEVG GMEDLLLQMK INYYPKCPQP ELALGVEAHT  240
DVSALTFILH NMVPGLQLFY EGQWVTAKCV PNSIIMHIGD TLEILSNGKY KSILHRGVVN  300
KEKIRISWAI FCEPPKEKII LKPLPETITE AEPPRFPPRT FAQHMAHKLF KKDDQDAAAE  360
HKVSKKDDPD SAAEHKPFKK DDQDAVAQQK VLKEDEQNAA AEHKVFKKDN QDAAAEESK   419

SEQ ID NO: 10          moltype = AA  length = 622
FEATURE                Location/Qualifiers
source                 1..622
                       mol_type = protein
                       organism = Nicotiana sp.
SEQUENCE: 10
MAMGHQDQDG VPNNLRKQLA LAVRGIQWSY AIFWSTPVTQ PGVLEWSDGY YNGDIKTRKT  60
VQVGEVNEDQ LGLHRTEQLR ELYSSLLTGE GEEDLQPQAK RPSAALSPED LTDTEWYFLV  120
CMSFVFNVGQ GLPGKTSATN QTIWLCNAHQ AESRVFSRSL LAKSASIQTV VCFPYLGGVI  180
ELGVTELVLE DPNLIQQIKN SFEVDHSVIS KRPNYNSNDA KDDMNVASRK LDHNVLESDA  240
YPVEINNSSP HDSSNGFVAN QEAEDSLMVV GVIGETSQAQ SWKFVDDNMS NGVHNSLNSS  300
DCISQNYEKL SPLSNGEKET KPCPIDRQEH NQNKLHLLDH QGDDAQYQAV ISTLLKSSDQ  360
LTLGPHFRNI NKKSSFAGWK NDTEAPRIGT AQKLLKKVLL EVPRMHGGVT HKFSRENRKK  420
NGLWRPEVDD IDRSRVISER RRREKINERF MHLASMLPTG GKVDKISLLD ETIEYMKELE  480
RRVQELEARS GKKTNDTAEQ TSDNCGTSKF NDVNGSLKRK ACDMDEMEPE SCNELLKGSS  540
ADGIVISMID KEVSIKMRCL WSEGLLLKIM EALTDLQMDC HTVQSSKIDG ILSIAIESKS  600
NGLKTVSVGA IREVLQRVVW KS                                          622

SEQ ID NO: 11          moltype = AA  length = 364
FEATURE                Location/Qualifiers
source                 1..364
                       mol_type = protein
                       organism = Nicotiana sp.
SEQUENCE: 11
MESSTKSQIP TQSEEERNCT YAMQLLSSSV LPFVLHSTIQ LEVFEILAKS NDTKLSASQI  60
VSQIPNCTKP EAPTMLNRML YVLASYSLFT CSIVEDEKNN GGQKRVYGLS QVGKFFVKNE  120
NGASMGPLLA LLQNKVFINS WFELKDAVLE GGVPFDRVHG VHAFEYPKSD PKFNDVFNKA  180
MINHTTVVMK KILENYKGFE NLKTLVDVGG GLGVNLKMIT SKYPTIKGTN FDLPHVVQHA  240
PSYPGVEHVG GDMFESVPEG DAIFMKWILH DWSDSHNLKL LKNCYKALPD NGKVIVVEAI  300
LPVKPDIDTA VVGVSQCDLI MMAQNPGGKE RSEEEFRALA TEAGFKGVNL ICCVCNFWVM  360
EFCK                                                              364

SEQ ID NO: 12          moltype = AA  length = 506
FEATURE                Location/Qualifiers
source                 1..506
                       mol_type = protein
                       organism = Nicotiana sp.
SEQUENCE: 12
MDLLLLEKTL IGLFFAIIVA IVVSKLRSKN FKLPPGPIPV PVFGNWLQVG DDLNHRNLTE  60
YAKKFGDMFL LRMGQRNLVV VSSPELAKEV LHTQGVEFGS RTRNVVFDIF TGKGQDMVFT  120
VYGEHWRKMR RIMTVPFFTN KVVQQYRRGW EDEVAHVVED VKKNPESATN GIVLRKRLQL  180
MMYNNMYRIM FDRRFESEDD PLFNKLKALN GERSRLAQSF EYNYGDFIPI LRPFLRGYLN  240
ICKEIKQRRL QLFKDYFVDE RKKLANTTKS MDNNSLKCAI DHILEAEQKG EINEDNVLYI  300
VENINVAAIE TTLWSIEWGI AELVNHPEIQ KKLRDEIDSV LGVGVQITEP ELNKLPYLQA  360
VIKETLRLRM AIPLLVPHMN LHDAKLAGYD IPAESKILVN AWWLANNPAT WKKPEEFRPE  420
RFFEEEKHVE ANGNDFRYLP FGVGRRSCPG IILALPILGI TLGRLVQNFE LLPPPGQSKL  480
DTTEKGGQFS LHILKHSTIV MKPRSF                                      506

SEQ ID NO: 13          moltype = AA  length = 298
FEATURE                Location/Qualifiers
source                 1..298
                       mol_type = protein
                       organism = Nicotiana sp.
SEQUENCE: 13
MGRKPCCVKE GLRKGPWSSK EDLLLTNYIK ENGEGQWRSL PKNAGLLRCG KSCRLRWMNY  60
LRPGIKRGNF SQDEEDLIVR LHSLLGNRWS LIAGRLPGRT DNEIKNYWNT HLIKKLKNAG  120
IEPKPHKNFS KCSKKESRKG PQQGKSRKIQ GKKSNNKNNK GQIVQVEKTK VFFPKPIRIS  180
CGISRNNSFE NVTLSTTCSS NSNSGEANLE NKENEVKLEE VSFFPRDLDF GKLLEGDAIY  240
DEFLMEESCH ISNKCSLPMN ESMLEKVYEE YLLLLSENCY LQDDHQNEQN FPVNVSDQ    298

SEQ ID NO: 14          moltype = AA  length = 381
FEATURE                Location/Qualifiers
source                 1..381
                       mol_type = protein
                       organism = Nicotiana sp.
SEQUENCE: 14
MASEAHAAVH APPPVAPTVC VTGAAGFIGS WLVMRLLERG YNVHATVRDP ENKKKVKHLF  60
ELPKADTNLT LWKADLSVEG SFDEAIQGCQ GVFHVATPMD FESEDPENEV IKPTVRGMLS  120
IIESCAKANT VKRLVFTSSA GTLDAQEHQK LFYDETSWSD LDFIYAKKMT GWMYFVSKIL  180
AEKAAMEAAK KKNFDFISII PPLVVGPFLT PTFPPSLITA LSLITGNEAH YCIIKQGQYV  240
HLDDLCEAHI FLYEQPKAEG RFICASHHAI IYDVAKMVRE KWPEYYVPTE FKGIDKDLPV  300
VYFSPKKLTD MGFQFKYTLE DMYKGAIETC RQKQLLPFST QSTADNGRDK ETIPLSAENY  360
```

```
ASGKENSPVA NGTGKSTNGE I                                          381

SEQ ID NO: 15          moltype = AA  length = 382
FEATURE                Location/Qualifiers
source                 1..382
                       mol_type = protein
                       organism = Nicotiana sp.
SEQUENCE: 15
MASEGHAAVH APSPPAAPTV CVTGAAGFIG SWLVMRLLER GYNVHATVRD PENKKKVKHL  60
LELPKADTNL TLWKADLSVE GSFDEAIQGC QGVFHVATPM DFESEDPENE VIKPTVRGML  120
SIIESCAKAN TVKRLVFTSS AGTVDVQEHQ KLLYDETSWS DLDFIYAKKM TGWMYFVSKI  180
LAEKAAMEAA KKKNIDFISI IPPLVVGPFL APTFPPSLIT ALSLITGNEA HYSIIKQGKY  240
VHLDDLCEAH IFLYEHPKAE GRFICASHHA IIYDVAKMVQ EKWPEYYVPT EFKGIDKDLS  300
VVYFSSKKLT DMGFQFKYTL EDMYKGAIET CRQKQLLPFS TRSTADNVRD KEAIPLSTEN  360
YASGKENSPV ANGTGKSTNG EI                                         382

SEQ ID NO: 16          moltype = AA  length = 213
FEATURE                Location/Qualifiers
source                 1..213
                       mol_type = protein
                       organism = Nicotiana sp.
SEQUENCE: 16
MGRKPCCSKE GLRKGTWTAK EDMLLTNYIN EHGEVGWRSL PMKAGSRWSL IAGRIPGRTD  60
NEIKNYWNTH LLKKLKSEGL EPKIHKSLAK NTRRQKEKAN VSSQINQKGY KEKKKRNKKG  120
NIEENCNNIE EKEQVAKKIE EQWHTQDSVQ AMSGFSSTSE VASEKETNCN NVHCPSSGQS  180
LEENDNEIYE KLQASGDSKR CKLNFSAEVN KTP                             213

SEQ ID NO: 17          moltype = AA  length = 435
FEATURE                Location/Qualifiers
source                 1..435
                       mol_type = protein
                       organism = Nicotiana sp.
SEQUENCE: 17
MKIEVKESTM VKPAAETPQQ RLWNSNVDLV VPNFHTPSVY FYRPTGSPNF FDGKVLKEAL  60
SKALVPFYPM AGRLCRDEDG RIEIDCKGQG VLFVEAESDG VVDDFGDFAP TLELRQLIPA  120
VDYSQGIQSY ALLVLQITHF KCGGVSLGVG MQHHAADGAS GLHFINTWSD MARGLDLTIP  180
PFIDRTLLRA RDPPQPQFPH VEYQPPPTLK VTPENTPISE AVPETSVSIF KLTRDQINTL  240
KAKSKEDGNT VNYSSYEMLA GHVWRSTCMA RGLAHDQETK LYIATDGRSR LRPSLPPGYF  300
GNVIFTTTPI AVAGDIQSKP IWYAASKLHD ALARMDNDYL RSALDYLELQ PDLKALVRGA  360
HTFKCPNLGI TSWSRLPIHD ADFGWGRPIF MGPGGIAYEG LSFILPSPTN DGSQSVAISL  420
QAEHMKLFEK FLYDF                                                 435

SEQ ID NO: 18          moltype = AA  length = 436
FEATURE                Location/Qualifiers
source                 1..436
                       mol_type = protein
                       organism = Nicotiana sp.
SEQUENCE: 18
MGSEKMMKIN IKESTLVKPS KPTPTKRLWS SNLDLIVGRI HLLTVYFYKP NGSSNFFDSK  60
IMKEALSNVL VSFYPMAGRL ARDEQGRIEI NCNGEGVLFV EAESDAFVDD FGDFTPSLEL  120
RKLIPTVDTS GDISTFPLII FQVTRFKCGG VSLGGGVFHT LSDGLSSIHF INTWSDIARG  180
LSVAIPPFID RTLLRARDPP TSSFEHVEYH PPPSLISSSK SLESTSPKPS TTTMLKFSSD  240
QLGLLKSKSK HDGSTYEILA AHIWRCTCKA RALSDDQLTK LHVATDGRSR LCPPLPPGYL  300
GNVVFTGTPM AKSSELLQEP LTNSAKRIHS ALSKMDDNYL RSALDYLELL PDLSALIRGP  360
TYFASPNLNI NSWTRLPVHD SDFGWGRPIH MGPACILYEG TVYILPSPNS KDRNLRLAVC  420
LDADHMPLFE KYLYEF                                                436

SEQ ID NO: 19          moltype = AA  length = 715
FEATURE                Location/Qualifiers
source                 1..715
                       mol_type = protein
                       organism = Nicotiana sp.
SEQUENCE: 19
MASNGHVNGG ENFELCKKSA DPLNWEMAAE SLRGSHLDEV KKMVSEFRKP MVKLGGESLT  60
VAQVAAIAVR DKSANGVKVE LSEEARAGVK ASSDWVMDSM NKGTDSYGVT TGFGATSHRR  120
TKNGGALQKE LIRFLNAGVF GNGTETSHTL PHSATRAAML VRINTLLQGY SGIRFEILEA  180
ITKLINSNIT PCLPLRGTIT ASGDLVPLSY IAGLLTGRPN SKAVGPNGET LNAEEAFRVA  240
GVNGGFFELQ PKEGLALVNG TAVGSGMASM VLFDSNILAV MSEVLSAIFA EVMNGKPEFT  300
DHLTHKLKHH PGQIEAAAIM EHILDGSSYV KAAQKLHEMD PLQKPKQDRY ALRTSPQWLG  360
PQIEVIRAAT KMIEREINSV NDNPLIDVSR NKALHGGNFQ GTPIGVSMDN ARLALASIGK  420
LMFAQFSELV NDYYNNGLPS NLTASRNPSL DYGFKGAEIA MASYCSELQF LANPVTNHVQ  480
SAEQHNQDVN SLGLISARKT AEAVDILKLM SSTYLVALCQ AIDLRHLEEN LKNAVKNTVS  540
QVAKRTLTMG ANGELHPARF CEKELLRIVD REYLFAYADD PCSCNYPLMQ KLRQVLVDHA  600
MNNGESEKNV NSSIFQKIGA FEDELKAVLP KEVESARAAL ESGNPAIPNR ITECRSYPLY  660
RFVRKELGTE LLTGEKVRSP GEECDKVFTA MCNGQIIDPM LECLKSWNGA PLPIC       715

SEQ ID NO: 20          moltype = AA  length = 341
FEATURE                Location/Qualifiers
source                 1..341
```

```
                        mol_type = protein
                        organism = Nicotiana sp.
SEQUENCE: 20
MDNSAPDSLS RSETAVTYDS PYPLYAMAFS SLRSSSGHRI AVGSFLEDYN NRIDILSFDS  60
DSMTVKPLPN LSFEHPYPPT KLMFSPPSLR RPSSGDLLAS SGDFLRLWEI NEDSSTVEPI  120
SVLNNSKTSE FCAPLTSFDW NDVEPKRLGT CSIDTTCTIW DIEKSVVETQ LIAHDKEVHD  180
IAWGEARVFA SVSADGSVRI FDLRDKEHST IIYESPQPDT PLLRLAWNKQ DLRYMATILM  240
DSNKVVILDI RSPTMPVAEL ERHQASVNAI AWAPQSCKHI CSGGDDTQAL IWELPTVAGP  300
NGIDPMSVYS AGSEINQLQW SSSQPDWIGI AFANKMQLLR V                     341

SEQ ID NO: 21           moltype = AA  length = 440
FEATURE                 Location/Qualifiers
source                  1..440
                        mol_type = protein
                        organism = Nicotiana sp.
SEQUENCE: 21
MSMSVALLWV VSPTSEVSNG TGLLDSVREG NRVFVSSRFL ARDRNLMWNG RIKKGGRQRW  60
NFGSLIADPR YSCLGGSRTE KGSSFSVQSS LVASPAGEMT VSSEKKVYDV VLKQAALVKR  120
QLRSTDELEV KPDIVVPGNL GLLSEAYDRC GEVCAEYAKT FYLGTKLMTP ERRRAIWSIY  180
VWCRRTDELV DGPNASHITP QALDRWEARL EDIFSGRPFD MLDAALSDTV SRFPVDIQPF  240
RDMIEGMRMD LWKSRYNNFD ELYLYCYYVA GTVGLMSVPV MGIAPESKAT TESVYNAALA  300
LGLANQLTNI LRDVGEDARR GRVYLPQDEL AQAGLSDEDI FAGRVTDKWR NFMKKQIQRA  360
RKFFDESEKG VTELDSASRW PVSTALLLYR KILDEIEAND YNNFTRRAYV SKPKKLLTLP  420
IAYAKSLVPP NRTSSPLAKT                                             440

SEQ ID NO: 22           moltype = AA  length = 440
FEATURE                 Location/Qualifiers
source                  1..440
                        mol_type = protein
                        organism = Nicotiana sp.
SEQUENCE: 22
MSMSVALLWV VSPTSEVSNG TGLLDSVREG NRVFVSSRFL ARDRNLMWNG RIKKGGRQRW  60
NFGSLIADPR YSCLGGSRTE KGSSFSVQSS LVASPAGEMT VSSEKKVYDV VLKQAALVKR  120
QLRSTDELEV KPDIVVPGNL GLLSEAYDRC GEVCAEYAKT FYLGTKLMTP ERRRAIWAIY  180
VWCRRTDELV DGPNASHITP QALDRWEARL EDIFSGRPFD MLDAALSDTV SRFPVDIQPF  240
RDMIEGMRMD LWKSRYNNFD ELYLYCYYVA GTVGLMSVPV MGIAPESKAT TESVYNAALA  300
LGLANQLTNI LRDVGEDARR GRVYLPQDEL AQAGLSDEDI FAGRVTDKWR NFMKKQIQRA  360
RKFFDESEKG VTELDSASRW PVLAALLLYR KILDEIEAND YNNFTRRAYV SKPKKLLTLP  420
IAYAKSLVPP NRTSSPLAKT                                             440

SEQ ID NO: 23           moltype = AA  length = 248
FEATURE                 Location/Qualifiers
source                  1..248
                        mol_type = protein
                        organism = Nicotiana sp.
SEQUENCE: 23
MEGSSKGLRK GAWTTEEDSL LRQCINKYGE GKWHQVPVRA GLNRCRKSCR LRWLNYLKPS  60
IKRGKLSSDE VDLLLRLHRL LGNRWSLIAG RLPGRTANDV KNYWNTHLSK KHEPCCKIKM  120
KKRDITPIPT TPALKNNVYK PRPRSFTVNN DCNHLNAPPK VDVNPPCLGL NINNVCDNSI  180
IYNKDKKKDQ LVNNLIDGDN MWLEKFLEES QEVDILVPEA TTTEKGDTLA FDVDQLWSLF  240
DGETVKFD                                                          248

SEQ ID NO: 24           moltype = DNA  length = 992
FEATURE                 Location/Qualifiers
source                  1..992
                        mol_type = other DNA
                        organism = Nicotiana sp.
SEQUENCE: 24
atggaaagca agagttccgg aggcggagaa ggaaaggttg tatgtgtaac aggggcctct  60
ggtttcatag cttcatggct tgttaagatg ctacttcaac gtggttacac tgtcaatgcc  120
actgttcgca acctcaagga tgcgagtaaa gtggatcacc tgttaggcct tgacggagct  180
aaagagaggc tgcatctttt caaagctgag ttacttggtg agcattcgtt tgatcctgcc  240
gttgatggtt gtgaaggtgt ctttcataca gcatcacctg tttctctcac agctaaatcc  300
aaggaggaac ttgtagaccc tgctgtgagc ggaacattaa acgtccttag gtcatgtacc  360
aaatcaacat ctgttagaag agtggtcata acctcttcta ccgcttctgt tatttgcaat  420
aaaaacatgt caacccctgg agctgtagct gatgagactt ggtattcaga tgcagaactc  480
tgtgaggaaa gaaaggaatg gtatcaactc tccaaaacct tggctgagga agctgcttgg  540
aaatttgcaa aggagaatgg gttggacttg gttacacttc atccaggtct agtcatcggt  600
ccacttctgc agcctacgct caatttctcg tgcgaggcta tagtgaactt cataaaagaa  660
ggaaaagaag catggtctgg cggaatatat agatttgtcg atgttaggga tgttgctaat  720
gcacatatac tagcatttga ggtcccttca gcaaatggaa gatattgttt agttggggta  780
aatggatatt cttctttggt tttgaagatt gtacaaaagc tttacccttc catcactctc  840
cctgagaatt ttgaagatgg attacctctt atcccaacct tccaagtatc aagcgaaaga  900
gcaaaaagtt taggcgtcaa tttcacatct cttgagttga gcgtgaagga cactgttgaa  960
agcttgatag agaagaactt cctcaagatt tg                               992

SEQ ID NO: 25           moltype = DNA  length = 1251
FEATURE                 Location/Qualifiers
source                  1..1251
```

```
                        mol_type = other DNA
                        organism = Nicotiana sp.
SEQUENCE: 25
atgatgtgca atattatttc acttgtgtcc atcatcaact tctttttgct gttttataga  60
gttgttgtcc taccacaaca tgctgctgct tctcactcta ccgttgaatt tcttcctgga  120
tttgaaggtc cacttccttt ccatcttgag actgggtata ttggagtagg tgaatatgaa  180
gaagtgcagc tcttttatta ttttcttaaa tcagaatcag aacccacaaa agatcctatt  240
ttgatttggc tctcaggagg acctggttgc tcttccttta ctgcacttgt ttatcaaata  300
gggcccttgt attttgagcc aaacgagtat aatgggagcc ttccaaagct aacattgaat  360
ccaaactcat ggaccaaggt agctaacata atattcttgg atcaacctgt gaatagtggc  420
ttctcttatg caacaacttc aacaacattc aagtctactg atctacaagc atgccaccat  480
atctaccagt ttttgcgaaa gtggttgatt aagcatcaag agttcattag gaatccaatg  540
tacattggtg gagattcata ttctggcatc actgttccag ttatcactca actaatatca  600
aatggaattg aagcagggca caagccatcg attaatctta agggatatat acttgggaat  660
cctagcacgt ttcctcttca atataactac tgggttcctt atgctcatgg aatgggactt  720
atctccgacg aactttatca ggctactact cttatccttt actttaaaat ttatcatatc  780
ataaatgcaa ttaatttagc ttacatggtt gaggtacaca ggttgtctac ttactgggca  840
aatgatccaa gagtacaaga agctcttaat gttcgtaagg gagctataac aagatggaca  900
agatgtaggg aaagtatcgt gaataaaact tacactatta ctttccaaga tagcatacct  960
tatcatgtgg aactcagcaa aaaactttat cgatcactta tatacagtgg cgatcatgat  1020
atgggcattc cattccaatc aactcaattt tggataaaat ctctaaatta ttctattgtg  1080
gatgaatggc ggccatggag ttttgatggt caagttgcag gatatacaag atcctattcc  1140
aaccagatga catttgcaac tgtcaaggga gcaggacatg tagctcctga gtacaagcct  1200
aaagagtgct ttaccatgtt tcaaagatgg ttgtctcatg aaccactttg a           1251

SEQ ID NO: 26           moltype = DNA  length = 1710
FEATURE                 Location/Qualifiers
source                  1..1710
                        mol_type = other DNA
                        organism = Nicotiana sp.
SEQUENCE: 26
atgttgagtg tagctagtgt tgaagcccag aaagcagagt tatcttcttc tgtaattcct  60
ccttctgatc aatctactga agagatacac gtgtttagat caagattacc agatatacaa  120
atttccaaca atgttcctct tcatgtttac ttgtttgaga ggctctctga atttcaagat  180
aggacatgtc ttatagcagg cagcagtgga caatcctaca cttttgctga aactcatctc  240
atttgccaga aaatagctgc tggcttaaca aatataggaa tcaaaaaggg agatgtaatc  300
atgacttttc tccagaactg cgcggaattt gtgtttactt ttctctcggc ttctatgatt  360
ggcgccgtta taactacagc taatccattt tacacaaaag cagaggcgtt taagcaatta  420
aaagcgtcga atgcaaaact aatcgttact caatctcagt acgtggataa atttcgtgat  480
tctggagaga atgacccgaa aattggcgaa gatttttcag tcattacaat tgatgacccc  540
cctgaaaatt gcttacattt ctctgtactt tctgaagcta acgaagagga aatgccaaag  600
ggaattgtaa tccaaccaga tgatccagta gctttaccat ttcttcagg aacaacaggg  660
ctaccaaaag gtgtgatttt aactcacaaa agtttaatca caggagtagc tcaattagtc  720
gacggagata atccaaattt gtacttaaaa caagacgacg tggtgctatg tgtgctacct  780
ttgtttcaca tatttgcgtt aaattcagtg cttttagtct cgttaagagc aggagctagt  840
gttttactaa tgcaaaaatt cgaaattggt gcattgctgg agctgataca aaaccaccgc  900
gtgtcagttg cagcagtagt tccgcccttg gttcttgcgt tggcgaaaaa tccgatggtt  960
gattcgttcg atttgagttc gattaggctc gtgttgtccg gggcggcgcc gctggggaaa  1020
gagttggagg aagcgctaca tcaaagagtc ccgcaagcta tatttggtca ggggtatggt  1080
atgacagagg caggaccagt agtaacaatg tgcccagcat ttgcaaagca accattttca  1140
accaaatctg gctcatgtgg ttcagtagtt cgaaatgcag acctcaaggt ggtcgacccc  1200
gaaactggtg gctccctcgg ccgcaaccaa cccggcgaaa tttgcatccg tggttcccaa  1260
atcatgaaag gttatctgaa tgatgatgag gccacggcac ggaccataga tgtcgatgga  1320
tggctccaca ctggtgatat aggatacgta gatgacgatg atgaaatata catcgtcgat  1380
agagtcaaag agcttatcaa gttcaaagga ttccaggtgc caccagctga gcttgagtcc  1440
cttctagtaa gccatccaga tattgcagat gctgctgttg taccgcaaaa agatgatgcg  1500
gcaggggaag tcccagttgc atttgtggtc cgctccgcca atggttttga aattactgaa  1560
gaagctataa aggaatttat tgccaaacag gtgatattct ataaaagatt gcacaaggtg  1620
tattttattc acgctattcc aaagtctccg tctggaaaga tactgaggaa agaactgaga  1680
gccaaactag ctgcgccctc cacccagtga                                 1710

SEQ ID NO: 27           moltype = DNA  length = 1656
FEATURE                 Location/Qualifiers
source                  1..1656
                        mol_type = other DNA
                        organism = Nicotiana sp.
SEQUENCE: 27
atgggaactc gtgcagtaga aagctcacag cagcaagaat gtgaacatat tttccggagt  60
agatatcctc cggttcaagt accggacaat gtgaccctcc cggattttgt gcttcacaat  120
gtagagttat acactgacaa aatggcattt gtggatgcta ccactggcaa aggctacact  180
tatggccaag ttgcaagaga cataaggagg ttcgccaagg ccttgagatc ccttggctta  240
aggaaaggac gggtggtggt ggtagttctt ccaaatgtac cagaatatgc tattgttgct  300
cttggaatca tggctgctgg tggcgtcttc tccggtgcaa atccagcagc tcattcatca  360
gaaatcgtga aacaagttga atctgctgat ggcaagctta ttgtctctga tctaccaacc  420
tatcacaagg ttaaagattg tgggctgcca gtaataatac taggtgaaga acatgtagaa  480
ggaacaattc attgggatga attgcttgaa gctgcagagc gtgccggttc cagaactgat  540
cacataacaa accatgaaga tgaaatggtg cagcaaaatg atttatgtgc actgcccttc  600
tcgtcaggca ctacggggct gtccaaggga gtgatgttaa cccacagaaa tctagtagca  660
aacctctgct ctacactctt cagtgttagc ccagaaatgg taggccaagt tacaacactg  720
```

```
ggtttgatac cattcttcca catttatggg ataactggaa tctgttgtgc aaccattaga  780
aacaaaggga aagtggtagt cttgcgtagg tacgaactga gggcatttct aaatgcactc  840
attacacatg aagtcacatt tgcaccaatt gtgccaccta tcatcttggc acttgttaag  900
aatcctattg tggatgaatt tgatctcagc aagcttaagc ttagatccat catgacagcg  960
gcagccccac ttgcccctga gattcttaat gaatttgaaa agaaatttcc cgatgttcag  1020
gtccaagagg catatgggat gactgagcac agctgcatta ctctttctca tagtgaccag  1080
catactgcta aaagaaattc tgttggtttt attctaccta atttggaggt aaagttcgtt  1140
gatcctgata ccggtagatc tctccccaaa aacaaaccag gcgagatatg tgtcaaaagc  1200
caatgtgtta tgaagggtta ctacaaaaat gaatttgaga cttgccttac cattgataag  1260
gatggatggc ttcagactgg tgacattggc tacattgacg atgatggaga tatcttccta  1320
gtcgatcgta tcaaagagct tatcaagtac aagggattcc aagttgctcc agctgagtta  1380
gaagggatcc ttctcacaca tccttcagta gaagatgctg cagtagttgg gctgccagat  1440
gaagaagcag gagagatacc agtggcatgg gtagtcttga actcaaaagc aaaagaaagc  1500
gaagaggaca ttatcaacta cattgcatcg actgttgcac agtataaacg agtgagagtg  1560
gtgcagttcg ttgatagtat tccaaaatct ccttctggaa aaatactgag aagacttatc  1620
aaggataaga tgctagagag acttaagaat gcatag                            1656

SEQ ID NO: 28          moltype = DNA  length = 2016
FEATURE                Location/Qualifiers
source                 1..2016
                       mol_type = other DNA
                       organism = Nicotiana sp.
SEQUENCE: 28
atgacggaga taccgcctaa cagccagatg aaaaccatgt tgcagaaggc agtgcaatcg  60
gttcaatgga catatactct tttctggcaa ttatgtcccc aacaaggggc gttagtgtgg  120
agagatggat attacaatgg ggctataaag actagaaaga cagtgcagcc aatggaagtt  180
agcgctgagg aagcttctct tcacagaagc caacagctta gagaacttta cgaatcactt  240
tccgccggcg agtcaaatca gccagcgaga aggccgtcgg cagctttgtc accggaggac  300
ttgacggagt ccgagtggtt ttatctcatg tgtgtttctt tctcttttcc tcctggcatc  360
ggattacctg gcaaggctta ttcgaagaaa catcacatat ggatcatggg cgcaaacgag  420
gttgatagca aagtcttctg tagagctatt cttgccaaga gcgcccgcat acagacggtc  480
gttggtattc ctctcttgga tggtgtactg gaactgggaa ctacagaaag ggttcaagaa  540
gagattggat tcataaacca tgtaaagagc tttttcactg agcaacaaca acctcagcta  600
ccaaagccag ccttatctga gcactccact tccaatccca ccaccttttc cgagccacat  660
ttttactccg gcaatacttc gccatctgct aatgttgata ttgcgcatca agatggcgga  720
gctgccggcg aagaagatga ggaggaggaa gaagaagaag atgatgatga agccgagttg  780
gactcggata gtatagcgat tcaaagcgcg gctaatccta ttgccgttga ggctagtgaa  840
ctcatgcagc ttgatgtgtc cgaggctata cagctcggct cgcccgatga tgactctgat  900
aatatggact ctgattttca tttggttggc gctggaaaca cggctcatga ctaccagcgc  960
caagctgact ctttcaaagc cgagaccgcc attagctggc cgcacttcca agaccttcaa  1020
caattaccag gtggctctag ttatgatgaa ttatcacaag aagacacaca ctattctcaa  1080
acagtgtcaa ccattctcga acaccgaagc tccaaatttt cctctacaac aatgggctgt  1140
atttctcatg actcggccca atctgccttc acattgtgcc ctagcaccac cgtctgcagc  1200
ccgaatcccg cccactgccg ccacgacgac tcacttgtcg acggtggcgg cgcctcccag  1260
tggctgctca aaagcatact cttcactgtc ccatttcttc acactaaata ccaatctgaa  1320
gcttctccaa agtcacgtga cgtcgccact gttgattcct ccagtactgc ttctcgcttt  1380
cgcaaaggct gtagtataac gtcgcaagaa gagccaagtg gaaaccatgt acttgcagaa  1440
cgacgtcgta gagagaagct aaatgagcgt tttatcatat taaggtctct tgtacctttt  1500
gtaacgaaaa tggacaaagc ctccattttg ggtgacacca tagagtatgt caagcagtta  1560
cgtaagaaag ttcaggatct tgaagctcgt gctcgcgaca cggagcactc cagagatgca  1620
gataaaaaag gtggcacagc tacagtgaag gtgttgcaag gaaggggtaa gaggagaatg  1680
aatacggtag atggaagtgt tggtggaggg caggcaacga taacggcgtc cccaccgtca  1740
acgacggaaa atgaggaggt tgtgcaagta caagtatcaa ttatcgaaag cgatgcattg  1800
gtggagctcc ggtgtccgta caaagagggg ttgctgttaa atgtaatgca gatgctaagg  1860
gaactcaaag tggaagttgt agccattcaa tcagctctta ataatggcgt cttcttggct  1920
gagttaagag ctaaggtaaa agagaatata tgtggaagga aagcaagcat tttggaagta  1980
aaaaggtcaa tacatcagat aatccctaga gattaa                            2016

SEQ ID NO: 29          moltype = DNA  length = 2052
FEATURE                Location/Qualifiers
source                 1..2052
                       mol_type = other DNA
                       organism = Nicotiana sp.
SEQUENCE: 29
atgacggaga taccgcctaa cagccagatg caaaccatgt tgcagaaggc tgtgcaatcg  60
gttcaatgga catatactct tttctggcaa ttatgttccc aacaaggggt gttagtgtgg  120
agagatggat attacaatgg ggctataaag actagaaaga ctgtgcagcc aatggaagtt  180
agcgctgagg aagcttctct tcacagaagc caacagctta gagaacttta cgaatcactt  240
tccgccggcg agtcaaatca gccggcgaga aggccgtcgg cagctttgtc accggaggac  300
ttgacggaat ccgagtggtt ttatctcatg tgtgtttctt tctcttttcc tcctggcatc  360
ggattacctg gcaaggctta ttcaaagaaa catcacatat ggattatgtg cgcaaacgag  420
gttgatagca aagtcttctg tagagctatt cttgccaaga gtgcccgcat acagacggtc  480
gtctgtattc ctctcttgga tggtgtactg gaactgggaa ctacagaaag ggttcaagaa  540
gacattggat tcataaacca tgtaaagagc tttttcactg agcaacaaca acctcagcca  600
ccaaagccag ccttatctga gcactccact tccaattcca ccaccttttc cgagccacac  660
ttttactccg gcaatactcc gccatctggc aatgctgata ttgcgcagca agatggcgga  720
gctgccggag aagaagatga ggaggaggaa gaagaagaag acgatgaagc cgagttggat  780
tcggatagta tagcaattca aagtgaggtt ggtggcgcgg ctaatcctat agcggctgag  840
gctagtgaac tcatgcagct tgatatgtct gaggctatac ggcttggctc gcccgatgat  900
```

```
ggctctaata atatggactc tgattttcat ttggttggcg ctggaaatac ggctgactac  960
cagcgtcaac ctgactcttt caaagccgag actgccatta gctgggctca cttccaagac  1020
cttcaacatt taccaggtgg ctctagttat gaagaattat cacaagaaga cacacattat  1080
tctcaaacag tgtcaaccat tcttgaacac ttctcaaacc gaagctccaa atttcctct  1140
accacaatgg gctgtatttc tcatgactca gcccaatctg ccttcacatt gtgccctagc  1200
accaccgtcg actgcagccc gaatcccgcc cactgccgcc gccgccacga cgattcactt  1260
ctcgacggtg gcggcgcctc cccctcctcc cagtggctgc tcaaaagcat actcttcact  1320
gtcccatttc ttcacactaa ataccaatct gaagcttctc cgaaatcagt tgacgtcgcc  1380
actgttgatt cctccagtac tgcttctcgc tttcgcaaag gctgtagtat aacgtcgcaa  1440
gaagagccca gtggaaacca tgtacttgca gaacgacgtc gtagagaaaa gctaaatgag  1500
cgttttatca tattaaggtc tcttgtacct tttgttacga aaatggataa agcctccatt  1560
ttgggtgaca ccatagagta tgtcaagcag ttacataaga aagttcagga tcttgaagct  1620
cgtgctcgtc acacggagca gtccaaagat gcagaccaaa aaagtggcac agctacagtg  1680
aaggtgttgc aagggagggg taagaggaga atgaatacgg tggaggccgg aaatattggt  1740
ggagggcagg caaagatgac ggcttttccg ctatcaacaa cggaggatga agaggttgtg  1800
caagtagaag tatcaattat tgaaagcgat gcattgttgg agctccgatg tccgtacaaa  1860
gaggggctgc tgttagatgt aatgcagatg ctaagggaac tcaaggtgga agttgtagcc  1920
attcaatcat ctcttaataa tggcatcttc ttggctgagt taagagctaa ggtaaaagag  1980
aatatatatg gaaggaaagc aagcattgtg gaagtaaaaa agtcaataca tcagataatc  2040
cctagagatt aa                                                      2052
```

```
SEQ ID NO: 30          moltype = DNA  length = 663
FEATURE                Location/Qualifiers
source                 1..663
                       mol_type = other DNA
                       organism = Nicotiana sp.
SEQUENCE: 30
atgaatattt gtactaataa gtcgtcgtca ggagtgaaga aaggtgcatg gactgaagaa  60
gaagatgttc tattgaaaaa atgcatcgag aaatatggag aaggaaagtg gcatcaagtt  120
cctcttagag ctggtttgaa tagatgcaga aagagctgca gattaaggtg gctaaattat  180
ctaaggccac atataaagag aggagacttc tcttttgatg aagtagatct cattttgagg  240
cttcataagc tgttaggcaa cagatggtca cttattgctg gtagacttcc tggaaggacg  300
gcaaacgatg tcaaaaacta ctggaacagc catcttcgca agaagttaat tgctcctcat  360
gatcaaaagg agagcaagca aaaagcaaag aagatcacca tattcagacc tcggcctcga  420
accttctcaa agacaaatac ttgtgttaaa agtaacacaa atactgtaga taaggatatt  480
gaaggcagca gcgaaataat tagattcaac gataatttga agccaacaac tgaagaattg  540
acggatgatg gaattcaatg gtgggccgat ttactagcta acaattacaa caataatggg  600
attgaggaag ctgataattc atcaccaact ttgttgcatg aggaaatgcc acttctcagt  660
tga                                                                663
```

```
SEQ ID NO: 31          moltype = DNA  length = 1260
FEATURE                Location/Qualifiers
source                 1..1260
                       mol_type = other DNA
                       organism = Nicotiana sp.
SEQUENCE: 31
atggtggtga tcagtgcagt agttccaact ccttcaagag ttgaaagctt ggctaaaagt  60
ggaatccagg ctatccctaa agagtatgtg aggccacaag aagagttaaa tggaatagga  120
aacatatttg aggaagagaa gaaagatgaa ggacctcaag taccgacgat tgatctgaaa  180
gaaatcgact cagaggacaa ggaaattcgc gagaaatgcc acaaagagtt gaagaaagca  240
gctatggagt ggggtgttat gtaccttgtt aaccatggca tatcagatca gctaattgat  300
cgtgtcaagg ttgctggaaa gaccttcttt gatcaacctg ttgaagaaaa ggagaagtat  360
gctaatgacc aaccctctgg caatgtccaa ggctatggca gcaagttagc aaatagtgct  420
tgtggtcagc ttgaatggga ggattatttc ttccattgcg ttttccccga ggacaagtgc  480
gacttatcca tctggcctaa aatccctact gactacattc cagcaacaag tgaatatgcc  540
aaacagatta ggaacctagc aacaaagatt ttggcagtgc tttctattgg gctgggacta  600
gaagaaggaa gactagagaa ggaagtcgga ggcaaggagg acctactgct tcaaatgaag  660
attaactact accccaaatg tccccaacca gaactagcac ttggcgttga agctcatact  720
gatgtgagtg cactgacttt tatcctccac aatatggtgc ctgggttaca acttttctat  780
gaaggacagt gggtaacggc aaagtgtgtg cctaattcca taatcatgca tattggggac  840
acccttgaaa tcctaagcaa tggaaagtac aaaagcattc ttcacagagg ggttgtgaat  900
aaagagaaag taagaatctc atgggctatt ttctgtgagc cgccaaagga gaagatcatc  960
cttaagcccc tatctgagac tatcactgag gctgaaccac ctcgattccc acctcgcacc  1020
tttgcacagc atatggccca taagctcttc aagaaggatg atcaggatgc tgctgctgaa  1080
cacaaagtct ccaagaagga tgacccggat tctgctgctg gacacaaacc cttcaagaag  1140
gatgatcagg atgctgttgt tcagcaaaaa gtcctcaagg aggatgaaca ggatgccgct  1200
gctgagcaca aagtcttcaa gaaggataat caggatgctg ctgctgaaga atctaaatag  1260
```

```
SEQ ID NO: 32          moltype = DNA  length = 1260
FEATURE                Location/Qualifiers
source                 1..1260
                       mol_type = other DNA
                       organism = Nicotiana sp.
SEQUENCE: 32
atggtggtga tcagtgcagt agttccaact ccttcaagag ttgaaagctt ggctaaaagt  60
ggaatccagg ctatccctaa agagtatgtg aggccacaag aagagttaaa tggaatagga  120
aacatatttg aggaagagaa gaaagatgaa ggacctcaag taccgacgat tgatctaaca  180
gaaatcgact cagaggacaa ggaaattcga gagaaatgcc accaagagtt gaagaaagca  240
gctatagaat ggggtgttat gcaccttgtt aaccatggca tatcagatga gctaattgat  300
```

```
cgtgtcaagg tttctggaga taccttcttt gatcaacctg ttgaagaaaa ggagaagtat  360
gctaatgacc aaccctctgg caatgtccaa ggctatggca gcaagctagc aaatagtgct  420
tgtggtcagc ttgagtggga ggattatttc ttccattgtg ttttccctga ggacaagtgc  480
aacttatcca tctggccgaa aacccctaca gactacattc cagcaacaag tgaatatgcc  540
aagcagatca ggaacctagc aacaaagatt ttggcagtgc tttctattgg gctgagacta  600
gaagaaggaa gactagagaa ggaagtcgga ggcatggagg acctgctgct tcaaatgaag  660
attaactact atcccaaatg cccccaacca gaactagcac ttggtgtcga agctcatact  720
gatgtcagtg cactgacttt tatcctccac aatatggtgc ctggcttgca acttttctac  780
gaaggacagt gggtaacggc aaagtgtgtg cctaattcca taatcatgca tattggggac  840
acccttgaaa ttctaagcaa tggaaagtac aagagcattc ttcacagagg ggttgtgaat  900
aaagagaaaa taagaatctc atgggctatt ttctgtgagc cgccgaagga gaagatcatc  960
cttaagcccc tacctgagac tataactgag gctgagccac ctcgattccc acctcgcacc  1020
tttgcacagc atatggccca taagctcttc aagaaggatg atcaggatgc tgctgctgaa  1080
cacaaagtct ccaagaagga tgacccggat tctgctgctg aacacaaacc cttcaagaag  1140
gatgatcagg atgctgttgc tcagcaaaaa gtcctcaagg aggatgaaca gaatgccgct  1200
gctgagcaca aagtcttcaa gaaggataat caggatgctg ctgctgaaga atctaaatag  1260

SEQ ID NO: 33          moltype = DNA  length = 1869
FEATURE                Location/Qualifiers
source                 1..1869
                       mol_type = other DNA
                       organism = Nicotiana sp.
SEQUENCE: 33
atggctatgg gacaccaaga ccaagatgga gttccaaaca acttgagaaa gcaacttgct  60
cttgctgtta gaggtattca atggagctat gcaatcttct ggtcaactcc agttacacag  120
ccaggggtgt tggaatggag tgatgggtac tataatgggg atatcaagac taggaagaca  180
gttcaggtgg gggaagttaa tgaagaccaa cttgggttgc acagaactga gcaattgcga  240
gaactttata gttcactctt aacaggtgaa ggtgaagaag acttacaacc tcaggctaaa  300
aggccctcag ctgcattatc tcctgaagat ctcactgata cggagtggta tttcttagta  360
tgcatgtctt tcgtcttcaa tgttggacaa gggttgccag ggaagacctc agcgacgaat  420
caaacaatct ggctatgcaa tgctcaccaa gcagagagta gagtattttc tcgctctctg  480
ctagcaaaga gtgcatctat ccagactgtc gtatgctttc catatttagg aggcgttatt  540
gagctgggag tcaccgagct tgtcttagaa gatcccaacc tcattcagca aataaaaaat  600
tcctttgagg ttgatcactc tgttatttcg aagaggccta attacaactc caatgatgca  660
aaagatgaca tgaatgttgc tagccgaaag cttgatcata atgtacttga aagtgatgct  720
tatccagttg aaataaacaa cagttcaccg catgatagtt caaacggttt tgtggccaat  780
caagaggcag aagattcttt aatggtggta ggcgttatag gggaaacttc acaagctcaa  840
agctggaagt tcgtggatga taatatgagt aacggtgtgc ataattcttt gaattccagt  900
gactgcatct ctcaaaatta tgaaaagttg tcccctcttt cgaatggaga aaaagaaact  960
aagccttgcc caatagaccg tcaagagcac aatcagaata aactgcatct tttagatcac  1020
caaggagatg acgctcaata tcaagctgtc atttctaccc ttttaaaaag ctctgaccaa  1080
ttaactttgg gaccacattt tagaaatatt aacaaaaagt caagctttgc tggttggaag  1140
aatgatactg aagcgccaag aataggaact gcacaaaaac tattgaagaa ggtacttctt  1200
gaagttccta gaatgcatgg tggtgttaca cataaattca gcagagagaa tcgtaaaaag  1260
aacggccttt ggagaccgga ggttgatgac attgatagaa gccgtgttat ttcagagaga  1320
aggcgaagag aaaagataaa cgagagattt atgcatcttg catcaatgct gccgactggt  1380
ggcaaggttg acaaaaatatc actacttgac gagacaatag aatacatgaa agagcttgag  1440
aggagagttc aagagctgga agctagatca ggaaaaaaaa caaatgatac tgcagagcag  1500
acatctgata attgtggcac tagtaaattc aatgacgtca atggatcgtt aaagaggaaa  1560
gcatgtgata tggatgaaat ggaacctgaa agctgtaatg aattactgaa aggcagttca  1620
gctgatggta ttgtcatcag tatgatcgat aaggaagtct cgatcaagat gaggtgtctt  1680
tggagcgagg gcttgttact taagattatg gaggcactaa ccgacctaca aatggattgc  1740
catacggttc aatcttccaa gattgatggg attttatcca ttgctattga atcaaagtca  1800
aatggattga aaactgtatc agttggagca attagagaag tacttcagcg agtagtctgg  1860
aaatcttga                                                          1869

SEQ ID NO: 34          moltype = DNA  length = 1095
FEATURE                Location/Qualifiers
source                 1..1095
                       mol_type = other DNA
                       organism = Nicotiana sp.
SEQUENCE: 34
atggaatcct caaccaaaag ccaaatacca acacaatcag aagaagagcg taactgcaca  60
tatgccatgc aactattgtc atcttcagtc ctccccttg tgttgcattc aacaattcaa  120
ttggaagttt ttgagatatt agccaaatct aatgacacta aactttctgc ttctcaaatt  180
gtttctcaaa ttcctaactg cacaaaacct gaagcaccta ctatgttaaa taggatgctt  240
tatgtcttgg ctagttactc cttgtttact tgttccattg ttgaagatga aaaaaataat  300
gggggccaaa aaagagtgta tggtttgtca caagtgggaa aattctttgt taaaaatgaa  360
aatggtgcat caatggggcc acttttggct ttgcttcaaa ataaagtatt cataaacagc  420
tggtttgaac taaaagatgc agttcttgaa ggaggagttc catttgacag ggtacacggt  480
gtgcatgcat ttgaatatcc aaaatcggac ccaaaattca atgatgtttt caacaaggca  540
atgatcaatc acacaactgt agtcatgaaa aaaatacttg aaaattacaa aggttttgag  600
aaccttaaaa ctttggttga tgttggaggt ggtcttggag ttaacctcaa gatgattaca  660
tctaaatacc ccacaattaa gggcactaat tttgatttgc cacatgttgt tcaacatgcc  720
ccttcctatc ctggggtgga acatgttggg ggagatatgt ttgaaagtgt tccagaagga  780
gatgctattt ttatgaagtg gattcttcat gactggagtg atagtcacaa cctcaagttg  840
ctaaagaact gctacaaggc tctaccagac aatggaaagg tgattgttgt tgaggccatt  900
ttaccagtga aaccagacat tgacaccgca gtggttggcg tttcgcaatg tgatttgatc  960
atgatggctc aaaatcctgg aggcaaagag cgatcggaag aggagtttcg agccttggct  1020
```

```
actgaagctg gattcaaagg cgttaactta atatgttgtg tctgtaattt ttgggtcatg  1080
gaattctgca agtag                                                    1095

SEQ ID NO: 35          moltype = DNA  length = 1521
FEATURE                Location/Qualifiers
source                 1..1521
                       mol_type = other DNA
                       organism = Nicotiana sp.
SEQUENCE: 35
atggatcttc tccttctaga gaagaccctt atagggttat tctttgctat cattgtagct  60
atagttgttt ctaagctacg tagcaagaat tttaagttgc ccccaggtcc gattcctgtg  120
ccagtttttg gcaattggct tcaagttggt gatgacttga atcacagaaa cctcactgaa  180
tatgccaaga aatttggtga catgttcttg ctaagaatgg gacagaggaa tcttgtggtg  240
gtgtcatccc ctgaactagc caaagaagtt ttgcatacac aaggggttga atttggatca  300
agaacaagga atgtggtctt tgatattttc actggaaaag gccaagatat ggtttttaca  360
gtatatggtg aacactggag gaaaatgagg aggattatga ctgttccatt ttttacaaac  420
aaagtggtgc agcagtatag gcgtgggtgg gaagatgaag tggcacatgt tgttgaggat  480
gtgaagaaaa atccagagtc agcaactaat gggattgtgt tgaggaaaag gttgcagctt  540
atgatgtaca ataacatgta caggattatg tttgatagga ggtttgagag tgaggatgat  600
cctttgttta acaagcttaa ggctttgaat ggggagagga gtagattggc tcagagtttt  660
gagtacaatt atggtgattt tatccctata ttgagacctt tcttgagagg ttacttgaac  720
atctgtaagg aaattaagca gaggaggttg cagcttttca aagattactt tgttgatgaa  780
agaaagaaac ttgcaaacac gacgaagagc atggacaata attcgctaaa gtgtgccatt  840
gatcacattc ttgaggctga acagaaggga gagatcaatg aggataatgt cctttacatt  900
gttgagaaca tcaatgttgc tgcaatagaa actacactgt ggtcaatcga gtggggtatt  960
gctgaactag tgaaccaccc tgaaatccag aagaaactcc gtgacgagat tgacagtgtt  1020
cttggagtag gagtgcaaat cactgagcca gaactcaaca agcttcctta ccttcaggct  1080
gtgatcaagg agacccttcg tctccgtatg gcaatccctc ttttagtccc acacatgaac  1140
cttcacgatg cgaagcttgc tggatatgac attcccgcgg agagcaagat cctggtaaac  1200
gcttggtggc tggctaacaa ccctgctacc tggaagaagc ccgaagagtt taggccagag  1260
aggttctttg aagaggagaa gcacgttgag gctaatggca atgacttcag atatcttcca  1320
tttggtgttg gtaggaggag ctgccctgga attatccttg cactgccaat tcttggcatt  1380
accttgggac gcttggtgca gaactttgag ttgttgcctc ctccaggaca gtcaaagctt  1440
gacacaacag agaaaggcgg gcaattcagt ctgcacattt tgaagcattc caccattgtg  1500
atgaaaccaa gatcttttta a                                             1521

SEQ ID NO: 36          moltype = DNA  length = 897
FEATURE                Location/Qualifiers
source                 1..897
                       mol_type = other DNA
                       organism = Nicotiana sp.
SEQUENCE: 36
atgggaagaa aaccatgttg tgtaaaagag ggattgagaa aaggtccatg gtcttctaaa  60
gaagatttat tacttactaa ttatatcaag gaaaatggtg aaggacaatg gagatctttg  120
cctaagaatg ctgggttgct taggtgtgga aaaagttgta gactaagatg gatgaactat  180
ttaagaccag ggattaaaag aggaaatttc agtcaagatg aagaagatct tatagtgaga  240
ctacattctc ttttgggtaa tcgttggtca ctaattgctg gaagattacc aggtcgtaca  300
gacaatgaaa tcaagaatta ttggaacaca catttaatca agaagctcaa aaatgctgga  360
attgaaccaa aaccccacaa aaatttctcc aaatgttcca aaaaggaatc aagaaaagga  420
ccccaacaag ggaaatcaag aaaaatacaa ggcaaaaaga gcaacaacaa aaacaataag  480
ggtcaaattg tacaagttga gaagaccaaa gtatttttcc caaaacccat caggatttct  540
tgtggaattt caaggaacaa tagttttgaa aatgttacat tgagtactac ttgttcctca  600
aatagtaatt ctggagaagc taatcttgaa aacaaggaaa atgaggtgaa attagaagaa  660
gtttcattct ttccaaggga cttagatttt ggtaaattac ttgaagggga tgcaatttat  720
gatgaatttc taatggaaga aagttgccac atttcaaaca aatgttcatt gccaatgaat  780
gagagcatgt tggagaaagt atatgaagaa tatcttttac ttctttctga aaattgttac  840
cttcaagatg atcatcaaaa tgagcaaaat ttccctgtaa atgtttctga tcagtga     897

SEQ ID NO: 37          moltype = DNA  length = 1146
FEATURE                Location/Qualifiers
source                 1..1146
                       mol_type = other DNA
                       organism = Nicotiana sp.
SEQUENCE: 37
atggcaagtg aagctcatgc agctgttcat gctcctcctc cggtagcacc gacggtttgc  60
gtcactggag cagctggatt tattggctct tggcttgtca tgagactcct tgaacgtggt  120
tataatgttc acgctactgt tcgtgatcct gagaacaaga agaaggtaaa gcatctattc  180
gaattgccaa aagctgacac aaacttaacg ctgtggaaag cggacttgtc agtggaagga  240
agctttgatg aagccattca aggctgtcaa ggagtattcc atgtggcaac acctatggat  300
ttcgagtccg aggaccctga gaatgaagta attaaaccaa cagtcagggg aatgttaagc  360
atcatagaat catgtgctaa agcaaacaca gtgaagaggc tggttttcac ttcatcggct  420
ggaactctcg atgcccaaga acaccaaaag cttttctatg acgagaccag ctggagcgac  480
ttggacttca tatatgctaa gaagatgaca ggatggatgt attttgtttc caagatactg  540
gcagagaagg ccgcaatgga agcagctaaa aagaagaact ttgattttat tagcatcata  600
ccgccgctgg ttgttggtcc attcctcacg cctacattcc cacctagctt aatcactgca  660
ctttcactaa ttactgggaa tgaagctcac tactgcatca ttaaacaagg tcaatatgtg  720
catttggatg atctttgtga ggctcatatt ttcctatatg agcagccaaa ggcagaggga  780
agattcatct gcgcgtccca tcatgctatc atctatgatg tggcaaagat ggtccgagag  840
aaatggccag agtactacgt ccctactgag tttaaaggca tcgataagga cttgcccgtg  900
```

```
gtgtattttt cgccaaagaa gctgacggat atggggtttc aattcaagta cactttggag  960
gatatgtata aaggggccat tgagacttgt cgacagaagc agttgcttcc cttttctacc  1020
caaagcacag cagataatgg acgtgacaaa gaaaccattc ccctttctgc tgaaaactat  1080
gcaagtggca aagagaattc accagttgca aatggtacag gaaagtcaac caatggggaa  1140
atctag                                                             1146

SEQ ID NO: 38          moltype = DNA  length = 1149
FEATURE                Location/Qualifiers
source                 1..1149
                       mol_type = other DNA
                       organism = Nicotiana sp.
SEQUENCE: 38
atggcaagtg aaggtcatgc agctgttcat gccccttctc ctccggcagc gccgacagtt  60
tgcgtcactg gagcagctgg atttattggc tcttggcttg tcatgagact ccttgaacgt  120
ggttataatg ttcacgctac tgttcgtgat cctgagaaca agaagaaggt aaagcatcta  180
ttggaattgc caaaagctga cacgaactta acgttgtgga aagcagactt gtcagtggaa  240
ggaagctttg atgaagccat tcaaggctgt caaggagtat tccatgtggc aacgcctatg  300
gatttcgagt ccgaggatcc tgagaatgaa gtaattaaac caacagtcag gggaatgtta  360
agcatcatag aatcatgtgc taaagcaaac acagtgaaga ggctggtttt cacttcatct  420
gctggaactg tcgatgtcca agagcaccaa aagctcttat atgacgagac cagctggagt  480
gacttggact ttatatatgc taagaagatg acaggatgga tgtattttgt ttccaagata  540
ctggcagaga aggccgcaat ggaagcagct aaaaagaaga acatcgattt cattagcatc  600
ataccgccac tggttgttgg tccattcctc gcgcctacat tcccacctag cttaatcact  660
gccctttcac taattactgg gaatgaagct cactacagca tcattaaaca aggtaaatat  720
gtgcatttgg atgatctttg tgaggctcat attttcctat atgagcaccc aaaggcagag  780
gggagattca tctgcgcgtc ccatcatgct atcatctatg atgtggcaaa gatggtccaa  840
gagaaatggc cggagtacta cgtccctact gagtttaaag gcatcgataa ggacttgtcc  900
gtggtgtatt tttcgtcaaa gaagctgacg gatatggggt ttcaattcaa gtacactttg  960
gaggatatgt ataaaggggc cattgagact tgtcgacaga agcagttgct tcccttttct  1020
acccgaagca ctgcagataa tgtacgtgac aaagaagcca ttcctctttc tactgaaaac  1080
tatgcaagtg gcaaagaaaa ttcaccagtt gcaaatggta cgggaaagtc aaccaatggt  1140
gaaatctag                                                          1149

SEQ ID NO: 39          moltype = DNA  length = 642
FEATURE                Location/Qualifiers
source                 1..642
                       mol_type = other DNA
                       organism = Nicotiana sp.
SEQUENCE: 39
atgggaagaa aaccctgttg ttctaaagaa ggtctgagga aaggtacatg gactgcaaaa  60
gaagatatgc tacttactaa ttatattaat gaacatggag aagttggatg gagatctctt  120
cctatgaaag ctggaagtcg ttggtctctc attgctggaa gaatacctgg tcgaacagac  180
aacgaaataa agaattattg gaacacacat cttctcaaga aactcaaatc cgaaggactt  240
gagccaaaaa tacacaaatc tcttgcaaaa aacactagaa gacaaaagga gaaagcaaat  300
gtttcttccc aaattaacca aaaaggttac aaggaaaaga agaagaggaa taaaaagggc  360
aatatcgaag aaaattgtaa caatattgaa gagaaagaac aagtagctaa gaagatagag  420
gagcagtggc atacgcagga ttccgtgcaa gcgatgtcag ggttttcaag tactagtgaa  480
gttgctagtg agaaggaaac taattgcaat aatgtccatt gtccttcttc tggtcaaagt  540
cttgaagaaa atgacaatga aatttatgag aagcttcagg ctagcggaga ttctaaacgt  600
tgcaaattga atttcagtgc agaggttaat aagacccctt aa                     642

SEQ ID NO: 40          moltype = DNA  length = 1308
FEATURE                Location/Qualifiers
source                 1..1308
                       mol_type = other DNA
                       organism = Nicotiana sp.
SEQUENCE: 40
atgaagatcg aggtgaaaga atcgacgatg gtaaagccgg cggcggagac gccacaacag  60
aggctgtgga actctaatgt ggatttggtg gtgccgaatt tccacacgcc aagtgtttat  120
ttttacaggc cgacgggatc cccaaatttc ttcgacggaa aagtgctgaa ggaagctcta  180
agcaaagcac ttgtgccgtt ttatcctatg gcggggaggc tgtgtaggga cgaagatggt  240
cgtattgaga ttgactgtaa aggtcagggg gtgctttttg tggaagctga gtcggatggt  300
gtggtggatg attttggtga ttttgccccg acgttagaac tccgtcaact catccccgcc  360
gttgattact cacaaggaat tcaatcgtat gctctcttag tgttgcagat aacacatttt  420
aaatgtgggg gagtttccct tggtgtgggc atgcaacatc atgcagcaga tggagcttct  480
ggtcttcact tcatcaacac atggtctgat atggctcgtg gtctggacct caccatccca  540
cctttcattg accggaccct cctccgtgct cgtgatccac ctcagcctca gtttccccat  600
gtcgagtacc agccacctcc cactctcaag gtaactccag aaaacacccc tatatctgaa  660
gctgttcctg aaaccagcgt gtccatcttc aaattaaccc gtgatcaaat caataccctc  720
aaagcgaagt ccaaggaaga tggaaatacc gttaactaca gctcctacga gatgttggca  780
ggacatgtgt ggcgctccac gtgcatggca cgaggactcg ctcatgatca agaaaccaaa  840
ttgtacatag caacagatgg acgttccagg cttcggccct ctctcccacc aggctatttc  900
ggtaatgtga tatttactac cactcctatt gcagtcgcag gtgatatcca atcgaagcct  960
atttggtatg ctgccagtaa attacatgat gcattggcta gaatggacaa cgattactta  1020
agatcagctc ttgattattt ggagttgcag cctgacttaa aggctcttgt tcgtggtgca  1080
catacgttta agtgcccgaa tttaggaata actagttggt ctaggctgcc aatccatgat  1140
gctgattttg gctggggtag gcctatattt atgggacctg gtggtattgc ttatgaaggt  1200
ttaagcttta tattgccaag tcctacaaat gatggcagtc aatctgttgc aatctctcta  1260
caagcagaac acatgaaact tttcgagaag ttcttgtatg acttttga               1308
```

```
SEQ ID NO: 41          moltype = DNA  length = 1311
FEATURE                Location/Qualifiers
source                 1..1311
                       mol_type = other DNA
                       organism = Nicotiana sp.
SEQUENCE: 41
atgggaagtg aaaaaatgat gaaaattaat atcaaggaat caacattagt aaaaccatca  60
aaaccaacac caacaaaaag actttggagt tctaacttag atttaatagt gggaagaatt  120
catcttttaa cagtatattt ctataaacca aatggatctt caaatttctt tgattcaaaa  180
ataatgaaag aagcattaag taatgttctt gtttcatttt acccaatggc tggaagatta  240
gctagagatg aacaaggaag aattgagata aattgtaatg gagaaggagt tttatttgtt  300
gaagctgaaa gtgatgcttt tgttgatgat tttggtgatt ttactccaag tttggaactt  360
aggaaactta ttcctactgt tgacacttct ggtgatattt ctactttccc cctcatcatc  420
tttcaggtta ctcgtttcaa atgtggtgga gtttcacttg gtggaggagt attccacact  480
ttatcagatg gtctctcatc aattcacttc atcaacacat ggtccgatat agcccgaggc  540
ctctccgtcg ccatcccgcc gttcatcgac cggaccctcc tccgtgcacg ggacccacca  600
acatcgtctt tcgagcacgt cgagtatcat cctcctccat ctctaatttc atcatcaaaa  660
agcttagaat ccactagccc aaagcctagt accacaacca tgttaaaatt ctctagtgac  720
caacttgggc ttctaaagtc caagtccaaa catgatggta gcacttacga aatcctcgcg  780
gcccatattt ggcgttgcac gtgcaaggca cgtgcactgt ccgacgatca attgaccaaa  840
ttacatgtgg ccactgatgg taggtctagg ctttgccctc ctttgccacc aggttactta  900
ggaaatgttg tgttcacagg cacacctatg gcaaaatcaa gtgaactttt acaagaacca  960
ttgacaaatt cagccaagag aattcatagt gcattatcaa aaatggatga caattaccta  1020
agatcagctc tcgattacct cgaattactg cccgatttat cggctttaat ccgtggaccg  1080
acgtactttg ctagccctaa tcttaatatt aatagttgga ctagattgcc tgttcatgat  1140
tcagattttg gatggggaag gccaattcat atgggaccag cttgcatttt atatgaaggg  1200
acagtttata tattgccaag tccaaatagt aaagatagga acttgcgttt ggctgtttgt  1260
ttagatgctg atcacatgcc actatttgag aagtatttgt atgaattttg a           1311

SEQ ID NO: 42          moltype = DNA  length = 2148
FEATURE                Location/Qualifiers
source                 1..2148
                       mol_type = other DNA
                       organism = Nicotiana sp.
SEQUENCE: 42
atggcatcaa atggtcatgt taatggagga gaaaactttg agttgtgcaa aaaatcagct  60
gatccattga attgggaaat ggcagctgaa tccttaagag ggagtcattt ggatgaagtg  120
aaaaaaatgg tgagtgaatt tagaaaacca atggtaaaac ttggtggtga aagtttaaca  180
gtggcacaag tggctgctat tgctgttagg gacaaaagtg caaatggtgt taaagttgaa  240
ctttctgaag aggcaagagc tggtgttaaa gctagtagtg attgggttat ggacagtatg  300
aataaaggaa ctgatagtta tggtgttact actggttttg gtgctacatc tcataggaga  360
accaagaatg gtggtgctct tcaaaaagaa cttattaggt tcttgaatgc tggtgttttt  420
ggcaatggaa cagaaacaag ccacacattg ccacattcag caacaagggc agctatgctt  480
gttaggatca acacactcct acaaggctac tctggcatca gatttgaaat cttggaagct  540
attacaaaat tgattaacag caacatcact ccatgtttac ctctccgtgg aacgatcact  600
gcctcgggtg atcttgtccc tttatcctac attgctggtt tgctcactgg taggcctaat  660
tccaaggctg ttggtcccaa tggtgagaca cttaatgctg aagaagcgtt ccgcgttgct  720
ggtgttaacg gtggattttt cgagttgcag cctaaggaag gacttgcact tgtgaatggt  780
acagctgttg gttctggtat ggcatcaatg gtcctctttg attccaacat tcttgctgta  840
atgtctgaag ttttatcagc aattttcgct gaagtaatga acggaaagcc cgaattcact  900
gaccatttga cacacaagtt gaagcaccac cctggtcaaa ttgaggctgc tgctattatg  960
gaacatattt tggatggaag ctcttatgtg aaggcggctc aaaagctaca tgaaatggat  1020
cctctacaaa aaccaaagca agatcgttat gctctccgaa catctccaca atggcttggc  1080
cctcaaattg aagtcattcg cgctgcaact aagatgattg agagggagat taactcagtg  1140
aacgataacc ctttgatcga tgtttcaaga aacaaggcgt tacatggtgg caacttccaa  1200
ggcactccta tcggtgtttc catggataat gcaagattgg ctcttgcatc aattgggaaa  1260
ttgatgtttg ctcaattctc ggaacttgtc aacgactatt acaacaacgg tttgccctct  1320
aatctcactg catcaaggaa tccaagcttg gactatggtt tcaagggagc tgaaatcgcc  1380
atggcttctt actgctcaga acttcaattc ttggcaaatc cagtgacaaa ccatgtccaa  1440
agtgctgaac aacacaacca agatgtcaac tccttaggct taatctcagc aaggaaaaca  1500
gctgaagctg ttgatatctt aaagctcatg tcatcaactt atctcgtggc actttgccaa  1560
gctatagact tgaggcattt ggaagaaaac ttaaagaatg cagtcaagaa cacagttagc  1620
caagtagcta agagaactct tacaatgggt gctaatggtg aacttcatcc agcaagattc  1680
tgtgaaaagg aattgcttcg aatcgtggat agggaatact tgttcgccta cgctgatgat  1740
ccttgcagtt gcaactaccc tttaatgcag aaactgagac aagtacttgt tgatcatgca  1800
atgaataatg gtgaaagtga gaagaatgtg aacagctcaa tctttcaaaa gattggagct  1860
ttcgaagatg aattgaaggc tgttttacca aaggaagttg agagtgcaag agctgcatta  1920
gaaagtggaa accctgctat tcctaacagg attacagaat gcagatctta tccattgtac  1980
aggtttgtga gaaaggagct tggaacagaa ttattgacag gagaaaaagt ccgatcaccg  2040
ggcgaggagt gtgacaaagt gttcacagca atgtgcaatg gacaaatcat tgatccaatg  2100
ttggagtgtc tcaagagctg gaatggtgct cctcttccta tctgttag               2148

SEQ ID NO: 43          moltype = DNA  length = 1026
FEATURE                Location/Qualifiers
source                 1..1026
                       mol_type = other DNA
                       organism = Nicotiana sp.
SEQUENCE: 43
```

```
atggataatt cagctccaga ttcgttatcc agatcggaaa ccgccgtcac atacgactca  60
ccatatccac tctacgccat ggctttctct tctctccgct catcctccgg tcacagaatc  120
gccgtcggaa gcttcctcga agattacaac aaccgcatcg acattctctc tttcgattcc  180
gattcaatga ccgttaagcc tctcccgaat ctctccttcg agcatcctta tcctccaaca  240
aagctaatgt tcagtcctcc ttctctccgt cgtccttcct ccggagatct cctcgcttcc  300
tccggcgatt tcctccgtct ttgggaaatt aacgaagatt catcaaccgt cgagccaatc  360
tcggttctca acaacagcaa aacgagcgag ttttgtgcgc cgttgacttc cttcgattgg  420
aacgatgtag agccgaaacg tctcggaact tgtagtattg atacgacgtg tacgatttgg  480
gatattgaga agtctgttgt tgagactcag cttatagctc atgataaaga ggttcatgac  540
attgcttggg gagaagctag ggttttcgca tcagtctctg ctgatggatc cgttaggatc  600
tttgatttac gtgataagga acattctaca atcatttacg agagtcctca gcctgatacg  660
cctttgttaa gacttgcttg gaacaaacaa gatcttagat atatggctac gattttgatg  720
gattctaata aggttgtgat tctcgatatt cgttcgccga ctatgcctgt tgctgagctt  780
gaaagacatc aggctagtgt gaatgctata gcttgggcgc ctcagagctg taaacatatt  840
tgttctggtg gtgatgatac acaggctctt atttgggagc ttcctactgt tgctggaccc  900
aatgggattg atccgatgtc ggtttattcg gctggttcgg agattaatca gttgcagtgg  960
tcttcttcgc agcctgattg gattggtatt gcttttgcta acaaaatgca gctccttaga  1020
gtttga                                                             1026
```

```
SEQ ID NO: 44           moltype = DNA  length = 1323
FEATURE                 Location/Qualifiers
source                  1..1323
                        mol_type = other DNA
                        organism = Nicotiana sp.
SEQUENCE: 44
atgagcatgt ctgttgcttt gttgtgggtt gtttctccca cttccgaggt ctcgaatggg  60
acaggattgt tggattcagt ccgagaagga aaccgcgtct ttgtatcatc caggttccta  120
gctcgagata ggaatttgat gtggaatggg agaatcaaga aaggtgggag acaaaggtgg  180
aattttggct ctttaattgc tgatccaaga tattcatgct tgggtggatc aagaactgaa  240
aagggaagca gtttctctgt acagtccagt ttggtggcta gcccagctgg agaaatgaca  300
gtgtcatcag agaaaaaggt ctatgatgtg gtattgaagc aagcagcttt agtgaagagg  360
cagctgagat ctaccgatga attagaagtg aaacctgata tagttgttcc agggaatttg  420
ggcttgttga gtgaagcata tgatcgttgt ggcgaagtat gtgcagagta tgcaaagaca  480
ttttacttag gaacaaagct aatgactcca gagagaagaa gagctatctg gtcaatatat  540
gtgtggtgca ggagaacgga tgagctagtc gatggcccta acgcatcaca cataactcca  600
caagctttag acaggtggga ggccaggctg gaagatattt tcagtgggcg gccatttgat  660
atgcttgatg ctgctttatc cgatactgtc tccagatttc ctgttgatat tcagccattc  720
agagatatga tagaaggaat gcgtatggac ttgtggaaat ccagatataa caacttcgat  780
gagctatatc tctattgtta ttatgttgct ggtacagtag gactgatgag tgttccagtt  840
atgggtattg cacctgaatc aaaggcaaca acagagagtg tatataatgc tgctttggct  900
ttagggcttg caaatcaact aaccaatata ctcagagatg taggagaaga tgccagaaga  960
ggacgagtat acttacctca agatgaatta gcacaggcag ggctttctga tgaagatata  1020
tttgctggaa gagtgaccga taagtggagg aactttatga agaaacaaat tcagagggcg  1080
aggaaattct ttgatgagtc agagaaaggt gtcacagaac tggactctgc tagtagatgg  1140
cctgtaagta cagcgctgct gttgtatcgc aagatattgg acgagattga agccaatgac  1200
tacaataact tcacaaggag ggcttatgtt agcaagccaa agaagcttct caccttgccc  1260
attgcttatg caaaatctct tgtgcccccct aatagaactt cctctccact agcaaaaaca  1320
tga                                                                1323
```

```
SEQ ID NO: 45           moltype = DNA  length = 1323
FEATURE                 Location/Qualifiers
source                  1..1323
                        mol_type = other DNA
                        organism = Nicotiana sp.
SEQUENCE: 45
atgagcatgt ctgttgcttt gttgtgggtt gtttctccca cttccgaggt ctcgaatggg  60
acaggattgt tggattcagt ccgagaagga aaccgcgtct ttgtatcatc caggttccta  120
gctcgagata ggaatttgat gtggaatggg agaatcaaga aaggtgggag acaaaggtgg  180
aattttggct ctttaattgc tgatccaaga tattcatgct tgggtggatc aagaactgaa  240
aagggaagca gtttctctgt acagtccagt ttggtggcta gcccagctgg agaaatgaca  300
gtgtcatcag agaaaaaggt ctatgatgtg gtattgaagc aagcagcttt agtgaagagg  360
cagctgagat ctaccgatga attagaagtg aaacctgata ttgttgttcc agggaatttg  420
ggcttgttga gtgaagcata tgatcgttgt ggcgaagtat gtgcagagta tgcaaagaca  480
ttttacttag gaacaaagct aatgactcca gagagaagaa gagctatctg ggcaatatat  540
gtgtggtgca ggagaacgga tgagctagtc gatggcccta acgcatcaca cataactcca  600
caagctttag acaggtggga ggccaggctg gaagatattt tcagtgggcg gccatttgat  660
atgcttgatg ctgctttatc cgatactgtc tccagatttc ctgttgatat tcagccattc  720
agagatatga tagaaggaat gcgtatggac ttgtggaaat ccagatataa caacttcgat  780
gagctatatc tctattgtta ttatgttgct ggtacagtag gactgatgag tgttccagtt  840
atgggtattg cacctgaatc aaaggcaaca acagagagtg tatataatgc tgctttggct  900
ttagggcttg caaatcaact aaccaatata ctcagagatg taggagaaga tgccagaaga  960
ggacgagtat acttacctca agatgaatta gcacaggcag ggctttctga tgaagatata  1020
tttgctggaa gagtgaccga taagtggagg aactttatga agaaacaaat tcagagggcg  1080
aggaaattct ttgatgagtc agagaaaggt gtcacagaac tggactctgc tagtagatgg  1140
cctgtgttag cagcgctgct gttgtatcgc aagatattgg acgagattga agccaatgac  1200
tacaataact tcacaaggag ggcttatgtt agcaagccaa agaagcttct caccttgccc  1260
attgcttatg caaaatctct tgtgcccccct aatagaactt cctctccact agcaaaaaca  1320
tga                                                                1323
```

```
SEQ ID NO: 46           moltype = DNA  length = 747
FEATURE                 Location/Qualifiers
source                  1..747
                        mol_type = other DNA
                        organism = Nicotiana sp.
SEQUENCE: 46
atggagggtt cgtccaaagg gctgcgaaaa ggtgcttgga ctactgaaga agatagtctc  60
ttgagacagt gcattaataa gtatggagaa ggcaaatggc accaagttcc tgtaagagct  120
gggctaaacc ggtgcaggaa aagttgtaga ttaagatggt tgaactattt gaagccaagt  180
atcaagagag gaaaacttag ctctgatgaa gtcgatcttc ttcttcgcct tcataggctt  240
ctagggaata ggtggtcttt aattgctgga agattacctg gtcggaccgc aaatgacgtc  300
aagaattact ggaacactca tctgagtaag aaacatgaac cgtgttgtaa gataaagatg  360
aaaaagagag acattacgcc cattcctaca acaccggcac taaaaaacaa tgtttataag  420
cctcgacctc gatccttcac agttaacaac gactgcaacc atctcaatgc cccaccaaaa  480
gttgacgtta atcctccatg ccttggactt aacatcaata atgtttgtga caatagtatc  540
atatacaaca aagataagaa gaaagaccaa ctagtgaata atttgattga tggagataat  600
atgtggttag agaaattcct agaggaaagc caagaggtag atattttggt tcctgaagcg  660
acgacaacag aaaaggggga caccttggct tttgacgttg atcaactttg gagtcttttc  720
gatggagaga ctgtgaaatt tgattag                                    747

SEQ ID NO: 47           moltype = AA  length = 717
FEATURE                 Location/Qualifiers
source                  1..717
                        mol_type = protein
                        organism = Nicotiana sp.
SEQUENCE: 47
MASNGHVNGG ENFELCKKSS ATDPLNWEMA AESLRGSHLD EVKKMVSEFR KPMVKLGGET  60
LTVAQVAAIA VRDKSANGVK VELSEEARAG VKASSDWVMD SMNKGTDSYG VTTGFGATSH  120
RRTKNGGALQ KELIRFLNAG VFGNGTETSH TLPHSATRAA MLVRINTLLQ GYSGIRFEIL  180
EAIAKLINSN ITPCLPLRGT ITASGDLVPL SYIAGLLTGR PNSKAVSPNG ETLNAEEAFR  240
VAGVNGGFFE LQPKEGLALV NGTAVGSGMA SMVLFDSNIL AVMSEVLSAI FAEVMNGKPE  300
FTDHLTHKLK HHPGQIEAAA IMEHILDGSS YVKAAQKLHE MDPLQKPKQD RYALRTSPQW  360
LGPQIEVIRA ATKMIEREIN SVNDNPLIDV SRNKALHGGN FQGTPIGVSM DNARLALASI  420
GKLMFAQFSE LVNDYYNNGL PSNLTASRNP SLDYGFKGAE IAMASYCSEL QFLANPVTNH  480
VQSAEQHNQD VNSLGLISAR KTAEAVDILK LMSSTYLVAL CQAIDLRHLE ENLKNAVKNT  540
VSQVAKRTLT MGANGELHPA RFCEKELLRV VDREYLFAYA DDPCSCNYPL MQKLRQVLVD  600
HAMNNGESEK NVNSSIFQKI GAFEDELKAV LPKEVESARA ALECGNPAIA NRITECRSYP  660
LYRFVRKELG TELLTGERVR SPGEECEKVF TAMCNGQIID PMLECLKSWN GAPLPIC     717

SEQ ID NO: 48           moltype = AA  length = 712
FEATURE                 Location/Qualifiers
source                  1..712
                        mol_type = protein
                        organism = Nicotiana sp.
SEQUENCE: 48
MAGVAQNGHQ EMDFCMKVDP LNWEMAADSL KGSHLDEVKK MVAEFRKPVV KLGGETLTVA  60
QVAAIAAKDN VKTVKVELSE GARAGVKASS DWVMDSMGKG TDSYGVTTGF GATSHRRTKN  120
GGALQKELIR FLNAGVFGNG TESCHTLPQS GTRAAMLVRI NTLLQGYSGI RFEILEAITK  180
LLNHNVTPCL PLRGTITASG DLVPLSYIAG LLTGRPNSKA VGPNGETLNA EEAFRVAGVN  240
GGFFELQPKE GLALVNGTAV GSGLASMVLF DANVLAVFSE VLSAIFAEVM NGKPEFTDHL  300
THKLKHHPGQ IEAAAIMEHI LDGSSYVKAA QKLHETDPLQ KPKQDRYALR TSPQWLGPQI  360
EVIRSATKMI EREINSVNDN PLIDVSRNKA LHGGNFQGTP IGVSMDNARL ALASIGKLMF  420
AQFSELVNDY YNNGLPSNLT AGRNPSLDYG FKGSEIAMAS YCSELQFLAN PVTNHVQSAE  480
QHNQDVNSLG LISARKTAEA VDILKLMSST YLVALCQAID LRHLEENLRN AVKNTVSQVA  540
KRTLTMGTNG ELHPSRFCEK DLLRVVDREY VFAYADDACS ANYPLMQKLR QVLVDHALQN  600
GENEKNANSS IFQKILAFED ELKAVLPKEV ESARAALESG NPAIANRIKE CRSYPLYRFV  660
RGELGAELLT GEKVRSPGEE CDKVFTAMCN GQIIDSLLEC LKEWNGAPLP IC          712

SEQ ID NO: 49           moltype = AA  length = 389
FEATURE                 Location/Qualifiers
source                  1..389
                        mol_type = protein
                        organism = Nicotiana sp.
SEQUENCE: 49
MVTVEEFRRA QRAEGPATVM AIGTATPSNC VDQSTYPDYY FRITNSEHKT ELKEKFKRMC  60
EKSMIKKRYM HLTEEILKEN PNICAYMAPS LDARQDIVVV EVPKLGKEAA QKAIKEWGQP  120
KSKISHLVFC TTSGVDMPGC DYQLTKLLGL RPSVKRFMMY QQGCFAGGTV LRMAKDLAEN  180
NKGARVLVVC SEITAVTFRG PNDTHLDSLV GQALFGDGAA AVIVGSDPIP DVERPLFELV  240
SAAQTLLPDS EGAIDGHLRE VGLTFHLLKD VPGLISKNIE KSLVEAFQPL GISDWNSLFW  300
IAHPGGPAIL DQVELKLGLK QEKLKATRNV LSNYGNMSSA CVLFILDEMR KASAKEGLGT  360
TGEGLEWGVL FGFGPGLTVE TVVLHSVAT                                  389

SEQ ID NO: 50           moltype = AA  length = 369
FEATURE                 Location/Qualifiers
source                  1..369
                        mol_type = protein
                        organism = Nicotiana sp.
SEQUENCE: 50
MAPSTLTALA EEKTLQTSFI RDEDERPKVA YNQFSDEIPI ISLKGIDDEG GINGRRGEIC  60
```

```
EKIVKACEDW GVFQVVDHGV DAQLISQMTT LAKQFFALPA EEKLRFDMSG GKKGGFIVSS  120
HLQGEVVQDW REIVTYFSYP IRARDYSRWP DKPEGWIDVT QKYSEKLMEL ACKLLEVLSE  180
AMGLEKEALT KACVDMDQKV VVNFYPKCPQ PDLTLGLKRH TDPGTITLLL QDQVGGLQAT  240
KDNGKTWITV QPVVGAFVVN LGDHGHFLSN GRFKNADHQA VVNSNSSRLS IATFQNPAPE  300
AIVYPLKIRE GEKAVMDEPV AFAEMYRRKM SKDLELARLK KLAKEQQIQA EEAAEKAKSE  360
TKPIDEILA                                                         369

SEQ ID NO: 51          moltype = AA  length = 145
FEATURE                Location/Qualifiers
source                 1..145
                       mol_type = protein
                       organism = Nicotiana sp.
SEQUENCE: 51
MFGPQSGKDG WTDLTFMYDM IRIRDKSLCS SFLQIFSSEG CKMLEMTCEE HDKLAARSQF  60
LTHTIGRILS EMEVEPTPID TKGFQKLVQV KESSVRDSFD LFSGLFIHNR FARQQMKNLE  120
VAVEKTKQKL EERSKELQDP IISKF                                       145

SEQ ID NO: 52          moltype = AA  length = 376
FEATURE                Location/Qualifiers
source                 1..376
                       mol_type = protein
                       organism = Nicotiana sp.
SEQUENCE: 52
MLSFTPLQSK PTPPTPTSNP TRWSWSHLTH HHPTTRRHFS ASSPSKVSYR RLSINAIDAA  60
QPYDYEALVS NQYAQSTRLK IAIVGFGNFG QFLAKAFVRQ GHVVFAHSRT DYSHIANSLG  120
VLFFQDPHDL CEQHPDVILL CTSIISTEPV LRSLPIQRLK RNTLFVDVLS VKEFPKNIFL  180
QVLPSHFDIL CTHPMFGPES GKDSWKDLAF VFDKVRIGEG ESRKGRVDRF LDIFEKEGCR  240
MVQMTCAEHD RYAAGSQFIT HTMGRVLEKL DLETTPINTK GYETLLNLVE NTSSDSFDLY  300
YGLFMYNKNA MEQLERLDLA FEALKKELFG HLHEVLRKQL FGKAEEAGQR RILTKLPKNG  360
YALPAPSSEA VKSENN                                                 376

SEQ ID NO: 53          moltype = DNA  length = 2154
FEATURE                Location/Qualifiers
source                 1..2154
                       mol_type = other DNA
                       organism = Nicotiana sp.
SEQUENCE: 53
atggcatcaa atggtcatgt taatggagga gaaaactttg agttgtgcaa gaaatcatca  60
gccactgatc cattgaattg ggaaatggca gctgaatctt taagagggag tcatttggat  120
gaagtgaaaa aaatggtgag tgaatttaga aaaccaatgg taaaacttgg tggtgaaact  180
ttaacagtgg cacaagtggc tgctattgct gttagggaca aaagtgcaaa tggtgttaaa  240
gttgaacttt ctgaagaggc aagagctggt gttaaagcta gtagtgattg ggttatggat  300
agtatgaata aaggaacaga tagttatggt gttactactg gttttggtgc tacatctcat  360
aggagaacca agaatggtgg tgctcttcaa aaagaactta ttaggttctt gaatgctggt  420
gtttttggca atggaacaga aacaagccac acattgccac attcagcaac aagggcagct  480
atgcttgtta ggatcaacac actcctacaa ggctactctg gcatcagatt tgaaatcttg  540
gaagcaattg caaaattgat taacagcaac attactccat gtttacctct ccgtggcacg  600
atcactgcct cgggcgatct tgttcctta tcctacattg ctggtttgct cactggtagg  660
cctaattcca aggctgttag tcccaatggt gagaccctta atgctgaaga agcgttccgc  720
gttgctggtg ttaacggtgg atttttcgag ttgcagccta aggaaggact tgcacttgtg  780
aatggtacag cagttggttc tggtatggca tcaatggtcc tctttgattc caacattctt  840
gctgttatgt ctgaagtttt atcagcaatt ttcgctgaag ttatgaacgg aaagcccgaa  900
tttactgacc atttgacaca caagttgaag caccaccctg gtcaaattga ggctgctgct  960
attatggaac atattttgga tggaagctct tatgtgaagg cggctcaaaa gctacatgaa  1020
atggatcctc tccaaaaacc aaagcaagat cgttatgctc tccgaacatc tccacaatgg  1080
cttggccctc aaattgaagt cattcgcgct gcaactaaga tgattgagag ggagattaac  1140
tcagtgaacg ataacccctt gatcgatgtt tcaagaaaca aggcattaca tggtggcaac  1200
ttccaaggca cccctatcgg tgtgtccatg gataatgcaa gattggctct tgcatcaatt  1260
gggaaattga tgtttgctca attctcggaa cttgtcaacg actattacaa caacggtttg  1320
ccatctaacc tcaccgcatc aaggaatcca agcttggact atggtttcaa gggagctgaa  1380
atcgccatgg catcttactg ctcagaactt caattcttgg caaatccagt gacaaaccat  1440
gtccaaagtg ctgagcaaca caaccaagat gtcaactcct tgggcttaat ctcagcaagg  1500
aaaacagctg aagctgtcga tatcttaaag ctcatgtcat caacttatct agtggcactt  1560
tgccaagcta tcgacttgag gcatttggag gaaaacttaa agaatgcagt caagaacaca  1620
gttagccaag tagctaagag aactcttaca atgggtgcta acggtgaact tcatccagca  1680
agattctgtg aaaaggaatt gctacgagtc gtggacaggg aatacttgtt cgcctacgct  1740
gatgatcctt gcagttgcaa ctacccttta atgcagaaac tgagacaagt acttgttgat  1800
catgcaatga ataatggtga aagtgagaag aatgtgaaca gctcaatctt ccaaaagatt  1860
ggagctttcg aagacgaatt aaaggctgtt ttaccaaagg aagttgagag tgcaagagct  1920
gcattggaat gtggcaaccc tgctattgct aacaggatta cagaatgcag atcttatcca  1980
ttgtacaggt ttgtgagaaa ggagcttgga acagaactac taacaggaga aagagtccga  2040
tcaccgggcg aggagtgtga gaaagtgttc acagcaatgt gcaatggaca gattattgat  2100
ccaatgttgg agtgtctcaa gagctggaat ggtgctcctc tacctatctg ttag       2154

SEQ ID NO: 54          moltype = DNA  length = 2139
FEATURE                Location/Qualifiers
source                 1..2139
                       mol_type = other DNA
                       organism = Nicotiana sp.
```

```
SEQUENCE: 54
atggctggtg ttgcacaaaa tggtcaccaa gaaatggatt tttgcatgaa agtggatcca  60
ttaaactggg aaatggcagc tgattcattg aaaggaagcc atttagatga agtgaagaaa  120
atggtggctg agtttaggaa accagtagtg aaacttggag gtgagacttt gacagtggct  180
caagttgcgg ctattgctgc aaaagataat gttaaaactg ttaaagtgga gctttctgaa  240
ggggcaagag ctggtgttaa agctagcagt gattgggtta tggacagtat gggtaaagga  300
actgatagtt atggtgttac aactggcttt ggtgctactt cacataggag gaccaagaat  360
ggtggtgctc ttcaaaagga acttattagg ttcttgaatg ctggagtttt tggcaatgga  420
acagagtcat gtcacacatt accacaatca gggacaaggg cagctatgtt agttaggatc  480
aacactctcc ttcaagggta ctctggcatc agatttgaaa tcttagaagc aatcactaaa  540
ttgcttaacc acaatgttac tccatgtttg ccccttcgcg gcaccatcac cgcctctggt  600
gatctcgtcc ccttgtccta cattgccggt ttactcactg gtcggcctaa ttctaaagca  660
gttggaccta atggcgaaac cctcaacgct gaagaagcgt ttcgtgttgc tggagttaac  720
ggtggatttt tcgagttgca gcctaaggaa ggccttgctc ttgtgaatgg tactgcagtt  780
ggttctggtt tggcctcaat ggttctcttt gatgctaatg ttctcgcggt cttttctgaa  840
gttctctcag ctatttttgc tgaggtaatg aatggaaagc ccgagttcac tgaccacttg  900
acacacaagt tgaagcatca ccccggacaa attgaggctg ctgctattat ggaacacatt  960
ttggatggta gctcttatgt gaaggcggct cagaagcttc acgaaacgga tcctctccaa  1020
aaaccaaagc aagatcgtta tgctcttaga acgtcgcccc aatggcttgg ccctcaaatt  1080
gaggtcatcc gttctgcaac caagatgatt gagagggaga ttaattcagt gaacgacaac  1140
cctttgatcg atgtttcaag aaacaaggca ttacacggtg gcaacttcca gggcactcca  1200
attggtgtct ctatggacaa tgctagatta gcccttgcat caatagggaa attgatgttt  1260
gcccaattct ccgagcttgt caacgattac tacaacaacg gattgccatc taatctgaca  1320
gcaggaagga atcctagctt ggactatggt ttcaagggat ctgagattgc catggcttca  1380
tactgttcag aacttcaatt cttggcaaat ccagtgacta accacgtaca aagcgccgag  1440
caacacaacc aagatgtgaa ctccttgggc ttaatctcag ctagaaaaac agctgaagcc  1500
gtggacatct taaagctaat gtcatccaca tatctagttg cactttgcca agcaatagac  1560
ttgaggcatt tggaagaaaa tctgaggaat gcagtcaaga acacggtgag ccaagtcgca  1620
aagagaactt taacaatggg taccaatgga gaacttcatc catcaagatt ctgtgaaaag  1680
gacttgcttc gagtcgtgga cagggaatac gtcttcgcct atgctgacga cgcctgcagc  1740
gctaactacc cactgatgca gaaactaagg caagtcctcg tcgaccacgc cttgcaaaat  1800
ggcgaaaatg agaagaacgc aaacagctca atcttccaaa agatactagc ttttgaagac  1860
gagctaaagg ccgtgttgcc aaaagaagtc gagagtgcaa gagccgcgct ggaaagtggg  1920
aaccctgcaa ttgccaacag gataaaagaa tgcagatctt atccacttta caggtttgtt  1980
agaggagaac ttggagctga attattgacg ggagaaaaag tcaggtcacc aggtgaagaa  2040
tgtgacaaag tgttcacagc aatgtgcaat ggacaaatta ttgattcatt gttagaatgt  2100
ctcaaggaat ggaatggtgc acctcttcca atctgttag                        2139

SEQ ID NO: 55           moltype = DNA  length = 1170
FEATURE                 Location/Qualifiers
source                  1..1170
                        mol_type = other DNA
                        organism = Nicotiana sp.
SEQUENCE: 55
atggtgacgg tcgaggagtt tcgtagggca caacgtgccg agggtccggc cacggtcatg  60
gccatcggaa cagccacacc ttccaactgt gttgatcaaa gcacttaccc cgattactat  120
tttcgtatca ctaatagcga gcataagact gagcttaagg agaaatttaa gcgcatgtgt  180
gaaaaatcaa tgattaagaa aaggtacatg cacttaacag aggaaatctt gaaagagaat  240
cctaatattt gtgcatacat ggcaccttcc cttgatgcta gacaagacat agtggtggtt  300
gaagtgccaa aacttggcaa agaggcagcc caaaaggcca tcaaagaatg gggccagccc  360
aagtccaaaa ttagtcattt ggtcttttgt acaactagtg gtgtagacat gcccgggtgt  420
gactaccaac tcactaagct actcgggctc cgtccttcgg tcaagcggtt catgatgtac  480
caacaaggtt gctttgccgg tgggacggta ctccggatgg ctaaggactt ggccgaaaac  540
aacaagggcg ctcgagtcct tgttgtttgc tcagagatca ccgctgtcac gttccgtggg  600
cccaatgaca cccacttgga tagtttggtt gggcaagccc tttttggtga tggggcagcc  660
gcggtcattg taggttctga tccaattcca gatgtcgaga ggcctttgtt cgagcttgtt  720
tccgcagccc aaaccctact ccccgatagc gaaggcgcta tcgacggtca tctccgtgaa  780
gttgggctta cattccactt actcaaagat gttcctgggc ttatctcgaa aaacattgag  840
aaaagccttg tggaagcatt ccaacctttg ggaatttctg attggaactc tttattttgg  900
attgctcacc ctggtgggcc tgccattttg gaccaagttg aactaaaatt gggcctaaag  960
caagagaaac ttaaggctac aagaaatgta ttaagtaact atggcaatat gtcaagtgct  1020
tgtgtgttgt ttattttgga tgaaatgagg aaagcctctg caaaagaagg tttaggaact  1080
actggtgaag ggcttgaatg ggtgtgcttt tttggatttg ggcctgggct tacagttgag  1140
actgttgtcc ttcacagtgt tgctacttag                                  1170

SEQ ID NO: 56           moltype = DNA  length = 1110
FEATURE                 Location/Qualifiers
source                  1..1110
                        mol_type = other DNA
                        organism = Nicotiana sp.
SEQUENCE: 56
atggcacctt cgacattgac agctctagca gaggaaaaga cacttcaaac aagtttcata  60
agagatgaag atgagcgacc aaaagtggcg tacaaccaat tcagcgatga gattccgatc  120
atatcgttga agggtattga tgatgagggt ggaattaatg gaagaagagg tgaaatatgt  180
gaaaagattg tcaaggcatg tgaagattgg ggcgttttcc aggtagttga tcatggtgtt  240
gatgctcaac ttatctcaca aatgacaact ctcgctaaac aattcttcgc tttgcctgct  300
gaggaaaagc tacggtttga catgtcgggt ggcaagaaag gtggcttcat tgtctctagc  360
catctacagg gtgaagtggt ccaagattgg cgtgaaatag tgacctactt ctcataccca  420
attcgggcta gagactactc tagatggcca gacaaaccag agggatggat agatgtgact  480
```

```
caaaagtaca gtgaaaagtt aatggagttg gcttgcaaat tattggaagt actatcagag  540
gctatgggct tagagaagga ggccttaacc aaggcatgtg tggatatgga ccaaaaagtg  600
gttgtcaatt tttacccaaa gtgtccacag cctgacctta cccttgggct gaaacgacac  660
actgatccag gaaccatcac cctcttgtta caagaccaag ttggtgggct tcaagccact  720
aaagataatg gcaaaacttg gattactgtt cagcccgttg ttggcgcttt tgttgtcaat  780
cttggtgacc atggtcattt tttgagcaat ggaaggttta agaacgctga tcatcaagca  840
gtggtgaact cgaatagcag cagattatcg atagctacgt ttcagaatcc agcaccagag  900
gcaatagtgt atcctttgaa aattagggaa ggagagaagg cagtgatgga cgagcccgta  960
gcatttgcag aaatgtatag gaggaaaatg agtaaggacc ttgagcttgc taggctcaag  1020
aaactagcca aggagcagca aatacaagct gaagaagctg ctgagaaggc caagtcggaa  1080
accaagccta ttgatgaaat tcttgcttaa                                  1110
```

```
SEQ ID NO: 57          moltype = DNA  length = 438
FEATURE                Location/Qualifiers
source                 1..438
                       mol_type = other DNA
                       organism = Nicotiana sp.
SEQUENCE: 57
atgtttggac cacaaagtgg aaaagatgga tggactgatt tgacttttat gtacgacatg  60
attcgaatta gagataaatc tctgtgttcc agttttctgc aaatattctc aagtgagggg  120
tgcaaaatgc tggaaatgac ttgtgaagag catgacaaat tggctgctcg aagtcaattt  180
ctgactcaca caattggcag gatcttatcc gaaatggagg ttgaacccac ccccatagac  240
acgaagggat ttcagaaact tgttcaagtg aaggagagct cagttagaga tagttttgat  300
ctattcagcg ggctattcat acacaatagg tttgccaggc aacagatgaa aaatttagaa  360
gtagcagtgg agaaaactaa acagaagctt gaagagaggt cgaaggagct gcaggatcct  420
atcatatcta agttctag                                               438
```

```
SEQ ID NO: 58          moltype = DNA  length = 1131
FEATURE                Location/Qualifiers
source                 1..1131
                       mol_type = other DNA
                       organism = Nicotiana sp.
SEQUENCE: 58
atgttgtctt tcacccctct tcaatccaag ccaacaccac ccacccccac ctcaaacccc  60
acccgttggt cttggtctca tctcacccac caccacccca ctacccgccg ccacttctct  120
gcctcttcac cctccaaagt cagttaccgc cgccttagca ttaatgccat tgatgcagca  180
cagccatatg attatgaagc attagtttca aatcaatatg ctcagtcaac aagactcaag  240
attgctatag tgggttttgg caacttcggt cagtttcttg ctaaagcctt tgttcgtcaa  300
ggtcatgttg tttttgctca ttcaagaact gattactcac acattgcaaa ttctttaggt  360
gttttgtttt ttcaagatcc acatgacctt tgtgagcaac atcctgatgt tattctactt  420
tgtacttcaa ttatatctac tgaacctgtc cttagatcac tccctattca aaggctaaaa  480
agaaacacat tatttgttga tgttttgtct gttaaagagt ttccaaagaa catttttcctt  540
caagttttgc cttcccattt tgatattttg tgtactcatc ctatgtttgg acctgaaagt  600
ggtaaggata gttggaaaga tttggccttt gtgtttgata aagttagaat tggtgaaggg  660
gaatcgagaa aaggaagggt tgataggttt cttgatatat ttgagaaaga agggtgtagg  720
atggtgcaga tgacgtgtgc ggagcatgat aggtatgctg caggttcgca gtttattaca  780
catacaatgg ggagagtatt ggagaagttg gatttggaga caactcctat taatacgaaa  840
gggtacgaga ctttgttgaa tttggttgag aatacttcta gtgatagctt tgacttgtac  900
tatgggttgt ttatgtacaa taagaatgcg atggagcagt tggaaagact tgatttggct  960
ttcgaggctt tgaagaagga gttatttggg catttgcatg aagtcttgag gaagcaattg  1020
ttcgggaagg cggaggaagc gggacagaga cgtatcttaa ccaagttgcc caagaatggg  1080
tatgcactac cagctccttc atcggaggct gttaaatctg agaacaattg a          1131
```

```
SEQ ID NO: 59          moltype = DNA  length = 2623
FEATURE                Location/Qualifiers
misc_feature           1..2623
                       note = comprises plant native sequences only
source                 1..2623
                       mol_type = other DNA
                       organism = synthetic construct
SEQUENCE: 59
cccgggttag tattcaaacc gaataaatca aagttaccaa accgaataaa tcgaaaccga  60
aaggagaaac cgcaccatac cgaatttaat taggtacgat attgatattg tattttaaaa  120
aatcgaatac caaaaatacc gaattaaaat atctaaatat cgtacagtac cgaccgataa  180
atactctata agcatcatca tgtcaccatt cctgcttgga aatagatgta ataatgtaat  240
tcaaggtgaa gatcattgaa aatgagatat ttggactctt agataattgt gcaactgata  300
tttttattta cttttttttct ttcatccaat aattgcgtta cattaaaaat gagatatttg  360
gattaatatt cttctccttg accacaaagc aaggaaagcc taaggaccga tagtaaagtt  420
gtattcgtgt ggttgcgtgt tagttttgag cggcaaaata aattatgtta aggtaaatta  480
tttttggaac aataataaaa ttatttctgt ataatatata aatcatatat ttgaaccgta  540
gaattatcag ttaatacttg tatatgagga ggctaactac gttagagcgc taacgagaat  600
acttcatata ccgtattttt tacgataata ataatgtaat gtgaaattgc tatccaaaag  660
gcacctaatt ttgtccaccg ttcaaaggaa aggacaagga agtagtagcg tgtaggtttg  720
gtgctgtaca aaataagcaa gacacgtgtt gccttattat aggataatcc ataaggcaat  780
ttcgtcttaa gtcggccatt gcacctttaa aaggagcctc tttgttccca aaatcttcat  840
cctttgattt ctctattctc aatatctcct caatttttct ctagtcttca aacacttctc  900
aaggtacatt aacttcttct ttctttttgt tcctcttatt ttatgctact tttatttaat  960
ttcgatctat atttttagga tctaaatact catttttgat ttgtttaatc gctctgtata  1020
tatgcaccaa gttgaaattt ttgtaagttt attttgttcg gtctatattt taagatctga  1080
```

```
aatacccttt actgagaaaa aaaaaactca accttgattt tgttgtacct ggttgaattt  1140
gttattgttg tgtatacagt taaaaaactc aagtcttgat tttattgttt ccccttttgta  1200
gtttgtatat acatagagct gaattggtgt tctaattttg gttgattttt atgtatacag  1260
tataaaatcg atcttagttt tgttcattga tttgtatttg cacaaagttg gaattttgcg  1320
tttgttattt tgatgattga aacctttttct gtatatacag ctcgagatgg agggttcgtc  1380
caaagggctg cgaaaaggtg cttggactac tgaagaagat agtctcttga gacagtgcat  1440
taataagtat ggagaaggca aatggcacca agttcctgta agagctgggc taaaccggtg  1500
caggaaaagt tgtagattaa gatggttgaa ctatttgaag ccaagtatca agagaggaaa  1560
acttagctct gatgaagtcg atcttcttct tcgccttcat aggcttctag ggaataggtg  1620
gtctttaatt gctggaagat tacctggtcg gaccgcaaat gacgtcaaga attactggaa  1680
cactcatctg agtaagaaac atgaaccgtg ttgtaagata aagatgaaaa agagagacat  1740
tacgcccatt cctacaacac cggcactaaa aaacaatgtt tataagcctc gacctcgatc  1800
cttcacagtt aacaacgact gcaaccatct caatgcccca ccaaaagttg acgttaatcc  1860
tccatgcctt ggacttaaca tcaataatgt ttgtgacaat agtatcatat acaacaaaga  1920
taagaagaaa gaccaactag tgaataattt gattgatgga gataatatgt ggttagagaa  1980
attcctagag gaaagccaag aggtagatat tttggttcct gaagcgacga caacagaaaa  2040
gggggacacc ttggcttttg acgttgatca actttggagt cttttcgatg gagagactgt  2100
gaaatttgat tagtctagaa ataacagagg gcgcgcgagc ggtggctact gatcgcctat  2160
gagttctgtg attctacttg taatttcaga agtgttttca gtgtcttgtt ttctggaagt  2220
ccgtctggtt tttagtaact tttagctcaa aaatgtgtct gtacgatggt atttgtatgt  2280
ttgtgggtct tttacatata cgcttgtaat cgatcaatgt agaatgctgt gtgccttttc  2340
cgtcaacagc ttatttagtg tttactctgt atacgtatat ctaatatata gtactgattc  2400
tttcatctgg tgatttgttt tcctaaagag attattatca tagctttaat tgaatgatac  2460
aaagaggtgt tgcctggctt caccagagca gaaattttca ttgatatagg gtacaaatgt  2520
cattcacata atgttaagag ataagttttt caatgtcctc aagagcccac caagagtttc  2580
ttccgggaat tgcttaaatt atcttaaatt taaattgtaa aac                    2623
```

```
SEQ ID NO: 60          moltype = DNA  length = 2539
FEATURE                Location/Qualifiers
misc_feature           1..2539
                       note = plant native sequences only
source                 1..2539
                       mol_type = other DNA
                       organism = synthetic construct
SEQUENCE: 60
cccgggttag tattcaaacc gaataaatca aagttaccaa accgaataaa tcgaaaccga  60
aaggagaaac cgcaccatac cgaatttaat taggtacgat attgatattg tattttaaaa  120
aatcgaatac caaaaatacc gaattaaaat atctaaatat cgtacagtac cgaccgataa  180
atactctata agcatcatca tgtcaccatt cctgcttgga aatagatgta ataatgtaat  240
tcaaggtgaa gatcattgaa aatgagatat ttggactctt agataattgt gcaactgata  300
tttttattta ctttttttct ttcatccaat aattgcgtta cattaaaaat gagatatttg  360
gattaatatt cttctccttg accacaaagc aaggaaagcc taaggaccga tagtaaagtt  420
gtattcgtgt ggttgcgtgt tagttttgag cggcaaaata aattatgtta aggtaaatta  480
tttttggaac aataataaaa ttatttctgt ataatatata aatcatatat ttgaaccgta  540
gaattatcag ttaatacttg tatatgagga ggctaactac gttagagcgc taacgagaat  600
acttcatata ccgtattttt tacgataata ataatgtaat gtgaaattgc tatccaaaag  660
gcacctaatt ttgtccaccg ttcaaaggaa aggacaagga agtagtagcg tgtaggtttg  720
gtgctgtaca aaataagcaa gacacgtgtt gccttattat aggataatcc ataaggcaat  780
ttcgtcttaa gtcggccatt gcacctttaa aaggagcctc tttgttccca aaatcttcat  840
cctttgattt ctctattctc aatatctcct caatttttct ctagtcttca aacacttctc  900
aaggtacatt aacttcttct ttctttttgt tcctcttatt ttatgctact tttatttaat  960
ttcgatctat atttttagga tctaaatact catttttgat ttgtttaatc gctctgtata  1020
tatgcaccaa gttgaaattt ttgtaagttt attttgttcg gtctatattt taagatctga  1080
aatacccttt actgagaaaa aaaaaactca accttgattt tgttgtacct ggttgaattt  1140
gttattgttg tgtatacagt taaaaaactc aagtcttgat tttattgttt ccccttttgta  1200
gtttgtatat acatagagct gaattggtgt tctaattttg gttgattttt atgtatacag  1260
tataaaatcg atcttagttt tgttcattga tttgtatttg cacaaagttg gaattttgcg  1320
tttgttattt tgatgattga aacctttttct gtatatacag ctcgagatga atatttgtac  1380
taataagtcg tcgtcaggag tgaagaaagg tgcatggact gaagaagaag atgttctatt  1440
gaaaaaatgc atcgagaaat atggagaagg aaagtggcat caagttcctc ttagagctgg  1500
tttgaataga tgcagaaaga gctgcagatt aaggtggcta aattatctaa ggccacatat  1560
aaagagagga gacttctctt ttgatgaagt agatctcatt ttgaggcttc ataagctgtt  1620
aggcaacaga tggtcactta ttgctggtag acttcctgga aggacggcaa acgatgtcaa  1680
aaactactgg aacagccatc ttcgcaagaa gttaattgct cctcatgatc aaaaggagag  1740
caagcaaaaa gcaaagaaga tcaccatatt cagacctcgg cctcgaacct tctcaaagac  1800
aaatacttgt gttaaaagta acacaaatac tgtagataag gatattgaag gcagcagcga  1860
aataattaga ttcaacgata atttgaagcc aacaactgaa gaattgacgg atgatggaat  1920
tcaatggtgg gccgatttac tagctaacaa ttacaacaat aatgggattg aggaagctga  1980
taattcatca ccaactttgt tgcatgagga aatgccactt ctcagttgat ctagaaataa  2040
cagagggcgc gcgagcggtg gctactgatc gcctatgagt tctgtgattc tacttgtaat  2100
ttcagaagtg ttttcagtgt cttgttttct ggaagtccgt ctggttttta gtaactttta  2160
gctcaaaaat gtgtctgtac gatggtattt gtatgtttgt gggtctttta catatacgct  2220
tgtaatcgat caatgtagaa tgctgtgtgc cttttccgtc aacagcttat ttagtgttta  2280
ctctgtatac gtatatctaa tatatagtac tgattctttc atctggtgat ttgttttcct  2340
aaagagatta ttatcatagc tttaattgaa tgatacaaag aggtgttgcc tggcttcacc  2400
agagcagaaa ttttcattga tatagggtac aaatgtcatt cacataatgt taagagataa  2460
gtttttcaat gtcctcaaga gcccaccaag agtttcttcc gggaattgct taaattatct  2520
taaatttaaa ttgtaaaac                                                2539
```

```
SEQ ID NO: 61           moltype = DNA  length = 3701
FEATURE                 Location/Qualifiers
misc_feature            1..3701
                        note = comprises plant native sequences only
source                  1..3701
                        mol_type = other DNA
                        organism = synthetic construct
SEQUENCE: 61
cccgggaaac taataagaac aagcaatata agagaattcg taaaaaactt tctagttctt  60
gaacatctac ccatgtgaat tctcttttat ttttgtacac tataattaaa ttaacatggc  120
taaaccaatt atgccaactg aataaattat caatattgat aaacttcagg tttacaccat  180
gacgtgtgca attatgaata aactccaagt ttattatgat atgagttttt atatcaataa  240
acttctactt tactgtgaca ttcttttgtt tgtgtagtac aaattggaga ataaagcgtg  300
taacttttca catacatatt accccgctat aagttgtagt aatagaagat attaaatctt  360
tcctttcttt atagtctcaa tataaccaat cgcttttgcg aatactttag aaactaaata  420
agtttctttg agacttacta caacataatg ccttattgat aatcaatttt gttccttcaa  480
aatagtaata attggctctt ccagagctct caattaattt tgtactacca catattcatc  540
aacatccata tggtgaatat ctcttttaaa gagaaagtta taccattatg gttatggtca  600
aaattatatg caatatttgt ttcttgcatt accgttgcct tttagtaatc acattgccaa  660
aatattttgg cctacaataa gtacgtgacc aatgaccatt tatgccataa tgacattatt  720
ttcttatttt ctctcaaacc tccttcaaga gatgagtgtg gtatatacta ctagcacgct  780
catattcttc caaaaatgaa tatgtattca taaatcacat attgtcacat tcacatcatg  840
aatggaccat aatcatctat atgtgcttta caaaatctca tgtcaaatcg atgataaata  900
ttactttcac atagtgaatg attattttga gaatacttat tattctcatt accacaatga  960
aaatgattat aatttcgtct attgtcacat ccacatccat tgatacattc atggtaataa  1020
ttttatcttc tttcagacgt atcatatatt gctatcacat tctcgtaagg gaatgagaat  1080
aaagcaaatt caatgggacg agtttccact ttttgtgctc acaatcatac atgaatttga  1140
tcatggcaat acatagaaat tttatcactt ttggtggtta taatttctta caaactctat  1200
tagagttata ataaaaattt attgtctttg cttgtattta aaatcaaatt ataaaatttt  1260
aaaaattcaa aagagaaaaa taaagtaaaa tacttacttt aaatccagaa tttaatcacg  1320
aaggaagttc atggaataat tgacgatcat tatgctcaat cccaaagctt ctactcaatt  1380
ggttacagtc tcgtgccgat aacgtgttat aaaacaataa aagaagaaca atattgcaga  1440
gaaagagaga gagggaattc ttattgaatt ttaggatgaa ttacaatgga ataggacccc  1500
tctatttata gggaaagagt gacttagcca ccaagtaaaa tccctaaaat ctctctaaaa  1560
tatagacatt caccttaaat aaaactctat ttataacaaa aacaaaattg ttctagacga  1620
gaatcatttt cactttttaa tgtttttctt ctactccttt agtttttcct taaaccaaaa  1680
taaaaaaaaa gtctatattt ttctatcctt tttcttctct agttttaata cattccataa  1740
aatttgtggt gaaattgtac tttctccttt tttttcctct ttagtttcat agaaattaaa  1800
caataaaacg aaaacatcaa aatatatcaa caaatagtaa atttcattac atttattttt  1860
ttgctcaaag tgctcttttg ttgaatactc aaagtatata gtatattaca gttctaatca  1920
ggaattattc actgaaatat tgactgattt taggttcgtg tgatcgatta aatacctctt  1980
gaaccactac aaatttaacg aattaataac ttttacctaa cattttgtta cccatgtatt  2040
aatttgaatt tatactatta cttcctattt atgagtaata taacataatt tctgtgtaaa  2100
ggacagaaaa tacagaattt gattaattca aaattaatta tacttcaaaa aatatcacaa  2160
ggatatcaaa atttatcaaa taaaggagca acgtcatttt cggctctccc acacaattca  2220
aaataattca aaacagaacc ggctagacct aacctaacca aaccatggtt aatacaaatc  2280
taaatcaccg aaaaacaatc ttaaccatag ttaataaccc gtattaatta acccgatatc  2340
catttcgcct tgcccttatt cattctccta taaaacagag gcccttcagt atagcgaaga  2400
ctcacaattc gaatttcgaa aactcatctc tttctgtttt aacggcgtct tgataaacgc  2460
cgctccttct ctcctcctct ttgaaatttg aatttttagg gtttcgtgaa actcgagaac  2520
aatgaatatt tgtactaata agtcgtcgtc aggagtgaag aaaggtgcat ggactgaaga  2580
agaagatgtt ctattgaaaa aatgcatcga gaaatatgga gaaggaaagt ggcatcaagt  2640
tcctcttaga gctggtttga atagatgcag aaagagctgc agattaaggt ggctaaatta  2700
tctaaggcca catataaaga gaggagactt ctcttttgat gaagtagatc tcattttgag  2760
gcttcataag ctgttaggca acagatggtc acttattgct ggtagacttc ctggaaggac  2820
ggcaaacgat gtcaaaaact actggaacag ccatcttcgc aagaagttaa ttgctcctca  2880
tgatcaaaag gagagcaagc aaaaagcaaa gaagatcacc atattcagac ctcggcctcg  2940
aaccttctca aagacaaata cttgtgttaa aagtaacaca aatactgtag ataaggatat  3000
tgaaggcagc agcgaaataa ttagattcaa cgataatttg aagccaacaa ctgaagaatt  3060
gacggatgat ggaattcaat ggtgggccga tttactagct aacaattaca acaataatgg  3120
gattgaggaa gctgataatt catcaccaac tttgttgcat gaggaaatgc cacttctcag  3180
ttgatctaga aataacagag ggcgcgcgag cggtggctac tgatcgccta tgagttctgt  3240
gattctactt gtaatttcag aagtgttttc agtgtcttgt tttctggaag tccgtctggt  3300
ttttagtaac ttttagctca aaaatgtgtc tgtacgatgg tatttgtatg tttgtgggtc  3360
ttttacatat acgcttgtaa tcgatcaatg tagaatgctg tgtgcctttt ccgtcaacag  3420
cttatttagt gtttactctg tatacgtata tctaatatat agtactgatt ctttcatctg  3480
gtgatttgtt ttcctaaaga gattattatc atagctttaa ttgaatgata caaagaggtg  3540
ttgcctggct tcaccagagc agaaattttc attgatatag ggtacaaatg tcattcacat  3600
aatgttaaga gataagtttt tcaatgtcct caagagccca ccaagagttt cttccgggaa  3660
ttgcttaaat tatcttaaat ttaaattgta cccgtttaaa c                       3701

SEQ ID NO: 62           moltype = DNA  length = 6230
FEATURE                 Location/Qualifiers
misc_feature            1..6230
                        note = comprises plant native sequences only
source                  1..6230
                        mol_type = other DNA
                        organism = synthetic construct
SEQUENCE: 62
```

```
cccgggttag tattcaaacc gaataaatca aagttaccaa accgaataaa tcgaaaccga  60
aaggagaaac cgcaccatac cgaatttaat taggtacgat attgatattg tattttaaaa  120
aatcgaatac caaaaatacc gaattaaaat atctaaatat cgtacagtac cgaccgataa  180
atactctata agcatcatca tgtcaccatt cctgcttgga aatagatgta ataatgtaat  240
tcaaggtgaa gatcattgaa aatgagatat ttggactctt agataattgt gcaactgata  300
tttttattta cttttttttct ttcatccaat aattgcgtta cattaaaaat gagatatttg  360
gattaatatt cttctccttg accacaaagc aaggaaagcc taaggaccga tagtaaagtt  420
gtattcgtgt ggttgcgtgt tagttttgag cggcaaaata aattatgtta aggtaaatta  480
tttttggaac aataataaaa ttatttctgt ataatatata aatcatatat ttgaaccgta  540
gaattatcag ttaatacttg tatatgagga ggctaactac gttagagcgc taacgagaat  600
acttcatata ccgtattttt tacgataata ataatgtaat gtgaaattgc tatccaaaag  660
gcacctaatt ttgtccaccg ttcaaaggaa aggacaagga agtagtagcg tgtaggtttg  720
gtgctgtaca aaataagcaa gacacgtgtt gccttattat aggataatcc ataaggcaat  780
ttcgtcttaa gtcggccatt gcacctttaa aaggagcctc tttgttccca aaatcttcat  840
cctttgattt ctctattctc aatatctcct caatttttct ctagtcttca aacacttctc  900
aaggtacatt aacttcttct ttctttttgt tcctcttatt ttatgctact tttatttaat  960
ttcgatctat attttagga tctaaatact catttttgat ttgtttaatc gctctgtata  1020
tatgcaccaa gttgaaattt ttgtaagttt attttgttcg gtctatattt taagatctga  1080
aatacccttt actgagaaaa aaaaaactca accttgattt tgttgtacct ggttgaattt  1140
gttattgttg tgtatacagt taaaaaactc aagtcttgat tttattgttt ccctttttgta  1200
gtttgtatat acatagagct gaattggtgt tctaattttg gttgattttt atgtatacag  1260
tataaaatcg atcttagttt tgttcattga tttgtatttg cacaaagttg gaattttgcg  1320
tttgttattt tgatgattga aaccttttct gtatatacag ctcgagatga atatttgtac  1380
taataagtcg tcgtcaggag tgaagaaagg tgcatggact gaagaagaag atgttctatt  1440
gaaaaaatgc atcgagaaat atggagaagg aaagtggcat caagttcctc ttagagctgg  1500
tttgaataga tgcagaaaga gctgcagatt aaggtggcta aattatctaa ggccacatat  1560
aaagagagga gacttctctt ttgatgaagt agatctcatt ttgaggcttc ataagctgtt  1620
aggcaacaga tggtcactta ttgctggtag acttcctgga aggacggcaa acgatgtcaa  1680
aaactactgg aacagccatc ttcgcaagaa gttaattgct cctcatgatc aaaaggagag  1740
caagcaaaaa gcaaagaaga tcaccatatt cagacctcgg cctcgaacct tctcaaagac  1800
aaatacttgt gttaaaagta acacaaatac tgtagataag gatattgaag gcagcagcga  1860
aataattaga ttcaacgata atttgaagcc aacaactgaa gaattgacgg atgatggaat  1920
tcaatggtgg gccgatttac tagctaacaa ttacaacaat aatgggattg aggaagctga  1980
taattcatca ccaactttgt tgcatgagga aatgccactt ctcagttgat ctagaaataa  2040
cagagggcgc gcgagcggtg gctactgatc gcctatgagt tctgtgattc tacttgtaat  2100
ttcagaagtg ttttcagtgt cttgttttct ggaagtccgt ctggttttta gtaactttta  2160
gctcaaaaat gtgtctgtac gatggtattt gtatgtttgt gggtcttttta catatacgct  2220
tgtaatcgat caatgtagaa tgctgtgtgc cttttccgtc aacagcttat ttagtgttta  2280
ctctgtatac gtatatctaa tatatagtac tgattctttc atctggtgat ttgttttcct  2340
aaagagatta ttatcatagc tttaattgaa tgatacaaag aggtgttgcc tggcttcacc  2400
agagcagaaa ttttcattga tatagggtac aaatgtcatt cacataatgt taagagataa  2460
gtttttcaat gtcctcaaga gcccaccaag agtttcttcc gggaattgct taaattatct  2520
taaatttaaa ttgtaaaact aataagaaca agcaatataa gagaattcgt aaaaaacttt  2580
ctagttcttg aacatctacc catgtgaatt ctcttttatt tttgtacact ataattaaat  2640
taacatggct aaaccaatta tgccaactga ataaattatc aatattgata aacttcaggt  2700
ttacaccatg acgtgtgcaa ttatgaataa actccaagtt tattatgata tgagttttta  2760
tatcaataaa cttctacttt actgtgacat tcttttgttt gtgtagtaca aattggagaa  2820
taaagcgtgt aacttttcac atacatatta ccccgctata agttgtagta atagaagata  2880
ttaaatcttt cctttcttta tagtctcaat ataaccaatc gcttttgcga atactttaga  2940
aactaaataa gtttctttga gacttactac aacataatgc cttattgata atcaattttg  3000
ttccttcaaa atagtaataa ttggctcttc cagagctctc aattaatttt gtactaccac  3060
atattcatca acatccatat ggtgaatatc tcttttaaag agaaagttat accattatgg  3120
ttatggtcaa aattatatgc aatatttgtt tcttgcatta ccgttgcctt ttagtaatca  3180
cattgccaaa atattttggc ctacaataag tacgtgacca atgaccattt atgccataat  3240
gacattattt tcttatttc tctcaaacct ccttcaagag atgagtgtgg tatatactac  3300
tagcacgctc atattcttcc aaaaatgaat atgtattcat aaatcacata ttgtcacatt  3360
cacatcatga atggaccata atcatctata tgtgctttac aaaatctcat gtcaaatcga  3420
tgataaatat tactttcaca tagtgaatga ttattttgag aatacttatt attctcatta  3480
ccacaatgaa aatgattata atttcgtcta ttgtcacatc cacatccatt gatacattca  3540
tggtaataat tttatcttct ttcagacgta tcatatattg ctatcacatt ctcgtaaggg  3600
aatgagaata aagcaaattc aatgggacga gtttccactt tttgtgctca caatcataca  3660
tgaatttgat catggcaata catagaaatt ttatcacttt tggtggttat aatttcttac  3720
aaactctatt agagttataa taaaaattta ttgtctttgc ttgtatttaa aatcaaatta  3780
taaaatttta aaaattcaaa agagaaaaat aaagtaaaat acttacttta aatccagaat  3840
ttaatcacga aggaagttca tggaataatt gacgatcatt atgctcaatc ccaaagcttc  3900
tactcaattg gttacagtct cgtgccgata acgtgttata aaacaataaa agaagaacaa  3960
tattgcagag aaagagagag agggaattct tattgaattt taggatgaat tacaatggaa  4020
taggacccct ctatttatag ggaaagagtg acttagccac caagtaaaat ccctaaaatc  4080
tctctaaaat atagacattc accttaaata aaactctatt tataacaaaa acaaaattgt  4140
tctagacgag aatcattttc actttttaat gtttttcttc tactccttta gtttttcctt  4200
aaaccaaaat aaaaaaaaag tctatatttt tctatccttt ttcttctcta gttttaatac  4260
attccataaa atttgtggtg aaattgtact ttctcctttt ttttcctctt tagtttcata  4320
gaaattaaac aataaaacga aaacatcaaa atatatcaac aaatagtaaa tttcattaca  4380
tttatttttt tgctcaaagt gctcttttgt tgaatactca aagtatatag tatattacag  4440
ttctaatcag gaattattca ctgaaatatt gactgatttt aggttcgtgt gatcgattaa  4500
atacctcttg aaccactaca aatttaacga attaataact tttacctaac attttgttac  4560
ccatgtatta atttgaattt atactattac ttcctattta tgagtaatat aacataattt  4620
ctgtgtaaag gacagaaaat acagaatttg attaattcaa aattaattat acttcaaaaa  4680
atatcacaag gatatcaaaa tttatcaaat aaaggagcaa cgtcattttc ggctctccca  4740
```

```
cacaattcaa aataattcaa aacagaaccg gctagaccta acctaaccaa accatggtta  4800
atacaaatct aaatcaccga aaaacaatct taaccatagt taataacccg tattaattaa  4860
cccgatatcc atttcgcctt gcccttattc attctcctat aaaacagagg cccttcagta  4920
tagcgaagac tcacaattcg aatttcgaaa actcatctct ttctgtttta acggcgtctt  4980
gataaacgcc gctccttctc tcctcctctt tgaaatttga atttttaggg tttcgtgaaa  5040
ctcgagaaca atgaatattt gtactaataa gtcgtcgtca ggagtgaaga aaggtgcatg  5100
gactgaagaa gaagatgttc tattgaaaaa atgcatcgag aaatatggag aaggaaagtg  5160
gcatcaagtt cctcttagag ctggtttgaa tagatgcaga aagagctgca gattaaggtg  5220
gctaaattat ctaaggccac atataaagag aggagacttc tcttttgatg aagtagatct  5280
cattttgagg cttcataagc tgttaggcaa cagatggtca cttattgctg gtagacttcc  5340
tggaaggacg gcaaacgatg tcaaaaacta ctggaacagc catcttcgca agaagttaat  5400
tgctcctcat gatcaaaagg agagcaagca aaaagcaaag aagatcacca tattcagacc  5460
tcggcctcga accttctcaa agacaaatac ttgtgttaaa agtaacacaa atactgtaga  5520
taaggatatt gaaggcagca gcgaaataat tagattcaac gataatttga agccaacaac  5580
tgaagaattg acggatgatg gaattcaatg gtgggccgat ttactagcta acaattacaa  5640
caataatggg attgaggaag ctgataattc atcaccaact ttgttgcatg aggaaatgcc  5700
acttctcagt tgatctagaa ataacagagg gcgcgcgagc ggtggctact gatcgcctat  5760
gagttctgtg attctacttg taatttcaga agtgttttca gtgtcttgtt ttctggaagt  5820
ccgtctggtt tttagtaact tttagctcaa aaatgtgtct gtacgatggt atttgtatgt  5880
ttgtgggtct tttacatata cgcttgtaat cgatcaatgt agaatgctgt gtgccttttc  5940
cgtcaacagc ttatttagtg tttactctgt atacgtatat ctaatatata gtactgattc  6000
tttcatctgg tgatttgttt tcctaaagag attattatca tagctttaat tgaatgatac  6060
aaagaggtgt tgcctggctt caccagagca gaaattttca ttgatatagg gtacaaatgt  6120
cattcacata atgttaagag ataagttttt caatgtcctc aagagcccac caagagtttc  6180
ttccgggaat tgcttaaatt atcttaaatt taaattgtac ccgtttaaac             6230
```

```
SEQ ID NO: 63           moltype = DNA  length = 7583
FEATURE                 Location/Qualifiers
misc_feature            1..7583
                        note = comprises plant native sequences only
source                  1..7583
                        mol_type = other DNA
                        organism = synthetic construct
SEQUENCE: 63
cccgggttag tattcaaacc gaataaatca aagttaccaa accgaataaa tcgaaaccga  60
aaggagaaac cgcaccatac cgaatttaat taggtacgat attgatattg tattttaaaa  120
aatcgaatac caaaaatacc gaattaaaat atctaaatat cgtacagtac cgaccgataa  180
atactctata agcatcatca tgtcaccatt cctgcttgga aatagatgta ataatgtaat  240
tcaaggtgaa gatcattgaa aatgagatat ttggactctt agataattgt gcaactgata  300
tttttattta cttttttct ttcatccaat aattgcgtta cattaaaaat gagatatttg   360
gattaatatt cttctccttg accacaaagc aaggaaagcc taaggaccga tagtaaagtt  420
gtattcgtgt ggttgcgtgt tagttttgag cggcaaaata aattatgtta aggtaaatta  480
tttttggaac aataataaaa ttatttctgt ataatatata aatcatatat ttgaaccgta  540
gaattatcag ttaatacttg tatatgagga ggctaactac gttagagcgc taacgagaat  600
acttcatata ccgtattttt tacgataata ataatgtaat gtgaaattgc tatccaaaag  660
gcacctaatt ttgtccaccg ttcaaaggaa aggacaagga agtagtagcg tgtaggtttg  720
gtgctgtaca aaataagcaa gacacgtgtt gccttattat aggataatcc ataaggcaat  780
ttcgtcttaa gtcggccatt gcacctttaa aaggagcctc tttgttccca aaatcttcat  840
cctttgattt ctctattctc aatatctcct caatttttct ctagtcttca aacacttctc  900
aaggtacatt aacttcttct ttctttttgt tcctcttatt ttatgctact tttatttaat  960
ttcgatctat atttttagga tctaaatact catttttgat ttgtttaatc gctctgtata  1020
tatgcaccaa gttgaaattt ttgtaagttt attttgttcg gtctatattt taagatctga  1080
aataccettt actgagaaaa aaaaaactca accttgattt tgttgtacct ggttgaattt  1140
gttattgttg tgtatacagt taaaaaactc aagtcttgat tttattgttt cccttttgta  1200
gtttgtatat acatagagct gaattggtgt tctaattttg gttgattttt atgtatacag  1260
tataaaatcg atcttagttt tgttcattga tttgtatttg cacaaagttg gaattttgcg  1320
tttgttattt tgatgattga aaccttttct gtatatacag ctcgagatga cggagatacc  1380
gcctaacagc cagatgaaaa ccatgttgca gaaggcagtg caatcggttc aatggacata  1440
tactcttttc tggcaattat gtccccaaca aggggcgtta gtgtggagag atggatatta  1500
caatggggct ataaagacta gaaagacagt gcagccaatg gaagttagcg ctgaggaagc  1560
ttctcttcac agaagccaac agcttagaga actttacgaa tcactttccg ccggcgagtc  1620
aaatcagcca gcgagaaggc cgtcggcagc tttgtcaccg gaggacttga cggagtccga  1680
gtggttttat ctcatgtgtg tttctttctc ttttcctcct ggcatcggat tacctggcaa  1740
ggcttattcg aagaaacatc acatatggat catgggcgca aacgaggttg atagcaaagt  1800
cttctgtaga gctattcttg ccaagagcgc ccgcatacag acggtcgttg gtattcctct  1860
cttggatggt gtactggaac tgggaactac agaaagggtt caagaagaga ttggattcat  1920
aaaccatgta aagagctttt tcactgagca acaacaacct cagctaccaa agccagcctt  1980
atctgagcac tccacttcca atcccaccac cttttccgag ccacattttt actccggcaa  2040
tacttcgcca tctgctaatg ttgatattgc gcatcaagat ggcggagctg ccggcgaaga  2100
agatgaggag gaggaagaag aagaagatga tgatgaagcc gagttggact cggatagtat  2160
agcgattcaa agcgcggcta atcctattgc cgttgaggct agtgaactca tgcagcttga  2220
tgtgtccgag gctatacagc tcggctcgcc cgatgatgac tctgataata tggactctga  2280
ttttcatttg gttggcgctg gaaacacggc tcatgactac cagcgccaag ctgactcttt  2340
caaagccgag accgccatta gctggccgca cttccaagac cttcaacaat taccaggtgg  2400
ctctagttat gatgaattat cacaagaaga cacacactat tctcaaacag tgtcaaccat  2460
tctcgaacac cgaagctcca aattttcctc tacaacaatg ggctgtattt ctcatgactc  2520
ggcccaatct gccttcacat tgtgccctag caccaccgtc tgcagcccga atcccgccca  2580
ctgccgccac gacgactcac ttgtcgacgg tggcggcgcc tcccagtggc tgctcaaaag  2640
catactcttc actgtcccat ttcttcacac taaataccaa tctgaagctt ctccaaagtc  2700
```

-continued

```
acgtgacgtc gccactgttg attcctccag tactgcttct cgctttcgca aaggctgtag  2760
tataacgtcg caagaagagc caagtggaaa ccatgtactt gcagaacgac gtcgtagaga  2820
gaagctaaat gagcgtttta tcatattaag gtctcttgta ccttttgtaa cgaaaatgga  2880
caaagcctcc attttgggtg acaccataga gtatgtcaag cagttacgta agaaagttca  2940
ggatcttgaa gctcgtgctc gcgacacgga gcactccaga gatgcagata aaaaaggtgg  3000
cacagctaca gtgaaggtgt tgcaaggaag gggtaagagg agaatgaata cggtagatgg  3060
aagtgttggt ggagggcagg caacgataac ggcgtcccca ccgtcaacga cggaaaatga  3120
ggaggttgtg caagtacaag tatcaattat cgaaagcgat gcattggtgg agctccggtg  3180
tccgtacaaa gaggggttgc tgttaaatgt aatgcagatg ctaagggaac tcaaagtgga  3240
agttgtagcc attcaatcag ctcttaataa tggcgtcttc ttggctgagt taagagctaa  3300
ggtaaaagag aatatatgtg gaaggaaagc aagcattttg gaagtaaaaa ggtcaataca  3360
tcagataatc cctagagatt aatctagaaa taacagaggg cgcgcgagcg gtggctactg  3420
atcgcctatg agttctgtga ttctacttgt aatttcagaa gtgttttcag tgtcttgttt  3480
tctggaagtc cgtctggttt ttagtaactt ttagctcaaa aatgtgtctg tacgatggta  3540
tttgtatgtt tgtgggtctt ttacatatac gcttgtaatc gatcaatgta gaatgctgtg  3600
tgccttttcc gtcaacagct tatttagtgt ttactctgta tacgtatatc taatatatag  3660
tactgattct ttcatctggt gatttgtttt cctaaagaga ttattatcat agctttaatt  3720
gaatgataca aagaggtgtt gcctggcttc accagagcag aaattttcat tgatataggg  3780
tacaaatgtc attcacataa tgttaagaga taagtttttc aatgtcctca agagcccacc  3840
aagagtttct tccgggaatt gcttaaatta tcttaaattt aaattgtaaa actaataaga  3900
acaagcaata taagagaatt cgtaaaaaac tttctagttc ttgaacatct acccatgtga  3960
attctctttt attttgtac actataatta aattaacatg gctaaaccaa ttatgccaac  4020
tgaataaatt atcaatattg ataaacttca ggtttacacc atgacgtgtg caattatgaa  4080
taaactccaa gtttattatg atatgagttt ttatatcaat aaacttctac tttactgtga  4140
cattcttttg tttgtgtagt acaaattgga gaataaagcg tgtaactttt cacatacata  4200
ttaccccgct ataagttgta gtaatagaag atattaaatc tttcctttct ttatagtctc  4260
aatataacca atcgcttttg cgaatacttt agaaactaaa taagtttctt tgagacttac  4320
tacaacataa tgccttattg ataatcaatt ttgttccttc aaaatagtaa taattggctc  4380
ttccagagct ctcaattaat tttgtactac cacatattca tcaacatcca tatggtgaat  4440
atctctttta aagagaaagt tataccatta tggttatggt caaaattata tgcaatattt  4500
gtttcttgca ttaccgttgc cttttagtaa tcacattgcc aaaatatttt ggcctacaat  4560
aagtacgtga ccaatgacca tttatgccat aatgacatta ttttcttatt ttctctcaaa  4620
cctccttcaa gagatgagtg tggtatatac tactagcacg ctcatattct tccaaaaatg  4680
aatatgtatt cataaatcac atattgtcac attcacatca tgaatggacc ataatcatct  4740
atatgtgctt tacaaaatct catgtcaaat cgatgataaa tattactttc acatagtgaa  4800
tgattatttt gagaatactt attattctca ttaccacaat gaaaatgatt ataatttcgt  4860
ctattgtcac atccacatcc attgatacat tcatggtaat aattttatct tctttcagac  4920
gtatcatata ttgctatcac attctcgtaa gggaatgaga ataaagcaaa ttcaatggga  4980
cgagtttcca ctttttgtgc tcacaatcat acatgaattt gatcatggca atacatagaa  5040
attttatcac ttttggtggt tataatttct tacaaactct attagagtta taataaaaat  5100
ttattgtctt tgcttgtatt taaaatcaaa ttataaaatt ttaaaaattc aaaagagaaa  5160
aataaagtaa aatacttact ttaaatccag aatttaatca cgaaggaagt tcatggaata  5220
attgacgatc attatgctca atcccaaagc ttctactcaa ttggttacag tctcgtgccg  5280
ataacgtgtt ataaaacaat aaaagaagaa caatattgca gagaaagaga gagagggaat  5340
tcttattgaa ttttaggatg aattacaatg gaataggacc cctctattta tagggaaaga  5400
gtgacttagc caccaagtaa aatccctaaa atctctctaa aatatagaca ttcaccttaa  5460
ataaaactct atttataaca aaaacaaaat tgttctagac gagaatcatt ttcacttttt  5520
aatgtttttc ttctactcct ttagtttttc cttaaaccaa aataaaaaaa aagtctatat  5580
ttttctatcc tttttcttct ctagttttaa tacattccat aaaatttgtg gtgaaattgt  5640
actttctcct tttttttcct ctttagtttc atagaaatta aacaataaaa cgaaaacatc  5700
aaaatatatc aacaaatagt aaatttcatt acatttattt ttttgctcaa agtgctcttt  5760
tgttgaatac tcaaagtata tagtatatta cagttctaat caggaattat tcactgaaat  5820
attgactgat tttaggttcg tgtgatcgat taaatacctc ttgaaccact acaaatttaa  5880
cgaattaata acttttacct aacattttgt tacccatgta ttaatttgaa tttatactat  5940
tacttcctat ttatgagtaa tataacataa tttctgtgta aaggacagaa aatacagaat  6000
ttgattaatt caaaattaat tatacttcaa aaaatatcac aaggatatca aaatttatca  6060
aataaaggag caacgtcatt ttcggctctc ccacacaatt caaaataatt caaaacagaa  6120
ccggctagac ctaacctaac caaaccatgg ttaatacaaa tctaaatcac cgaaaaacaa  6180
tcttaaccat agttaataac ccgtattaat taacccgata tccatttcgc cttgccctta  6240
ttcattctcc tataaaacag aggcccttca gtatagcgaa gactcacaat tcgaatttcg  6300
aaaactcatc tctttctgtt ttaacggcgt cttgataaac gccgctcctt ctctcctcct  6360
ctttgaaatt tgaattttta gggtttcgtg aaactcgaga acaatgaata tttgtactaa  6420
taagtcgtcg tcaggagtga agaaaggtgc atggactgaa gaagaagatg ttctattgaa  6480
aaaatgcatc gagaaatatg gagaaggaaa gtggcatcaa gttcctctta gagctggttt  6540
gaatagatgc agaaagagct gcagattaag gtggctaaat tatctaaggc cacatataaa  6600
gagaggagac ttctcttttg atgaagtaga tctcattttg aggcttcata agctgttagg  6660
caacagatgg tcacttattg ctggtagact tcctggaagg acggcaaacg atgtcaaaaa  6720
ctactggaac agccatcttc gcaagaagtt aattgctcct catgatcaaa aggagagcaa  6780
gcaaaaagca aagaagatca ccatattcag acctcggcct cgaaccttct caaagacaaa  6840
tacttgtgtt aaaagtaaca caaatactgt agataaggat attgaaggca gcagcgaaat  6900
aattagattc aacgataatt tgaagccaac aactgaagaa ttgacggatg atggaattca  6960
atggtgggcc gatttactag ctaacaatta caacaataat gggattgagg aagctgataa  7020
ttcatcacca actttgttgc atgaggaaat gccacttctc agttgatcta gaaataacag  7080
agggcgcgcg agcggtggct actgatcgcc tatgagttct gtgattctac ttgtaatttc  7140
agaagtgttt tcagtgtctt gttttctgga agtccgtctg gtttttagta acttttagct  7200
caaaaatgtg tctgtacgat ggtatttgta tgtttgtggg tcttttacat atacgcttgt  7260
aatcgatcaa tgtagaatgc tgtgtgcctt ttccgtcaac agcttattta gtgtttactc  7320
tgtatacgta tatctaatat atagtactga ttctttcatc tggtgatttg ttttcctaaa  7380
gagattatta tcatagcttt aattgaatga tacaaagagg tgttgcctgg cttcaccaga  7440
```

```
gcagaaattt tcattgatat agggtacaaa tgtcattcac ataatgttaa gagataagtt  7500
tttcaatgtc ctcaagagcc caccaagagt ttcttccggg aattgcttaa attatcttaa  7560
atttaaattg tacccgttta aac                                           7583

SEQ ID NO: 64          moltype = AA  length = 299
FEATURE                Location/Qualifiers
source                 1..299
                       mol_type = protein
                       organism = Nicotiana sp.
SEQUENCE: 64
MGRKPCCAKE GLRKGPWSSK EDLLLTNYIK ENGEGQWRSL PKNAGLLRCG KSCRLRWMNY  60
LRPGIKRGNF SQDEEDLILR LHSLLGNRWS LIAGRLPGRT DNEIKNYWNT HLIKKLKSAG  120
IEPKPHKKFS KCSKKESRKG PQQEKSRKKQ GKKSNNKNNE GQIVQVEKIQ VFTPKPIRIS  180
SEVLSRNNSF ENVTLSTNCS SNSNFEEADV DIKETELKLE EVSFFPRDLD FGKLLEGDAN  240
LDEFLIQESS YISNKYSVPM NESMLEKVYE EYLLLLSENC YLQDDHQKEQ NFPVNVSDQ   299

SEQ ID NO: 65          moltype = AA  length = 240
FEATURE                Location/Qualifiers
source                 1..240
                       mol_type = protein
                       organism = Nicotiana sp.
SEQUENCE: 65
MNYLRPGIKR GNFTQDEEDL IVRLHSLLGN RWSLIAGRLP GRTDNEIKNY WNTHLIKKLK  60
SAGIERKPHK NFSKCSKKES RKGPQQEKSR KKQGKKSNNK NNEGQIVQVE KIQVFTPKPI  120
RISSEVLSRN NSFENVTLST TCSSNSNFEE ADVENKEKEV KLEEVSFFPR DLNFGKLLEG  180
DENLDEFLIQ ENSCISNKHS MLMNESMLEK VYEEYLLLLS ENCYLQDDHQ KEQNFPCKCL  240

SEQ ID NO: 66          moltype = DNA  length = 900
FEATURE                Location/Qualifiers
source                 1..900
                       mol_type = other DNA
                       organism = Nicotiana sp.
SEQUENCE: 66
atgggaagaa aaccatgttg tgcaaaagag ggattgcgaa aaggtccttg gtcttctaaa  60
gaagatttgt tacttactaa ttatatcaag gaaaatggtg aaggacaatg gagatctttg  120
cctaagaatg ctgggttgct taggtgtgga aaaagttgca gactaagatg gatgaactat  180
ttaagaccag ggattaaaag aggaaacttc agtcaagatg aagaagatct tatattgaga  240
ctacattctc ttttgggtaa tcgttggtca ctaattgctg ggagattacc aggtcgaaca  300
gataatgaaa tcaagaatta ttggaacacc catttaatca agaagctcaa aagtgctgga  360
attgaaccaa aaccccacaa aaaattctcc aaatgttcca aaaaggaatc aagaaaagga  420
ccccaacaag agaaatcaag aaaaaaacaa ggtaaaaaga gcaacaacaa aaacaatgag  480
ggtcaaattg tacaagttga gaaaattcaa gtgtttaccc caaaacccat caggatttct  540
tctgaggtac tttcaaggaa caatagtttt gaaaatgtta cattgagtac taattgttcc  600
tcaaatagta attttgaaga agctgatgtt gacatcaagg aaactgagtt gaaattagaa  660
gaagtttcat tctttccaag ggacttagat tttggcaaat tacttgaagg ggatgcaaat  720
ttagatgaat ttcttattca agaaagcagc tacatttcaa acaaatattc agtgccaatg  780
aatgagagca tgttggagaa agtgtatgaa gaatatcttt tacttctttc tgaaaattgt  840
taccttcaag atgatcatca aaaggagcaa aatttccctg taaatgtctc tgatcagtga  900

SEQ ID NO: 67          moltype = DNA  length = 723
FEATURE                Location/Qualifiers
source                 1..723
                       mol_type = other DNA
                       organism = Nicotiana sp.
SEQUENCE: 67
atgaactatt taagaccagg gattaaaaga ggaaacttca ctcaagatga agaagatctt  60
atagtgagac tacattctct tttgggtaat cgttggtcac taattgctgg aagattacca  120
ggtcgaacag ataatgaaat caaaaattat tggaacaccc atttaatcaa gaagctcaaa  180
agtgctggaa ttgaacgtaa accccacaaa aatttctcca aatgttccaa aaaggaatca  240
agaaaaggac cccaacaaga gaaatcaaga aaaaaacaag gcaaaaagag caacaacaaa  300
aacaatgagg gtcaaattgt acaagttgag aaaattcaag tgtttacccc aaaacccatc  360
aggatttctt ctgaggtact ttcaaggaac aatagttttg aaaatgttac attgagtact  420
acttgttcct caaatagtaa ttttgaagaa gctgatgttg aaaacaagga aaaagaggtg  480
aaattagaag aagtttcatt ctttccaagg gacttaaatt ttggtaaatt acttgaaggg  540
gatgaaaatt tagatgaatt tcttattcaa gaaaacagct gcatttcaaa caaacattca  600
atgctaatga atgagagcat gttggagaaa gtatatgaag aatatctttt acttctttct  660
gaaaattgtt accttcaaga tgatcatcaa aaggagcaaa atttcccctg taaatgtctc  720
tga                                                                 723

SEQ ID NO: 68          moltype = AA  length = 318
FEATURE                Location/Qualifiers
source                 1..318
                       mol_type = protein
                       organism = Nicotiana sp.
SEQUENCE: 68
MEAQLLKLPS PSLTSTNSSK HSTLLPRQKW SNFCKFQLPN STSTITIRPL QASATSLGLG  60
PKKRIDETES YTLDGIRNSL IRQEDSIIFS LVERAQYCYN AETYDPDVFL MDGFHGSLVE  120
YIVKETEKLH AKVGRYKSPD EHPFFPKELP EPMLPPMQFP KVLHSVADSI NINVKIWEMY  180
FKNLLPRLVK EGDDGNFGST AVCDTICLQA LSKRIHYGKF VAEAKFRASP DVYKAAIRAQ  240
```

```
DRNGLMDLLT YPTVEEAITR RVEMKTRTYG QEFNINGPEN GGDPVYKIKP SLVAELYGDW  300
IMPLTKEVQV EYLLRRLD                                               318

SEQ ID NO: 69          moltype = AA  length = 262
FEATURE                Location/Qualifiers
source                 1..262
                       mol_type = protein
                       organism = Nicotiana sp.
SEQUENCE: 69
MALISGDANN KLSLDSIRDS LIRQEDTIIF NLIERIKYPI NSTLYKEPSS SSSWNISGSL  60
FHYLFQETEA LQSKVGRYLS PEENPFFPDN LPASIIPPSK CTPVLHPAAE SVNVNEKILD  120
VYIKQLLPLF CITDQADEGN FATIASCDIQ LLQALSRRIH YGKFVAEIKF RDCTDQYKPL  180
ILAKDRDALM KLLTFEAVEE MVKKRVAKKA LTFGQQVTLN IDDSSKEVKC KVDPSLVSRL  240
YDEWIMPLTK LVEVEYLLRR LD                                          262

SEQ ID NO: 70          moltype = AA  length = 257
FEATURE                Location/Qualifiers
source                 1..257
                       mol_type = protein
                       organism = Nicotiana sp.
SEQUENCE: 70
MASDNNKLSL DSIRDSLIRQ EDTIIFNLIE RIKYPITPTL YKEASSSSWN ISGSLFHYLF  60
QETEALHSKV GRYLSAEENP FFPDKLPASI IPPSKCTPVL HPAAECVNVN EKILDVYKKQ  120
LLPLFCTDQA DDEENFATTA SCDIQLLQAL SRRIHYGKFV AKVKFRDCTD QYKPLILAKD  180
RDALMKLLTF EAVEEVVKKR VAKKAFVFGQ QVTLNIDDNT KEAKYKVDPS LVSRLYDEWI  240
MPLTKLVEVE YLLRRLD                                                257

SEQ ID NO: 71          moltype = DNA  length = 957
FEATURE                Location/Qualifiers
source                 1..957
                       mol_type = other DNA
                       organism = Nicotiana sp.
SEQUENCE: 71
atggaagccc aattgttaaa actcccttct ccttccttaa caagtaccaa ttcttcaaaa  60
cacagtaccc ttttaccccg tcaaaaatgg tcaaattttt gtaagtttca attacccaat  120
tcaactagta ccattactat tcgtcccctt caagcttctg ctacttctct tggacttggg  180
ccaaagaaga gaatagatga gacggagagt tacactcttg atggtataag gaactcttta  240
attcgacaag aagatagcat aatattcagc cttgtggaga gagctcagta ctgttacaat  300
gcggagacat atgatcctga tgttttttg atggatgggt ttcatggctc tttggttgaa  360
tatattgtca aagaaactga aaagcttcat gctaaggttg gaagatataa aagccctgat  420
gagcacccat tcttcccaaa agaattaccc gagccaatgt tgccacccat gcagttccca  480
aaggttctgc attcagttgc tgattcaata aatatcaatg tcaaaatatg ggaaatgtat  540
ttcaagaatc tcctcccaag attagtaaag gaaggcgacg atggtaattt tggatctaca  600
gcagtttgtg acactatttg cttgcaggcc ctgtcgaaga gaattcatta tgggaaattt  660
gtcgctgaag caaaatttcg agcctcacca gatgtctata aggctgccat aagagcacaa  720
gacagaaacg gactgatgga tttgttaacc taccctactg ttgaagaggc tatcacgagg  780
agggtagaaa tgaaaaccag aacttacgga caagaattta acatcaatgg accggaaaat  840
ggaggtgacc cagtgtacaa aataaaacca agcctagttg ctgaattgta cggcgactgg  900
atcatgccat tgacaaagga agttcaagtt gagtatctcc tgagaagact ggattag    957

SEQ ID NO: 72          moltype = DNA  length = 789
FEATURE                Location/Qualifiers
source                 1..789
                       mol_type = other DNA
                       organism = Nicotiana sp.
SEQUENCE: 72
atggctttaa ttagtggtga tgctaataat aaactgagtc ttgattcaat aagggatagt  60
ttaataagac aagaagacac catcattttc aaccttatag agagaatcaa atacccaata  120
aattccacct tgtacaaaga accttcttct tcttcttctt ggaatatttc agggtccttg  180
ttccactatt tgtttcaaga aacagaagct cttcaatcta aggttggtag atacctatca  240
ccagaagaaa atcctttctt cccagataac ttgcctgcct caatcatacc acctagcaaa  300
tgcacaccag ttttgcatcc tgcagcagaa tctgtcaacg taaatgagaa gatattggat  360
gtttatataa agcagttgct tccactattt tgtattactg atcaggctga tgaaggaaac  420
tttgcaacta ttgcttcctg tgatattcag ttattgcagg cactctctag aaggattcat  480
tatggaaaat ttgttgctga gattaaattc agggattgta ctgatcaata taaaccactt  540
attcttgcta aggataggga tgctctaatg aagctattga catttgaagc agttgaagag  600
atggtaaaga agagagttgc aaagaaagcc ttgacgtttg ggcaacaagt gaccctaaat  660
attgatgata gctccaaaga agtaaagtgc aaggttgatc catcgctagt ttcgcgctta  720
tatgatgaat ggattatgcc tttgacaaaa cttgttgaag ttgagtacct tctacgacgt  780
ctcgattag                                                         789

SEQ ID NO: 73          moltype = DNA  length = 774
FEATURE                Location/Qualifiers
source                 1..774
                       mol_type = other DNA
                       organism = Nicotiana sp.
SEQUENCE: 73
atggcatcgg ataataataa actgagtctt gattcaataa gggatagttt aattagacaa  60
gaagacacca tcattttcaa ccttatagag agaatcaaat acccaataac tcccaccttg  120
```

-continued

```
tacaaagaag cttcttcttc ttcttggaat atttcagggt cattgttcca ctacttgttt  180
caagaaacag aagctcttca ttctaaggtt ggtagatacc tatcagcaga ggaaaatcct  240
ttcttcccag ataagttgcc tgcctcaatc ataccaccta gcaaatgcac accagttttg  300
catcctgcag cagaatgtgt gaacgtaaat gagaagatat tggatgttta taaaaagcag  360
ttgcttccac tattttgtac tgatcaggct gacgatgaag aaaactttgc aactactgct  420
tcctgtgata ttcagttatt gcaggcactc tctagaagga ttcattatgg gaaatttgtt  480
gctaaggtta aattcaggga ttgtactgat caatataaac cacttattct tgctaaggat  540
agggatgctc taatgaagct attgacattt gaagcagttg aagaggtggt aaaaaagaga  600
gttgcaaaga aagcatttgt gtttgggcaa caagtgaccc taaatattga tgataacacc  660
aaagaagcaa agtacaaggt tgatccatca ctggtttcgc gcttatatga tgaatggata  720
atgcctttga caaaacttgt cgaagttgag taccttctac gccgtcttga ttag        774
```

COMPOSITION AND METHODS FOR PRODUCING TOBACCO PLANTS AND PRODUCTS HAVING INCREASED PHENYLALANINE AND REDUCED TOBACCO-SPECIFIC NITROSAMINES (TSNAs)

CROSS-REFERENCE TO RELATED APPLICATION

This application is a Divisional application of the U.S. patent application Ser. No. 17/830,072, filed Jun. 1, 2022, now U.S. Pat. No. 11,999,961, issued Jun. 4, 2024, which is a Continuation of U.S. patent application Ser. No. 16/372,833, filed Apr. 2, 2019, now U.S. Pat. No. 11,377,665, issued on Jul. 5, 2022, which claims priority to U.S. Provisional Application No. 62/652,092, filed on Apr. 3, 2018, and is incorporated by reference herein in its entirety.

INCORPORATION OF SEQUENCE LISTING

A sequence listing contained in the file named "P34599US03_SL.xml" which is 145,175 bytes (measured in MS-Windows®) and created on Jun. 24, 2024, comprises 73 sequences, is filed electronically herewith and incorporated by reference in its entirety.

FIELD

The present disclosure relates generally to methods for reducing tobacco specific nitrosamines (TSNAs) comprising modulating the levels of phenylalanine, antioxidants, nitrite, or antioxidant capacity. Also provided are methods and compositions related to reducing or eliminating TSNAs in cured leaf from tobacco plants and products, their development via breeding or transgenic approaches, and production of tobacco products from those tobacco plants.

BACKGROUND

Tobacco-specific nitrosamines (TSNAs), such as N-nitrosonornicotine (NNN) and 4-(methylnitrosamino)-1-(3-pyridyl)-1-butanone (NNK), can be found in smokeless tobacco; mainstream smoke; and side stream smoke of cigarettes. It has been reported that air-cured and flue-cured tobacco contain tobacco-specific nitrosamines. See, "Effect of Air-Curing on the Chemical Composition of Tobacco", Wiernik et al., *Recent Adv. Tob. Sci*, (1995), 21, pp. 39-80. According to Wiernik et al., TSNAs are not present in significant quantities in growing tobacco plants or fresh cut tobacco (green tobacco), but are formed during the curing process. Bacterial populations which reside on the tobacco leaf are stated to largely cause the formation of nitrites from nitrate during curing and possibly affect the direct catalysis of the nitrosation of secondary amines at physiological pH values. The affected secondary amines include tobacco alkaloids, which form TSNAs when nitrosated.

Prior reports suggest several approaches to reduce TSNA levels. For example, WO2003/022081 proposed methods for reducing tobacco-specific nitrosamine (TSNA) content in cured tobacco by increasing the levels of antioxidants in the tobacco prior to harvesting. Specifically, WO2003/022081 proposed root pruning of the tobacco plant prior to harvesting; severing the xylem tissue of the tobacco plant prior to harvesting; and administering antioxidants and/or chemicals which increase antioxidants to the tobacco plant after harvesting. Despite previous attempts and proposals, simpler, more uniform, more economical and non-labor-intensive methods are desirable for reducing TSNA levels in cured tobacco leaf. Here, the inventors address this need by providing methods and compositions for reducing TSNAs by manipulating antioxidant levels via, inter alia, modification of genes involved in antioxidant biosynthesis or regulation thereof.

SUMMARY

In one aspect, the present disclosure provides a method for reducing the amount of one or more Tobacco Specific Nitrosamines (TSNAs) in a cured leaf of a tobacco plant, the method comprising the steps of increasing the amount of phenylalanine in the tobacco plant via a transgene encoding or targeting a phenylalanine biosynthetic enzyme, a regulator of phenylalanine biosynthesis, or a phenylalanine metabolic enzyme; and reducing the amount of one or more TSNAs in a cured leaf of the tobacco plant or a tobacco product made from the cured tobacco leaf.

In one aspect, the present disclosure provides a method for reducing the amount of one or more TSNAs in a cured leaf of a tobacco plant, the method comprising the steps of increasing the amount of phenylalanine in the tobacco plant via a genetic modification in an endogenous gene, wherein the endogenous gene encodes a phenylalanine biosynthetic enzyme, a regulator of phenylalanine biosynthesis, or a phenylalanine metabolic enzyme; and reducing the amount of one or more TSNAs in a cured leaf of the tobacco plant or a tobacco product made from the cured tobacco leaf.

In one aspect, the present disclosure provides a method for increasing the amount of one or more anthocyanins in a cured leaf of a tobacco plant, the method comprising the steps of increasing the amount of phenylalanine in the tobacco plant via a transgene encoding or targeting a phenylalanine biosynthetic enzyme, a regulator of phenylalanine biosynthesis, or a phenylalanine metabolic enzyme; and increasing the amount of one or more anthocyanins in a cured leaf of the tobacco plant or a tobacco product made from the cured tobacco leaf.

In one aspect, the present disclosure provides a method for increasing the amount of one or more anthocyanins in a cured leaf of a tobacco plant, the method comprising the steps of increasing the amount of phenylalanine in the tobacco plant via a genetic modification in an endogenous gene, wherein the endogenous gene encodes a phenylalanine biosynthetic enzyme, a regulator of phenylalanine biosynthesis, or a phenylalanine metabolic enzyme; and increasing the amount of one or more anthocyanins in a cured leaf of the tobacco plant or a tobacco product made from the cured tobacco leaf.

In one aspect, the present disclosure provides a cured tobacco leaf of a modified tobacco plant, wherein the cured tobacco leaf comprises a decreased amount of one or more TSNAs and an increased amount of at least one Chorismate Mutase-like polypeptide, wherein the decreased and increased amounts are compared to an unmodified control tobacco plant.

In one aspect, the present disclosure provides a cured tobacco leaf of a modified tobacco plant, wherein the cured tobacco leaf comprises a decreased amount of one or more TSNAs and an increased amount of phenylalanine, wherein the decreased and increased amounts are compared to an unmodified control tobacco plant.

In one aspect, the present disclosure provides a cured tobacco leaf of a modified tobacco plant, wherein the cured tobacco leaf comprises a decreased amount of one or more TSNAs and an increased amount of one or more phenylalanine biosynthetic enzymes, regulators of phenylalanine biosynthesis, or phenylalanine metabolic enzymes, wherein the decreased and increased amounts are compared to an unmodified control tobacco plant.

BRIEF DESCRIPTION OF THE SEQUENCES

SEQ ID NOs: 1 to 23, 47 to 52, 64 to 65, and 68 to 70 are amino acid sequences of selected genes that are involved in antioxidant production. SEQ ID NOs: 24 to 46, 53 to 58, 66 to 67, and 71 to 73 are corresponding nucleic acid sequences that encode SEQ ID NOs: 1 to 23, 47 to 52, 64 to 65, and 68 to 70, respectively. SEQ ID NOs: 59 to 63 are polynucleotides encoding recombinant DNA molecules comprising cisgenic promoters, coding regions, and terminators.

BRIEF DESCRIPTION OF THE DRAWINGS

FIG. 2: Cloning of AtPAP1, NtAN2, and NtAN1 into 45-2-7 binary vector.

FIG. 10: Accumulation of Chlorogenic Acid is inversely correlated with TSNA levels. A negative correlation is observed between CGA levels and total TSNA levels as shown in Table 4 and FIG. 10A. This correlation is also observed between CGA levels and individual TSNAs NNN (FIG. 10B), NNK (FIG. 10C), NAB (FIG. 10D), and NAA (FIG. 10E).

FIG. 11: The phenylpropanoid pathway can be targeted to reduce TSNA levels in tobacco by increasing antioxidant levels.

DETAILED DESCRIPTION

Figure 1:
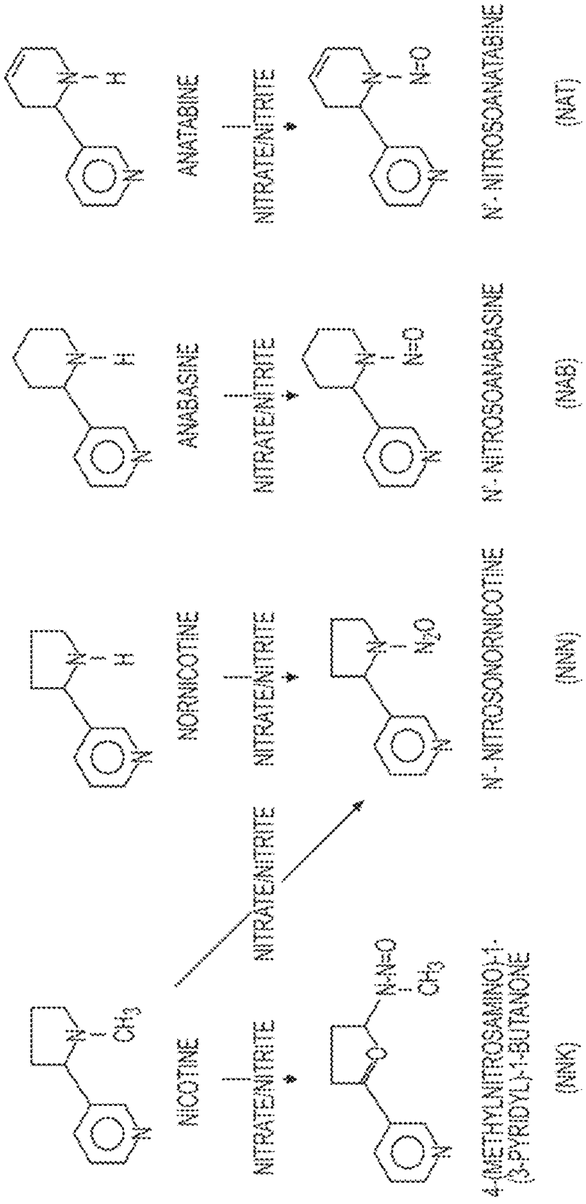
FIG. 1: TSNAs are formed when alkaloids nitrosinate in the presence of nitrite.

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents, published patent applications, and non-patent publications, are incorporated by reference in their entirety.

As used herein, the singular form "a," "an," and "the" include plural references unless the context clearly dictates otherwise. For example, the term "a compound" or "at least one compound" may include a plurality of compounds, including mixtures thereof.

The term "about" is used herein to mean approximately, roughly, around, or in the region of. When the term "about" is used in conjunction with a number or numerical range, it modifies that number or range by extending the boundaries above and below the numerical values set forth by 10%.

As used herein, a tobacco plant can be from any plant from the *Nicotiana tabacum* genus including, but not limited to *Nicotiana tabacum tabacum; Nicotiana tabacum amplexicaulis* PI 271989; *Nicotiana tabacum benthamiana* PI 555478; *Nicotiana tabacum bigelovii* PI 555485; *Nicotiana tabacum debneyi; Nicotiana tabacum excelsior* PI 224063; *Nicotiana tabacum glutinosa* PI 555507; *Nicotiana tabacum goodspeedii* PI 241012; *Nicotiana tabacum gossei* PI 230953; *Nicotiana tabacum hesperis* PI271991; *Nicotiana tabacum knightiana* PI 555527; *Nicotiana tabacum maritima* PI 555535; *Nicotiana tabacum megalosiphon* PI 555536; *Nicotiana tabacum nudicaulis* PI 555540; *Nicotiana tabacum paniculata* PI 555545; *Nicotiana tabacum plumbaginifolia* PI 555548; *Nicotiana tabacum repanda* PI 555552; *Nicotiana tabacum rustica; Nicotiana tabacum suaveolens* PI 230960; *Nicotiana tabacum sylvestris* PI 555569; *Nicotiana tabacum tomentosa* PI 266379; *Nicotiana tabacum tomentosiformis*; and *Nicotiana tabacum trigonophylla* PI 555572.

In one aspect, this disclosure provides methods and compositions related to modified tobacco plants, seeds, plant components, plant cells, and products made from modified tobacco plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct provided herein. In another aspect, cured tobacco material or tobacco products provided herein comprise modified tobacco plants, plant components, plant cells, or plant genomes provided herein.

As used herein, "modified" refers to plants, seeds, plant components, plant cells, and plant genomes that have been subjected to mutagenesis, genome editing, genetic transformation, or a combination thereof.

In one aspect, the present disclosure provides a modified tobacco plant capable of producing cured tobacco leaf comprising a decreased amount of one or more tobacco-specific nitrosamines (TSNAs) and further comprising an increased amount of at least one Chorismate Mutase-like polypeptide, wherein the decreased and increased amounts are compared to an unmodified control tobacco plant. In one aspect, a reduced level of one or more TSNAs is less than 50% of the level of the one or more TSNAs in cured leaf from a control plant. In one aspect, a modified tobacco plant further comprises an increased amount of at least one polypeptide having at least 80% homology to a sequence selected from the group consisting of SEQ ID Nos. 1 to 23, 47 to 52, and 64 to 65. In one aspect, a modified tobacco plant further comprises an increased amount of at least one polypeptide having a sequence selected from the group consisting of SEQ ID Nos. 1 to 23, 47 to 52, and 64 to 65.

In one aspect, the present disclosure provides a modified tobacco plant capable of producing cured tobacco leaf comprising a decreased amount of one or more TSNAs and an increased amount of phenylalanine, wherein the decreased and increased amounts are compared to an unmodified control tobacco plant. In one aspect, a reduced level of one or more TSNAs is less than 50% of the level of the one or more TSNAs in cured leaf from a control plant. In one aspect, a modified tobacco plant further comprises an increased amount of at least one polypeptide having at least 80% homology to a sequence selected from the group consisting of SEQ ID Nos. 1 to 23, 47 to 52, and 64 to 65. In one aspect, a modified tobacco plant further comprises an increased amount of at least one polypeptide having a sequence selected from the group consisting of SEQ ID Nos. 1 to 23, 47 to 52, and 64 to 65.

In one aspect, the present disclosure provides a modified tobacco plant capable of producing cured tobacco leaf comprising decreased amount of one or more TSNAs and an increased amount of one or more phenylalanine biosynthetic enzymes, regulators of phenylalanine biosynthesis, or phenylalanine metabolic enzymes, wherein said decreased and increased amounts are compared to an unmodified control tobacco plant. In one aspect, a reduced level of one or more TSNAs is less than 50% of the level of the one or more TSNAs in cured leaf from a control plant. In one aspect, a modified tobacco plant further comprises an increased amount of at least one polypeptide having at least 80% homology to a sequence selected from the group consisting of SEQ ID Nos. 1 to 23, 47 to 52, and 64 to 65. In one aspect, a modified tobacco plant further comprises an increased amount of at least one polypeptide having a sequence selected from the group consisting of SEQ ID Nos. 1 to 23, 47 to 52, and 64 to 65. In a further aspect, a regulator of phenylalanine biosynthesis is a regulatory transcription factor.

In a further aspect, a transgene disclosed in the present disclosure encodes a Chorismate Mutase-like polypeptide. In a further aspect, a transgene disclosed in the present disclosure targets an endogenous gene encoding a Chorismate Mutase-like polypeptide. In a further aspect, a Chorismate Mutase-like polypeptide has at least 80% homology to a sequence from the group consisting of SEQ ID NOs: 68 to 70. In a further aspect, a Chorismate Mutase-like polypeptide has at least 85% homology to a sequence from the group consisting of SEQ ID NOs: 68 to 70. In a further aspect, a Chorismate Mutase-like polypeptide has at least 90% homology to a sequence from the group consisting of SEQ ID NOs: 68 to 70. In a further aspect, a Chorismate Mutase-like polypeptide has at least 91% homology to a sequence from the group consisting of SEQ ID NOs: 68 to 70. In a further aspect, a Chorismate Mutase-like polypeptide has at least 92% homology to a sequence from the group consisting of SEQ ID NOs: 68 to 70. In a further aspect, a Chorismate Mutase-like polypeptide has at least 93% homology to a sequence from the group consisting of SEQ ID NOs: 68 to 70. In a further aspect, a Chorismate Mutase-like polypeptide has at least 94% homology to a sequence from the group consisting of SEQ ID NOs: 68 to 70. In a further aspect, a Chorismate Mutase-like polypeptide has at least 95% homology to a sequence from the group consisting of SEQ ID NOs: 68 to 70. In a further aspect, a Chorismate Mutase-like polypeptide has at least 96% homology to a sequence from the group consisting of SEQ ID NOs: 68 to 70. In a further aspect, a Chorismate Mutase-like polypeptide has at least 97% homology to a sequence from the group consisting of SEQ ID NOs: 68 to 70. In a further aspect, a Chorismate Mutase-like polypeptide has at least 98% homology to a sequence from the group consisting of SEQ ID NOs: 68 to 70. In a further aspect, a Chorismate Mutase-like polypeptide has at least 99% homology to a sequence from the group consisting of SEQ ID NOs: 68 to 70. In a further aspect, a Chorismate Mutase-like polypeptide has 100% homology to a sequence from the group consisting of SEQ ID NOs: 68 to 70.

In a further aspect, a Chorismate Mutase-like polypeptide is encoded by a polynucleotide sequence having at least 80% homology to a sequence selected from the group consisting of SEQ ID NOs: 71 to 73. In a further aspect, a Chorismate Mutase-like polypeptide is encoded by a polynucleotide sequence having at least 85% homology to a sequence selected from the group consisting of SEQ ID NOs: 71 to 73. In a further aspect, a Chorismate Mutase-like polypeptide is encoded by a polynucleotide sequence having at least 90% homology to a sequence selected from the group consisting of SEQ ID NOs: 71 to 73. In a further aspect, a Chorismate Mutase-like polypeptide is encoded by a polynucleotide sequence having at least 91% homology to a sequence selected from the group consisting of SEQ ID NOs: 71 to 73. In a further aspect, a Chorismate Mutase-like polypeptide is encoded by a polynucleotide sequence having at least 92% homology to a sequence selected from the group consisting of SEQ ID NOs: 71 to 73. In a further aspect, a Chorismate Mutase-like polypeptide is encoded by a polynucleotide sequence having at least 93% homology to a sequence selected from the group consisting of SEQ ID NOs: 71 to 73. In a further aspect, a Chorismate Mutase-like polypeptide is encoded by a polynucleotide sequence having at least 94% homology to a sequence selected from the group consisting of SEQ ID NOs: 71 to 73. In a further aspect, a Chorismate Mutase-like polypeptide is encoded by a polynucleotide sequence having at least 95% homology to a sequence selected from the group consisting of SEQ ID NOs: 71 to 73. In a further aspect, a Chorismate Mutase-like polypeptide is encoded by a polynucleotide sequence having at least 96% homology to a sequence selected from the group consisting of SEQ ID NOs: 71 to 73. In a further aspect, a Chorismate Mutase-like polypeptide is encoded by a polynucleotide sequence having at least 97% homology to a sequence selected from the group consisting of SEQ ID NOs: 71 to 73. In a further aspect, a Chorismate Mutase-like polypeptide is encoded by a polynucleotide sequence having at least 98% homology to a sequence selected from the group consisting of SEQ ID NOs: 71 to 73. In a further aspect, a Chorismate Mutase-like polypeptide is encoded by a polynucleotide sequence having at least 99% homology to a sequence selected from the group consisting of SEQ ID NOs: 71 to 73. In a further aspect, a Chorismate Mutase-like polypeptide is encoded by a polynucleotide sequence having 100% homology to a sequence selected from the group consisting of SEQ ID NOs: 71 to 73.

In one aspect, the present disclosure provides a modified tobacco plant capable of producing cured tobacco leaf comprising a reduced level of one or more tobacco-specific nitrosamines (TSNAs) and further comprising an increased level of one or more antioxidants, wherein the reduced and increased levels are compared to a control tobacco plant or cured leaf from a control tobacco plant of the same variety when grown and cured under comparable conditions. In one aspect, a reduced level of one or more TSNAs is less than 50% of the level of the one or more TSNAs in cured leaf from a control plant. In another aspect, a modified tobacco plant further comprises an increased level of oxygen radical absorbance capacity (ORAC) compared to a control tobacco plant when grown and cured under comparable conditions. In a further aspect, cured leaf from a modified tobacco plant comprises a reduced level of nitrite compared to cured leaf from a control tobacco plant when grown and cured under comparable conditions.

In another aspect, cured leaf from a modified tobacco plant comprises a reduced level of total TSNAs compared to the cured leaf from a control tobacco plant when grown and cured under comparable conditions. In one aspect, reduced one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In one aspect, the level of total TSNAs or an individual TSNA is measured based on a freeze-dried cured leaf sample using liquid chromatograph with tandem mass spectrometry (LC/MS/MS).

In one aspect, the present disclosure provides cured leaf from a modified tobacco plant comprising a reduced level of 4-methylnitrosoamino-1-(3-pyridyl)-1-butanone (NNK) compared to cured leaf from a control tobacco plant of the same variety when grown and cured under comparable conditions. In one aspect, a reduced level of NNK is less than 50% of the level of the NNK in cured leaf from a control plant. In one aspect, a modified tobacco plant or cured leaf from a modified tobacco plant further comprises an increased level of one or more antioxidants compared to a control tobacco plant or cured tobacco leaf from a control plant of the same variety when grown and cured under comparable conditions. In another aspect, a modified tobacco plant or cured leaf from a modified tobacco plant further comprises an increased level of oxygen radical absorbance capacity (ORAC) compared to a control tobacco or cured tobacco leaf from a control plant when grown and cured under comparable conditions. In a further aspect, cured leaf from a modified tobacco plant comprises a reduced level of nitrite compared to cured leaf from a control tobacco plant when grown and cured under comparable conditions. The role of nitrite in the formation is nitrosamines and TSNAs is linked to the reduction of nitrate by the activity of bacteria during the curing process. Nitrite is believed to generate nitrosating compounds which then react with secondary amines such as the tobacco alkaloids nicotine, nornicotine, anabasine, and anatabine to form TSNAs. Reducing the amount of nitrite and therefore the nitrosation of tobacco alkaloids, the production of TSNAs can be prevented during the curing process.

In one aspect, a modified tobacco plant or cured leaf from a modified tobacco plant comprises an increased level of one or more anthocyanins selected from the group consisting of Delphnidin, Cyanidin, Procyanidin, Prodelphinidin, Hesperetin, Perlargonidin, Peonidin, and Petunidin.

As used herein, "anthocyanins" are antioxidants that are derived from the aromatic amino acid phenylalanine. Biosynthesis of phenylalanine is the first step in many different biosynthetic pathways leading to various downstream molecules, including flavonoids and anthocyanins, through the phenylpropanoid biosynthesis pathway. See, for example, FIG. 2 of Rommens et al., *Plant Biotechnology Journal,* 6:870-886 (2008) and FIG. 9 of Tzin et al., *The Plant Journal,* 60:156-167 (2009). Phenylalanine is produced via the shikimate pathway which, through a series of steps, transforms chorismate into phenylalanine, tyrosine, and tryptophan. Chorismate Mutase catalyzes a reaction transforming chorismate into prephenate. Prephenate is subsequently used to create both tyrosine and phenylalanine. See, for example, FIG. 20 of the present disclosure which is based on FIG. 3 of Tzin and Galili., Molecular Plant, 3(6):956-972 (2010) and FIG. 1 of Oliva et al., *Frontiers in Plant Science,* 8:769 (2017).

In one aspect, a modified tobacco plant or cured leaf from a modified tobacco plant comprises an increased level of one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin.

In another aspect, a modified tobacco plant or cured leaf from a modified tobacco plant comprises an increased level of one or more antioxidants selected from the group consisting of Delphnidin, Cyanidin, Procyanidin, Prodelphinidin, Hesperetin, Perlargonidin, Peonidin, Petunidin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Unless specified otherwise, measurements of alkaloid, polyamine, or nicotine levels (or another leaf chemistry or property characterization) or leaf grade index values mentioned herein for a tobacco plant, variety, cultivar, or line refer to average measurements, including, for example, an average of multiple leaves of a single plant or an average measurement from a population of tobacco plants from a single variety, cultivar, or line. Unless specified otherwise, the nicotine, alkaloid, or polyamine level (or another leaf chemistry or property characterization) of a tobacco plant described here is measured 2 weeks after topping in a pooled leaf sample collected from leaf number 3, 4, and 5 after topping. In another aspect, the nicotine, alkaloid, or polyamine level (or another leaf chemistry or property characterization) of a tobacco plant is measured after topping in a leaf having the highest level of nicotine, alkaloid, or polyamine (or another leaf chemistry or property characterization). In an aspect, the nicotine, alkaloid, or polyamine level of a tobacco plant is measured after topping in leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In another aspect, the nicotine, alkaloid, or polyamine level (or another leaf chemistry or property characterization) of a tobacco plant is measured after topping in a pool of two or more leaves with consecutive leaf numbers selected from the group consisting of leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. In another aspect, the nicotine, alkaloid, or polyamine level (or another leaf chemistry or property characterization) of a tobacco plant is measured after topping in a leaf with a leaf number selected from the group consisting of between 1 and 5, between 6 and 10, between 11 and 15, between 16 and 20, between 21 and 25, and between 26 and 30. In another aspect, the nicotine, alkaloid, or polyamine level (or another leaf chemistry or property characterization) of a tobacco plant is measured after topping in a pool of two or more leaves with leaf numbers selected from the group consisting of between 1 and 5, between 6 and 10, between 11 and 15, between 16 and 20, between 21 and 25, and between 26 and 30. In another aspect, the nicotine, alkaloid, or polyamine level (or another leaf chemistry or property characterization) of a tobacco plant is measured after topping in a pool of three or more leaves with leaf numbers selected from the group consisting of between 1 and 5, between 6 and 10, between 11 and 15, between 16 and 20, between 21 and 25, and between 26 and 30.

Alkaloid levels can be assayed by methods known in the art, for example by quantification based on gas-liquid chromatography, high performance liquid chromatography, radio-immunoassays, and enzyme-linked immunosorbent assays. For example, nicotinic alkaloid levels can be measured by a GC-FID method based on CORESTA Recommended Method No. 7, 1987 and ISO Standards (ISO TC 126N 394 E. See also Hibi et al., *Plant Physiology* 100: 826-35 (1992) for a method using gas-liquid chromatography equipped with a capillary column and an FID detector. Unless specified otherwise, all alkaloid levels described here are measured using a method in accordance with CORESTA Method No 62*, Determination of Nicotine in Tobacco and Tobacco Products by Gas Chromatographic Analysis*, February 2005, and those defined in the Centers for Disease Control and *Prevention's Protocol for Analysis of Nicotine, Total Moisture and pH in Smokeless Tobacco Products*, as published in the Federal Register Vol. 64, No. 55 Mar. 23, 1999 (and as amended in Vol. 74, No. 4, Jan. 7, 2009).

Alternatively, tobacco total alkaloids can be measured using a segmented-flow colorimetric method developed for analysis of tobacco samples as adapted by Skalar Instrument Co (West Chester, PA) and described by Collins et al., *Tobacco Science* 13:79-81 (1969). In short, samples of tobacco are dried, ground, and extracted prior to analysis of total alkaloids and reducing sugars. The method then employs an acetic acid/methanol/water extraction and charcoal for decolorization. Determination of total alkaloids was based on the reaction of cyanogen chloride with nicotine alkaloids in the presence of an aromatic amine to form a colored complex which is measured at 460 nm. Unless specified otherwise, total alkaloid levels or nicotine levels shown herein are on a dry weight basis (e.g., percent total alkaloid or percent nicotine).

In one aspect, a modified tobacco plant or cured leaf from a modified tobacco plant comprises an antioxidant that is undetectable in the control plant or leaf. In another aspect, a modified tobacco plant or cured leaf from a modified tobacco plant comprises an antioxidant that does not exist in the control plant.

In another aspect, the present disclosure provides cured leaf from a modified tobacco plant comprising a reduced level of one or more tobacco-specific nitrosamines (TSNAs) and further comprising a reduced level of nitrite, wherein the reduced levels are compared to cured leaf from a control tobacco plant of the same variety when grown and cured under comparable conditions. In another aspect, a modified tobacco plant or cured leaf from a modified tobacco plant further comprises an increased level of oxygen radical absorbance capacity (ORAC) compared to the control tobacco plant or cured leaf from the control tobacco plant when grown and cured under comparable conditions.

In a further aspect, the present disclosure provides a modified tobacco plant capable of producing cured leaf comprising a reduced level of one or more tobacco-specific nitrosamines (TSNAs) and further comprising an increased level of oxygen radical absorbance capacity (ORAC), and wherein the reduced and increased levels are compared to a control tobacco plant or cured leaf from a control tobacco plant of the same variety when grown and cured under comparable conditions.

In one aspect, a reduced or increased level is within about 10%, within about 20%, within about 30%, within about 40%, within about 50%, within about 60%, within about 70%, within about 80%, within about 90%, within about 92%, within about 94%, within about 95%, within about 96%, within about 97%, within about 98%, or within about 99% lower or higher than the level in a control tobacco plant or cured leaf from a control tobacco plant when grown and cured under comparable conditions.

In another aspect, a reduced or increased level is within about 1 fold, within about 2 folds, within about 3 folds, within about 4 folds, within about 5 folds, within about 6 folds, within about 7 folds, within about 8 folds, within about 9 folds, within about 10 folds, within about 15 folds, within about 20 folds, within about 25 folds, or within about 30 folds lower or higher than the level in a control tobacco plant or cured leaf from a control tobacco plant when grown and cured under comparable conditions.

In one aspect, a reduced or increased level is at least about 10%, at least about 20%, at least about 30%, at least about 40%, at least about 50%, at least about 60%, at least about 70%, at least about 80%, at least about 90%, at least about 92%, at least about 94%, at least about 95%, at least about 96%, at least about 97%, at least about 98%, or at least about 99% lower or higher than the level in a control tobacco plant or cured leaf from a control tobacco plant when grown and cured under comparable conditions.

In another aspect, a reduced or increased level is at least about 1 fold, at least about 2 folds, at least about 3 folds, at least about 4 folds, at least about 5 folds, at least about 6 folds, at least about 7 folds, at least about 8 folds, at least about 9 folds, at least about 10 folds, at least about 15 folds, at least about 20 folds, at least about 25 folds, or at least about 30 folds lower or higher than the level in a control tobacco plant or cured leaf from a control tobacco plant when grown and cured under comparable conditions.

In one aspect, a reduced or increased level is about 10%, about 20%, about 30%, about 40%, about 50%, about 60%, about 70%, about 80%, about 90%, about 92%, about 94%, about 95%, about 96%, about 97%, about 98%, or about 99% lower or higher than the level in a control tobacco plant or cured leaf from a control tobacco plant when grown and cured under comparable conditions.

In another aspect, a reduced or increased level is about 1 fold, about 2 folds, about 3 folds, about 4 folds, about 5 folds, about 6 folds, about 7 folds, about 8 folds, about 9 folds, about 10 folds, about 15 folds, about 20 folds, about 25 folds, or about 30 folds lower or higher than the level in a control tobacco plant or cured leaf from a control tobacco plant when grown and cured under comparable conditions.

In one aspect, a reduced or increased level is about 1-2 folds, about 2-3 folds, about 3-4 folds, about 4-5 folds, about 5-6 folds, about 6-7 folds, about 7-8 folds, about 8-9 folds, about 9-10 folds, about 10-15 folds, about 15-20 folds, about 20-25 folds, about 25-30 folds, or about 30-50 folds lower or higher than the level in a control tobacco plant or cured leaf from a control tobacco plant when grown and cured under comparable conditions.

In another aspect, a reduced or increased level is about 1-10 folds, about 2-10 folds, about 3-10 folds, about 4-10 folds, about 5-10 folds, about 6-10 folds, about 7-10 folds, about 8-10 folds, about 9-10 folds, about 10-50 folds, about 15-50 folds, about 20-50 folds, about 25-50 folds, or about 30-50 folds lower or higher than the level in a control tobacco plant or cured leaf from a control tobacco plant when grown and cured under comparable conditions.

In one aspect, cured leaf from a modified tobacco plant produces or comprises less than 2, less than 1.8, less than 1.5, less than 1.2, less than 1.0, less than 0.8, less than 0.6, less than 0.4, less than 0.3, less than 0.2, less than 0.15, less than 0.1, or less than 0.05 ppm total TSNAs. In one aspect, cured leaf from a modified tobacco plant comprises between 2 and 0.05, between 1.8 and 0.05, between 1.5 and 0.05, between 1.2 and 0.05, between 1.0 and 0.05, between 0.8 and 0.05, between 0.6 and 0.05, between 0.4 and 0.05, between 0.3 and 0.05, between 0.2 and 0.05, between 0.15 and 0.05, or between 0.1 and 0.05 ppm total TSNAs. In one aspect, cured leaf from a modified tobacco plant comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs.

In one aspect, cured leaf from a modified tobacco plant comprises or produces less than 0.08 ppm NNK, wherein the level of the NNK level is measured based on a freeze-dried cured leaf sample using liquid chromatograph with tandem mass spectrometry (LC/MS/MS).

As used herein, "comparable conditions" refers to similar environmental conditions, agronomic practices, and/or curing process for growing or curing tobacco and making meaningful comparisons between two or more plant genotypes so that neither environmental conditions nor agronomic practices (including curing process) would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, suckering, and curing. See Chapters 4B and 4C of Tobacco, Production, Chemistry and Technology, Davis & Nielsen, eds., Blackwell Publishing, Oxford (1999), pp. 70-103.

As used herein, a "reduced" or "increased" level refers to a statistically significant change (reduction or increase) from a reference point. As used herein, "statistically significant" refers to a p-value of less than 0.05, a p-value of less than 0.025, a p-value of less than 0.01, or a p-value of less than 0.001 when using an appropriate measure of statistical significance (e.g., a one-tailed two sample t-test).

As used herein, a "control plant" refers to a comparator plant that is an unmodified tobacco plant of the same variety or a tobacco plant having no transgene of interest, depending on the context or the purpose of the control plant. Control tobacco plants and plants of interest are grown and cured under comparable conditions.

In one aspect, a modified tobacco plant provided herein has similar or higher leaf yield compared to a control tobacco plant when grown and cured under comparable conditions. In an aspect, leaf yield is selected from the group consisting of fresh yield, dry yield, and cured yield. In one aspect, a modified tobacco plant provided herein produces a leaf yield mass within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plant when grown and cured under comparable conditions. In another aspect, a modified tobacco plant provided herein produces a leaf yield mass at least 0.25%, 0.5%, 1%, 2.5%, 5%, 10%, 15%, 20%, 25%, 30%, 40%, 50%, 60%, 70%, 80%, 90%, 100%, or more than 100% higher compared to a control tobacco plant when grown and cured under comparable conditions. In another aspect, a modified tobacco plant provided herein produces a leaf yield mass 0.25%-100%, 0.5%-100%, 1%-100%, 2.5%-100%, 5%-100%, 10%-100%, 15%-100%, 20%-100%, 25%-100%, 30%-100%, 40%-100%, 50%-100%, 60%-100%, 70%-100%, 80%-100%, 90%-100%, 100%-200%, 100%-175%, 100%-150%, 100%-125%, 0.25%-50%, 0.5%-50%, 1%-50%, 2.5%-50%, 5%-50%, 10%-50%, 15%-50%, 20%-50%, 25%-50%, 30%-50%, 40%-50%, 50%-200%, 50%-175%, 50%-150%, 50%-125%, 0.25%-25%, 0.5%-25%, 1%-25%, 2.5%-25%, 5%-25%, 10%-25%, 15%-25%, 20%-25%, 25%-200%, 25%-175%, 25%-150%, or 25%-125% higher compared to a control tobacco plant when grown and cured under comparable conditions.

In one aspect, a modified tobacco plant provided herein has a similar or comparable plant height compared to a control tobacco plant when grown and cured under comparable conditions. In one aspect, a modified tobacco plant provided herein comprises a height within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plants when grown and cured under comparable conditions. In another aspect, a modified tobacco plant provided herein comprises a height 0.25%, 0.5%, 1%, 2.5%, 5%, 10%, 15%, 20%, 25%, 30%, 40%, 50%, 60%, 70%, 80%, 90%, 100%, or more than 100% taller compared to a control tobacco plant when grown and cured under comparable conditions. In another aspect, a modified tobacco plant comprises a height 0.25%-100%, 0.5%-100%, 1%-100%, 2.5%-100%, 5%-100%, 10%-100%, 15%-100%, 20%-100%, 25%-100%, 30%-100%, 40%-100%, 50%-100%, 60%-100%, 70%-100%, 80%-100%, 90%-100%, 100%-200%, 100%-175%, 100%-150%, 100%-125%, 0.25%-50%, 0.5%-50%, 1%-50%, 2.5%-50%, 5%-50%, 10%-50%, 15%-50%, 20%-50%, 25%-50%, 30%-50%, 40%-50%, 50%-200%, 50%-175%, 50%-150%, 50%-125%, 0.25%-25%, 0.5%-25%, 1%-25%, 2.5%-25%, 5%-25%, 10%-25%, 15%-25%, 20%-25%, 25%-200%, 25%-175%, 25%-150%, or 25%-125% taller compared to a control tobacco plant when grown and cured under comparable conditions.

In one aspect, a modified tobacco plant provided herein produces leaf that has a similar or higher USDA grade index value compared to a control tobacco plant when grown and cured under comparable conditions. In one aspect, a modified tobacco plant provided herein produces leaf with a USDA grade index value within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% compared to a control tobacco plant when grown and cured under comparable conditions. In one aspect, a modified tobacco plant provided herein is capable of producing leaf having a USDA grade index value of 55 or more, 60 or more, 65 or more, 70 or more, 75 or more, 80 or more, 85 or more, 90 or more, or 95 or more. In one aspect, a modified tobacco plant provided herein produces leaf with a USDA grade index value at least 1, 2, 3, 4, 5, 6, 7, 8, 9, 10, 12, 13, 14, 15, 16, 17, 18, 19, 20, 21, 22, 23, 24, 25, 26, 27, 28, 29, 30, 35, 40, 45, 50, or more than 50 units higher compared to a control tobacco plant when grown and cured under comparable conditions. In one aspect, a modified tobacco plant provided herein produces leaf with a USDA grade index value 1-50, 1-45, 1-40, 1-35, 1-30, 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2,2-50,2-45,2-40,2-35,2-30,2-29, 2-28,2-27, 2-26, 2-25, 2-24, 2-23, 2-22, 2-21, 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-50, 3-45, 3-40, 3-35, 3-30, 3-29, 3-28, 3-27, 3-26, 3-25, 3-24, 3-23, 3-22, 3-21, 3-20, 3-19, 3-18, 3-17, 3-16, 3-15, 3-14, 3-13, 3-12, 3-11, 3-10, 3-9, 3-8, 3-7, 3-6, 3-5, 3-4, 4-50, 4-45, 4-40, 4-35, 4-30, 4-29, 4-28, 4-27, 4-26, 4-25, 4-24, 4-23, 4-22, 4-21, 4-20, 4-19, 4-18, 4-17, 4-16, 4-15, 4-14, 4-13, 4-12, 4-11, 4-10, 4-9, 4-8, 4-7, 4-6, 4-5, 5-50, 5-45, 5-40, 5-35, 5-30, 5-29, 5-28, 5-27, 5-26, 5-25, 5-24, 5-23, 5-22, 5-21, 5-20, 5-19, 5-18, 5-17, 5-16, 5-15, 5-14, 5-13, 5-12, 5-11, 5-10, 5-9, 5-8, 5-7, 5-6, 10-50, 10-40, 10-30, 10-20, 20-50, 20-30, 20-40, or 20-30 units higher compared to a control tobacco plant when grown and cured under comparable conditions.

Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaf to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science,* 32:39-40 (1988); Legacy Tobacco Document Library (Bates Document #523267826-523267833, Jul. 1, 1988, Memorandum on the Proposed Burley Tobacco Grade Index); and Miller et al., 1990, *Tobacco Intern.,* 192:55-57 (all foregoing references are incorporated by inference in their entirety). Alternatively, leaf grade can be determined via hyper-spectral imaging. See e.g., WO 2011/027315 (published on Mar. 10, 2011, and incorporated by inference in its entirety).

In one aspect, a modified tobacco plant provided herein comprises tobacco leaf with reduced total TSNAs and further comprises one or more desirable or enhanced properties, e.g., inhibited or reduced sucker growth prior to or after topping. In one aspect, a modified plant provided herein comprises fewer total suckers, smaller suckers, or both compared to a control plant lacking such modification when grown and cured under comparable conditions. In one aspect, smaller suckers of a modified plant provided herein comprise reduced mass, reduced length, reduced diameter, or a combination thereof compared to suckers of a control plant grown and cured under comparable conditions.

Unless specified otherwise, measurements of the level of total TSNAs, individual TSNA, total or individual alkaloid, total or individual antioxidant, leaf yield, or leaf grade index values mentioned herein for cured leaf from a tobacco plant, variety, cultivar, or line refer to average measurements, including, for example, an average of multiple leaves (e.g., 2, 3, 4, 5, 6, 7, 8, 9, 10, 11, 12, 13, 14, 15, 16, 17, 18, 19, or 20 or more leaves) of a single plant or an average measurement from a population of tobacco plants from a single variety, cultivar, or line. A population of tobacco plants or a collection of tobacco leaf for determining an average measurement (e.g., fresh weight or leaf grading) can be of any size, for example, 5, 10, 15, 20, 25, 30, 35, 40, or 50. Industry-accepted standard protocols are followed for determining average measurements or grade index values.

In one aspect, a modified tobacco plant or leaf provided here has a similar leaf chemistry profile compared to a control plant when grown and cured under comparable conditions. Without being limiting, a leaf chemistry profile can comprise the amount of alkaloids (e.g., nicotine, nornicotine, anabasine, anatabine), malic acid, and reducing sugars (e.g., dextrose), or a combination thereof in a tobacco plant or tobacco leaf. In one aspect, a modified plant or leaf provided herein comprises a total alkaloids level within about 90%, within about 80%, within about 70%, within about 60%, within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the total alkaloids level of a control plant when grown and cured under comparable conditions. In one aspect, a modified plant or leaf provided herein comprises a total alkaloids level that is reduced by at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% compared to a control plant when grown and cured under comparable conditions. In one aspect, a modified plant or leaf provided herein comprises a nicotine level within about 90%, within about 80%, within about 70%, within about 60%, within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nicotine level of a control plant when grown and cured under comparable conditions. In one aspect, a modified plant or leaf provided herein comprises a nornicotine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nornicotine level of a control plant when grown and cured under comparable conditions. In one aspect, a modified plant or leaf provided herein comprises an anabasine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anabasine level of a control plant when grown and cured under comparable conditions. In one aspect, a modified plant or leaf provided herein comprises an anatabine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anatabine level of a control plant when grown and cured under comparable conditions. In one aspect, a modified plant or leaf provided herein comprises a malic acid level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the malic acid level of a control plant when grown and cured under comparable conditions. In one aspect, a modified plant or leaf provided herein comprises a reducing sugars level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the reducing sugars level of a control plant when grown and cured under comparable conditions. In one aspect, a modified plant or leaf provided herein comprises a dextrose level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the dextrose level of a control plant when grown and cured under comparable conditions.

In one aspect, a plant component provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a tobacco plant chloroplast. In a further aspect, this disclosure provides an epidermal cell, a stomata cell, a leaf hair (trichome), a root hair, or a storage root. In another aspect, this disclosure provides a tobacco protoplast.

Skilled artisans understand that tobacco plants naturally reproduce via seeds, not via asexual reproduction or vegetative propagation. In one aspect, this disclosure provides tobacco endosperm. In another aspect, this disclosure provides a tobacco endosperm cell. In a further aspect, this disclosure provides a male or female sterile tobacco plant, which cannot reproduce without human intervention.

In one aspect, a modified plant, seed, plant part, or plant cell provided herein comprises one or more non-naturally occurring mutations. In one aspect, a mutation provided herein suppresses TSNA levels in cured leaf from a tobacco plant. Types of mutations provided herein include, for example, substitutions (point mutations), deletions, insertions, duplications, and inversions. Such mutations are desirably present in the coding region of a gene; however, mutations in a promoter or other regulatory region, an intron, an intron-exon boundary, or an untranslated region of a gene may also be desirable.

In one aspect, a modified tobacco plant comprises one or more mutations or modifications capable of providing the reduced level of one or more TSNAs. In another aspect, one or more mutations are further capable of providing one or more traits selected from the group consisting of: i. a reduced level of nitrite, ii. an increased level of oxygen radicle absorbance capacity (ORAC), and iii. an increased level of one or more antioxidants; wherein the reduced or increased level is compared to a control tobacco plant or cured leaf from a control tobacco plant when grown and cured under comparable.

In one aspect, a mutation comprises a mutation type selected from the group consisting of an insertion, a deletion, an inversion, a duplication, a substitution, and a combination thereof.

In one aspect, a modified tobacco plant comprises one or more mutations or modifications capable of activating one or more genes encoding a biosynthetic enzyme, a regulatory transcription factor, a transporter, a catabolic enzyme, or a combination thereof, for one or more antioxidants. In another aspect, one or more mutations or modifications are in one or more genes encoding a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect, one or more mutations or modifications are in one or more genes encoding a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Perlargonidin, Peonidin, Petunidin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

In one aspect, a modified tobacco plant of the present disclosure comprises tobacco leaves with increased levels of anthocyanins. In a further aspect, a modified tobacco plant with increased levels of anthocyanins further comprises leaves that have a purple or crimson visual appearance. In one aspect, a modified tobacco plant of the present disclosure comprises tobacco leaves with increased levels of antioxidants and without increased levels of anthocyanins. In a further aspect, a modified tobacco plant comprising increased levels of antioxidants and without increased levels of anthocyanins further comprises leaves with a visual appearance similar to an unmodified tobacco plant.

As used herein, a "biosynthetic enzyme" refers to a protein that functions in the synthesis of phenylalanine, antioxidants, alkaloids, TSNAs, nitrite, nitrate, Chlorogenic Acid or other proteins affecting the activity or stability of phenylalanine, antioxidants, alkaloids, TSNAs, nitrite, nitrate or Chlorogenic Acid. These proteins catalyze reactions that result in the transformation of one molecular structure into another structure as part of a biosynthesis pathway. Exemplary biosynthetic enzymes include but are not limited to Chorismate Mutase (CM), CM-like proteins, Prephenate Aminotransferase (PAT), PAT-like proteins, Arogenate Dehydratase (ADT), ADT-like proteins, Prephenate Dehydratase (PDT), PDT-like proteins, Aromatic Amino Acid Aminotransferase (AAAAT), AAAAT-like proteins, Anthocyanidin synthase2 (NtANS2), Dihyfroflavonol-4-reductase (NtDFR2), Shikimate O-hydroxycinnamoyl transferase (HCT), HCT-like proteins, Hydroxycinnamoyl CoA quinate Transferase (HQT), and HQT-like proteins. The activity of a biosynthetic enzyme effects the total concentration of different molecule species that compose a biosynthetic pathway.

Figure 20:
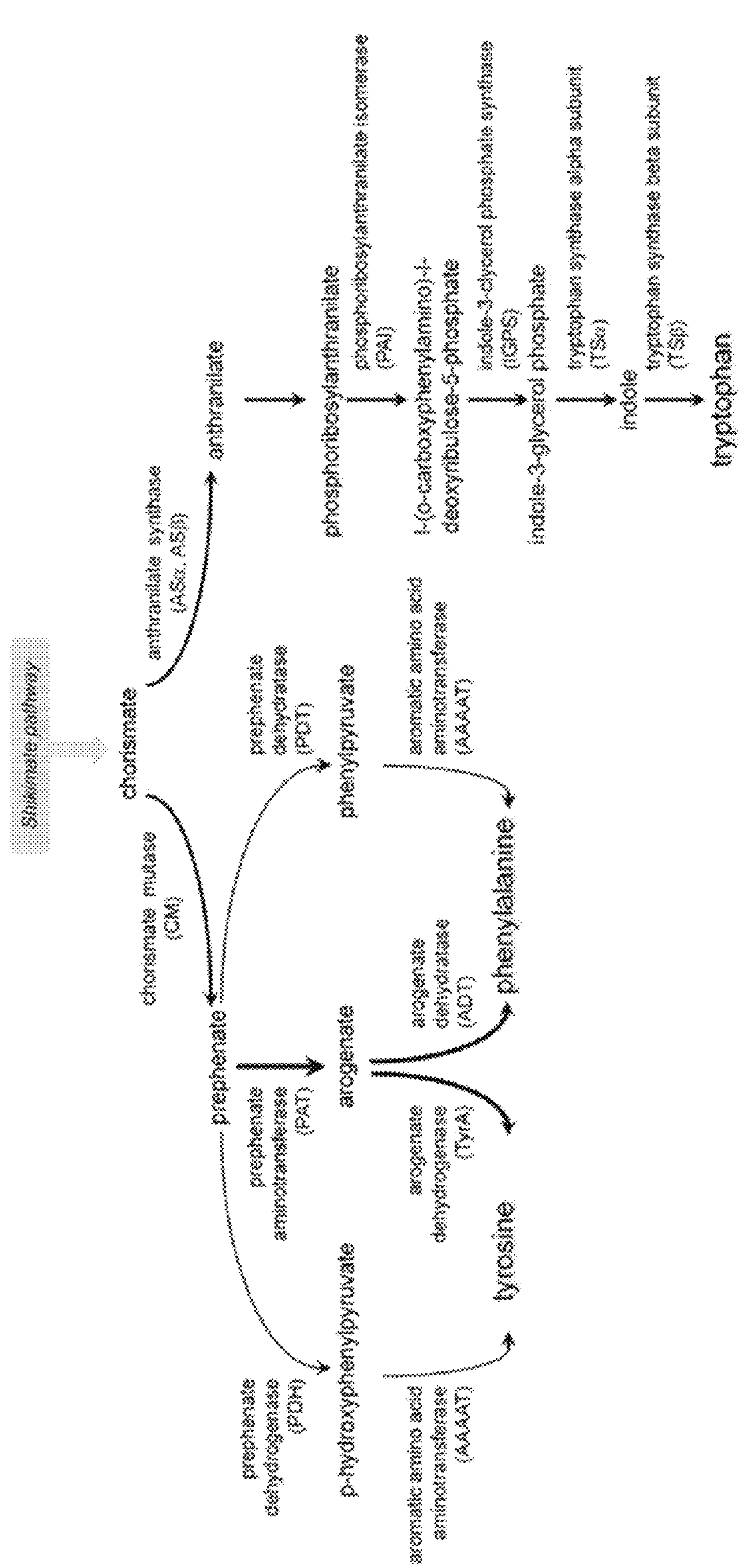
FIG. 20: Overview of the Shikimate pathway for the biosynthesis of aromatic amino acids. Based on FIG. 3 of Tzin and Galili., Molecular Plant, 3(6):956-972 (2010) (incorporated by reference herein in its entirety).

It is known that CM, PAT, ADT, PDT, and AAAAT play roles in the metabolism of aromatic amino acids, specifically, phenylalanine biosynthesis. See Zhang et al. 2013, *The Plant Journal* 73:628-639; Li et al. 2015, *Metabolic Engineering* 32:1-11; Tzin et al. 2009, *The Plant Journal* 60:156-167; Rommens et al. 2008, *Plant Biotechnology Journal* 6:870-886; Rippert et al. 2004, *Plant Physiology* 134:92-100; Oliva et al. 2017, *Frontiers in Plant Science* Vol 8, Article 769, Cho et al. 2007, *Journal of Biological Chemistry* 282:42 20827-20835, Tzin and Galili 2010, *The Arabidopsis Book* e0132. 10.119/tab.0132 (each reference is incorporated herein in its entirety). The consequences of CM down-regulation have been studied is various plant species. For example, downregulation of CM in petunia results in a significant decrease in both prephenate and phenylalanine. See Qian et al. 2019, *Nature Communications* 10:15 (incorporated herein in its entirety) at FIG. 2C. Likewise, down regulation of ADT1 in petunia results in a significant decrease in phenylalanine. See Yoo et al. 2013, *Nature Communications* 4:2833 (incorporated herein in its entirety) at FIG. 2C. Overexpression of a dual function chorimstae mutase/prephrenate dehydratase gene from Arabidopsis results in increased levels of phenylalanine. See Tzin et al. 2009, *The Plant Journal* 60:156-167 at FIG. 3. FIG. 20 outlines the phenylalanine metabolic pathway downstream of the Shikimate pathway.

As used herein, a "regulatory transcription factor" is a protein that binds a promoter element of a target gene to modulate the transcription of one or more genes involved in antioxidant biosynthesis, transport, catabolism, or other processes affecting the level of one or more antioxidants. Exemplary regulatory transcription factors include AtPAP1, NtPAP1, NtMYB3-like, NtJAF13, and AtTTG1. A regulatory transcription factor can bind DNA as part of a protein complex or individually. A regulatory transcription factor can have a single target or multiple targets and can bind different targets with varying affinities. The activity of a regulatory transcription factor can be to activate, repress, or attenuate transcription from a target loci.

As used herein, a "transport protein" can be a transmembrane protein that actively or passively moves molecules across a biological membrane. A transport protein can aid in the movement of ions, small molecules or macromolecules. A transport protein can be referred to as a transmembrane transporter, a transmembrane pump, an anion transport protein, a cation transport protein, or an escort protein. Transport proteins can also facilitate the movement of molecules or proteins in vesicles composed of biological membrane. A transport protein can be integrated into a biological membrane. A Transport protein can be anchored to a biological membrane via different modifications such as but not limited to myristolation, prenylation or palmitoylation.

In one aspect, a modified tobacco plant comprises one or more mutations in a gene encoding a polypeptide having at least 50%, 55%, 60%, 65%, 70%, 75%, 80%, 85%, 90%, 95%, 97%, 98%, 99%, or 100% identity to a sequence selected from the group consisting of SEQ ID No. 1 to 23, 47 to 52, 64 to 65, and 68 to 70. In another aspect, a modified tobacco plant comprises one or more mutations in a gene comprise a coding sequence having at least 50%, 55%, 60%, 65%, 70%, 75%, 80%, 85%, 90%, 95%, 97%, 98%, 99%, or 100% identity to a sequence selected from the group consisting of SEQ ID No. 24 to 46, 53 to 58, 66 to 67, and 71 to 73.

In one aspect, a modified plant, seed, plant component, plant cell, or plant genome provided herein comprises one or more transgenes. As used herein, a "transgene" refers to a polynucleotide that has been transferred into a genome by any method known in the art. In one aspect, a transgene is an exogenous polynucleotide. In one aspect, a transgene is an endogenous polynucleotide that is integrated into a new genomic locus where it is not normally found.

As used herein, "modified", in the context of plants, seeds, plant components, plant cells, and plant genomes, refers to a state containing changes or variations from their natural or native state. For instance, a "native transcript" of a gene refers to an RNA transcript that is generated from an unmodified gene. Typically, a native transcript is a sense transcript. Modified plants or seeds contain molecular changes in their genetic materials, including either genetic or epigenetic modifications. Typically, modified plants or seeds, or a parental or progenitor line thereof, have been subjected to mutagenesis, genome editing (e.g., without being limiting, via methods using site-specific nucleases), genetic transformation (e.g., without being limiting, via methods of *Agrobacterium* transformation or microprojectile bombardment), or a combination thereof. In one aspect, a modified plant provided herein comprises no non-plant genetic material or sequences. In yet another aspect, a modified plant provided herein comprises no interspecies genetic material or sequences. In one aspect, this disclosure provides methods and compositions related to modified plants, seeds, plant components, plant cells, and products made from modified plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct or vector provided herein. In another aspect, a product provided herein comprises a modified plant, plant component, plant cell, or plant chromosome or genome provided herein. The present disclosure provides modified plants with desirable or enhanced properties, e.g., without being limiting, disease, insect, or pest tolerance (for example, virus tolerance, bacteria tolerance, fungus tolerance, nematode tolerance, arthropod tolerance, gastropod tolerance); herbicide tolerance; environmental stress resistance; quality improvements such as yield, nutritional enhancements, environmental or stress tolerances; any desirable changes in plant physiology, growth, development, morphology or plant product(s) including starch production, modified oils production, high oil production, modified fatty acid content, high protein production, fruit ripening, enhanced animal and human nutrition, biopolymer production, pharmaceutical peptides and secretable peptides production; improved processing traits; improved digestibility; low raffinose; industrial enzyme production; improved flavor; nitrogen fixation; hybrid seed production; and fiber production.

As used herein, "genome editing" or editing refers to targeted mutagenesis, insertion, deletion, inversion, substitution, or translocation of a nucleotide sequence of interest in a genome using a targeted editing technique. A nucleotide sequence of interest can be of any length, e.g., at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides. As used herein, a "targeted editing technique" refers to any method, protocol, or technique that allows the precise and/or targeted editing of a specific location in a genome (e.g., the editing is not random). Without being limiting, use of a site-specific nuclease is one example of a targeted editing technique. Another non-limiting example of a targeted editing technique is the use of one or more tether guide Oligos (tgOligos). As used herein, a "targeted edit" refers to a targeted mutagenesis, insertion, deletion, inversion, or substitution caused by a targeted editing technique. A nucleotide sequence of interest can be an endogenous genomic sequence or a transgenic sequence.

In one aspect, a "targeted editing technique" refers to any method, protocol, or technique that allows the precise and/or targeted editing of a specific location in a genome (e.g., the editing is not random). Without being limiting, use of a site-specific nuclease is one example of a targeted editing technique.

In one aspect, a targeted editing technique is used to edit an endogenous locus or an endogenous gene. In another aspect, a targeted editing technique is used to edit a transgene. As used herein, an "endogenous gene" or a "native copy" of a gene refers to a gene that originates from within a given organism, cell, tissue, genome, or chromosome. An "endogenous gene" or a "native copy" of a gene is a gene that was not previously modified by human action.

In one aspect, a modified tobacco plant described here comprises one or more mutations are introduced via a system selected from the group consisting of chemical mutagenesis, irradiation mutagenesis, transposon mutagenesis, *Agrobacterium*-mediated transformation, a meganuclease, a zinc-finger nuclease (ZFN), a transcription activator-like effector nuclease (TALEN), a clustered regularly-interspaced short palindromic repeats (CRISPR)/Cas9 system, a CRISPR/Cpf1 system, a CRISPR/CasX system, a CRISPR/CasY system, a CRISPR/Csm1 system, and a combination thereof (see, for example, U.S. Patent Application publication 2017/0233756).

In one aspect, methods provided herein are capable of producing a tobacco plant comprising a reduced level of one or more TSNAs using mutagenesis. Mutagenesis methods include, without limitation, chemical mutagenesis, for example, treatment of seeds with ethyl methylsulfate (EMS) (Hildering and Verkerk, In, The use of induced mutations in plant breeding. Pergamon Press, pp. 317-320, 1965); or UV-irradiation, X-rays, electron beams, ion beams (e.g., carbon ion beam, helium ion beam, neon ion beam), and fast neutron irradiation (see, for example, Verkerk, Neth. *J. Agric. Sci.* 19:197-203, 1971; Poehlman, Breeding Field Crops, Van Nostrand Reinhold, New York (3.sup.rd ed.), 1987; and Tanaka, *J. Radiat. Res.* 51:223-233, 2010); transposon tagging (Fedoroff et al., 1984; U.S. Pat. Nos. 4,732,856; 5,013,658); and T-DNA insertion methodologies (Hoekema et al., 1983; U.S. Pat. No. 5,149,645). EMS-induced mutagenesis consists of chemically inducing random point mutations over the length of a genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes provided herein can be determined using methods that are well known in the art. Insertional mutations in gene exons usually result in null-mutants. Mutations in conserved residues can be particularly effective in inhibiting the function of a protein.

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In one aspect, a modified plant or plant genome provided herein is mutated or edited by a nuclease selected from the group consisting of a meganuclease, a zinc-finger nuclease (ZFN), a transcription activator-like effector nuclease (TALEN), a CRISPR/Cas9 nuclease, a CRISPR/Cpf1 nuclease, a CRISPR/CasX nuclease, a CRISPR/CasY nuclease, or a CRISPR/Csm1 nuclease. As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In one aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide selected from the group consisting of SEQ ID NOs: 24 to 46, 53 to 58, 64 to 65, 68 to 70, and fragments thereof. In another aspect, an edited nucleic acid sequence provided herein has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide encoding a polypeptide selected from the group consisting of SEQ ID NOs: 1 to 23, 47 to 52, 64 to 65, and 68 to 70.

Meganucleases, ZFNs, TALENs, CRISPR/Cas9, CRISPR/Csm1, CRISPR/CasX, CRISPR/CasY, and CRISPR/Cpf1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In one aspect, a method provided herein comprises editing a plant genome with a nuclease provided herein to mutate at least 1, at least 2, at least 3, at least 4, at least 5, at least 6, at least 7, at least 8, at least 9, at least 10, or more than 10 nucleotides in the plant genome via HR with a donor polynucleotide. In one aspect, a mutation provided herein is caused by genome editing using a nuclease. In another aspect, a mutation provided herein is caused by non-homologous end-joining or homologous recombination.

In one aspect, a mutation provided herein provides a dominant mutant that activates the expression or activity of a gene of interest, e.g., a gene selected from the group consisting of a biosynthetic enzyme, a regulatory transcription factor, a transporter, a catabolic enzyme, or a combination thereof, for one or more antioxidants. Exemplary proteins include, but are not limited to, AtPAP1, NtPAP1, NtMYB3-like, NtJAF13, and AtTTG1.

In one aspect, a mutation provided herein provides a dominant mutant that activates the expression or activity of a gene of interest, e.g., a gene selected from the group consisting of a biosynthetic enzyme, a regulatory transcription factor, a transporter, a catabolic enzyme, or a combination thereof, for one or more anthocyanins. Exemplary proteins include, but are not limited to, AtPAP1, NtPAP1, NtMYB3-like, NtJAF13, AtTTG1, Chorismate Mutase (CM), CM-like proteins, Prephenate Aminotransferase (PAT), PAT-like proteins, Arogenate Dehydratase (ADT), ADT-like proteins, Prephenate Dehydratase (PDT), PDT-like proteins, Aromatic Amino Acid Aminotransferase (AAAAT), AAAAT-like proteins, Anthocyanidin synthase2 (NtANS2), Dihyfroflavonol-4-reductase (NtDFR2), Shikimate O-hydroxycinnamoyl transferase (HCT), HCT-like proteins, Hydroxycinnamoyl CoA quinate Transferase (HQT), and HQT-like proteins.

In one aspect, a mutation provided herein provides a dominant mutant that activates the expression or activity of a gene of interest, e.g., a gene selected from the group consisting of a phenylalanine biosynthetic enzyme, a regulator of phenylalanine biosynthesis, or a phenylalanine metabolic enzyme, or a combination thereof, for one or more anthocyanins. Exemplary proteins include, but are not limited to, Chorismate Mutase (CM), CM-like proteins, Prephenate Aminotransferase (PAT), PAT-like proteins, Arogenate Dehydratase (ADT), ADT-like proteins, Prephenate Dehydratase (PDT), PDT-like proteins, Aromatic Amino Acid Aminotransferase (AAAAT), AAAAT-like proteins, Anthocyanidin synthase2 (NtANS2), Dihyfroflavonol-4-reductase (NtDFR2), Shikimate O-hydroxycinnamoyl transferase (HCT), HCT-like proteins, Hydroxycinnamoyl CoA quinate Transferase (HQT), and HQT-like proteins Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011). 39:e82; and tale-nt.cac.cornell.edu/about.

A CRISPR/Cas9 system, CRISPR/Csm1, CRISPR/CasX, CRISPR/CasY, or a CRISPR/Cpf1 system are alternatives to the FokI-based methods ZFN and TALEN. The CRISPR systems are based on RNA-guided engineered nucleases that use complementary base pairing to recognize DNA sequences at target sites.

CRISPR/Cas9, CRISPR/Csm1, CRISPR/CasX, CRISPR/CasY, and a CRISPR/Cpf1 systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA.

In still another aspect, a modified tobacco plant provided herein further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187,759; 9,228,194; 9,228,195; 9,247,706) compared to control plant lacking one or more mutations in one or more loci encoding a nicotine demethylase. In one aspect, a tobacco variety comprising mutations in three nicotine demethylase genes is referred to as an SRC variety. In another aspect, an SRC variety comprises at least one mutation in each of CYP82E4, CYP82E5, and CYP82E10. These varieties will have the letters SRC as part of their names to differentiate from the Low Converter (LC) varieties. SRC stands for Stable Reduced Converter which identified the effect of the technology in reducing the conversion of nicotine to nornicotine. In still another aspect, SRC varieties will further comprise blank shank resistance. In one aspect, a modified tobacco plant described herein further comprises reduced nicotine demethylase activity compared to a control plant when grown and cured under comparable conditions. In another aspect, a modified tobacco plant described herein further comprises a reduced level of total alkaloids compared to the control plant when grown and cured under comparable conditions.

In another aspect, a tobacco plant provided herein further comprises one or more mutations in a Nic1 locus, a Nic2 locus, or both, which confer reduced amounts of nicotine compared to a control plant lacking one or more mutations in a Nic1 locus, a Nic2 locus, or both. In another aspect, a modified tobacco plant described herein further comprises a reduced level of nicotine compared to the control plant when grown and cured under comparable conditions. In a further aspect, a modified tobacco plant described herein comprises a substantially similar level of nicotine compared to the control plant when grown and cured under comparable conditions.

In one aspect, a modified tobacco plant described herein is a cisgenic plant. As used herein, "cisgenesis" or "cisgenic" refers to genetic modification of a plant, plant cell, or plant genome in which all components (e.g., promoter, donor nucleic acid, selection gene) have only plant origins (i.e., no non-plant origin components are used). In one aspect, a modified plant, plant cell, or plant genome provided herein is cisgenic. Cisgenic plants, plant cells, and plant genomes provided herein can lead to ready-to-use tobacco lines. In another aspect, a modified tobacco plant provided herein comprises no non-tobacco genetic material or sequences. In one aspect, a cisgenic construct of the present disclosure encodes a polynucleotide selected from the group consisting of Ubi4-P:PAP1-HSP-T (SEQ ID NO:59), Ubi4-P:NtAN2-HSP-T (SEQ ID NO:60), Tub-P:NtAN2-HSP-T (SEQ ID NO:61), Ubi4-P:NtAN2-HSP-T:Tub-P:NtAN2-HSP-T (SEQ ID NO:62), and Ubi4-P:NtAN1a-HSP-T:Tub-P:NtAN2-HSP-T (SEQ ID NO:63).

In one aspect, a modified tobacco plant described herein comprises one or more transgenes or recombinant DNA constructs capable of providing a reduced level of one or more TSNAs compared to a control plant without the one or more transgenes. In another aspect, a modified tobacco plant comprises one or more transgenes or recombinant DNA constructs further providing the one or more traits selected from the group consisting of: i. a reduced level of nitrite, ii. an increased level of oxygen radicle absorbance capacity (ORAC), and iii. an increased level of one or more antioxidants; wherein the reduced or increased level is compared to a control tobacco plant when grown and cured under comparable.

In another aspect, a modified tobacco plant comprises one or more transgenes or recombinant DNA constructs encoding a biosynthetic enzyme, a regulatory transcription factor, a transporter, a catabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In another aspect, a modified tobacco plant comprises one or more transgenes or recombinant DNA constructs encoding a biosynthetic enzyme, a regulatory transcription factor, a transporter, a catabolic enzyme, or a combination thereof, for one or more antioxidants selected from the group consisting of Delphnidin, Cyanidin, Procyanidin, Prodelphinidin, Hesperetin, Perlargonidin, Peonidin, Petunidin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C. In another aspect, a modified tobacco plant comprises one or more transgenes or recombinant DNA constructs encoding phenylalanine biosynthetic enzymes, regulators of phenylalanine biosynthesis, or phenylalanine metabolic enzymes, or a combination thereof. In one aspect, one or more transgenes or recombinant DNA constructs encode a polypeptide having at least 50%, 55%, 60%, 65%, 70%, 75%, 80%, 85%, 90%, 95%, 97%, 98%, 99%, or 100% identity to a sequence selected from the group consisting of SEQ ID Nos: 1 to 23, 47 to 52, 64 to 65, and 68 to 70. In another aspect, one or more transgenes or recombinant DNA constructs encode a gene comprise a coding sequence having at least 50%, 55%, 60%, 65%, 70%, 75%, 80%, 85%, 90%, 95%, 97%, 98%, 99%, or 100% identity to a sequence selected from the group consisting of SEQ ID Nos: 24 to 46, 53 to 58, 66 to 67, and 71 to 73.

In one aspect, a recombinant DNA construct of the present disclosure comprises a promoter capable of driving gene transcription in a plant, operably linked to a polynucleotide encoding a polypeptide having at least 70%, at least 75%, at least 80%, at least 85%, at least 90%, at least 95%, at least 96%, at least 97%, at least 98%, at least 99% or 100% sequence identity to a polypeptide selected from the group consisting of SEQ ID NOs: 1 to 23, 47 to 52, 64 to 65, and 68 to 70. In one aspect, a recombinant DNA construct or expression cassette in a transgene provided herein comprises a promoter selected from the group consisting of a constitutive promoter, an inducible promoter, and a tissue-preferred promoter (for example, without being limiting, a leaf-specific promoter, a shoot-specific promoter, a root-specific promoter, or a meristem-specific promoter).

Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659,026), and the like.

Exemplary chemical-inducible promoters include the tobacco PR-1a promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used herein are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wunl), organ specific gene expression (for example, of the tuber-specific storage protein gene; the 23-kDa zein gene from maize described by; or the French bean (ß-phaseolin gene), or pathogen-inducible promoters (for example, the PR-1, prp-1, or (ß-1,3 glucanase promoters, the fungal-inducible wirla promoter of wheat, and the nematode-inducible promoters, TobRB7-5A and Hmg-1, of tobacco arid parsley, respectively).

Additional exemplary tissue-preferred promoters include those disclosed in Yamamoto et al. (1997) Plant J. 12(2): 255-265; Kawamata et al. (1997) Plant Cell Physiol. 38(7): 792-803; Hansen et al. (1997) Mol. Gen. Genet. 254(3):337-343; Russell et al. (1997) Transgenic Res. 6(2):157-168; Rinehart et al. (1996) Plant Physiol. 112(3):1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

In one aspect, a transgene provided herein comprises a heterologous or non-tobacco promoter or coding sequence. In another aspect, a transgene provided herein comprises a endogenous or tobacco-origin promoter or coding sequence. As used herein, "heterologous" refers to a sequence that originates from a foreign species, or, if from the same species, is substantially modified from its native form in composition and/or genomic locus by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic locus by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest.

In one aspect, a recombinant DNA construct, modified plant, seed, plant component, plant cell, or plant genome provided herein comprises a heterologous promoter operably linked to a polynucleotide encoding a polypeptide having at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a polypeptide selected from the group consisting of SEQ ID NOs: 24 to 46, 53 to 58, 66 to 67, and 71 to 73.

Enhancer elements are regions of DNA that can be bound by proteins to activate RNA transcription. In one aspect, a promoter sequence used herein is operably linked to an enhancer element. In one aspect, an enhancer element provided herein is a CsVMV promoter.

Also provided herein are the transformation of tobacco plants with recombinant constructs or expression cassettes described herein using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into a genome of the plant and is capable of being inherited by the progeny thereof "Transient transformation" is intended to mean that a sequence is introduced into the plant and is only temporally expressed or is only transiently present in the plant.

In one aspect, methods and compositions provided herein comprise the introduction of one or more polynucleotides into one or more plant cells. In one aspect, a plant genome provided herein is modified to include an introduced polynucleotide or recombinant DNA construct. As used herein, "plant genome" refers to a nuclear genome, a mitochondrial genome, or a plastid (e.g., chloroplast) genome of a plant cell. In another aspect, a polynucleotide provided herein is integrated into an artificial chromosome. In one aspect, an artificial chromosome comprising a polynucleotide provided herein is integrated into a plant cell.

In one aspect, transgenes provided herein comprise a recombinant DNA construct. In one aspect, recombinant DNA constructs or expression cassettes provided herein can comprise a selectable marker gene for the selection of transgenic cells. Selectable marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, triazolopyrimidines, sulfonylurea (e.g., chlorsulfuron and sulfometuron methyl), and 2,4-dichlorophenoxyacetate (2,4-D). Additional selectable markers include phenotypic markers such as β-galactosidase and fluorescent proteins such as green fluorescent protein (GFP).

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* $T_1$ plasmid or derived from an *Agrobacterium* $T_1$ plasmid.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., $T_1$ plasmid). Without being limited, one skilled in the art can create a synthetic plasmid de novo via synthesizing a plasmid by individual nucleotides, or by splicing together nucleic acid molecules from different pre-existing plasmids.

Vectors are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST)).

Suitable methods of introducing polynucleotides (e.g., transgenes, recombinant vectors, recombinant DNA constructs, expression constructs) into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149,645, 5,177,010, 5,231,019, 5,463,174, 5,464,763, 5,469,976, 4,762,785, 5,004,863, 5,159,135, 5,563,055, and 5,981,840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in Plant Cell, Tissue, and Organ Culture Fundamental Methods, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation). In one aspect, a bacterial cell provided herein comprises a recombinant DNA construct or recombinant vector provided herein.

In another aspect, recombinant constructs or expression cassettes provided herein may be introduced into plants by contacting plants with a virus or viral nucleic acids. Generally, such methods involve incorporating an expression cassette of the present disclosure within a viral DNA or RNA molecule. It is recognized that promoters for use in the expression cassettes provided herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette provided herein. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described herein include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

It is understood that any modified tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance, high yield, high grade index value, curability, curing quality, mechanical harvestability, holding ability, leaf quality, height, plant maturation (e.g., early maturing, early to medium maturing, medium maturing, medium to late maturing, or late maturing), stalk size (e.g., a small, medium, or a large stalk), or leaf number per plant (e.g., a small (e.g., 5-10 leaves), medium (e.g., 11-15 leaves), or large (e.g., 16-21) number of leaves), or any combination. In one aspect, tobacco plants capable of producing cured leaf with reduced TSNA or seeds provided herein comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In another aspect, tobacco plants provided herein further comprise an introgressed trait conferring resistance to brown stem rot (U.S. Pat. No. 5,689,035) or resistance to cyst nematodes (U.S. Pat. No. 5,491,081).

The level and/or activity of polypeptides provided herein may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984; each of which is incorporated herein by reference as if set forth in its entirety. See also, International Patent Application Publication Nos. WO 98/149350, WO 99/107865 and WO 99/125921; and Beetham et al. (1999) Proc. Natl. Acad. Sci. USA 96:8774-8778; each of which is incorporated herein by reference as if set forth in its entirety.

The present disclosure also provides compositions and methods for inhibiting the expression or function of one or more polypeptides that suppress, directly or indirectly, the production or accumulation of one or more antioxidants in a plant, particularly plants of the *Nicotiana tabacum* genus, including tobacco plants of various commercial varieties.

In one aspect, inhibition of the expression of one or more polypeptides provided herein may be obtained by RNA interference (RNAi) by expression of a transgene capable of producing an inhibitory sequence provided herein. In one aspect, RNAi comprises expressing a non-coding RNA. As used herein, a "non-coding RNA" is selected from the group consisting of a microRNA (miRNA), a small interfering RNA (siRNA), a trans-acting siRNA (ta-siRNA), a transfer RNA (tRNA), a ribosomal RNA (rRNA), an intron, a hairpin RNA (hpRNA), and an intron-containing hairpin RNA (ihpRNA). In one aspect, a single non-coding RNA provided herein inhibits the expression of at least 1, at least 2, at least 3, at least 4, at least 5, at least 6, at least 7, at least 8, at least 9, at least 10, or more than 10 polypeptides. In one aspect, a non-coding RNA provided herein is stably transformed into a plant genome. In another aspect, a non-coding RNA provided herein is transiently transformed into a plant genome.

As used herein, the terms "suppress," "inhibit," "inhibition," "inhibiting", and "downregulation" are defined as any method known in the art or described herein that decreases the expression or function of a gene product (e.g., an mRNA, a protein, a non-coding RNA). "Inhibition" can be in the context of a comparison between two cells, for example, a modified cell versus a control cell. Inhibition of expression or function of a gene product can also be in the context of a comparison between plant cells, organelles, organs, tissues, or plant components within the same plant or between different plants, and includes comparisons between developmental or temporal stages within the same plant or plant component or between plants or plant components. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product. "Inhibition" need not comprise complete elimination of expression of a gene product. In an aspect, a gene product in a modified cell provided herein comprises expression that is at least 1%, at least 2%, at least 3%, at least 4%, at least 5%, at least 10%, at least 20%, at least 25%, at least 30%, at least 40%, at least 50%, at least 60%, at least 70%, at least 80%, at least 90%, at least 95%, or 100% lower than the expression of the gene product in a control cell. In another aspect, a gene product in a modified cell provided herein comprises expression that is between 1% and 100%, between 1% and 95%, between 1% and 90%, between 1% and 80%, between 1% and 70%, between 1% and 60%, between 1% and 50%, between 1% and 40%, between 1% and 30%, between 1% and 25%, between 1% and 20%, between 1% and 15%, between 1% and 10%, between 1% and 5%, between 5% and 25%, between 5% and 50%, between 5% and 75%, between 5% and 100%, between 10% and 25%, between 10% and 50%, between 10% and 75%, between 10% and 100%, between 25% and 50%, between 25% and 75%, between 25% and 100%, or between 50% and 100% lower than the expression of the gene product in a control cell.

As used herein, a "target site" refers to a location of a polynucleotide sequence that is bound to and cleaved by a site-specific nuclease introducing a double stranded break into the nucleic acid backbone. In another aspect a target site comprises at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. In another aspect, a target site provided herein is at least 10, at least 20, at least 30, at least 40, at least 50, at least 75, at least 100, at least 125, at least 150, at least 200, at least 250, at least 300, at least 400, or at least 500 nucleotides. In one aspect a site-specific nuclease binds to a target site. In another aspect a site-specific nuclease binds to a target site via a guiding non-coding RNA (i.e., such as, without being limiting, a CRISPR RNA or single-guide RNA (both described in detail below)). In one aspect, a non-coding RNA provided herein is complementary to a target site. It will be appreciated that perfect complementarity is not required for a non-coding RNA to bind to a target site; at least 1, at least 2, at least 3, at least 4, or at least 5, at least 6, at least 7 or at least 8 mismatches between a target site and a non-coding RNA can be tolerated. As used herein, a "target region" or a "targeted region" refers to a polynucleotide sequence that is desired to be modified. In one aspect, a "target region," "targeted region," or a "target gene" is flanked by two or more, three or more, four or more, five or more, six or more, seven or more, eight or more, nine or more, or ten or more target sites. A "target gene" refers to a polynucleotide sequence encoding a gene that is desired to be modified or from which transcript expression is desired to be modulated. In one aspect, a polynucleotide sequence comprising a target gene further comprises one or more target sites. In another aspect, a transgene is said to be targeting a target site or a target gene. In another aspect, a target region comprises one or more, two or more, three or more, four or more, five or more, six or more, seven or more, eight or more, nine or more, or ten or more target genes. Without being limiting, in one aspect a target region can be subject to deletion or inversion. As used herein, "flanked" when used to describe a target region, refers to two or more target sites physically surrounding the target region, with one target site on each side of the target region.

As used herein, in the context of a transgene "directly modulating" or "directly modulates" refers to inducing a change in the transcript or protein level of a target gene by an agent produced by the transgene and sharing sufficient homology with at least a portion of the target gene. Direct modulation can result in a change in transcriptional activity, transcript stability, transcript constitution, or transcript expression level which can either increase or decrease the number of transcripts available for translation and can either increase or decrease the number of protein molecules.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can be also be positioned upstream or downstream of a sequence encoding a leader, an enhancer, a transcriptional start site, a promoter, a 5'-UTR, an exon, an intron, a 3'-UTR, a polyadenylation site, or a termination sequence. In one aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

As used herein, "upstream" refers to a nucleic acid sequence that is positioned before the 5' end of a linked nucleic acid sequence. As used herein, "downstream" refers to a nucleic acid sequence is positioned after the 3' end of a linked nucleic acid sequence. As used herein, "5'" refers to the start of a coding DNA sequence or the beginning of an RNA molecule. As used herein, "3'" refers to the end of a coding DNA sequence or the end of an RNA molecule. It will be appreciated that an "inversion" refers to reversing the orientation of a given polynucleotide sequence. For example, if the sample sequence 5'-ATGATC-3' is inverted it will read 5'-CTAGTA-3' in reverse orientation. Additionally, the sample sequence 5'-ATGATC-3' is considered to be in "opposite orientation" to the sample sequence 5'-CTAGTA-3'.

The term "inhibitory sequence" encompasses any polynucleotide or polypeptide sequence capable of inhibiting the expression or function of a gene in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense—or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

Inhibitory sequences are designated herein by the name of the target gene product. Thus, as a non-limiting example, an "gene X inhibitory sequence" refers to an inhibitory sequence that is capable of inhibiting the expression of a gene X locus in a plant, for example, at the level of transcription and/or translation, or which is capable of inhibiting the function of a gene product. When the phrase "capable of inhibiting" is used in the context of a transgene containing polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (e.g., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (e.g., inhibits expression or function of the target gene product).

An inhibitory sequence provided herein can be a sequence triggering gene silencing via any silencing pathway or mechanism known in the art, including, but not limited to, sense suppression/co-suppression, antisense suppression, double-stranded RNA (dsRNA) interference, hairpin RNA interference and intron-containing hairpin RNA interference, amplicon-mediated interference, ribozymes, small interfering RNA, artificial or synthetic microRNA, and artificial trans-acting siRNA.

One aspect of the present application relates to methods of screening and selecting cells for targeted edits and methods of selecting cells comprising targeted edits. Nucleic acids can be isolated using various techniques. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Also provided herein is cured tobacco material made from tobacco leaf, tobacco plants, or plant components provided herein. "Curing" is a post-harvest process that reduces moisture and brings about the destruction of chlorophyll giving tobacco leaf a golden color and by which starch is converted to sugar. Cured tobacco therefore has a higher reducing sugar content and a lower starch content compared to harvested green leaf. In one aspect, tobacco plants or plant components provided herein can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, for example, U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cured, aged, and fermented tobacco can be further processed (e.g., cut, shredded, expanded, or blended). See, for example, U.S. Pat. Nos. 4,528,993; 4,660,577; and 4,987,907. In one aspect, the cured tobacco material of the present disclosure is flue-cured, sun-cured, air-cured, or fire-cured.

Tobacco material obtained from modified tobacco lines, varieties or hybrids of the present disclosure can be used to make tobacco products. As used herein, "tobacco product" is defined as any product made or derived from tobacco that is intended for human use or consumption. In an aspect, a tobacco product provided herein comprises cured components from a modified tobacco plant provided herein. In another aspect, a tobacco product provided herein comprises cured tobacco leaf from a modified tobacco plant provided herein.

Tobacco products provided herein include, without limitation, cigarette products (e.g., cigarettes, bidi cigarettes, kreteks), cigar products (e.g., cigars, cigar wrapping tobacco, cigarillos), pipe tobacco products, products derived from tobacco, tobacco-derived nicotine products, smokeless tobacco products (e.g., moist snuff, dry snuff, snus, chewing tobacco, moist smokeless tobacco, fine cut chewing tobacco, long cut chewing tobacco, pouched chewing tobacco), films, chewables (e.g., gum), lozenges, dissolving strips, tabs, tablets, shaped parts, gels, consumable units, insoluble matrices, hollow shapes, reconstituted tobacco, expanded tobacco, and the like. See, for example, U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

In one aspect, this disclosure provides nicotine derived from and a method of producing nicotine from a modified tobacco plant provided herein for use in a product.

In one aspect, a method provided herein comprises preparing a tobacco product using cured tobacco leaf from a modified tobacco plant provided herein.

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokeable material includes cured tobacco within a tobacco blend. In an aspect, a tobacco product of the present disclosure is selected from the group consisting of a cigarillo, a non-ventilated recess filter cigarette, a vented recess filter cigarette, a bidi cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

The present disclosure further provides a method for manufacturing a tobacco product comprising tobacco material from tobacco plants provided herein. In one aspect, methods provided herein comprise conditioning aged tobacco material made from tobacco plants provided herein to increase its moisture content from between about 12.5% and about 13.5% to about 21%, blending the conditioned tobacco material to produce a desirable blend. In one aspect, the method of manufacturing a tobacco product provided herein further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided herein can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In one aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided herein can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with a copolymer and, optionally, flavorants and other additives.

In one aspect, tobacco material provided herein can be processed to a desired size. In certain aspects, tobacco fibers can be processed to have an average fiber size of less than 200 micrometers. In one aspect, tobacco fibers are between 75 and 125 micrometers. In another aspect, tobacco fibers are processed to have a size of 75 micrometers or less. In one aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided herein can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. An oral product can have a different overall oven volatiles content than the oven volatiles content of the tobacco fibers used to make the oral product. The processing steps described herein can reduce or increase the oven volatiles content.

In one aspect, tobacco plants, seeds, plant components, plant cells, and plant genomes provided herein are from a tobacco type selected from the group consisting of flue-cured tobacco, sun-cured tobacco, air-cured tobacco, dark air-cured tobacco, and dark fire-cured tobacco. In another aspect, tobacco plants, seeds, plant components, plant cells, and plant genomes provided herein are from a tobacco type selected from the group consisting of Burley tobacco, Maryland tobacco, bright tobacco, Virginia tobacco, Oriental tobacco, Turkish tobacco, dark tobacco, and Galpão tobacco. In one aspect, a tobacco plant or seed provided herein is a hybrid plant or seed. As used herein, a "hybrid" is created by crossing two plants from different varieties or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

Flue-cured tobaccos (also called Virginia or bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S. In one aspect, modified tobacco plants or seeds provided herein are in a flue-cured tobacco background selected from the group consisting of CC 13, CC 27, CC 33, CC35, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, modified tobacco plants or seeds provided herein are in a flue-cured tobacco background selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In further aspects, modified tobacco plants, seeds, hybrids, varieties, or lines provided herein are in any flue cured background selected from the group consisting of K326, K346, and NC196.

Air-cured tobaccos include Burley, Maryland, and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, have good burning properties, low nicotine and a neutral aroma. Major Maryland growing countries include the U.S. and Italy. In one aspect, modified tobacco plants or seeds provided herein are in a Burley tobacco background selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, HB4488PLC, PD 7319LC, Bu 21×Ky 10, HB04P, Ky 14×L 8, Kt 200, Newton 98, Pedigo 561, Pf561 and Va 509. In further aspects, modified tobacco plants, seeds, hybrids, varieties, or lines provided herein are in any Burley background selected from the group consisting of TN 90, KT 209, KT 206, KT212, and HB 4488. In another aspect, modified tobacco plants or seeds provided herein are in a Maryland tobacco background selected from the group consisting of Md 10, Md 40, Md 201, Md 609, Md 872 and Md 341.

Dark air-cured tobaccos are distinguished from other types primarily by its curing process which gives dark air-cured tobacco its medium- to dark-brown color and distinct aroma. Dark air-cured tobaccos are mainly used in the production of smokeless tobacco products including chewing tobacco and snuff. In one aspect, modified tobacco plants or seeds provided herein are in a dark air-cured tobacco background selected from the group consisting of Sumatra, Jatim, Dominican Cubano, Besuki, One sucker, Green River, Virginia sun-cured, and Paraguan Passado.

Dark fire-cured tobaccos are generally cured with low-burning wood fires on the floors of closed curing barns. Dark fire-cured tobaccos are used for making pipe blends, cigarettes, chewing tobacco, snuff and strong-tasting cigars. Major growing regions for dark fire-cured tobaccos are Tennessee, Kentucky, and Virginia, USA. In one aspect, modified tobacco plants or seeds provided herein are in a dark fire-cured tobacco background selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries. In one aspect, modified tobacco plants or seeds provided herein are in an Oriental tobacco background selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

In one aspect, modified tobacco plants, seeds, hybrids, varieties, or lines provided herein are essentially derived from or in the genetic background of BU 64, CC 101, CC 200, CC 13, CC 27, CC 33, CC 35, CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpão, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119, KDH 959, KT 200, KT204LC, KY 10, KY 14, KY 160, KY 17, KY 171, KY 907, KY 907LC, KTY14×L8 LC, Little Crittenden, McNair 373, McNair 944, male sterile KY 14×L8, Narrow Leaf Madole, MS KY171, Narrow Leaf Madole (phph), MS Narrow Leaf Madole, MS TND950, PD 7302LC, PD 7305LC, PD 7309LC, PD 7312LC, PD 7318LC, PD 7319LC, MSTKS 2002, TKF 2002, TKF 6400, TKF 4028, TKF 4024, KT206LC, KT209LC, KT210LC, KT212LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique', PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, a TR (Tom Rosson) Madole, VA 309, VA 359, or any commercial tobacco variety according to standard tobacco breeding techniques known in the art.

All foregoing mentioned specific varieties of dark air-cured, Burley, Maryland, dark fire-cured, or Oriental type are only listed for exemplary purposes. Any additional dark air-cured, Burley, Maryland, dark fire-cured, or Oriental varieties are also contemplated in the present application.

Also provided herein are populations of tobacco plants described herein. In one aspect, a population of tobacco plants provided herein has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants provided herein is in a soil type with low to medium fertility.

Also provided herein are containers of tobacco leaves used to store, transport, or otherwise house cured or uncured tobacco leaves from tobacco plants described herein. As a non-limiting example, a container can be a box, a bag, a barrel, a crate, or any other suitable container.

Also provided herein are bales of the cured tobacco leaves from tobacco plants described herein. Also provided herein are bales of the uncured tobacco leaves from tobacco plants described herein. A bale can be any size known in the art. A bale can be about 50 pounds, about 75 pounds, about 100 pounds, about 125 pounds, about 150 pounds, about 175 pounds, about 200 pounds, about 225 pounds, about 250 pounds, about 300 pounds, about 350 pounds, about 400 pounds, about 450 pounds, about 500 pounds, about 600 pounds, about 700 pounds, about 800 pounds, about 900 pounds, or about 1000 pounds. A bale can take any shape such as, by a non-limiting example, conical, rectangular, or cuboidal.

Also provided herein are containers of seeds from tobacco plants described herein. A container of tobacco seeds of the present disclosure may contain any number, weight, or volume of seeds. For example, a container can contain at least, or greater than, about 100, at least, or greater than, about 200, at least, or greater than, about 300, at least, or greater than, about 400, at least, or greater than, about 500, at least, or greater than, about 600, at least, or greater than, about 700, at least, or greater than, about 800, at least, or greater than, about 900, at least, or greater than, about 1000, at least, or greater than, about 1500, at least, or greater than, about 2000, at least, or greater than, about 2500, at least, or greater than, about 3000, at least, or greater than, about 3500, at least, or greater than, or about 4000 or more seeds. Alternatively, the container can contain at least, or greater than, about 1 ounce, at least, or greater than, about 5 ounces, at least, or greater than, about 10 ounces, at least, or greater than, about 1 pound, at least, or greater than, about 2 pounds, at least, or greater than, about 3 pounds, at least, or greater than, about 4 pounds, at least, or greater than, about 5 pounds or more seeds. Containers of tobacco seeds may be any container available in the art. By way of non-limiting example, a container may be a box, a bag, a packet, a pouch, a tape roll, a tube, or a bottle.

Also provided herein are containers of tobacco products from tobacco leaves harvested and cured from tobacco plants described herein. By way of non-limiting example, a container may be a box, a bag, a packet, a pack, a pouch, a tin, or any other container known in the art.

The present disclosure also provides methods for breeding tobacco lines, cultivars, or varieties comprising cured leaf with reduced or eliminated TSNAs (and, optionally, also comprising increased phenylalanine, increased Chorismate Mutase-like protein activity, increased antioxidants or decreased nitrite). Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in an $F_2$ or backcross generation using Fi hybrid plants provided herein or further crossing the Fi hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. In one aspect, a recurrent parent in the present disclosure can be a flue-cured variety, a Burley variety, a dark air-cured variety, a dark fire-cured variety, or an Oriental variety. In another aspect, a recurrent parent can be a modified tobacco plant, line, or variety. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using modified tobacco plants described herein includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In one aspect, the present disclosure provides a method for reducing the amount of one or more Tobacco Specific Nitrosamines (TSNAs) in a cured leaf of a tobacco plant, the method comprising the steps of increasing the amount of phenylalanine in the tobacco plant via a transgene encoding or targeting a phenylalanine biosynthetic enzyme, a regulator of phenylalanine biosynthesis, or a phenylalanine metabolic enzyme; and reducing the amount of one or more TSNAs in a cured leaf of the tobacco plant or a tobacco product made the cured tobacco leaf.

In one aspect, the present disclosure provides a method for reducing the amount of one or more TSNAs in a cured leaf of a tobacco plant, the method comprising the steps of increasing the amount of phenylalanine in the tobacco plant via a genetic modification in an endogenous gene, wherein the endogenous gene encodes a phenylalanine biosynthetic enzyme, a regulator of phenylalanine biosynthesis, or a phenylalanine metabolic enzyme; and reducing the amount of one or more TSNAs in a cured leaf of the tobacco plant or a tobacco product made from the cured tobacco leaf.

In one aspect, the present disclosure provides a method for increasing the amount of one or more anthocyanins in a cured leaf of a tobacco plant, the method comprising the steps of increasing the amount of phenylalanine in the tobacco plant via a transgene encoding or targeting a phenylalanine biosynthetic enzyme, a regulator of phenylalanine biosynthesis, or a phenylalanine metabolic enzyme; and increasing the amount of one or more anthocyanins in a cured leaf of the tobacco plant or a tobacco product made from the cured tobacco leaf.

In one aspect, the present disclosure provides a method for increasing the amount of one or more anthocyanins in a cured leaf of a tobacco plant, the method comprising the steps of increasing the amount of phenylalanine in the tobacco plant via a genetic modification in an endogenous gene, wherein the endogenous gene encodes a phenylalanine biosynthetic enzyme, a regulator of phenylalanine biosynthesis, or a phenylalanine metabolic enzyme; and increasing the amount of one or more anthocyanins in a cured leaf of the tobacco plant or a tobacco product made from the cured tobacco leaf.

In one aspect, the present disclosure provides a method of producing a tobacco plant comprising crossing at least one tobacco plant of a first tobacco variety with at least one tobacco plant of a second tobacco variety, where the at least one tobacco plant of the first tobacco variety comprising one or more desired traits, e.g., comprising a reduced level of one or more tobacco-specific nitrosamines (TSNAs) in cured leaf and further comprising one or more traits selected from the group consisting of: a reduced level of nitrite, an increased level of oxygen radical absorbance capacity (ORAC), and an increased level of one or more antioxidants, wherein said reduced or increased level is compared to a control tobacco plant of the same cross grown and cured under comparable conditions; and selecting for progeny tobacco plants that exhibit the one or more desired traits.

In one aspect, a first tobacco variety provided herein comprises modified tobacco plants. In another aspect, a second tobacco variety provided herein comprises modified tobacco plants. In one aspect, a first or second tobacco variety is male sterile. In another aspect, a first or second tobacco variety is cytoplasmically male sterile. In another aspect, a first or second tobacco variety is female sterile. In one aspect, a first or second tobacco variety is an elite variety. In another aspect, a first or second tobacco variety is a hybrid.

In one aspect, the present disclosure provides a method of introgressing one or more transgenes or mutations into a tobacco variety, the method comprising: (a) crossing a first tobacco variety comprising one or more transgenes or mutations provided herein with a second tobacco variety without the one or more transgenes or mutations to produce one or more progeny tobacco plants; (b) genotyping the one or more progeny tobacco plants for the one or more transgenes or mutations; and (c) selecting a progeny tobacco plant comprising the one or more transgenes or mutations. In another aspect, these methods further comprise backcrossing the selected progeny tobacco plant with the second tobacco variety. In further aspects, these methods further comprise: (d) crossing the selected progeny plant with itself or with the second tobacco variety to produce one or more further progeny tobacco plants; and (e) selecting a further progeny tobacco plant comprising the one or more transgenes or mutations. In one aspect, the second tobacco variety is an elite variety.

In one aspect, the present disclosure provides a method of growing a population of modified tobacco plants disclosed herein, where the method comprises planting a population of tobacco seeds comprising one or more mutations, one or more transgenes, or both as described herein, where the one or more modified tobacco plants or cured leaf of one or more modified tobacco plants comprise a reduced level of one or more TSNAs and further comprises one or more traits selected from the group consisting of an increased level of one or more antioxidants, an increased level of oxygen radical absorbance capacity (ORAC), and a reduced level of nitrite, wherein said reduced or increased level is compared to control tobacco plants or cured leaf of a control tobacco plant of the same variety when grown and cured under comparable conditions.

In one aspect, the present disclosure provides a method of growing a modified tobacco plant described herein comprising planting a modified tobacco seed described herein; and growing the modified tobacco plant from the seed. In an aspect, growing comprises germinating a seed. In another aspect, growing comprises placing a seedling in soil, agar, agar-based media, or a hydroponics system. In another aspect, growing comprises providing a seed or plant with water, light (e.g., artificial light, sunlight), fertilizer, a rooting media, or a combination thereof. In an aspect, growing can take place indoors (e.g., a greenhouse) or outdoors (e.g., a field). In one aspect, growing comprises placing a seed or a plant in a container.

In one aspect, this disclosure provides a method for manufacturing a modified seed, comprising introducing a recombinant DNA construct provided herein into a plant cell; screening a population of plant cells for the recombinant DNA construct; selecting one or more plant cells from the population; generating one or more modified plants from the one or more plant cells; and collecting one or more modified seeds from the one or more modified plants.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, a chromosome in a diploid plant is "hemizygous" when only one copy of a locus is present. For example, an inserted transgene is hemizygous when it only inserts into one sister chromosome (i.e., the second sister chromosome does not contain the inserted transgene).

In one aspect, a modified plant, seed, plant component, plant cell, or plant genome is homozygous for a transgene provided herein. In another aspect, a modified plant, seed, plant component, plant cell, or plant genome is heterozygous for a transgene provided herein. In one aspect, a modified plant, seed, plant component, plant cell, or plant genome is hemizygous for a transgene provided herein. In one aspect, a modified plant, seed, plant component, plant cell, or plant genome is homozygous for a mutation provided herein. In another aspect, a modified plant, seed, plant component, plant cell, or plant genome is heterozygous for a mutation provided herein. In one aspect, a modified plant, seed, plant component, plant cell, or plant genome is hemizygous for a mutation provided herein.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between different plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the $F_1$ generation. The term "$BC_1$" refers to the second use of the recurrent parent, "$BC_2$" refers to the third use of the recurrent parent, and so on. In one aspect, a backcross is performed repeatedly, with a progeny individual of each successive backcross generation being itself backcrossed to the same parental genotype.

As used herein, "elite variety" means any variety that has resulted from breeding and selection for superior agronomic performance.

As used herein, "selecting" or "selection" in the context of breeding refer to the act of picking or choosing desired individuals, normally from a population, based on certain pre-determined criteria.

In one aspect, tobacco plants provided herein are hybrid plants. Hybrids can be produced by preventing self-pollination of female parent plants (e.g., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting $F_1$ seed is harvested. Additionally, female sterile plants can also be used to prevent self-fertilization.

Plants can be used to form single-cross tobacco $F_1$ hybrids. Pollen from a male parent plant is manually transferred to an emasculated female parent plant or a female parent plant that is male sterile to form $F_1$ seed. Alternatively, three-way crosses can be carried out where a single-cross $F_1$ hybrid is used as a female parent and is crossed with a different male parent. As another alternative, double-cross hybrids can be created where the $F_1$ progeny of two different single-crosses are themselves crossed. Self-incompatibility can be used to particular advantage to prevent self-pollination of female parents when forming a double-cross hybrid.

In one aspect, a tobacco variety provided herein is male sterile. In another aspect, a tobacco variety provided herein is cytoplasmic male sterile (CMS). Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp. In another aspect, a tobacco variety provided herein is female sterile. As a non-limiting example, female sterile plants can be made by mutating the STIG1 gene. See, for example, Goldman et al. 1994, *EMBO Journal* 13:2976-2984.

As used herein, the term "sequence identity" or "identity" in the context of two polynucleotide or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity."

The use of the term "polynucleotide" is not intended to limit the present disclosure to polynucleotides comprising DNA. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, the term "polypeptide" refers to a chain of at least two covalently linked amino acids.

Nucleic acid molecules, polypeptides, or proteins provided herein can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized. In another aspect, an isolated polypeptide provided herein is substantially free of cellular material in preparations having less than about 30%, less than about 20%, less than about 10%, less than about 5%, or less than about 1% (by dry weight) of chemical precursors or non-protein-of-interest chemicals. Fragments of the disclosed polynucleotides and polypeptides encoded thereby are also encompassed by the present invention. Fragments of a polynucleotide may encode polypeptide fragments that retain the biological activity of the native polypeptide. Alternatively, fragments of a polynucleotide that are useful as hybridization probes or PCR primers using methods known in the art generally do not encode fragment polypeptides retaining biological activity. Fragments of a polynucleotide provided herein can range from at least about 20 nucleotides, about 50 nucleotides, about 70 nucleotides, about 100 nucleotides, about 150 nucleotides, about 200 nucleotides, about 250 nucleotides, about 300 nucleotides, and up to the full-length polynucleotide encoding the polypeptides of the invention, depending on the desired outcome.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting in plant cells one or more recombinant nucleic acids and polypeptides described here. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

In one aspect, the present disclosure also provides a method of reducing the level of one or more TSNAs in cured leaf from a tobacco plant, the method comprising increasing the level of one or more antioxidants in the tobacco plant by expressing a biosynthetic enzyme, a regulatory transcription factor, a transporter, a catabolic enzyme, or a combination thereof, for the one or more antioxidants. In another aspect, a method comprises expressing a gene promoting the production or accumulation of one or more antioxidants are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect, a method comprises expressing a gene promoting the production or accumulation of one or more antioxidants are selected from the group consisting of Delphnidin, Cyanidin, Procyanidin, Prodelphinidin, Hesperetin, Perlargonidin, Peonidin, Petunidin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C. In one aspect, a method does not substantially reduce the level of total alkaloids in the tobacco plant. In another aspect, a method does not substantially reduce the level of nicotine in the tobacco plant.

In one aspect, the present disclosure provides a method for reducing the level of one or more TSNAs in cured tobacco leaf or a tobacco product made therefrom, the method comprising increasing the level of one or more antioxidants in a tobacco plant via a transgene encoding or directly modulating an antioxidant biosynthetic enzyme, a regulatory transcription factor of an antioxidant, an antioxidant transporter, an antioxidant metabolic enzyme, or a combination thereof; and reducing the level of one or more TSNAs in cured tobacco leaf from the tobacco plant or a tobacco product made from the cured tobacco leaf.

In another aspect of a method described herein, a modified tobacco plant or leaf provided here has a similar leaf chemistry profile compared to a control plant when grown and cured under comparable conditions. Without being limiting, a leaf chemistry profile can comprise the amount of alkaloids (e.g., nicotine, nornicotine, anabasine, anatabine), malic acid, and reducing sugars (e.g., dextrose), or a combination thereof in a tobacco plant or tobacco leaf. In another aspect of a method described herein, a modified plant or leaf provided herein comprises a total alkaloids level within about 90%, within about 80%, within about 70%, within about 60%, within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the total alkaloids level of a control plant when grown and cured under comparable conditions. In another aspect of a method described herein, a modified plant or leaf provided herein comprises a total alkaloids level that is reduced by at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% compared to a control plant when grown and cured under comparable conditions. In another aspect of a method described herein, a modified plant or leaf provided herein comprises a nicotine level within about 90%, within about 80%, within about 70%, within about 60%, within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nicotine level of a control plant when grown and cured under comparable conditions. In another aspect of a method described herein, a modified plant or leaf provided herein comprises a nornicotine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the nornicotine level of a control plant when grown and cured under comparable conditions. In another aspect of a method described herein, a modified plant or leaf provided herein comprises an anabasine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anabasine level of a control plant when grown and cured under comparable conditions. In another aspect of a method described herein, a modified plant or leaf provided herein comprises an anatabine level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the anatabine level of a control plant when grown and cured under comparable conditions. In another aspect of a method described herein, a modified plant or leaf provided herein comprises a malic acid level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the malic acid level of a control plant when grown and cured under comparable conditions. In another aspect of a method described herein, a modified plant or leaf provided herein comprises a reducing sugars level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the reducing sugars level of a control plant when grown and cured under comparable conditions. In another aspect of a method described herein, a modified plant or leaf provided herein comprises a dextrose level within about 50%, within about 45%, within about 40%, within about 35%, within about 30%, within about 25%, within about 20%, within about 15%, within about 10%, within about 5%, within about 4%, within about 3%, within about 2%, within about 1%, or within about 0.5% of the dextrose level of a control plant when grown and cured under comparable conditions.

In another aspect of a method described herein, the level of one or more TSNAs reduces by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In a further aspect of a method described herein, cured leaf of the modified tobacco plant produces or comprises less than 2, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.15, less than 0.1, or less than 0.05 ppm total TSNAs. In a further aspect of a method described herein, cured leaf of the modified tobacco plant comprises between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 ppm total TSNAs. In a further aspect of a method described herein, cured leaf of the modified tobacco plant comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs. In a further aspect of a method described herein, one or more TSNAs are selected from the group consisting of N'-nitrosonornicotine (NNN), 4-methylnitrosoamino-1-(3-pyridyl)-1-butanone (NNK), N'-nitrosoanatabine (NAT), N'-nitrosoanabasine (NAB), and any combination thereof. In a further aspect of a method described herein, the TSNA reduction comprises a reduction of NNK. In a further aspect of a method described herein, the TSNA reduction consists of a reduction of NNK. In a further aspect of a method described herein, NNK is reduced below 0.08 parts per million, below 0.07 parts per million, below 0.06 parts per million, or below 0.05 parts per million, as measured in freeze-dried cured leaf samples using liquid chromatography with tandem mass spectrometry.

In another aspect of a method described herein, the tobacco plant comprises reduced nicotine demethylase activity compared to a control plant. In a further aspect of a method described herein, the tobacco plant comprises at least one mutation in a nicotine demethylase gene selected from the group consisting of CYP82E4, CYP82E5, CYP82E10, and a combination thereof. In another aspect of a method described herein, a method reduces nitrite levels in cured tobacco leaf comprising the transgene. In another aspect of a method described herein, a method increases the oxygen radical absorbance capacity level in cured tobacco leaf comprising the transgene. In another aspect of a method described herein, the one or more antioxidants that are increased in cured tobacco leaf comprising the transgene are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect of a method described herein, the one or more antioxidants that are increased in cured tobacco leaf comprising the transgene are selected from the group consisting of Delphnidin, Cyanidin, Procyanidin, Prodelphinidin, Hesperetin, Perlargonidin, Peonidin, Petunidin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C In a further aspect of a method described herein, a method does not substantially reduce the level of total alkaloids in a tobacco plant. In a further aspect of a method described herein, a method does not substantially reduce the level of nicotine in a tobacco plant. In an aspect of a method described herein, a transgene encodes or directly modulates a biosynthetic enzyme, a regulatory transcription factor, a transporter, a metabolic enzyme, or a combination thereof, for one or more antioxidants selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect of a method described herein, a transgene encodes or directly modulates a biosynthetic enzyme, a regulatory transcription factor, a transporter, a metabolic enzyme, or a combination thereof, for one or more antioxidants selected from the group consisting of Delphnidin, Cyanidin, Procyanidin, Prodelphinidin, Hesperetin, Perlargonidin, Peonidin, Petunidin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C In another aspect of a method described herein, the transgene encodes a protein comprising a sequence having at least 50%, 55%, 60%, 65%, 70%, 75%, 80%, 85%, 90%, 95%, 97%, 98%, 99%, or 100% identity to a sequence selected from the group consisting of SEQ ID Nos: 1 to 23, 47 to 52, 64 to 65, and 68 to 70.

In one aspect, the present disclosure provides a method for reducing the level of one or more TSNAs in cured tobacco leaf or a tobacco product made therefrom, a method comprising increasing the level of one or more antioxidants in a tobacco plant via a genetic modification in an endogenous gene, wherein the endogenous gene encodes an antioxidant biosynthetic enzyme, a regulatory transcription factor of an antioxidant, an antioxidant transporter, an antioxidant metabolic enzyme, or a combination thereof; and reducing the level of one or more TSNAs in cured tobacco leaf from the tobacco plant or a tobacco product made from the cured tobacco leaf. In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In a further aspect of a method described herein, one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In further aspect of a method described herein, the TSNA reduction comprises a reduction of NNK. In a further aspect of a method described herein, the TSNA reduction consists of a reduction of NNK. In a further aspect of a method described herein, NNK is reduced below 0.08 parts per million as measured in freeze-dried cured leaf samples using liquid chromatography with tandem mass spectrometry.

In another aspect of a method described herein, a tobacco plant comprises reduced nicotine demethylase activity compared to a control plant. In a further aspect of a method described herein, a tobacco plant comprises at least one mutation in a nicotine demethylase gene selected from the group consisting of CYP82E4, CYP82E5, CYP82E10, and a combination thereof. In another aspect of a method described herein, a method reduces nitrite levels in cured tobacco leaf comprising a transgene. In another aspect of a method described herein, a method increases the oxygen radical absorbance capacity level in cured tobacco leaf comprising a transgene. In another aspect of a method described herein, a method increases the oxygen radical absorbance capacity level in cured tobacco leaf comprising a transgene. In another aspect of a method described herein, one or more increased antioxidants are tobacco native antioxidants. In another aspect of a method described herein, the one or more antioxidants that are increased in cured tobacco leaf comprising a transgene are selected from the group consisting of anthocyanidin, flavanone, flavanol, flavone, flavonol, isoflavone, hydroxybenzoic acid, hydroxycinnamic acid, ellagitannin, stibene, lignan, carotenoids, and glycyrrhzin. In a further aspect of the method, the one or more antioxidants that are increased in cured tobacco leaf comprising the transgene are selected from the group consisting of Delphnidin, Cyanidin, Procyanidin, Prodelphinidin, Hesperetin, Perlargonidin, Peonidin, Petunidin, Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

In a further aspect of a method described herein, a method does not substantially reduce the level of total alkaloids in a tobacco plant. In a further aspect of a method described herein, a method does not substantially reduce the level of nicotine in a tobacco plant. In another aspect of a method described herein, an endogenous gene encodes a protein comprising a sequence having at least 50%, 55%, 60%, 65%, 70%, 75%, 80%, 85%, 90%, 95%, 97%, 98%, 99%, or 100% identity to a sequence selected from the group consisting of SEQ ID Nos: 1 to 23, 47 to 52, 64 to 65, and 68 to 70.

In one aspect, the present disclosure provides a method for manufacturing a tobacco product, the method comprising obtaining cured tobacco leaf comprising a transgene or comprising a genetic modification in an endogenous gene, and further comprising an increased level of one or more antioxidants compared to cured tobacco leaf control lacking a transgene or a genetic modification, wherein an endogenous gene encodes an antioxidant biosynthetic enzyme, a regulatory transcription factor of an antioxidant, an antioxidant transporter, an antioxidant metabolic enzyme, or a combination thereof, wherein a transgene encodes or directly modulates an antioxidant biosynthetic enzyme, a regulatory transcription factor of an antioxidant, an antioxidant transporter, an antioxidant metabolic enzyme, or a combination thereof; and producing a tobacco product from cured tobacco leaf, wherein a tobacco product comprises a reduced level of one or more TSNAs relative to a control tobacco product prepared from a control cured tobacco leaf. In another aspect of a method described herein, cured tobacco leaf comprises a transgene encoding or directly modulating an antioxidant biosynthetic enzyme, a regulatory transcription factor of an antioxidant, an antioxidant transporter, an antioxidant metabolic enzyme, or a combination thereof. In another aspect of a method described herein, cured tobacco leaf comprises a genetic modification in an antioxidant biosynthetic enzyme, a regulatory transcription factor of an antioxidant, an antioxidant transporter, an antioxidant metabolic enzyme, or a combination thereof.

In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a genetic modification in an endogenous gene. In another aspect of a method described herein, cured tobacco leaf comprises a reduced nitrite level compared to a control plant without a transgene. In another aspect of a method described herein, the cured tobacco leaf comprises a reduced nitrite level compared to a control plant without a genetic modification in an endogenous gene. In another aspect of a method described herein, cured tobacco leaf comprises an increased amount of phenylalanine compared to a control plant without a transgene. In another aspect of a method described herein, cured tobacco leaf comprises an increased amount of phenylalanine compared to a control plant without a genetic modification in an endogenous gene.

In one aspect, the present disclosure provides a method for preparing cured tobacco leaf, the method comprising growing a tobacco plant comprising a transgene or a genetic modification in an endogenous gene, and further comprising an increased level of one or more antioxidants compared to a control cured tobacco leaf lacking a transgene or a genetic modification, wherein an endogenous gene encodes an antioxidant biosynthetic enzyme, a regulatory transcription factor of an antioxidant, an antioxidant transporter, an antioxidant metabolic enzyme, or a combination thereof, wherein a transgene encodes or directly modulates an antioxidant biosynthetic enzyme, a regulatory transcription factor of an antioxidant, an antioxidant transporter, an antioxidant metabolic enzyme, or a combination thereof; and preparing cured leaf from a tobacco plant, wherein cured leaf comprises a reduced level of one or more TSNAs relative to a control cured leaf from a control tobacco plant not comprising a transgene or a genetic modification. In another aspect of a method described herein, cured tobacco leaf comprises a transgene encoding or directly modulating an antioxidant biosynthetic enzyme, a regulatory transcription factor of an antioxidant, an antioxidant transporter, an antioxidant metabolic enzyme, or a combination thereof. In another aspect of a method described herein, cured tobacco leaf comprises a genetic modification in an antioxidant biosynthetic enzyme, a regulatory transcription factor of an antioxidant, an antioxidant transporter, an antioxidant metabolic enzyme, or a combination thereof.

In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a transgene. In another aspect of a method described herein, the level of one or more TSNAs is reduced by at least 50%, by at least 45%, by at least 40%, by at least 35%, by at least 30%, by at least 25%, by at least 20%, by at least 15%, by at least 10%, or by at least 5%, compared to cured leaf from a control tobacco plant not comprising a genetic modification in an endogenous gene. In another aspect of a method described herein, cured tobacco leaf comprises a reduced nitrite level compared to a control plant without a transgene. In another aspect of a method described herein, cured tobacco leaf comprises a reduced nitrite level compared to a control plant without a genetic modification in an endogenous gene. In another aspect of a method described herein, cured tobacco leaf comprises an increased amount of phenylalanine compared to a control plant without a transgene. In another aspect of a method described herein, cured tobacco leaf comprises an increased amount of phenylalanine compared to a control plant without a genetic modification in an endogenous gene.

In one aspect, the present disclosure provides cured leaf of a modified tobacco plant, wherein cured leaf comprises a reduced level of one or more tobacco-specific nitrosamines (TSNAs) and further comprises an increased level of one or more antioxidants and a reduced nitrite level, wherein reduced and increased levels are compared to a control cured leaf of an unmodified tobacco plant of the same variety when grown and cured under comparable conditions, wherein a modification comprises a transgene or a genetic modification in an endogenous gene, wherein a transgene or an endogenous gene encodes an antioxidant biosynthetic enzyme, a regulatory transcription factor of an antioxidant, an antioxidant transporter, an antioxidant metabolic enzyme, or a combination thereof; wherein a modified tobacco plant does not comprise a transgene overexpressing an *Arabidopsis* PAP1 protein.

In a further aspect of a method described herein, cured leaf of the modified tobacco plant produces or comprises less than 2, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.15, less than 0.1, or less than 0.05 ppm total TSNAs. In a further aspect of a method described herein, cured leaf of the modified tobacco plant comprises between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 ppm total TSNAs. In a further aspect of a method described herein, cured leaf of the modified tobacco plant comprises between 2 and 0.05, between 1.8 and 0.1, between 1.5 and 0.15, between 1.2 and 0.2, between 1.0 and 0.3, between 0.8 and 0.4, or between 0.6 and 0.5 ppm total TSNAs. In a further aspect of a method described herein, one or more TSNAs are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof. In a further aspect of a method described herein, the TSNA reduction comprises a reduction of NNK. In a further aspect of a method described herein, the TSNA reduction consists of a reduction of NNK. In a further aspect of a method described herein, NNK is reduced below 0.08 parts per million, below 0.07 parts per million, below 0.06 parts per million, or below 0.05 parts per million, as measured in freeze-dried cured leaf samples using liquid chromatography with tandem mass spectrometry. In another aspect of a method described herein, a tobacco plant comprises reduced nicotine demethylase activity compared to a control plant. In a further aspect of a method described herein, a tobacco plant comprises at least one mutation in a nicotine demethylase gene selected from the group consisting of CYP82E4, CYP82E5, CYP82E10, and a combination thereof. In a further aspect of a method described herein, a method provides a tobacco product comprising cured leaf of a modified tobacco plant.

Having now generally described the disclosure, the same will be more readily understood through reference to the following examples that are provided by way of illustration, and are not intended to be limiting of the present disclosure, unless specified.

The following are exemplary embodiments of the present disclosure.

Embodiment 1. A method for reducing the amount of one or more Tobacco Specific Nitrosamines (TSNAs) in a cured leaf of a tobacco plant, said method comprising the steps of:
- increasing the amount of phenylalanine in said tobacco plant via a transgene encoding or targeting a phenylalanine biosynthetic enzyme, a regulator of phenylalanine biosynthesis, or a phenylalanine metabolic enzyme; and
- reducing the amount of said one or more TSNAs in a cured leaf of said tobacco plant or a tobacco product made from said cured tobacco leaf.

Embodiment 2. A method for reducing the amount of one or more TSNAs in a cured leaf of a tobacco plant, said method comprising the steps of:
- increasing the amount of phenylalanine in said tobacco plant via a genetic modification in an endogenous gene, wherein said endogenous gene encodes a phenylalanine biosynthetic enzyme, a regulator of phenylalanine biosynthesis, or a phenylalanine metabolic enzyme; and
- reducing the amount of said one or more TSNAs in a cured leaf of said tobacco plant or a tobacco product made from said cured tobacco leaf.

Embodiment 3. A method for increasing the amount of one or more anthocyanins in a cured leaf of a tobacco plant, said method comprising the steps of:
- increasing the amount of phenylalanine in said tobacco plant via a transgene encoding or targeting a phenylalanine biosynthetic enzyme, a regulator of phenylalanine biosynthesis, or a phenylalanine metabolic enzyme; and
- increasing the amount of one or more anthocyanins in a cured leaf of said tobacco plant or a tobacco product made from said cured tobacco leaf.

Embodiment 4. A method for increasing the amount of one or more anthocyanins in a cured leaf of a tobacco plant, said method comprising the steps of:
- increasing the amount of phenylalanine in said tobacco plant via a genetic modification in an endogenous gene, wherein said endogenous gene encodes a phenylalanine biosynthetic enzyme, a regulator of phenylalanine biosynthesis, or a phenylalanine metabolic enzyme; and
- increasing the amount of one or more anthocyanins in a cured leaf of said tobacco plant or a tobacco product made from said cured tobacco leaf.

Embodiment 5. The method of any one of embodiments 1 to 4, wherein said method further comprises reducing the amount of total alkaloids by at least 10% in a cured leaf compared to a cured tobacco leaf or a tobacco product from a control tobacco plant not comprising said modification.

Embodiment 6. The method of embodiment 1 or 2, wherein the amount of said one or more TSNAs is reduced by at least 50% compared to a cured tobacco leaf or a tobacco product from a control tobacco plant not comprising said transgene.

Embodiment 7. The method of embodiment 1 or 2, wherein said cured tobacco leaf comprises less than 2 ppm total TSNAs.

Embodiment 8. The method of embodiment 1 or 2, wherein said cured tobacco leaf comprises between 2 and 0.05 ppm total TSNAs.

Embodiment 9. The method of embodiment 1 or 2, wherein said cured tobacco leaf comprises less than 0.08 ppm 4-methylnitrosoamino-1-(3-pyridyl)-1-butanone (NNK), wherein the level of said total TSNAs is measured based on a freeze-dried cured leaf sample using liquid chromatograph with tandem mass spectrometry (LC/MS/MS).

Embodiment 10. The method of embodiment 1 or 2, wherein said one or more tobacco-specific nitrosamines (TSNAs) are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof.

Embodiment 11. The method of embodiment 3 or 4, wherein said one or more anythocyanins is selected from the group consisting of Delphnidin, Cyanidin, Procyanidin, Prodelphinidin, Hesperetin, Perlargonidin, Peonidin, and Petunidin.

Embodiment 12. The method of embodiment 3 or 4, further comprising the step of reducing the amount of said one or more TSNAs in a cured leaf of said tobacco plant or a tobacco product made from said cured tobacco leaf.

Embodiment 13. The method of embodiment 12, wherein the amount of said one or more TSNAs is reduced by at least 50% compared to a cured tobacco leaf or a tobacco product from a control tobacco plant not comprising said transgene.

Embodiment 14. The method of embodiment 12, wherein said cured tobacco leaf comprises less than 2 ppm total TSNAs.

Embodiment 15. The method of embodiment 12, wherein said cured tobacco leaf comprises between 2 and 0.05 ppm total TSNAs.

Embodiment 16. The method of embodiment 12, wherein said cured tobacco leaf comprises less than 0.08 ppm 4-methylnitrosoamino-1-(3-pyridyl)-1-butanone (NNK), wherein the level of said total TSNAs is measured based on a freeze-dried cured leaf sample using liquid chromatograph with tandem mass spectrometry (LC/MS/MS).

Embodiment 17. The method of embodiment 12, wherein said one or more tobacco-specific nitrosamines (TSNAs) are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof.

Embodiment 18. The method of any one of embodiments 1 to 4, wherein said regulator of phenylalanine biosynthesis is a regulatory transcription factor.

Embodiment 19. The method of any one of embodiments 1 to 4, wherein said cured leaf of a tobacco plant is selected from the group consisting of air-cured Burley tobacco, air-cured dark tobacco, fire-cured dark tobacco, and Oriental tobacco.

Embodiment 20. The method of any one of embodiments 1 to 4, wherein said tobacco plant is selected from the group consisting of a flue-cured variety, a Burley variety, a Maryland variety, a dark variety, and an Oriental variety.

Embodiment 21. The method of any one of embodiments 1 to 4, further comprising increasing the amount of one or more antioxidants in said cured leaf of a tobacco plant.

Embodiment 22. The method of embodiment 21, wherein said one or more antioxidants are selected from the group consisting of flavanone, flavanol, flavone, flavonol, isoflavone, hydroxybenzoic acid, hydroxycinnamic acid, ellagitannin, stibene, lignan, carotenoids, and glycyrrhzin.

Embodiment 23. The method of embodiment 21, wherein said one or more antioxidants are selected from the group consisting of Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 24. The method of embodiments 1 or 3, wherein said transgene encodes a chorismate mutase-like polypeptide.

Embodiment 25. The method of embodiment 24, wherein said chorismate mutase-like polypeptide has at least 80% homology to a sequence selected from the group consisting of SEQ ID NOs: 68 to 70.

Embodiment 26. The method of embodiment 24, wherein said chorismate mutase-like polypeptide comprises a sequence selected from the group consisting of SEQ ID NOs: 68 to 70.

Embodiment 27. The method of embodiment 24, wherein said chorismate mutase-like polypeptide is encoded by a polynucleotide sequence having at least 80% homology to a sequence selected from the group consisting of SEQ ID NOs: 71 to 73.

Embodiment 28. The method of embodiment 24, wherein said chorismate mutase-like polypeptide is encoded by a polynucleotide sequence selected from the group consisting of SEQ ID NOs: 71 to 73.

Embodiment 29. The method of embodiments 2 or 4, wherein said endogenous gene encodes a chorismate mutase-like polypeptide.

Embodiment 30. The method of embodiment 29, wherein said chorismate mutase-like polypeptide has at least 80% homology to a sequence selected from the group consisting of SEQ ID NOs: 68 to 70.

Embodiment 31. The method of embodiment 29, wherein said chorismate mutase-like polypeptide comprises a sequence selected from the group consisting of SEQ ID NOs: 68 to 70.

Embodiment 32. The method of embodiment 29, wherein said chorismate mutase-like polypeptide is encoded by a polynucleotide sequence having at least 80% homology to a sequence selected from the group consisting of SEQ ID NOs: 71 to 73.

Embodiment 33. The method of embodiment 29, wherein said chorismate mutase-like polypeptide is encoded by a polynucleotide sequence selected from the group consisting of SEQ ID NOs: 71 to 73.

Embodiment 34. The method of embodiment 21, wherein said tobacco plant further comprises a transgene encoding or targeting an antioxidant biosynthetic enzyme, a regulatory transcription factor of an antioxidant, an antioxidant transporter, an antioxidant metabolic enzyme.

Embodiment 35. The method of embodiment 34, wherein said transgene encodes or targets a biosynthetic enzyme, a regulatory transcription factor, a transporter, a metabolic enzyme, or a combination thereof, for one or more antioxidants selected from the group consisting of flavanone, flavanol, flavone, flavonol, isoflavone, hydroxybenzoic acid, hydroxycinnamic acid, ellagitannin, stibene, lignan, carotenoids, and glycyrrhzin.

Embodiment 36. The method of embodiment 34, wherein said transgene encodes or targets a biosynthetic enzyme, a regulatory transcription factor, a transporter, a metabolic enzyme, or a combination thereof, for one or more antioxidants selected from the group consisting of Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 37. The method of embodiment 34, wherein said transgene encodes a protein comprising a sequence having at least 80% identity to a sequence selected from the group consisting of SEQ ID Nos. 1 to 23, 47 to 52, and 64 to 65.

Embodiment 38. The method of embodiment 34, wherein said endogenous gene encodes a protein comprising a sequence having at least 80% identity to a sequence selected from the group consisting of SEQ ID Nos. 1 to 23, 47 to 52, and 64 to 65.

Embodiment 39. A cured tobacco leaf of a modified tobacco plant, wherein said cured tobacco leaf comprises a decreased amount of one or more TSNAs and an increased amount of at least one Chorismate Mutase-like polypeptide, wherein said decreased and increased amounts are compared to an unmodified control tobacco plant.

Embodiment 40. A cured tobacco leaf of a modified tobacco plant, wherein said cured tobacco leaf comprises a decreased amount of one or more TSNAs and an increased amount of phenylalanine, wherein said decreased and increased amounts are compared to an unmodified control tobacco plant.

Embodiment 41. A cured tobacco leaf of a modified tobacco plant, wherein said cured tobacco leaf comprises a decreased amount of one or more TSNAs and an increased amount of one or more phenylalanine biosynthetic enzymes, regulators of phenylalanine biosynthesis, or phenylalanine metabolic enzymes, wherein said decreased and increased amounts are compared to an unmodified control tobacco plant.

Embodiment 42. The cured tobacco leaf of any one of embodiments 39 to 41, further comprising a reduced amount of total alkaloids that is a least 10% less than the total amount of alkaloids in an unmodified control tobacco plant.

Embodiment 43. The cured tobacco leaf of any one of embodiments 39 to 41, further comprising an increased amount of at least one polypeptide having at least 80% homology a sequence selected from the group consisting of SEQ ID Nos. 1 to 23, 47 to 52, and 64 to 65.

Embodiment 44. The cured tobacco leaf of any one of embodiments 39 to 41, further comprising an increased amount of at least one polypeptide having a sequence selected from the group consisting of SEQ ID Nos. 1 to 23, 47 to 52, and 64 to 65.

Embodiment 45. The cured tobacco leaf of any one of embodiments 39 to 41, wherein said chorismate mutase-like polypeptide has at least 80% homology to a sequence selected from the group consisting of SEQ ID NOs: 68 to 70.

Embodiment 46. The cured tobacco leaf of any one of embodiments 39 to 41, wherein said chorismate mutase-like polypeptide comprises a sequence selected from the group consisting of SEQ ID NOs: 68 to 70.

Embodiment 47. The cured tobacco leaf of any one of embodiments 39 to 41, wherein said chorismate mutase-like polypeptide is encoded by a polynucleotide sequence having at least 80% homology to a sequence selected from the group consisting of SEQ ID NOs: 71 to 73.

Embodiment 48. The cured tobacco leaf of any one of embodiments 39 to 41, wherein said chorismate mutase-like polypeptide is encoded by a polynucleotide sequence selected from the group consisting of SEQ ID NOs: 71 to 73.

Embodiment 49. The cured tobacco leaf of any one of embodiments 39 to 41, wherein the amount of said one or more TSNAs is reduced by at least 50% compared to a cured tobacco leaf or a tobacco product from a control tobacco plant not comprising said transgene.

Embodiment 50. The cured tobacco leaf of any one of embodiments 39 to 41, wherein said cured tobacco leaf comprises less than 2 ppm total TSNAs.

Embodiment 51. The cured tobacco leaf of any one of embodiments 39 to 41, wherein said cured tobacco leaf comprises between 2 and 0.05 ppm total TSNAs.

Embodiment 52. The cured tobacco leaf of any one of embodiments 39 to 41, wherein said cured tobacco leaf comprises less than 0.08 ppm 4-methylnitrosoamino-1-(3-pyridyl)-1-butanone (NNK), wherein the level of said total TSNAs is measured based on a freeze-dried cured leaf sample using liquid chromatograph with tandem mass spectrometry (LC/MS/MS).

Embodiment 53. The cured tobacco leaf of any one of embodiments 39 to 41, wherein said one or more tobacco-specific nitrosamines (TSNAs) are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof.

Embodiment 54. The cured tobacco leaf of any one of embodiments 39 to 41, wherein said cured leaf of a tobacco plant is selected from the group consisting of air-cured Burley tobacco, air-cured dark tobacco, fire-cured dark tobacco, and Oriental tobacco.

Embodiment 55. The cured tobacco leaf of any one of embodiments 39 to 41, wherein said tobacco plant is selected from the group consisting of a flue-cured variety, a Burley variety, a Maryland variety, a dark variety, and an Oriental variety.

Embodiment 56. The cured tobacco leaf of any one of embodiments 39 to 41, wherein said cured tobacco leaf is from a tobacco plant selected from the group consisting a BU 64 plant, a CC 101 plant, a CC 200 plant, a CC 13 plant, a CC 27 plant, a CC 33 plant, a CC 35 plant, a CC 37 plant, a CC 65 plant, a CC 67 plant, a CC 301 plant, a CC 400 plant, a CC 500 plant, CC 600 plant, a CC 700 plant, a CC 800 plant, a CC 900 plant, a CC 1063 plant, a Coker 176 plant, a Coker 319 plant, a Coker 371 Gold plant, a Coker 48 plant, a CU 263 plant, a DF911 plant, a *Galpao* plant, a GL 26H plant, a GL 338 plant, a GL 350 plant, a GL 395 plant, a GL 600 plant, a GL 737 plant, a GL 939 plant, a GL 973 plant, a GF 157 plant, a GF 318 plant, an RJR 901 plant, an HB 04P plant, a K 149 plant, a K 326 plant, a K 346 plant, a K 358 plant, a K394 plant, a K 399 plant, a K 730 plant, an NC 196 plant, an NC 37NF plant, an NC 471 plant, an NC 55 plant, an NC 92 plant, an NC2326 plant, an NC 95 plant, an NC 925 plant, a PVH 1118 plant, a PVH 1452 plant, a PVH 2110 plant, a PVH 2254 plant, a PVH 2275 plant, a VA 116 plant, a VA 119 plant, a KDH 959 plant, a KT 200 plant, a KT204LC plant, a KY 10 plant, a KY 14 plant, a KY 160 plant, a KY 17 plant, a KY 171 plant, a KY 907 plant, a KY 907LC plant, a KTY14×L8 LC plant, a Little Crittenden plant, a McNair 373 plant, a McNair 944 plant, a male sterile KY 14×L8 plant, a Narrow Leaf Madole plant, a MS KY171 plant, a Narrow Leaf Madole (phph) plant, a MS Narrow Leaf Madole plant, a MS TND950 plant, a PD 7302LC plant, a PD 7305LC plant, a PD 7309LC plant, a PD 7312LC plant, a PD 7318LC plant, a PD 7319LC plant, a MSTKS 2002 plant, a TKF 2002 plant, a TKF 6400 plant, a TKF 4028 plant, a TKF 4024 plant, a KT206LC plant, a KT209LC plant, a KT210LC plant, a KT212LC plant, an NC 100 plant, an NC 102 plant, an NC 2000 plant, an NC 291 plant, an NC 297 plant, an NC 299 plant, an NC 3 plant, an NC 4 plant, an NC 5 plant, an NC 6 plant, an NC7 plant, an NC 606 plant, an NC 71 plant, an NC 72 plant, an NC 810 plant, an NC BH 129 plant, an NC 2002 plant, a Neal Smith Madole plant, an OXFORD 207 plant, a 'Perique' plant, a PVH03 plant, a PVH09 plant, a PVH19 plant, a PVH50 plant, a PVH51 plant, an R 610 plant, an R 630 plant, an R 7-11 plant, an R 7-12 plant, an RG 17 plant, an RG 81 plant, an RG H51 plant, an RGH 4 plant, an RGH 51 plant, an RS 1410 plant, a Speight 168 plant, a Speight 172 plant, a Speight 179 plant, a Speight 210 plant, a Speight 220 plant, a Speight 225 plant, a Speight 227 plant, a Speight 234 plant, a Speight G-28 plant, a Speight G-70 plant, a Speight H-6 plant, a Speight H20 plant, a Speight NF3 plant, a TI 1406 plant, a TI 1269 plant, a TN 86 plant, a TN86LC plant, a TN 90 plant, a TN90LC plant, a TN 97 plant, a TN97LC plant, a TN D94 plant, a TN D950 plant, a TR (Tom Rosson) Madole plant, a VA 309 plant, and a VA 359 plant.

Embodiment 57. A tobacco product comprising the cured tobacco leaf of any one of embodiments 39 to 41.

Embodiment 58. The tobacco product of embodiment 57, wherein said tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

Embodiment 59. A bale of the cured tobacco leaf of any one of embodiments 39 to 41.

Embodiment 60. A container of tobacco product comprising the cured tobacco leaf of any one of embodiments 39 to 41.

Embodiment 61. The container of tobacco product of embodiment 60, wherein said contained is selected from the group consisting of a box, a can, a pack, a tin, and a pouch.

Embodiment 62. A population of the modified tobacco plants capable of producing the cured tobacco leaf of any one of embodiments 39 to 41.

Embodiment 63. The cured tobacco leaf of embodiment 41, wherein said wherein said regulator of phenylalanine biosynthesis is a regulatory transcription factor.

Embodiment 64. A method for reducing the amount of one or more Tobacco Specific Nitrosamines (TSNAs) in a cured leaf of a tobacco plant, said method comprising the steps of: introducing a transgene encoding or targeting a phenylalanine biosynthetic enzyme, a regulator of phenylalanine biosynthesis, or a phenylalanine metabolic enzyme; and reducing the amount of said one or more TSNAs in a cured leaf of said tobacco plant or a tobacco product made from said cured tobacco leaf.

Embodiment 65. A method for reducing the amount of one or more TSNAs in a cured leaf of a tobacco plant, said method comprising the steps of:

introducing a genetic modification in an endogenous gene, wherein said endogenous gene encodes a phenylalanine biosynthetic enzyme, a regulator of phenylalanine biosynthesis, or a phenylalanine metabolic enzyme; and reducing the amount of said one or more TSNAs in a cured leaf of said tobacco plant or a tobacco product made from said cured tobacco leaf.

Embodiment 66. The method of embodiment 64 or 65, wherein said method further comprises reducing the amount of total alkaloids by at least 10% in a cured leaf compared to a cured tobacco leaf or a tobacco product from a control tobacco plant not comprising said modification.

Embodiment 67. The method of embodiment 64 or 65, wherein the amount of said one or more TSNAs is reduced by at least 50% compared to a cured tobacco leaf or a tobacco product from a control tobacco plant not comprising said transgene.

Embodiment 68. The method of embodiment 64 or 65, wherein said cured tobacco leaf comprises less than 2 ppm total TSNAs.

Embodiment 69. The method of embodiment 64 or 65, wherein said cured tobacco leaf comprises between 2 and 0.05 ppm total TSNAs.

Embodiment 70. The method of embodiment 64 or 65, wherein said cured tobacco leaf comprises less than 0.08 ppm 4-methylnitrosoamino-1-(3-pyridyl)-1-butanone (NNK), wherein the level of said total TSNAs is measured based on a freeze-dried cured leaf sample using liquid chromatograph with tandem mass spectrometry (LC/MS/MS).

Embodiment 71. The method of embodiment 64 or 65, wherein said one or more tobacco-specific nitrosamines (TSNAs) are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof.

Embodiment 72. The method of embodiment 64 or 65, wherein the amount of said one or more TSNAs is reduced by at least 50% compared to a cured tobacco leaf or a tobacco product from a control tobacco plant not comprising said transgene.

Embodiment 73. The method of embodiment 64 or 65, wherein said regulator of phenylalanine biosynthesis is a regulatory transcription factor.

Embodiment 74. The method of embodiment 64 or 65, wherein said cured leaf of a tobacco plant is selected from the group consisting of air-cured Burley tobacco, air-cured dark tobacco, fire-cured dark tobacco, and Oriental tobacco.

Embodiment 75. The method of embodiment 64 or 65, wherein said tobacco plant is selected from the group consisting of a flue-cured variety, a Burley variety, a Maryland variety, a dark variety, and an Oriental variety.

Embodiment 76. The method of embodiment 64 or 65, further comprising increasing the amount of one or more antioxidants in said cured leaf of a tobacco plant.

Embodiment 77. The method of embodiment 76, wherein said one or more antioxidants are selected from the group consisting of flavanone, flavanol, flavone, flavonol, isoflavone, hydroxybenzoic acid, hydroxycinnamic acid, ellagitannin, stibene, lignan, carotenoids, and glycyrrhzin.

Embodiment 78. The method of embodiment 76, wherein said one or more antioxidants are selected from the group consisting of Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 79. The method of embodiment 64, wherein said transgene encodes a chorismate mutase-like polypeptide.

Embodiment 80. The method of embodiment 79, wherein said chorismate mutase-like polypeptide has at least 80% homology to a sequence selected from the group consisting of SEQ ID NOs: 68 to 70.

Embodiment 81. The method of embodiment 79, wherein said chorismate mutase-like polypeptide comprises a sequence selected from the group consisting of SEQ ID NOs: 68 to 70.

Embodiment 82. The method of embodiment 79, wherein said chorismate mutase-like polypeptide is encoded by a polynucleotide sequence having at least 80% homology to a sequence selected from the group consisting of SEQ ID NOs: 71 to 73.

Embodiment 83. The method of embodiment 79, wherein said chorismate mutase-like polypeptide is encoded by a polynucleotide sequence selected from the group consisting of SEQ ID NOs: 71 to 73.

Embodiment 84. The method of embodiment 65, wherein said endogenous gene encodes a chorismate mutase-like polypeptide.

Embodiment 85. The method of embodiment 84, wherein said chorismate mutase-like polypeptide has at least 80% homology to a sequence selected from the group consisting of SEQ ID NOs: 68 to 70.

Embodiment 86. The method of embodiment 84, wherein said chorismate mutase-like polypeptide comprises a sequence selected from the group consisting of SEQ ID NOs: 68 to 70.

Embodiment 87. The method of embodiment 84, wherein said chorismate mutase-like polypeptide is encoded by a polynucleotide sequence having at least 80% homology to a sequence selected from the group consisting of SEQ ID NOs: 71 to 73.

Embodiment 88. The method of embodiment 84, wherein said chorismate mutase-like polypeptide is encoded by a polynucleotide sequence selected from the group consisting of SEQ ID NOs: 71 to 73.

Embodiment 89. The method of embodiment 64 or 65, wherein said tobacco plant further comprises a second transgene encoding or targeting an antioxidant biosynthetic enzyme, a regulatory transcription factor of an antioxidant, an antioxidant transporter, an antioxidant metabolic enzyme.

Embodiment 90. The method of embodiment 89, wherein said second transgene encodes or targets a biosynthetic enzyme, a regulatory transcription factor, a transporter, a metabolic enzyme, or a combination thereof, for one or more antioxidants selected from the group consisting of flavanone, flavanol, flavone, flavonol, isoflavone, hydroxybenzoic acid, hydroxycinnamic acid, ellagitannin, stibene, lignan, carotenoids, and glycyrrhzin.

Embodiment 91. The method of embodiment 89, wherein said second transgene encodes or targets a biosynthetic enzyme, a regulatory transcription factor, a transporter, a metabolic enzyme, or a combination thereof, for one or more antioxidants selected from the group consisting of Naringenin, Catechin, Epicatechin, Apigenin, Luteonin, Quercetin, Myricetin, Rutin, Genistein, Daidzein, Gallic acid, Vanillic acid, Protocatechuic acid, Ferunic acid, Cinnamic acid, Coumeric acid, Chlorogenic acid, Coffeic acid, ferulic acid, Sanguiin, Resveratrol, Sesamin, Caretonoids, and Vitamin C.

Embodiment 92. The method of embodiment 89, wherein said second transgene encodes a protein comprising a sequence having at least 80% identity to a sequence selected from the group consisting of SEQ ID NOs: 1 to 23, 47 to 52, and 64 to 65.

Embodiment 93. The method of embodiment 65, wherein said endogenous gene encodes a protein comprising a sequence having at least 80% identity to a sequence selected from the group consisting of SEQ ID NOs: 1 to 23, 47 to 52, and 64 to 65.

EXAMPLES

Example 1. Plant Transformation

Tobacco plants overexpressing a gene of interest are generated via *Agrobacterium*-mediated transformation. An expression vector, p45-2-7 (FIG. 2), is used as a backbone to generate multiple transformation vectors. p45-2-7 contains a CsVMV promoter, a NOS terminator, and a cassette comprising a kanamycin selection marker (NPT II) operably linked to an Actin2 promoter and a NOS terminator. Nucleic acid vectors comprising transgenes of interest are introduced into tobacco leaf discs via *Agrobacterium* transformation. See, for example, Mayo et al., 2006, *Nat Protoc.* 1:1105-11 and Horsch et al., 1985, *Science* 227:1229-1231.

Narrow Leaf Madole (NLM) tobacco plants are grown in Magenta™ GA-7 boxes and leaf discs are cut and placed into Petri plates. *Agrobacterium tumefaciens* cells comprising a transformation vector are collected by centrifuging a 20 mL cell suspension in a 50 mL centrifuge tube at 3500 RPM for 10 minutes. The supernatant is removed and the *Agrobacterium tumefaciens* cell pellet is re-suspended in 40 mL liquid re-suspension medium. Tobacco leaf, avoiding the midrib, are cut into eight 0.6 cm discs with a #15 razor blade and placed upside down in a Petri plate. A thin layer of Murashige & Skoog with B5 vitamins liquid re-suspension medium is added to the Petri plate and the leaf discs are poked uniformly with a fine point needle. About 25 mL of the *Agrobacterium tumefaciens* suspension is added to the Petri plate and the leaf discs are incubated in the suspension for 10 minutes.

Leaf discs are transferred to co-cultivation Petri plates (½ MS medium) and discs are placed upside down in contact with filter paper overlaid on the co-cultivation TOM medium (MS medium with 20 g/L sucrose; 1 mg/L indole-3-acetic acid; and 2.5 mg/L 6-benzyl aminopurine (BAP)). The Petri plate is sealed with parafilm prior to incubation in dim light (60-80 mE/ms) with 18 hours on, 6 hours off photoperiods at 24 degrees Celsius for three days. After incubation, leaf discs are transferred to regeneration/selection TOM K medium Petri plates (TOM medium plus 300 mg/L kanamycin). Leaf discs are sub-cultured bi-weekly to fresh TOM K medium in dim light with 18 hours on, 6 hours off photoperiods at 24 degrees Celsius until shoots become excisable. Shoots from leaf are removed with forceps and inserted in MS basal medium with 100 mg/L kanamycin. Shoots on MS basal medium with 100 mg/L kanamycin are incubated at 24 degrees Celsius with 18 hours on, 6 hours off photoperiods with high intensity lighting (6080 mE/ms) to induce rooting.

When plantlets containing both shoots and roots grow large enough (e.g., reach approximately half the height of a Magenta™ GA-7 box), they are transferred to soil. Established seedlings are transferred to a greenhouse for further analysis and to set seed. Control plants are either NLM plants that have not been transformed or NLM plants that have been transformed with an empty p45-2-7 vector.

Example 2. AtPAP1 Overexpressing Plants Comprise Reduced TSNAs

Figure 3:
FIG. 3: A control plant (left) exhibits a similar growth profile compared AtPAP1 overexpression plants (right). AtPAP1 plants exhibit a purple color due to anthocyanin accumulation.

Tobacco plants overexpressing AtPAP1 are generated via *Agrobacterium*-mediated transformation. AtPAP1, comprising SEQ ID NO:46, is incorporated into an overexpression vector and transformed into tobacco as described in Example 1. After transformation, established seedlings are transferred to a greenhouse for further analysis and to set seed. Transformed plants are developmentally similar to control plants except that they exhibit a purple color due to anthocyanin accumulation as shown in FIG. 3. To determine TSNA amounts, tobacco plants are grown under standard conditions and topped at flowering. Four to six weeks after topping, plants are harvested and leaf is cured using either air or fire curing methods.

Leaves are cured using both air and fire curing methods. The standard fire curing method used in this study is based on the 2017-2018 Burley and Dark Tobacco production guide (B. Pearce ed., (2017)). After the pre-curing methods described in Example 1 above, 15 sticks of tobacco from each of the five experimental varieties are placed in a barn. Each experimental barn is filled with all varieties at the same time. The first phase is the yellowing phase. Tobacco is allowed to yellow and the first firing is performed when yellowing is nearly complete. The first firing is performed between five and eight days after housing and the initial fires are about 100° F. Barn top ventilators are left open during this phase.

The second phase is color setting. Color setting begins when yellowing is completed which is indicated by a solid yellow leaf lamina with little or no brown color. During color setting the temperature is increased to between 37.7° C. and 46.1° C. (100° F. and 115° F.) with additional fires. Barn top ventilators are closed during this phase. Color setting conditions are maintained until the leaf lamina is a solid brown color. This phase lasts between 7 and 14 days and involves multiple firings. Ventilators are opened between firings. Brown color appearing one-half to two-thirds up the leaf indicates the end of the color setting phase.

The third phase is drying. During drying, ventilators are opened and heat is increase to no greater than 54.4° C. (130° F.). Drying is complete when little to no green color is present and when the tobacco lamina shatters when touched.

The final phase is finishing phase. After drying, barn temperatures are maintained at no greater than 48.9° C. (120° F.). The barn is ventilated for several days before two slow firings over a 10 to 14 day period to impart a smoke finish. Smoke volume is maximized to impart smoke finish characteristics to the leaf surface. The firing phase uses little to no ventilation.

The standard air curing method used in this study is based on the 2017-2018 Burley and Dark Tobacco production guide (B. Pearce ed., (2017)). After the pre-curing phase, 15 sticks of tobacco from each of the five experimental varieties are placed in a barn. Each experimental barn is filled with all varieties at the same time. Ventilators are used to maintain adequate air flow and to modulate temperature and humidity inside the barn. When mean daytime temperatures are above 26.6° C. (80° F.) and mean nighttime temperatures are above 15.5° C. (60° F.) barn doors and ventilators are open during the yellowing and color setting stages. During cool temperature conditions (mean daytime temperature below 18.3° C. (65° F.)), heat sources can be used to increase the barn temperature to no more than 32.2° C. (90° F.). At the end of the air-curing process, the tobacco is sampled for chemistry analysis.

The amounts of four TSNAs are measured: N'-nitrosonornicotine (NNN), 4-methylnitrosoamino-1-(3-pyridyl)-1-butanone (NNK), N'-nitrosoanatabine (NAT) and N'-nitrosoanabasine (NAB) are measured. Cured leaf samples are freeze dried and crushed to 1 mm. For TSNA analysis, 750 mg of crushed, freeze-dried leaf is added to 30 mls of 10 mM ammonium acetate. After incubation in a shaker for 30 minutes, approximately 4 mls of sample is transferred into disposable culture tubes containing 0.25 ml of concentrated ammonium hydroxide. The sample is vortexed briefly and 1.5 mls is added to a prewashed and conditioned extraction cartridge with a flow rate of 1 to 2 drops per second. Analytes are eluted from the sample using 1.5 mls of 70:30 methanol with 0.1% acetic acid. Samples are analyzed using liquid chromatography with tandem mass spectrometry (LC/MS/MS).

Figure 4A:
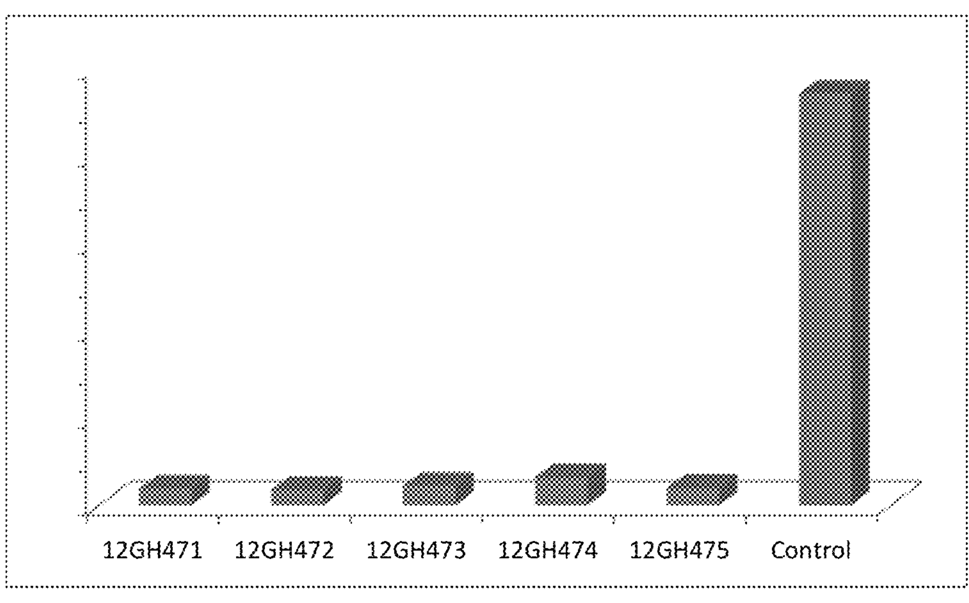
FIG. 4A: total TSNAs are reduced in AtPAP1 overexpression lines.
Figures 4B, 4C, 4D, 4E:
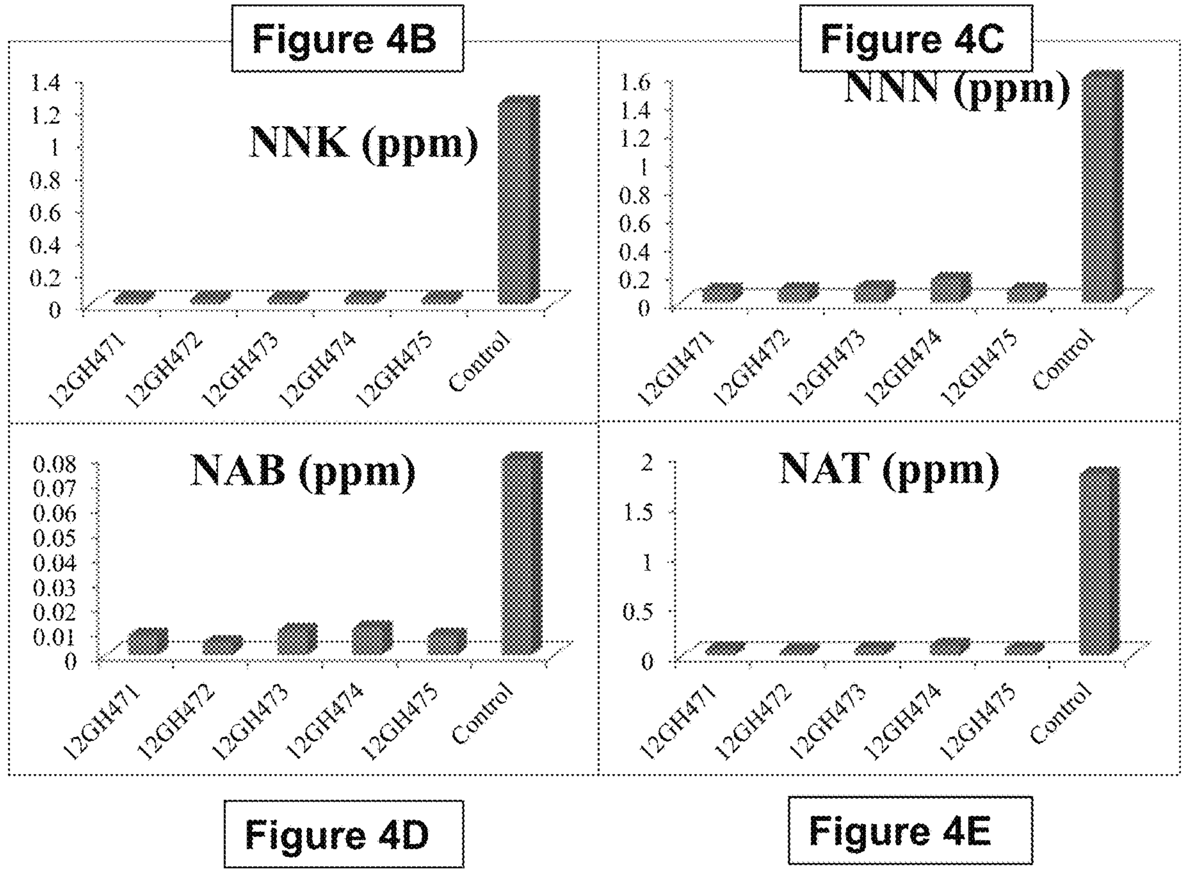
FIG. 4B: NNN levels are reduced in AtPAP1 overexpression lines compared to controls.
FIG. 4C: NNK levels are reduced in AtPAP1 overexpression lines compared to controls.
FIG. 4D: NAB levels are reduced in AtPAP1 overexpression lines compared to controls.
FIG. 4E: NAT levels are reduced in AtPAP1 overexpression lines compared to controls.

The effect of AtPAP1 overexpression on TSNA levels is determined for five $T_1$ AtPAP1 overexpression lines (six plants each) after cultivation in the greenhouse. Measurements of NNN, NNK, NAB, and NAT in $T_0$ AtPAP1 overexpressing plants are shown in Table 1. Total TSNA levels are considerably reduced in AtPAP1 plants as shown in FIG. 4A. Considerable reductions in NNK levels (FIG. 4B), NNN levels (FIG. 4C), NAB levels (FIG. 4D), and NAT levels (FIG. 4E) are also observed.

The effect of AtPAP1 overexpression on TSNA levels is consistent in subsequent generations grown under field conditions. Total TSNA levels, as well as the levels of NNN, NNK, NAT, and NAB, are consistently reduced under both air and fire cured conditions for $T_2$. (See Table 2).

TABLE 1

TSNA levels in AtPAP1 overexpression plants are reduced compared to controls.

| Plant ID | Variety | NNN (ppm) | NNK (ppm) | NAB (ppm) | NAT (ppm) | Total TSNA (ppm) | % TSNA Reduction |
|---|---|---|---|---|---|---|---|
| 12GH471 | t-NL Madole LC T821 (PAP1 OEX) | 0.087 | 0.035 | 0.008 | 0.059 | 0.189 | 95.98 |
| 12GH472 | t-NL Madole LC T824 (PAP1 OEX) | 0.091 | 0.031 | 0.005 | 0.048 | 0.175 | 96.28 |

TABLE 1-continued

TSNA levels in AtPAP1 overexpression plants are reduced compared to controls.

| Plant ID | Variety | NNN (ppm) | NNK (ppm) | NAB (ppm) | NAT (ppm) | Total TSNA (ppm) | % TSNA Reduction |
|---|---|---|---|---|---|---|---|
| 12GH473 | t-NL Madole LC T827 (PAP1 OEX) | 0.105 | 0.037 | 0.01 | 0.069 | 0.221 | 95.30 |
| 12GH474 | t-NL Madole LC T827 (PAP1 OEX) | 0.164 | 0.043 | 0.011 | 0.103 | 0.321 | 93.18 |
| 12GH475 | t-NL Madole LC T836 (PAP1 OEX) | 0.089 | 0.036 | 0.008 | 0.067 | 0.2 | 95.75 |
| Control | NL Madole | 1.581 | 1.232 | 0.079 | 1.812 | 4.704 | — |

TABLE 2

TSNA levels in AtPAP1 overexpressing plants grown in a field and air or fire cured. S5759 is a control line and TS3615 and TS3617 are independently derived AtPAP1 overexpressing lines.

| | | NNN (ppm) | NNK (ppm) | NAB (ppm) | NAT (ppm) | Total TSNA (ppm) |
|---|---|---|---|---|---|---|
| Fire-Cured | S5759 | 2.96 | 0.85 | 0.27 | 4.36 | 8.44 |
| | TS3615 | 0.66 | 0.29 | 0.06 | 0.82 | 1.83 |
| | TS3617 | 0.88 | 0.37 | 0.08 | 1.06 | 2.39 |
| Air-Cured | S5759 | 0.62 | 0.08 | 0.03 | 0.68 | 1.41 |
| | TS3615 | 0.16 | 0.06 | 0.01 | 0.14 | 0.37 |
| | TS3617 | 0.13 | 0.06 | 0.01 | 0.12 | 0.32 |

Example 3. AtPAP1 Overexpressing Plants Exhibit Increased Oxygen Radical Absorbance Capacity The effect of AtPAP1 overexpression on oxidative capacity is determined for five $T_1$ AtPAP1 overexpression lines (six plants each) after cultivation in the greenhouse. Oxygen Radical Absorbance Capacity (ORAC) is measured to determine antioxidant activity in AtPAP1 overexpressing plants. Quenching of a Progallol Red (PGR) florescent probe is used to determine the ORAC measurement according to manufactures instruction (BioTek, Winooski, VT). Antioxidants are extracted from crushed tissue samples with a methanol/HCL extraction buffer (6/1, v/v). The samples are incubated for 30 minutes at 37° C. in a reaction mixture containing 75 mM phosphate buffer, pH 7.4, and 5 μM PGR. After incubation, 37° C. AAPH solution is added to the reaction mixture to a final concentration of 10 mM. Controls with all the solution components, but without the tissue samples, are used for comparison.

Figure 5:
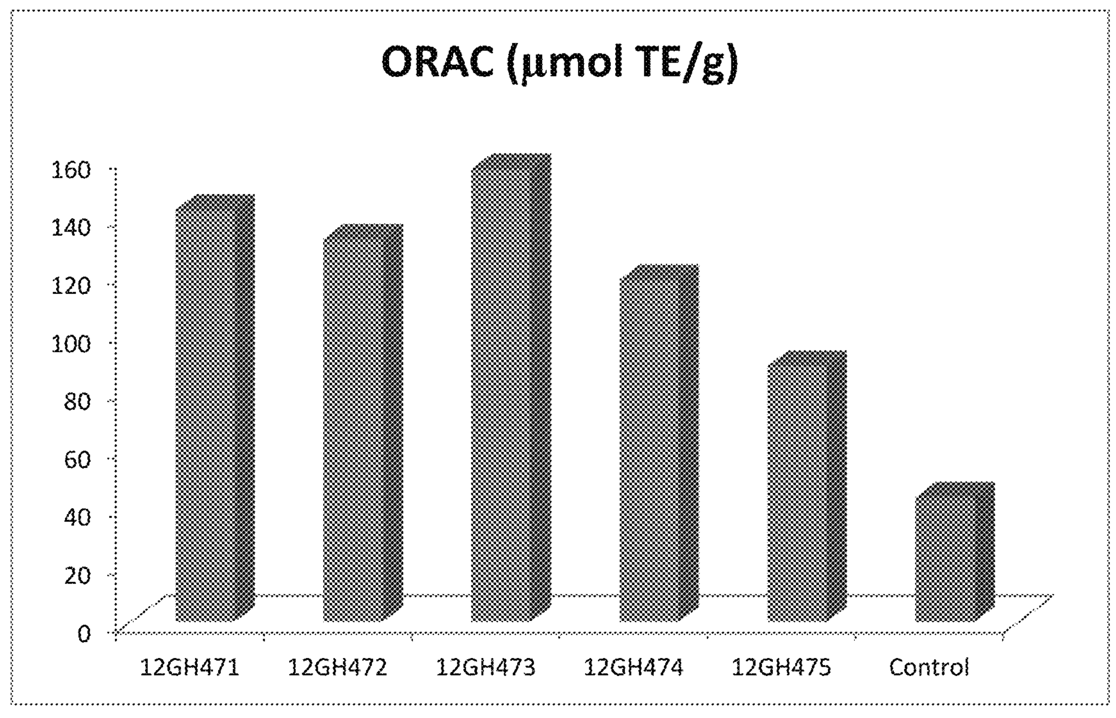
FIG. 5: Oxygen radical absorbance capacity (ORAC) values in AtPAP1 overexpression plants are increased compared to controls.

Reaction and control samples are shaken and the absorption (A) is recorded every 30 seconds for 180 minutes. The kinetic values are recorded as $A/A_{time0}$. ORAC scores are determined based on the Area Under Curve (AUC) values determined scores from the sample and blank. ORAC scores are assessed for all time-points until the $A/A_{time0}$ reaches a value of 0.2 using MicroCal Origin (R17.0, Boston, MA). ORAC values are recorded in FIG. 5 demonstrating increased ORAC values in AtPAP1 overexpression lines.

Example 4. Alkaloid Levels in Tobacco Plants Expressing AtPAP1

The effect of AtPAP1 overexpression on total alkaloid levels is determined for five T1 AtPAP1 overexpression lines (six plants each) after cultivation in the greenhouse. The levels of the alkaloids nicotine, nornicotine, anatabine, and anabasine are determined with Gas Chromatography followed by Mass Spectrometry (GC-MS). For example, measurement of anatabine is performed by mixing one gram of cured leaf tissue with 10 mls of 2N NaOH, followed by incubation at room temperature for fifteen minutes. Anatabine is then extracted by addition of 50 mls of 0.04% quinolone (w/v) dissolved in methyl-tert-butyl ether followed by rotation on a linear shaker for three hours. After phase separation, alkaloid levels are determined using an Agilent 6890 Gas Chromatograph and an Agilent 5973N Mass Spectrometer. The results of measurements for the alkaloids nicotine, nornicotine, anatabine, and anabasine are recorded in Table 3.

Alkaloid levels in field grown plants are also reduced after both air-curing and fire-curing. Tobacco plants overexpressing AtPAP1 are grown in a field, harvested, and both air and fire cured as described in Example 2. Total alkaloid levels are reduced under both air and fire curing conditions (See Table 4). The levels of nicotine, nornicotine, anatabine, and anabasine are also reduced under both air and fire curing conditions (SeeTable 4).

TABLE 3

Alkaloid levels in greenhouse grown AtPAPI overexpressing plants are mildly reduced compared to controls.

| Plant ID | Variety | Nicotine (% by wt) | Nornicotine (% by wt) | Anabasine (% by wt) | Anatabine (% by wt) |
|---|---|---|---|---|---|
| 12GH471 | t-NL Madole LC T821 (PAP1 OEX) | 3.679 | 0.046 | 0.009 | 0.038 |
| 12GH472 | t-NL Madole LC T824 (PAP1 OEX) | 3.009 | 0.089 | 0.008 | 0.034 |
| 12GH473 | t-NL Madole LC T827 (PAP1 OEX) | 4.323 | 0.073 | 0.011 | 0.048 |
| 12GH474 | t-NL Madole LC T827 (PAP1 OEX) | 4.609 | 0.052 | 0.009 | 0.037 |
| 12GH475 | t-NL Madole LC T836 (PAP1 OEX) | 3.329 | 0.036 | 0.008 | 0.034 |
| Control | NL Madole | 5.921 | 0.09 | 0.014 | 0.074 |

TABLE 4

TSNA levels in AtPAP1 overexpressing plants grown in a field and air or fire cured S5759 is a control line and TS3615 and TS3617 are independently derived AtPAP1 overexpressing lines.

| | | Nicotine (%) | Nornicotine (%) | Anabasine (%) | Anatabine (%) | Total Alkaloids (%) |
|---|---|---|---|---|---|---|
| Fire-Cured | S5759 | 5.973 | 0.073 | 0.018 | 0.101 | 6.164 |
| | TS3615 | 4.215 | 0.037 | 0.01 | 0.049 | 4.311 |
| | TS3617 | 4.533 | 0.038 | 0.011 | 0.048 | 4.629 |
| Air-Cured | S5759 | 7.117 | 0.181 | 0.022 | 0.13 | 7.449 |
| | TS3615 | 5.217 | 0.078 | 0.013 | 0.062 | 5.369 |
| | TS3617 | 5.51 | 0.059 | 0.014 | 0.063 | 5.646 |

Example 5. AtPAP1 Overexpressing Plants Comprise Reduced Nitrite

Figure 6A:
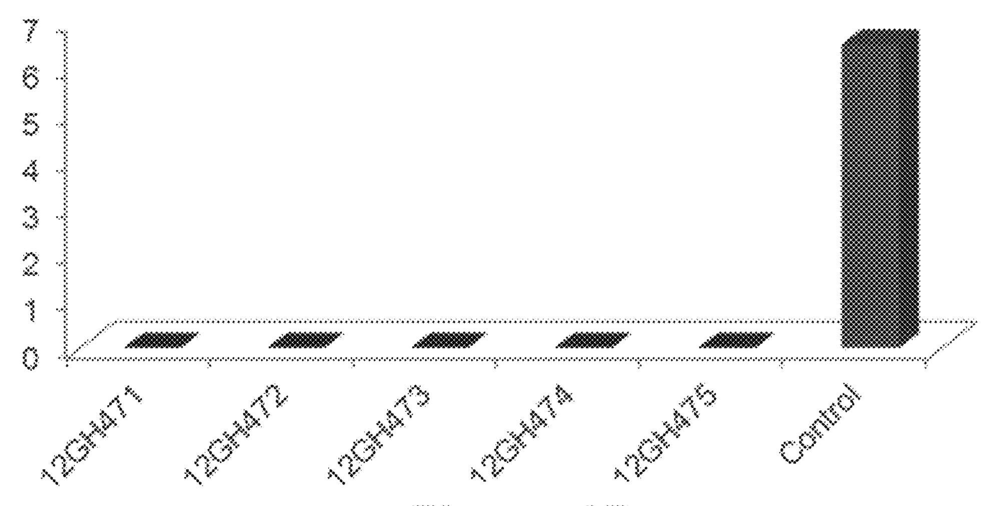
FIG. 6A: Nitrite levels in AtPAP1 overexpression plants are reduced compared to controls.
Figure 6B:
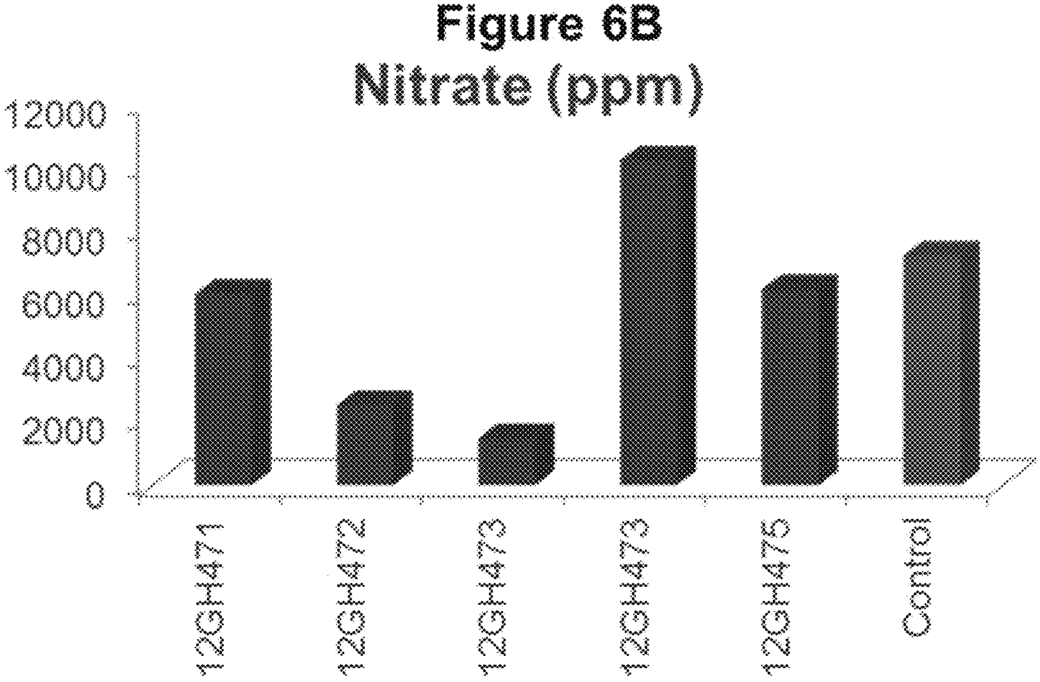
FIG. 6B: Nitrate levels in AtPAP1 overexpression plants are not consistently different from controls.

The effect of AtPAP1 overexpression on nitrite and nitrate levels is determined for five $T_1$ AtPAP1 overexpression lines (six plants each) after cultivation in the greenhouse. Cured leaf Samples are prepared as in Example 2 for LC/MS/MS and tested. Nitrite and nitrate levels as shown in FIG. 6A and FIG. 6B. The overexpression of AtPAP1 reduces the level of nitrite but not nitrate.

Figure 7:
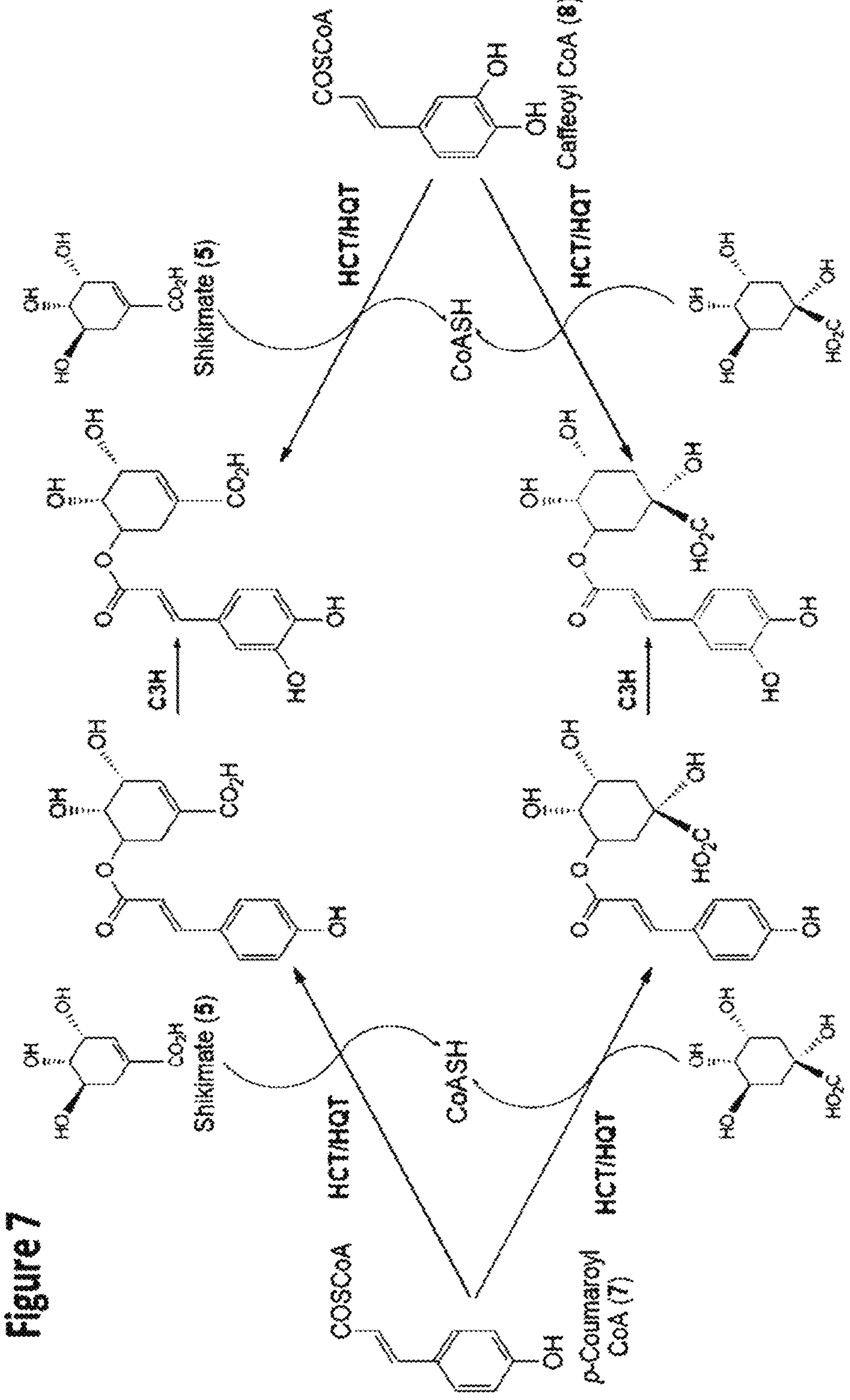
FIG. 7: HCT and HQT function in the biosynthetic pathway of Chlorogenic Acid.
Figure 8:
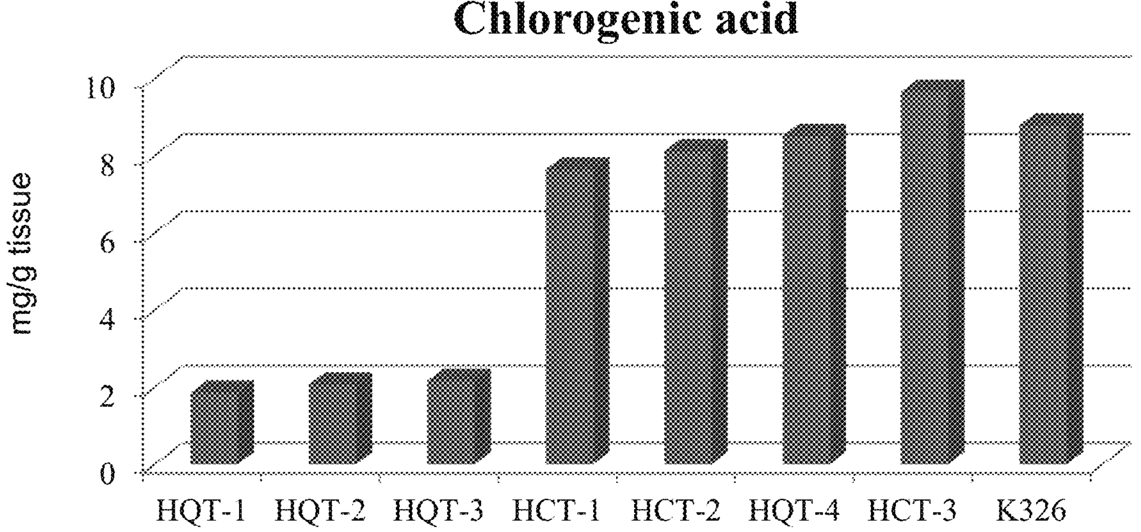
FIG. 8: Chlorogenic Acid levels are reduced in 3 of 4 HQT RNAi lines but not in HCT RNAi lines.
Figure 9:
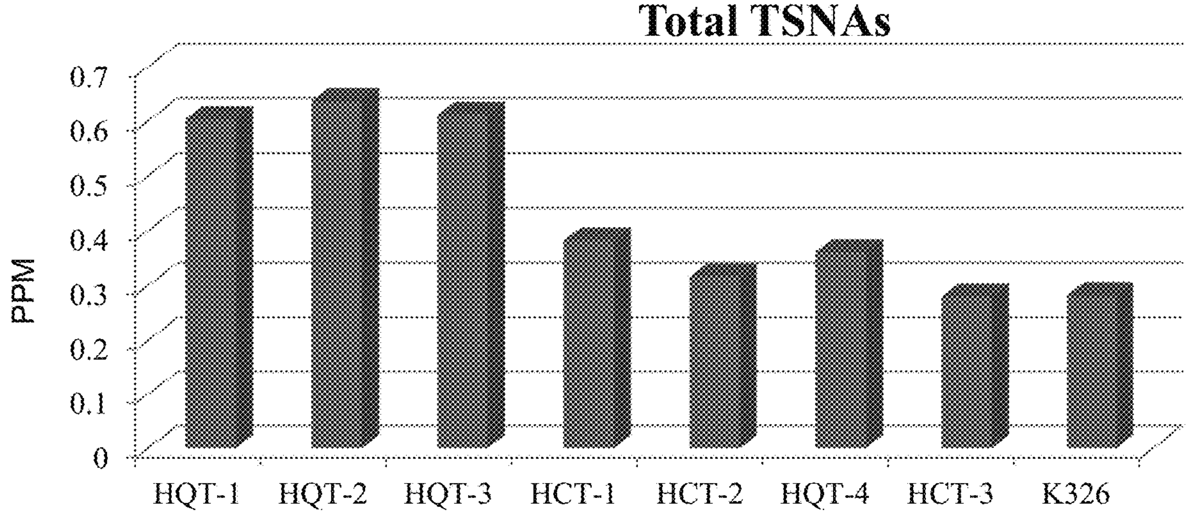
FIG. 9: Total TSNAs are increased in the 3 HQT RNAi lines with decreased Chlorogenic Acid levels.
Figure 12:
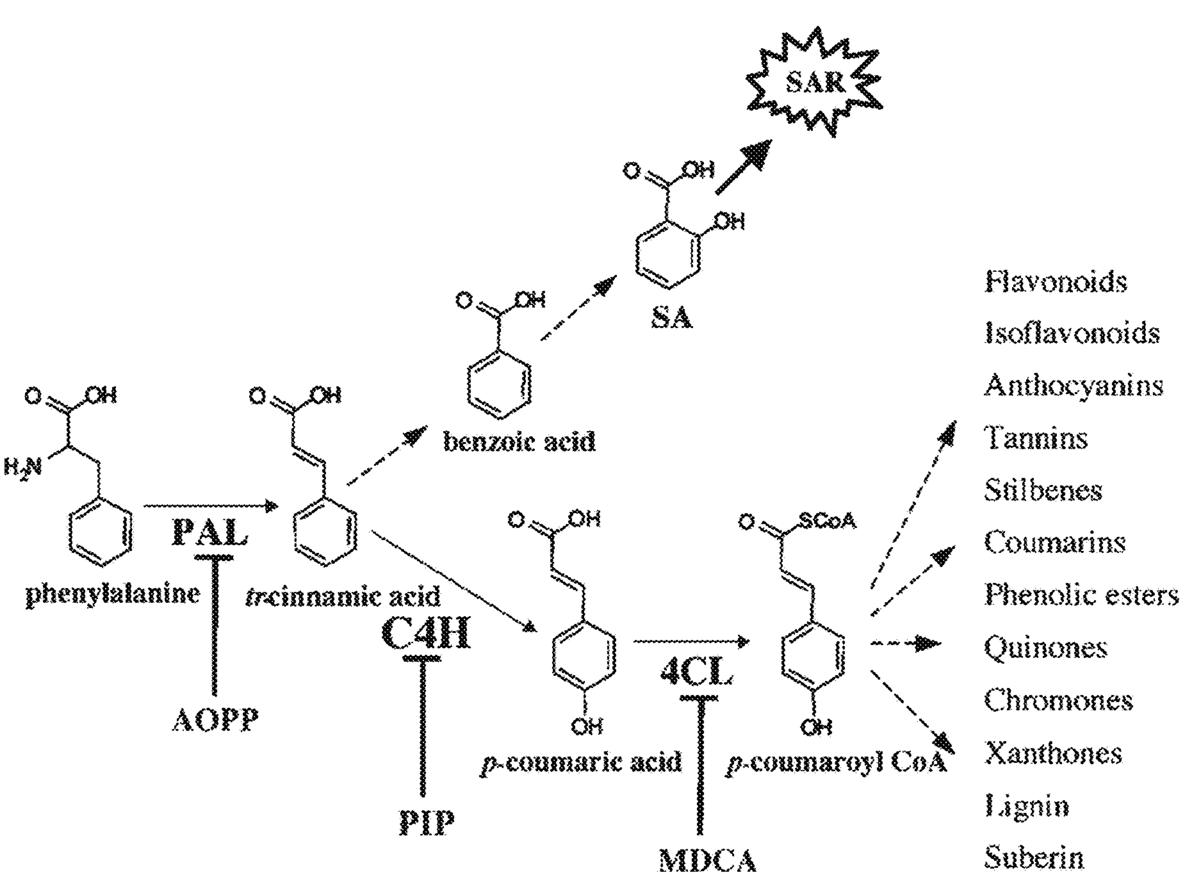
FIG. 12: The phenylpropanoid pathway leads to the biosynthesis of many antioxidants.

Example 6. Reduced Chlorogenic Acid in Tobacco Leaf Correlates with Elevated TSNA Levels The level of additional antioxidants are modulated to further demonstrate a negative correlation between antioxidants and TSNAs. Reduction of Chlorogenic acid (CGA) levels results in an increase in total TSNAs and total alkaloids. CGA or Caffeoyl quinate is generated from Caffeoyl CoA or p-Coumaroyl CoA through the activity of hydroxycinnamoyl-CoA quinate hydroxycinnamoyl transferase (HQT) and hydroxycinnamoyl-CoA shikimate/quinate hydroxycinnamoyl transferase (HCT) (Payyavula et al., 2015, Plant Biotechnology Journal, Hoffmann et al., 2004, The Plant Cell, FIG. 7). The activity of these enzymes is reduced in tobacco by silencing HCT and HQT with RNAi. Silencing HQT and HCT results in a reduction of CGA as shown in FIG. 8 and an increase in total TSNAs as shown in FIG. 9.

Transformation vectors comprising RNAi constructs are designed to inhibit the expression of tobacco genes that promote the conversion of Caffeoyl CoA or p-Coumaroyl CoA to CGA. Modified tobacco plants and control tobacco plants are created and grown as described in Example 1. Cured leaf samples from the modified tobacco plants are prepared for evaluation of TSNAs, alkaloids, and nitrite/nitrate as described in Examples 2, 4 and 5. Alkaloid levels show mild modulations as shown in Table 5. A negative correlation is observed between CGA levels and TSNA levels, as well as the levels of individual TSNAs (NNN, NNK, NAB, and NNA) as shown in FIG. 10A-E and Table 6. Nitrite levels are unchanged and nitrate levels show reductions compared to controls (Table 6).

TABLE 5

Alkaloid and CGA levels in HCT and HQT RNAi lines grown in a greenhouse.

| | | Nicotine (% by wt) | Nornicotine (% by wt) | Myosmine (% by wt) | Anabasine (% by wt) | Anatabine (% by wt) | CGA (mg/g) |
|---|---|---|---|---|---|---|---|
| K326 | HQT-1 | 3.90 | 0.10775 | 0.007918 | 0.0217 | 0.109775 | 1.8525 |
| K326 | HQT-2 | 4.10 | 0.112275 | 0.006815 | 0.022825 | 0.106125 | 2.07 |
| K326 | HQT-3 | 4.04 | 0.115 | 0.006995 | 0.021025 | 0.103175 | 2.17 |
| K326 | HCT-1 | 3.59 | 0.095625 | 0.006978 | 0.018425 | 0.091025 | 7.6375 |
| K326 | HCT-2 | 3.45 | 0.083525 | 0.005678 | 0.0178 | 0.085525 | 8.1075 |
| K326 | HQT-4 | 3.93 | 0.0972 | 0.00643 | 0.01985 | 0.10085 | 8.5025 |
| K326 | HCT-3 | 3.28 | 0.07795 | 0.006198 | 0.0154 | 0.074925 | 9.65 |
| K326 | Control | 3.45 | 0.09165 | 0.007213 | 0.018575 | 0.094975 | 8.775 |

TABLE 6

TSNA, CGA, Nitrite and Nitrate levels in HQT and HCT RNAi plants grown in a greenhouse.

| | | LL NNN (ppm) | LL NNK (ppm) | LL NAB (ppm) | LL NAT (ppm) | LL TSNA (ppm) | LL Nitrite (ppm) | LL Nitrate (ppm) | CGA (mg/g) |
|---|---|---|---|---|---|---|---|---|---|
| K326 | HQT-1 | 0.205 | 0.08425 | 0.02675 | 0.2875 | 0.6035 | 0.245 | 3192.5 | 1.8525 |
| K326 | HQT-2 | 0.2175 | 0.09825 | 0.0285 | 0.2925 | 0.63675 | 0.2 | 3257.5 | 2.07 |
| K326 | HQT-3 | 0.195 | 0.1265 | 0.02475 | 0.265 | 0.61125 | 0.22 | 2685 | 2.17 |
| K326 | HCT-1 | 0.13325 | 0.0635 | 0.02 | 0.165 | 0.38175 | 0.2 | 3285 | 7.6375 |
| K326 | HCT-2 | 0.0955 | 0.07025 | 0.02 | 0.13075 | 0.3165 | 0.2225 | 3202.5 | 8.1075 |
| K326 | HQT-4 | 0.11475 | 0.07 | 0.0215 | 0.155 | 0.36125 | 0.215 | 2655 | 8.5025 |

TABLE 6-continued

| TSNA, CGA, Nitrite and Nitrate levels in HQT and HCT RNAi plants grown in a greenhouse. | | | | | | | | |
|---|---|---|---|---|---|---|---|---|
| | LL NNN (ppm) | LL NNK (ppm) | LL NAB (ppm) | LL NAT (ppm) | LL TSNA (ppm) | LL Nitrite (ppm) | LL Nitrate (ppm) | CGA (mg/g) |
| K326 HCT-3 | 0.088 | 0.0635 | 0.02 | 0.1085 | 0.28 | 0.2525 | 2945.5 | 9.65 |
| K326 Control | 0.0885 | 0.0575 | 0.02 | 0.1165 | 0.2825 | 0.2 | 1862.5 | 8.775 |

Example 7: Increased antioxidant capacity in field grown AtPAP1 Overexpressing Plants A Ferric Reducing Antioxidant Power (FRAP) analysis is conducted on field grown tobacco plants overexpressing AtPAPL. AtPAP1 overexpression constructs are transformed into TN90 and Narrow Leaf Madole (NLM) tobacco plants as described in Example 1. Modified and unmodified control plants are grown in a field under standard field conditions. Plants are topped at flowering and leaves for analysis are collected harvest stage (4 weeks) later. At least five plants from two independent transgenic events in both the TN90 background and the NLM background and at least five plants from unmodified TN90 and NLM plants are sampled and tested. 10 mg of freeze dried leaf is taken into an Eppendorf tube and 1500 µl of 80% ethanol is added and sonicated for 10 minutes. After centrifuge, 5-10 µl of supernatant is used to measure antioxidant capacity.

The Ferric Reducing Antioxidant Power (FRAP) method is based on the reduction of complexes of 2,4,6-tripyridyl-s-triazine (TPTZ) with ferric chloride hexahydrate (FeCl3·6H2O) which forms blue ferrous complexes after its reduction (Benzie & Strain, 1996, Analytical Biochemistry, 239, 70-76). Three solutions are used for the assay: Solution 1) 10 mmol-L-1 solution of TPTZ (0.07802 g/25 mL), in 40 mM of hydrochloric acid; Solution 2) 20 mM solution of ferric chloride hexahydrate (0.13513 g/25 mL) in ACS water; Solution 3) 20 mM acetate buffer, pH 3.6 (weight of sodium acetate trihydrate is 0.27216 g in 100 mL ACS water, adjusted to the desired pH using HCl). These three solutions (TPTZ, FeCl3, acetate buffer) are mixed in a 1:1:10 ratio. A 245 L volume of the mixed solution is pipetted into a plastic cuvette with subsequent addition of a 5 µL sample (gallic acid, Trolox®). Absorbance is measured at primary X 593 nm wavelength. Different concentrations of Trolox® was used to make a standard curve and samples are compared to standard curve. Total antioxidants are calculated using the following equation $$\text{Antioxidants (nmol/mg)} = \frac{\text{nmoles present in the sample } X \text{ total sample extraction volume}}{\text{total wt of the sample } X \text{ volume used for measurement}}$$

Figure 13:
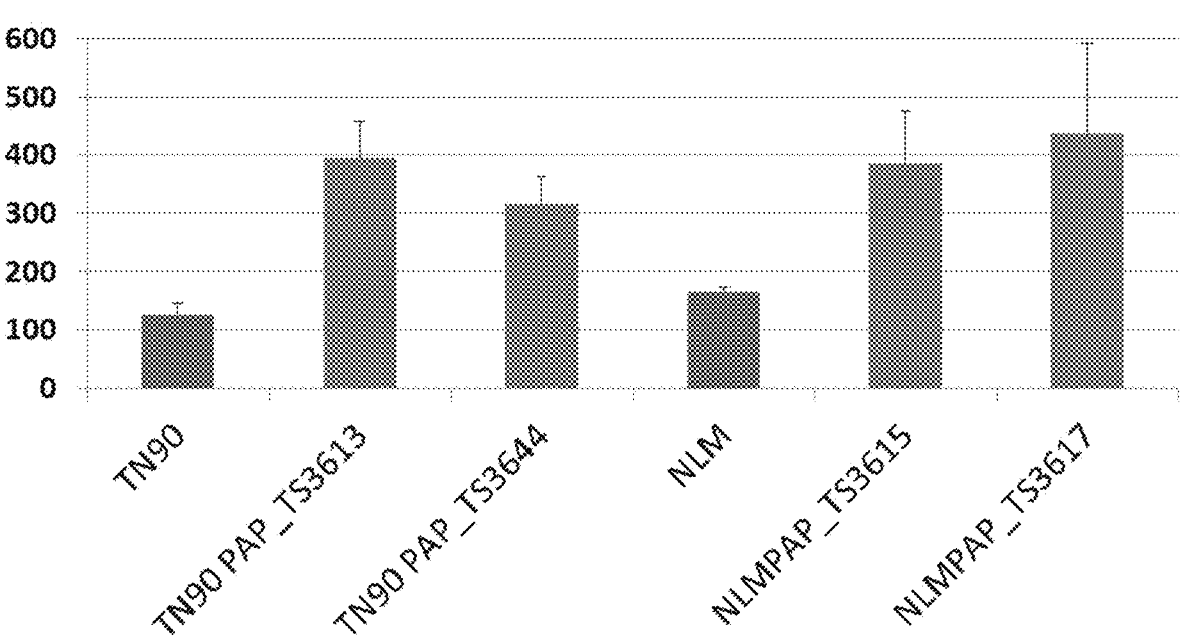
FIG. 13: Overexpression of AtPAP1 in TN90 and Narrow Leaf Madole (NLM) results in increased antioxidant capacity as measured using a FRAP assay. Measurements from leaves from at least five plants are averaged together for unmodified TN90 and NLM, two independent lines overexpressing AtPAP1 in TN90, and two independent lines overexpressing AtPAP1 in NLM are tested using a FRAP assay. Both independent lines overexpressing AtPAP1 in TN90 exhibit a highly significant increase in average antioxidant capacity ($P<0.01$) compared to unmodified TN90 plants. Both independent lines overexpressing AtPAP1 in NLM exhibit a highly significant increase in average antioxidant capacity ($P<0.01$) compared to unmodified NLM plants.

Modified tobacco plants overexpressing AtPAP1 show a significantly increased antioxidant capacity as measured by FRAP analysis compared to the unmodified controls (P<0.01) (FIG. 13).

Example 8. Secondary Metabolite accumulation in field grown AtPAP1 Overexpressing Plants A secondary metabolite accumulation analysis is conducted on field grown AtPAP1 overexpressing plants. AtPAP1 overexpression constructs are transformed into Narrow Leaf Madole (NLM) tobacco plants as described in Example 1. Modified and unmodified control plants are grown in a field under standard conditions. Plants are topped at flowering and leaves for analysis are collected two weeks later from two independently modified NLM plants (D1 and D2) and one unmodified NLM plant. A set of Benzenoids, Flavonoids, and Phenylpropanoids show significantly increased levels in modified plants compared to unmodified plants (P<0.01) (See Table 7).

The levels of the alkaloids nicotine, nornicotine, anatabine, and anabasine are determined with Gas Chromatography followed by Mass Spectrometry (GC-MS). For example, measurement of anatabine is performed by mixing one gram of cured leaf tissue with 10 mls of 2N NaOH, followed by incubation at room temperature for fifteen minutes. Anatabine is then extracted by addition of 50 mls of 0.04% quinolone (w/v) dissolved in methyl-tert-butyl ether followed by rotation on a linear shaker for three hours. After phase separation, alkaloid levels are determined using an Agilent 6890 Gas Chromatograph and an Agilent 5973N Mass Spectrometer.

TABLE 7

| Secondary metabolite accumulation in 35:AtPAP1 overexpressing Narrow Leaf Madole tobacco plants. | | | | | | | | | | | |
|---|---|---|---|---|---|---|---|---|---|---|---|
| | | Transgene Effects (FLOWERING) | | | | Transgene Effects (HARVEST) | | | | Transgene Effects (CURED) | |
| Sub Pathway | Biochemical Name | NP1_F/ NLMC_F | NP2_F/ NLMC_F | TP1_F/ TNC_F | TP2_F/ TNC_F | NP1_H/ NLMC_H | NP2_H/ NLMC_H | TP1_H/ TNC_H | TP2_H/ TNC_H | NP1_C/ NLMC_C | NP2_C/ NLMC_C |
| Alkaloids | cotinine | 0.38 | 0.51 | 0.41 | 0.64 | 0.47 | 0.32 | 0.41 | 0.35 | 0.76 | 0.72 |
| | nornicotine | 0.44 | 0.52 | 0.54 | 0.81 | 0.55 | 0.49 | 0.62 | 0.49 | 0.57 | 0.58 |
| | anatabine | 0.67 | 0.69 | 0.65 | 0.82 | 0.62 | 0.52 | 0.71 | 0.56 | 0.69 | 0.63 |
| | nicotine | 0.57 | 0.64 | 0.8 | 1.12 | 0.82 | 0.74 | 0.88 | 0.75 | 0.81 | 0.83 |
| | norcotinine | 0.09 | 0.26 | 0.1 | 0.2 | 0.39 | 0.34 | 0.44 | 0.25 | 0.49 | 0.5 |
| Benzenoids | 4-hydroxybenzoate | 5.33 | 4.8 | 3.52 | 2.91 | 3.25 | 2.85 | 6.87 | 7.37 | 1.95 | 1.9 |
| | protocatechuic acid-3-glucoside | 7.99 | 7.52 | 10.01 | 8.44 | 5.08 | 4.09 | 7.5 | 6.99 | 1 | 1 |

TABLE 7-continued

Secondary metabolite accumulation in 35:AtPAP1 overexpressing Narrow Leaf Madole tobacco plants.

| | | Transgene Effects (FLOWERING) | | | | Transgene Effects (HARVEST) | | | | Transgene Effects (CURED) | |
|---|---|---|---|---|---|---|---|---|---|---|---|
| Sub Pathway | Biochemical Name | NP1_F/ NLMC_F | NP2_F/ NLMC_F | TP1_F/ TNC_F | TP2_F/ TNC_F | NP1_H/ NLMC_H | NP2_H/ NLMC_H | TP1_H/ TNC_H | TP2_H/ TNC_H | NP1_C/ NLMC_C | NP2_C/ NLMC_C |
| Flavonoids | dihydrokaempferol | 4.48 | 7.74 | 16.46 | 7.73 | 13.57 | 15.88 | 22.2 | 14.24 | 8.64 | 11.66 |
| | dihydroquercetin | 2.8 | 1.35 | 1.13 | 1 | 1 | 15.84 | 2.38 | 9.99 | 1.41 | 1 |
| | naringenin | 4.55 | 5.71 | 3.52 | 2.37 | 3.27 | 3.48 | 2.84 | 2.78 | 4.67 | 8.62 |
| | naringenin 7-O-glucoside | 7.03 | 9.54 | 24.63 | 16.99 | 4.3 | 8.95 | 5.13 | 5.09 | 1 | 1 |
| | quercetin 3-galactoside | 1.44 | 1.52 | 1.64 | 2.19 | 0.73 | 51.7 | 3.93 | 19.21 | 8.46 | 8.43 |
| | rutin (quercetin 3-rutinoside) | 0.76 | 0.71 | 1.11 | 1.6 | 0.45 | 4.22 | 1.11 | 4.21 | 3.08 | 4.58 |
| | 3-methoxyapigenin | 1.04 | 1 | 0.49 | 0.67 | 0.69 | 0.69 | 0.52 | 1.03 | 1.12 | 0.93 |
| | kaempferol 3-O-glucoside/galactoside | 0.42 | 0.47 | 0.88 | 0.97 | 0.44 | 0.97 | 0.87 | 0.86 | 3.02 | 3.6 |
| | rutinose | 44.98 | 36.54 | 101.69 | 81.72 | 21.31 | 21.37 | 47.26 | 50.06 | 3.31 | 2.94 |
| Phenylpropanoids | chlorogenate | 2.1 | 2.01 | 2.25 | 2.13 | 2.63 | 47.37 | 1.33 | 8.85 | 3.61 | 5.35 |
| | 4-hydroxycinnamate | 2.03 | 2.13 | 5.11 | 2.55 | 5.85 | 4.17 | 5.2 | 5.04 | 3.21 | 3.31 |
| | ferulate | 2.28 | 4.44 | 2.31 | 2.11 | 1.6 | 1.13 | 1.13 | 1.04 | 1.38 | 1.4 |
| | sinapoyl aldehyde | 2.03 | 2.38 | 2.25 | 1.55 | 2.04 | 2.27 | 2.77 | 2.39 | 1.17 | 0.96 |
| | dihydroferulic acid | 2.61 | 3.58 | 4.61 | 5.16 | 3.37 | 2.52 | 3.72 | 3.76 | 1.04 | 1.03 |
| | coumaroylquinate (2) | 1.99 | 1.88 | 5.17 | 4.2 | 6.75 | 8.6 | 9.49 | 9.97 | 9.23 | 13.81 |
| | coumaroylquinate (4) | 3.71 | 3.28 | 7.38 | 5.59 | 8.46 | 10.56 | 7.56 | 8.59 | 4.44 | 7.28 |
| | coumaroylquinate (5) | 1.41 | 1.22 | 5.03 | 4.11 | 3.24 | 4.04 | 8.14 | 9.35 | 4.5 | 7.37 |
| | coumaroylquinate (3) | 0.99 | 0.92 | 2.95 | 2.62 | 1.84 | 2.15 | 3.58 | 4.39 | 2.88 | 4.82 |

NP1_F represents NLMPAP_TS3615 at flowering time;
NP2_F represents NLMPAP_TS3617 at flowering time;
NP1_H represents NLMPAP_TS3615 at harvest time;
NP2_H represents NLMPAP_TS3617 at harvest time;
NLMCF represents NL Madole Control at flowering time;
NLMC_H represents NL Madole Control at harvest time;
TP1_F represents TN90PAP_TS3613 at flowering time;
TP2_F represents NLMPAP_TS3644 at flowering time;
TP1_F represents TN90PAP_TS3613 at harvest time;
TP2_F represents NLMPAP_TS3644 at harvest time;
TNC_F represents TN90 Control at flowering time; and
TNC_H represents TN90 Control at harvest time.

Example 9. Expression of Additional Genes to Modulate TSNA Levels

Transformation vectors and modified tobacco plants are generated to overexpress full-length coding sequences from tobacco genes (e.g., SEQ ID NOs: 24-42, 44, 45, 53 to 58, 66 to 67, and 71 to 73) or non-tobacco origin genes (e.g., SEQ ID NOs: 43 and 46) that promote or are involved in the production or accumulation of one or more antioxidants (See Table 8). The overexpression of transcription factors that promote or are involved in the production or accumulation of one or more antioxidants is described below.

Figure 14:
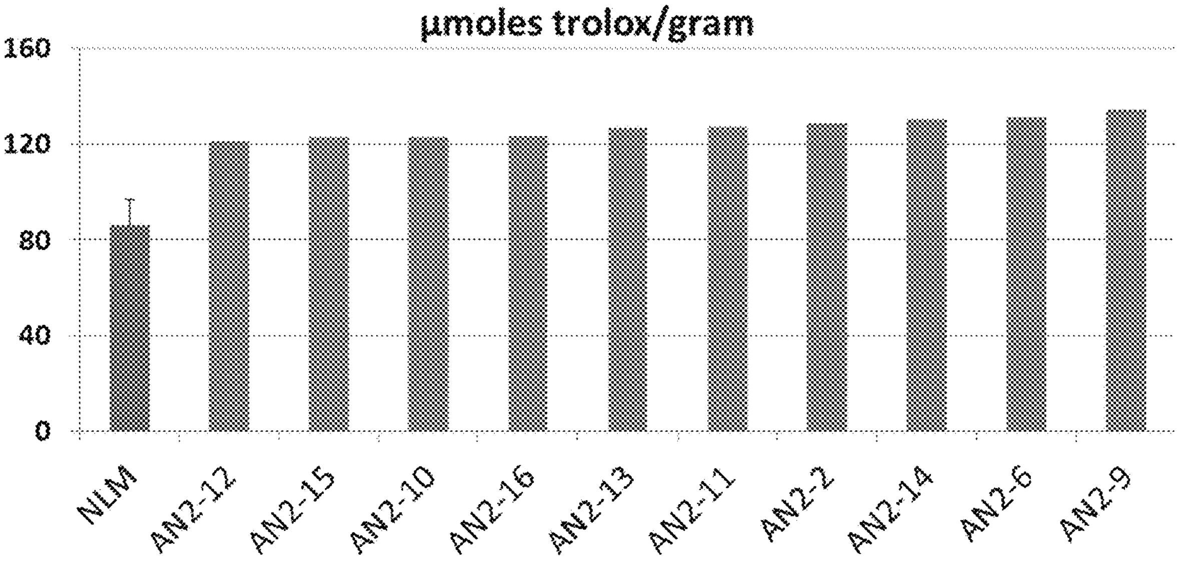
FIG. 14: Overexpression of NtAN2 (SEQ ID NO: 30) in NLM results in increased antioxidant capacity as measured using a FRAP assay. Greenhouse grown, individually tested TO plants overexpressing NtAN2 show increased antioxidant capacity compared to the average antioxidant capacity determined for at least five unmodified NLM plants.

NtAN2, SEQ ID NO: 30, is incorporated into a p45-2-7 transformation vector, and modified tobacco plants are generated, according to Example 1. Modified NLM tobacco plants (To and $T_1$ generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in $T_0$ plants as described in Example 7. Increased antioxidant capacity is detected in individual field grown $T_0$ plants compared to the average antioxidant capacity determined for at least five unmodified Narrow leaf Madole plants (FIG. 14).

Figure 15:
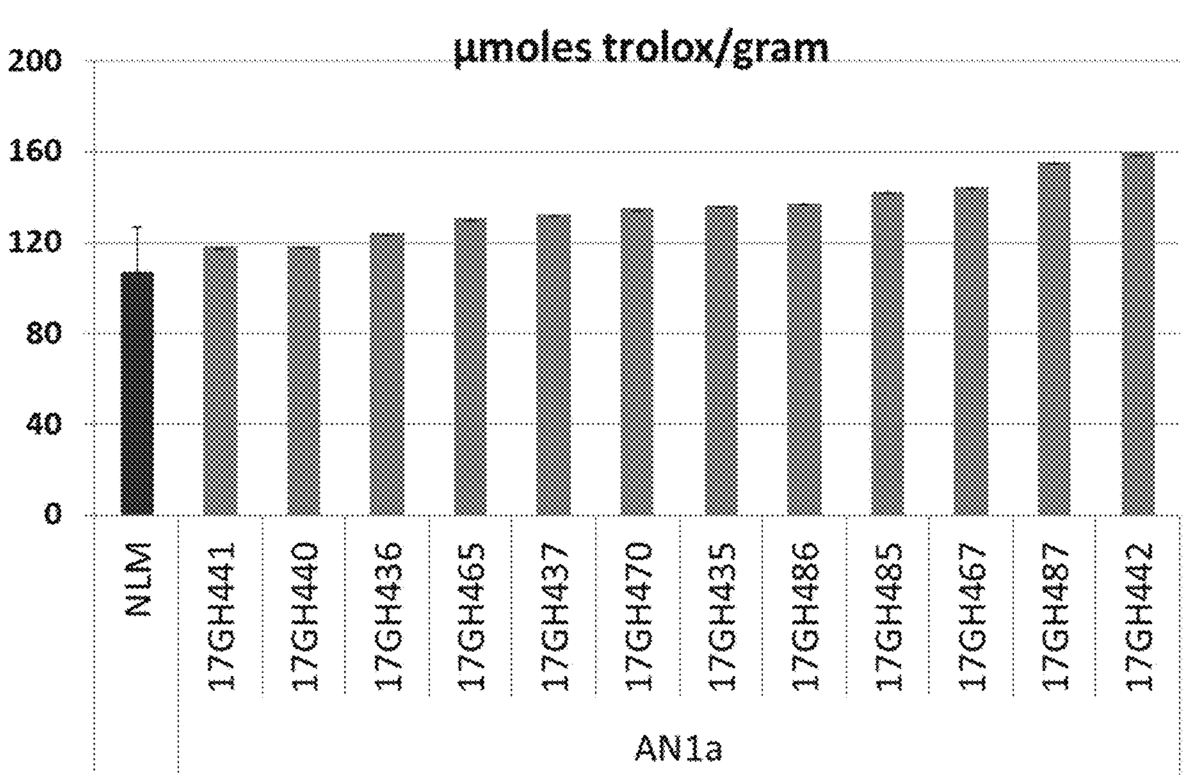
FIG. 15: Overexpression of NtAN1a (SEQ ID NO: 28) in NLM results in increased antioxidant capacity as measured using a FRAP assay. Greenhouse grown, individually tested TO plants overexpressing NtAN1a show increased antioxidant capacity compared to the average antioxidant capacity determined for at least five unmodified NLM plants.

NtAN1a, SEQ ID NO: 28, is incorporated into a p45-2-7 transformation vector, and modified tobacco plants are generated, according to Example 1. Modified NLM tobacco plants (To and $T_1$ generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in $T_0$ plants as described in Example 7. Increased antioxidant capacity is detected in individual greenhouse grown $T_0$ plants compared to the average antioxidant capacity determined for at least five unmodified Narrow leaf Madole plants (FIG. 15).

Figure 16:
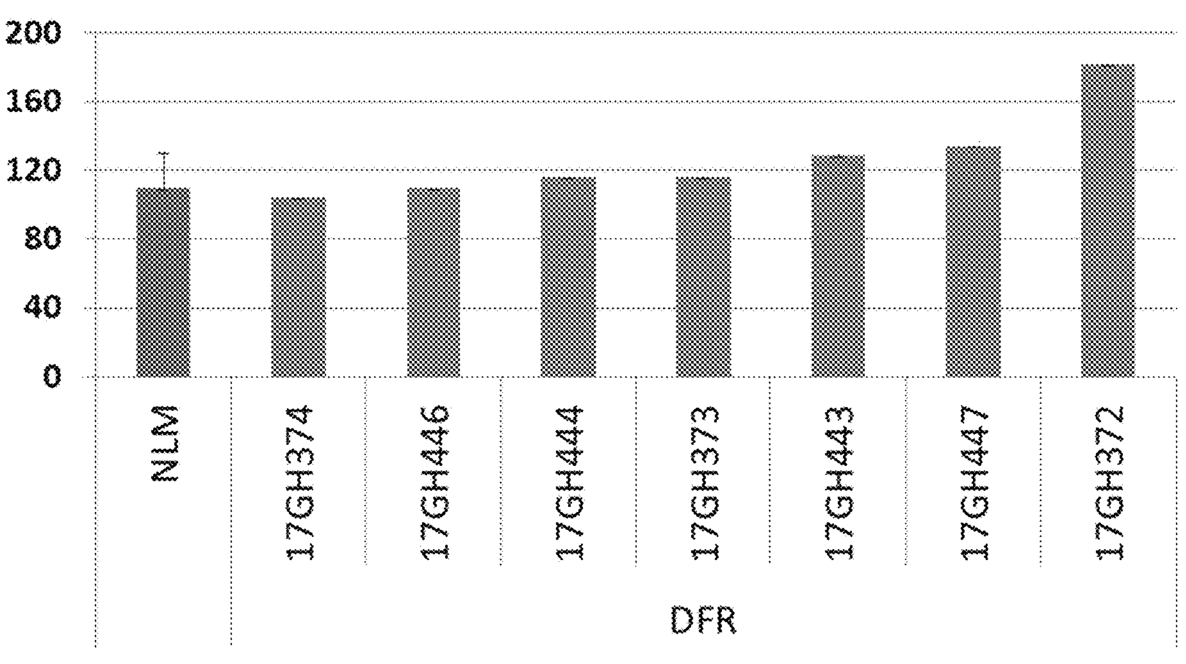
FIG. 16: Overexpression of NtDFR (SEQ ID NO: 37) in NLM results in increased antioxidant capacity as measured using a FRAP assay. Greenhouse grown, individually tested $T_0$ plants overexpressing NtDFR show increased antioxidant capacity compared to the average antioxidant capacity determined for at least five unmodified NLM plants.

NtDFR, SEQ ID NO: 37, is incorporated into a p45-2-7 transformation vector, and modified tobacco plants are generated, according to Example 1. Modified NLM tobacco plants (To and $T_1$ generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in $T_0$ plants as described in Example 7. Increased antioxidant capacity is detected in individual greenhouse grown $T_0$ plants compared to the average antioxidant capacity determined for at least five unmodified Narrow leaf Madole plants (FIG. 16).

Figure 17:
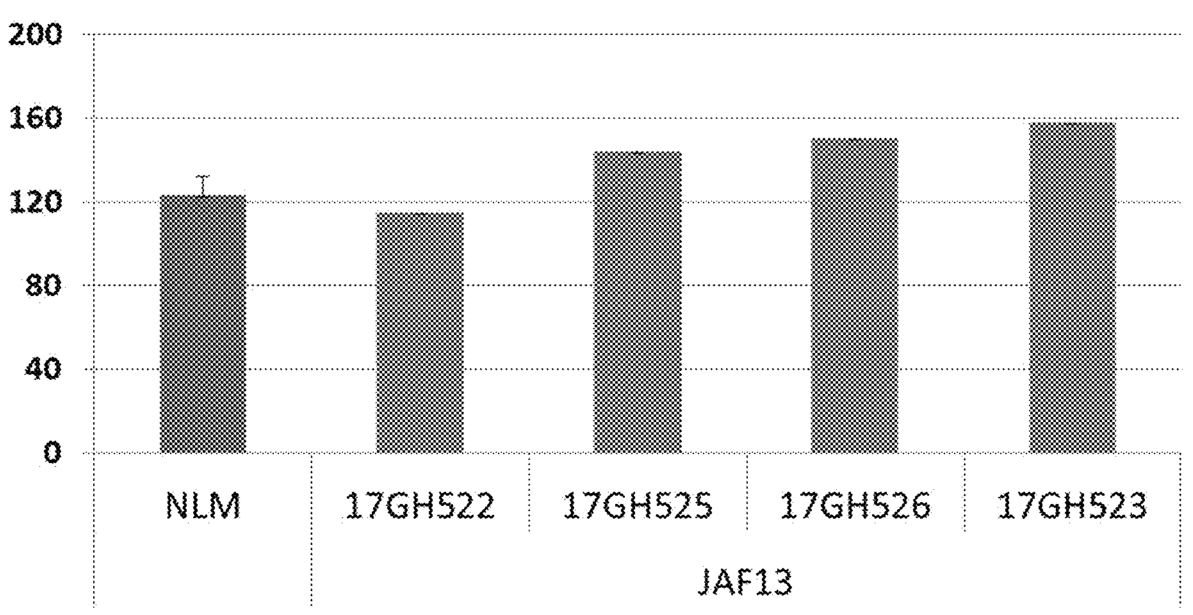
FIG. 17: Overexpression of NtJAF13 (SEQ ID NO: 33) in NLM results in increased antioxidant capacity as measured using a FRAP assay. Greenhouse grown, individually tested $T_0$ plants overexpressing NtJAF13 show increased antioxidant capacity compared to the average antioxidant capacity determined for at least five unmodified NLM plants.

NtJAF13, SEQ ID NO: 33, is incorporated into a p45-2-7 transformation vector, and modified tobacco plants are generated, according to Example 1. Modified NLM tobacco plants (To and $T_1$ generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in $T_0$ plants as described in Example 7. Increased antioxidant capacity is detected in individual greenhouse grown $T_0$ plants compared to the average antioxidant capacity determined for at least five unmodified Narrow leaf Madole plants (FIG. 17).

Figure 18:
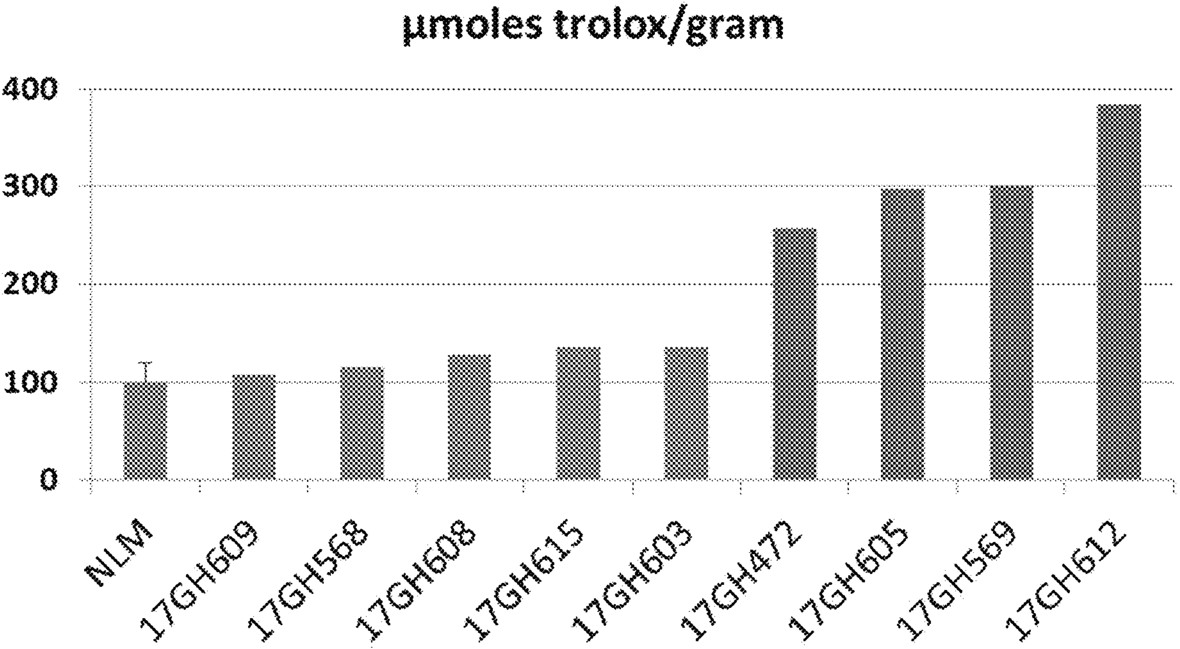
FIG. 18: Overexpression of NtMYB3 (SEQ ID NO: 36) in NLM results in increased antioxidant capacity as measured using a FRAP assay. Greenhouse grown, individually tested $T_0$ plants overexpressing NtMYB3 show increased antioxidant capacity compared to the average antioxidant capacity determined for at least five unmodified NLM plants.
Figure 19:
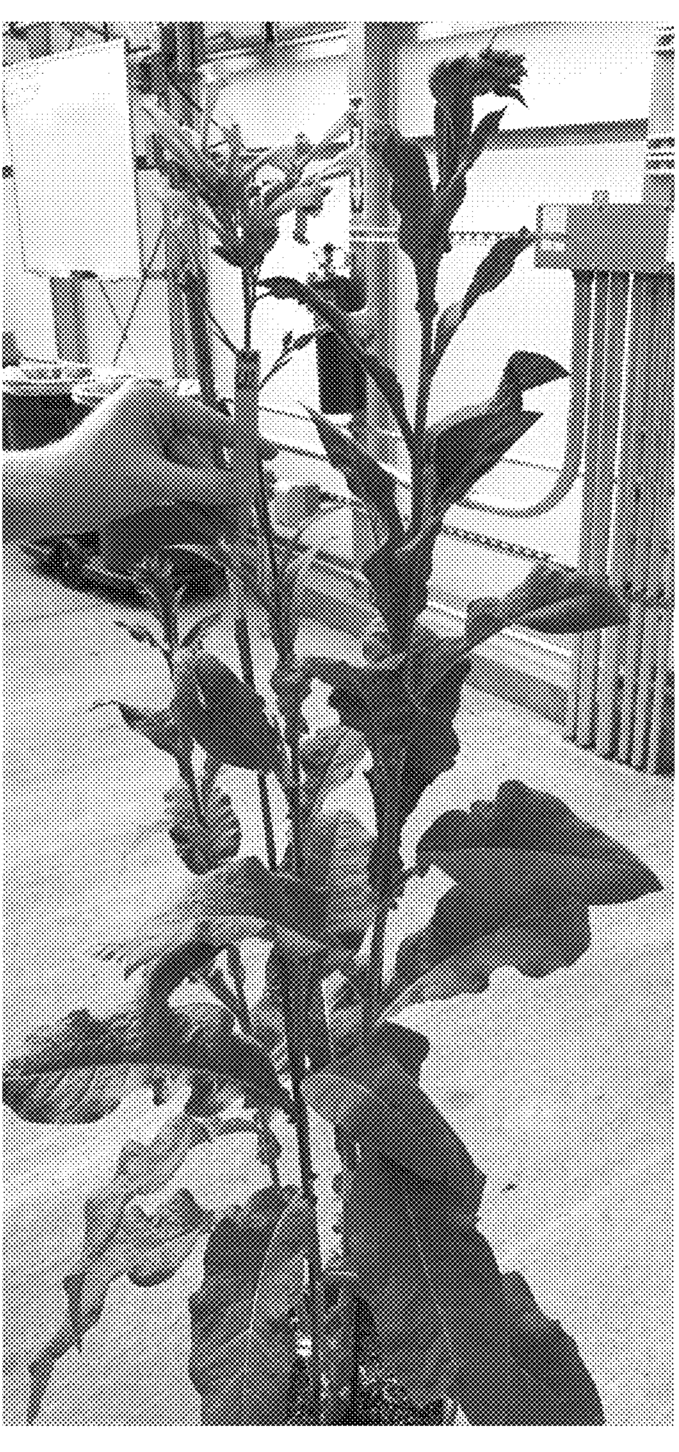
FIG. 19: Overexpression of NtMYB3 (SEQ ID NO: 36) in NLM results in tobacco plants with normal leaf color in $T_0$ plants grown in the greenhouse.

NtMYB3, SEQ ID NO: 13, is incorporated into a p45-2-7 transformation vector, and modified tobacco plants are generated, according to Example 1. Modified tobacco plants ($T_0$ and $T_1$ generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in $T_0$ plants as described in Example 7. Increased antioxidant capacity is detected in individual greenhouse grown $T_0$ plants compared to the average antioxidant capacity determined for at least five unmodified Narrow leaf Madole plants (FIG. 18). Plants overexpressing NtMYB3 show a normal leaf color in the $T_0$ generation (FIG. 19). NtMYB3-like 1, 2, and 3, SEQ ID Nos: 64 to 65 are also incorporated into a p45-2-7 transformation vector, and modified tobacco plants are generated, according to Example 1. Increased antioxidant capacity is detected in plants overexpressing either NtMYB3-like 1, 2, or 3.

Chorismate mutase-like 1, 2a, and 2b, SEQ ID NOs: 68 to 70, are incorporated into a p45-2-7 transformation vector, and modified tobacco plants are generated, according to Example 1. Modified NLM tobacco plants (To and $T_1$ generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 5. A FRAP assay is used to determine antioxidant capacity in $T_0$ plants as described in Example 7. Increased antioxidant capacity is detected in individual greenhouse grown $T_0$ plants compared to the average antioxidant capacity determined for at least five unmodified Narrow leaf Madole plants (FIG. 17).

TABLE 8

Nucleotide and protein sequences.

| Target Antioxidant | Gene Function annotation | Source | Protein SEQ ID No. | Coding SEQ ID No. |
|---|---|---|---|---|
| Anthocyanin | Putative alcohol dehydrogenase; [*Solanumlycopersicum* (Tomato) (*Lycopersicon esculentum*).] | tobacco | 1 | 24 |
| Anthocyanin | 1-O-acylglucose: anthocyanin-O-acyltransferase; [*Clitoria ternatea* (Butterfly pea).] | tobacco | 2 | 25 |
| Chlorogenic acid | 4-coumarate:CoA ligase; [*Ipomoea batatas* (Sweet potato) (*Convolvulus batatas*).]. Also called 4CL | tobacco | 3 | 26 |
| Chlorogenic acid | 4-coumarate: CoA ligase-like; [*Nicotiana sylvestris* (Wood tobacco) (South American tobacco).]. Also called 4CL. | tobacco | 4 | 27 |
| Anthocyanin | Anthocyanin 1a; [*Nicotiana tabacum* (Common tobacco).]. Also called AN1a. | tobacco | 5 | 28 |
| Anthocyanin | Anthocyanin 1b; [*Nicotiana tabacum* (Common tobacco).]. Also called AN1b. | tobacco | 6 | 29 |
| Anthocyanin | Anthocyanin 2; [*Nicotiana tomentosiformis* (Tobacco).] | tobacco | 7 | 30 |
| Anthocyanin | anthocyanidin synthase 2 [Nicotiana tabacum]. Also called ANS2. | tobacco | 8 | 31 |
| Anthocyanin | leucoanthocyanidin dioxygenase [*Nicotiana tabacum*] | tobacco | 9 | 32 |
| Anthocyanin | BHLH transcription factor JAF13; [*Petunia hybrida* (*Petunia*).] | tobacco | 10 | 33 |
| Ferulic acid | *Nicotiana tabacum* caffeic acid O-methyltransferase II gene | tobacco | 11 | 34 |
| chlorogenic acid | trans-cinnamate 4-monooxygenase-like [*Nicotiana tomentosiformis*], Also called C4H. | tobacco | 12 | 35 |
| Anthocyanin | transcription factor MYB3-like [*Nicotiana tabacum*]; tobacco homolog of AtPAP1 | tobacco | 13 | 36 |
| Anthocyanin | *Nicotiana tabacum* dihydroflavonol-4-reductase (LOC107797232) | tobacco | 14 | 37 |
| Anthocyanin | *Nicotiana tabacum* NtDFR2 gene for dihydroflavonol-4-reductase | tobacco | 15 | 38 |
| Anthocyanin | *Nicotiana tabacum* myb-related protein 308-like (LOC107782378), mRNA-XM_016603259. | tobacco | 16 | 39 |
| Chlorogenic acid | *Nicotiana tabacum* shikimate O-hydroxy cinnamoyltransferase-like; also called HCT. | tobacco | 17 | 40 |
| Chlorogenic acid | *Nicotiana tabacum* mRNA for hydroxycinnamoyl CoA quinate transferase (hqt gene); also called HQT. | tobacco | 18 | 41 |
| Anthocyanin, CGA, ferulic acid, cinnamate, coumarate caffeic acid | *Nicotiana tabacum* phenylalanine ammonia lyase (tpa1) gene; also called PAL. | tobacco | 19 | 42 |

TABLE 8-continued

| Nucleotide and protein sequences. | | | | |
|---|---|---|---|---|
| Target Antioxidant | Gene Function annotation | Source | Protein SEQ ID No. | Coding SEQ ID No. |
| Anthocyanin | *Arabidopsis thaliana* ttg1 gene; WD40. | *Arabidopsis* | 20 | 43 |
| carotenoids | phytoene synthase 1 [*Nicotiana tabacum*] | tobacco | 21 | 44 |
| carotenoids | phytoene synthase 2, chloroplastic [*Nicotiana sylvestris*] | tobacco | 22 | 45 |
| Anthocyanin | Production of anthocyanin pigment 1; PAPI. | *Arabidopsis* | 23 | 46 |
| Flavonoids and anthocyanins | Phenylalanine ammonia-lyase 4 (NtPAL4) | tobacco | 47 | 53 |
| Flavonoids and anthocyanins | Phenylalanine ammonia-lyase 2 (NtPAL2) | tobacco | 48 | 54 |
| Flavonoids and anthocyanins | Chaicone synthase (NtCHS) | tobacco | 49 | 55 |
| Flavonoids and anthocyanins | Flavonol 3-hydratase (NtF3H) | tobacco | 50 | 56 |
| | Arogenate dehydrogenase 1 (NtADT1) | tobacco | 51 | 57 |
| Chlorogenic acid, Flavonoids and anthocyanins | Arogenate dehydrogenase 2 (NtADT2) | tobacco | 52 | 58 |
| Anthocyanin | transcription factor Myb3-like 2 [*Nicotiana tabacum*] | tobacco | 64 | 66 |
| Anthocyanin | transcription factor Myb3-like 3 [*Nicotiana tabacum*] | tobacco | 65 | 67 |
| | Chorismate mutase-like 1 | tobacco | 68 | 71 |
| | Chorismate mutase-like 2a | tobacco | 69 | 72 |
| | Chorismate mutase-like 2b | tobacco | 70 | 73 |

Example 10. Secondary Metabolite Accumulation in Greenhouse Grown Tobacco Plants Overexpressing NtMYB3

A secondary metabolite accumulation analysis is conducted on greenhouse grown NtMYB3 overexpressing plants. NtMYB3 overexpression constructs are created as described in Example 9 and transformed into Narrow Leaf Madole (NLM) tobacco plants as described in Example 1. Modified and unmodified control plants are grown in a greenhouse under standard conditions. Plants are topped at flowering and leaves for analysis are collected two weeks later from two independently modified NLM plants (D1 and D2) and one unmodified NLM plant. A set of Benzenoids, Flavonoids, and Phenylpropanoids show significantly increased levels in modified plants compared to unmodified plants ($P<0.01$) (See Table 9). The levels of the alkaloids nicotine, nornicotine, anatabine, and anabasine are determined with Gas Chromatography followed by Mass Spectrometry (GC-MS) as described in Example 8.

Example 11. TSNA and Alkaloid Accumulation in Field Grown Tobacco Plants Overexpressing AtPAP1 or NtMYB3

A TSNA and alkaloid accumulation analysis is conducted on field grown AtPAP1 and NtMYB3 overexpressing plants. AtPAP1 and NtMYB3 overexpression constructs are created as described in Examples 2 and 9 and transformed into Narrow Leaf Madole (NLM) dark tobacco plants as described in Example 1. The AtPAP1 and NtMYB3 overexpression constructs are transformed into both NLM LC and NLM SRC plants. The accumulation in NLM LC is set to 100% as the control. Modified and unmodified control plants are also grown under the same conditions. Plants are topped at flowering and leaves for analysis are collected two weeks later. Each sample for analysis comprises 15 leaves with each leaf representing an individual plant. The levels of the alkaloids nicotine, nornicotine, anatabine, and anabasine are determined as described in Example 8. TSNAs are measured as described in Example 2.

Figure 22:
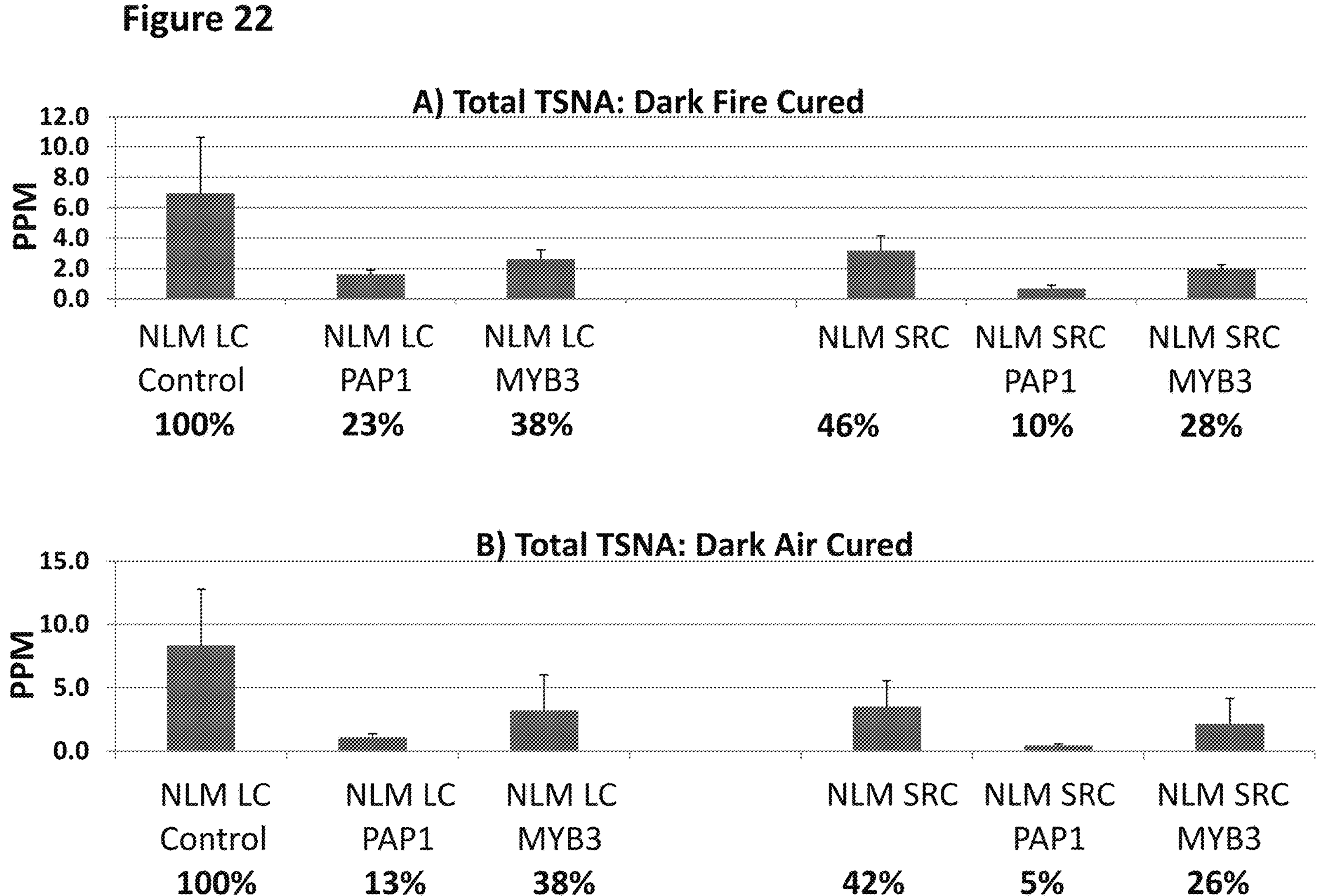
FIG. 22: Total TSNA accumulation measured in parts per million (PPM) in dark tobacco leaves. PAP1 and MYB2 are expressed in both NLM dark tobacco and NLM SRC dark tobacco. Plants are grown in the field and harvested using normal techniques before being cured. A) Total TSNA accumulation in fire cured leaves. B) Total TSNA accumulation in air cured leaves. Error bars represent standard error.
Figure 23:
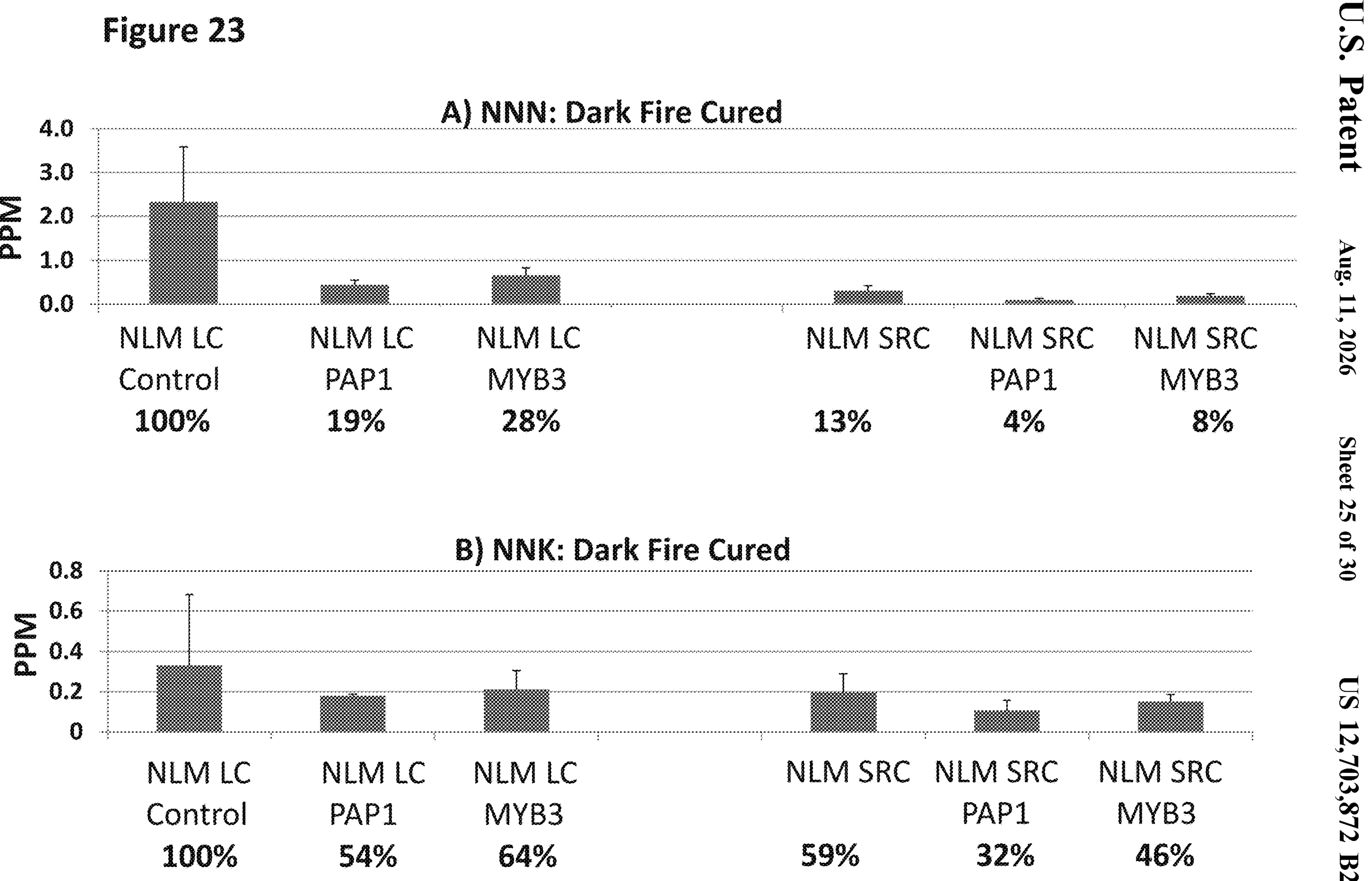
FIG. 23: Specific TSNA accumulation measured in PPM in dark tobacco leaves that are fire cured. PAP1 and MYB2 are expressed in both NLM dark tobacco and NLM SRC dark tobacco. Plants are grown in the field and harvested using normal techniques before being fire cured. A) NNN accumulation in fire cured leaves. B) NNK accumulation in fire cured leaves. Error bars represent standard error.
Figure 24:
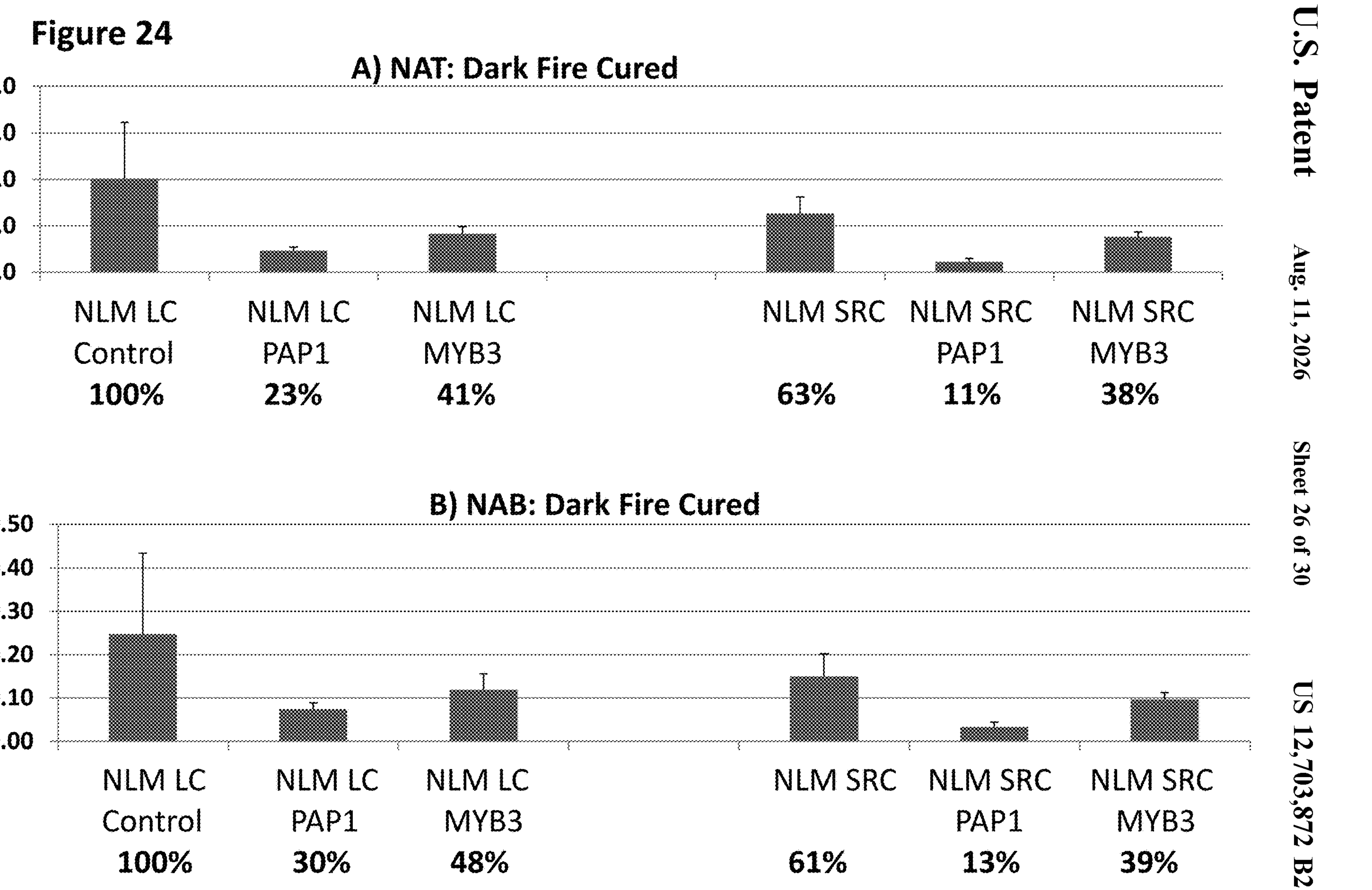
FIG. 24: Specific TSNA accumulation measured in PPM in dark tobacco leaves that are fire cured. PAP1 and MYB2 are expressed in both NLM dark tobacco and NLM SRC dark tobacco. Plants are grown in the field and harvested using normal techniques before being fire cured. A) NAT accumulation in fire cured leaves. B) NAB accumulation in fire cured leaves. Error bars represent standard error.
Figure 25:
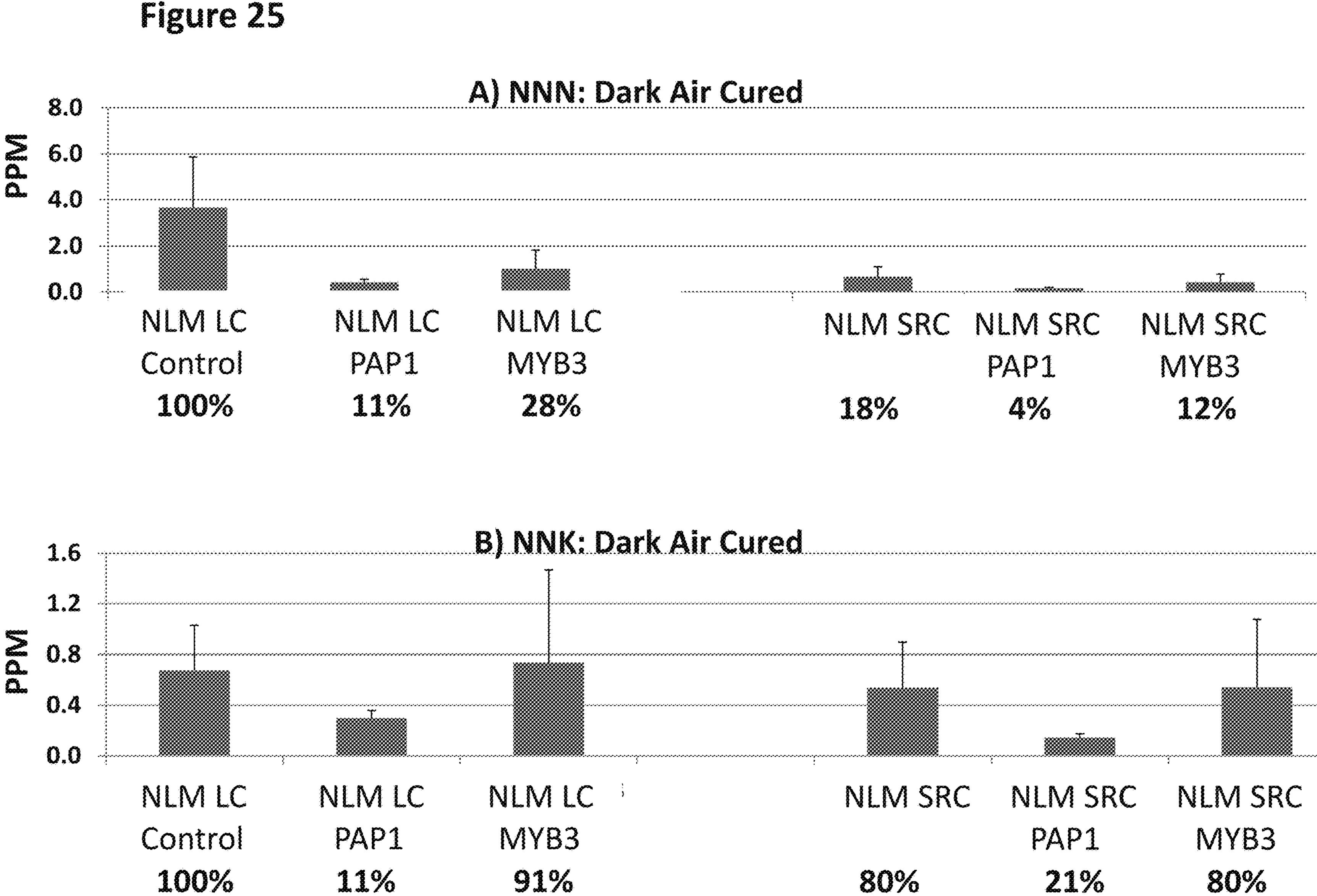
FIG. 25: Specific TSNA accumulation measured in PPM in dark tobacco leaves that are air cured. PAP1 and MYB2 are expressed in both NLM dark tobacco and NLM SRC dark tobacco. Plants are grown in the field and harvested using normal techniques before being air cured. A) NNN accumulation in air cured leaves. B) NNK accumulation in air cured leaves. Error bars represent standard error.
Figure 26:
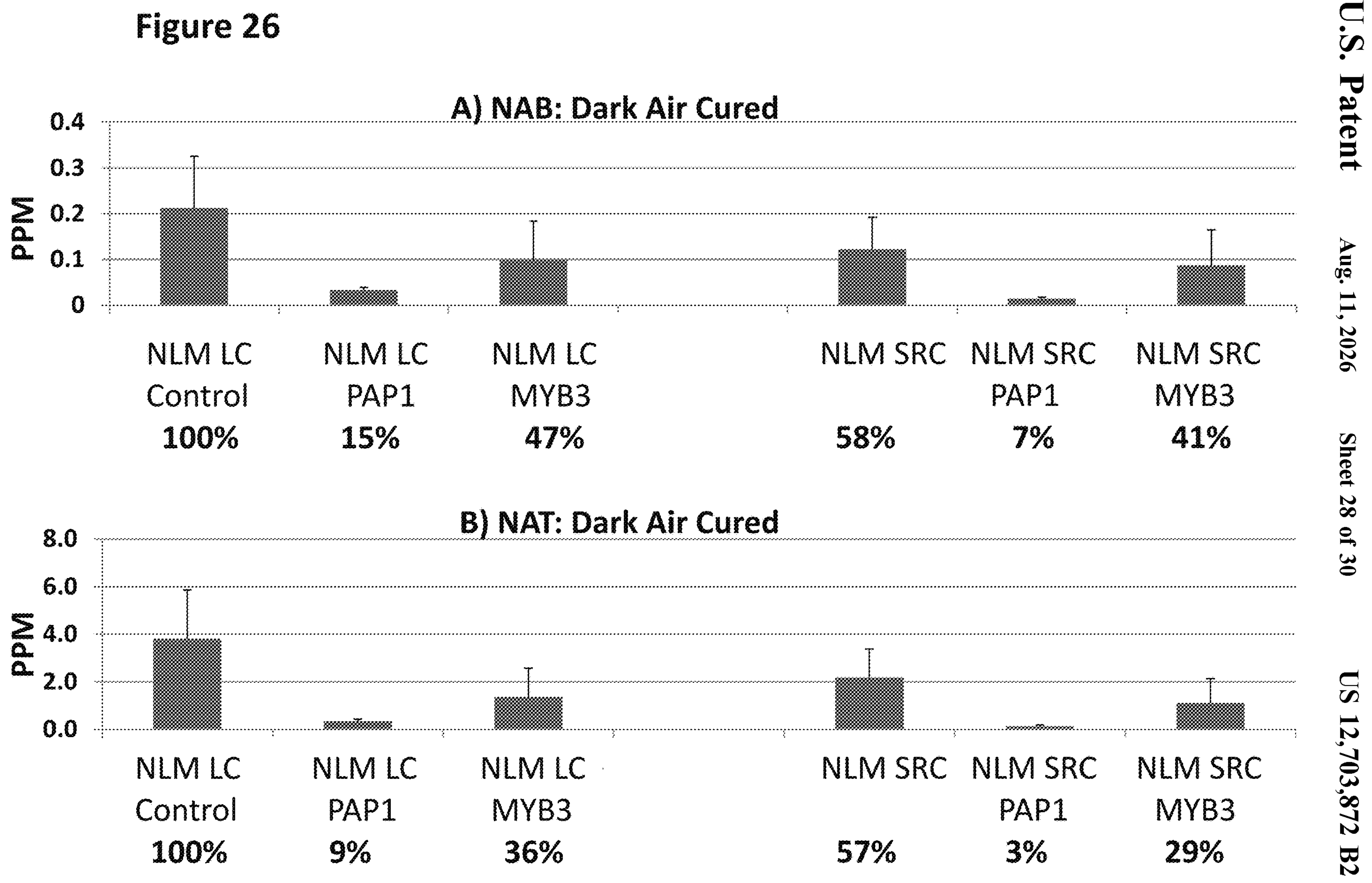
FIG. 26: Specific TSNA accumulation measured in PPM in dark tobacco leaves that are air cured. PAP1 and MYB2 are expressed in both NLM dark tobacco and NLM SRC dark tobacco. Plants are grown in the field and harvested using normal techniques before being air cured. A) NAT accumulation in air cured leaves. B) NAB accumulation in air cured leaves. Error bars represent standard error.
Figure 27:
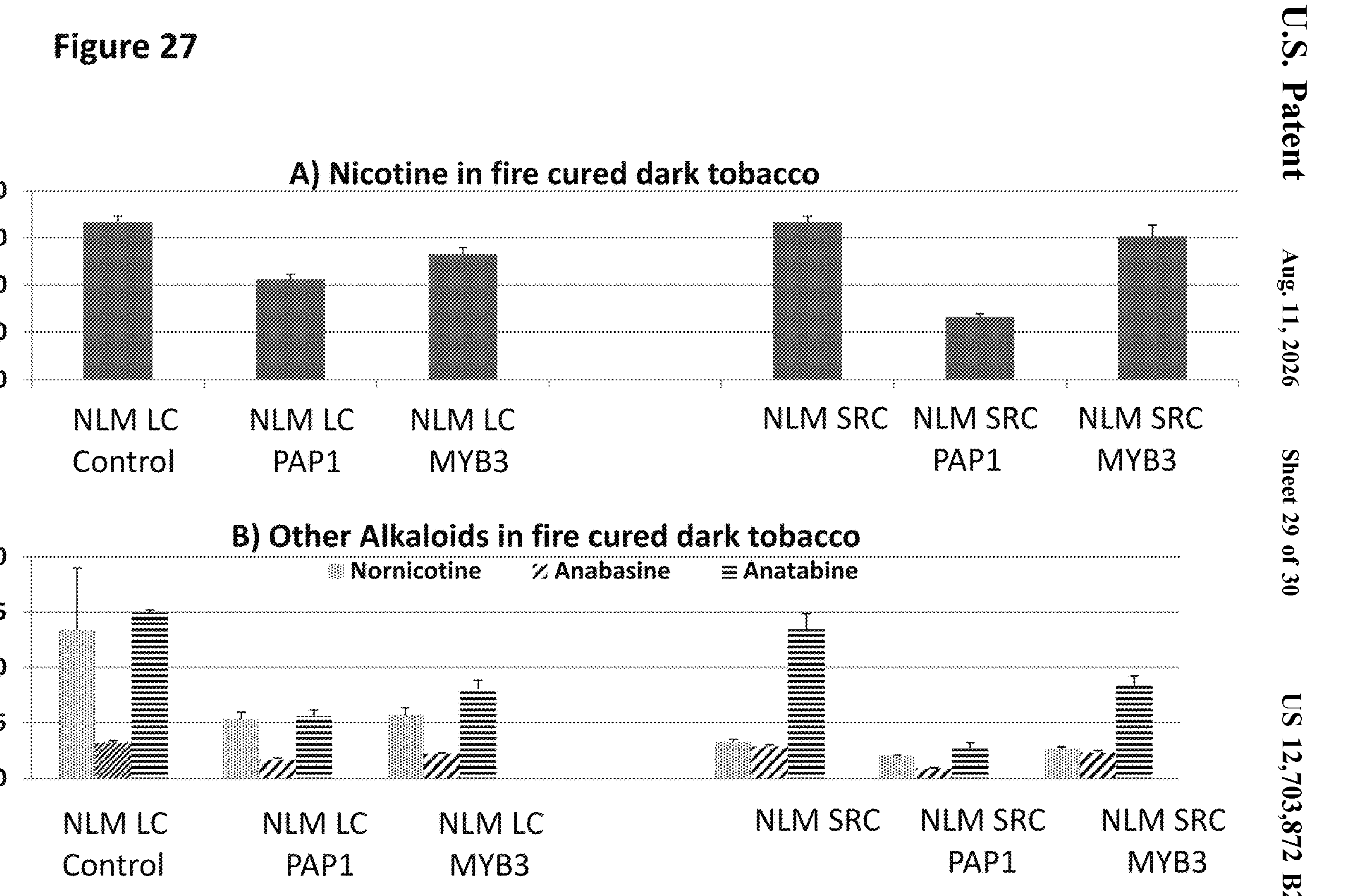
FIG. 27: Total alkaloid accumulation measured as percent per gram in dark tobacco leaves that are fire cured. PAP1 and MYB2 are expressed in both NLM dark tobacco and NLM SRC dark tobacco. Plants are grown in the field and harvested using normal techniques before being fire cured. A) The amounts of nicotine measured as percent per gram. B) The amounts of anatabine, anabasine, and nornicotine measured as percent per gram. Error bars represent standard error.
Figure 28:
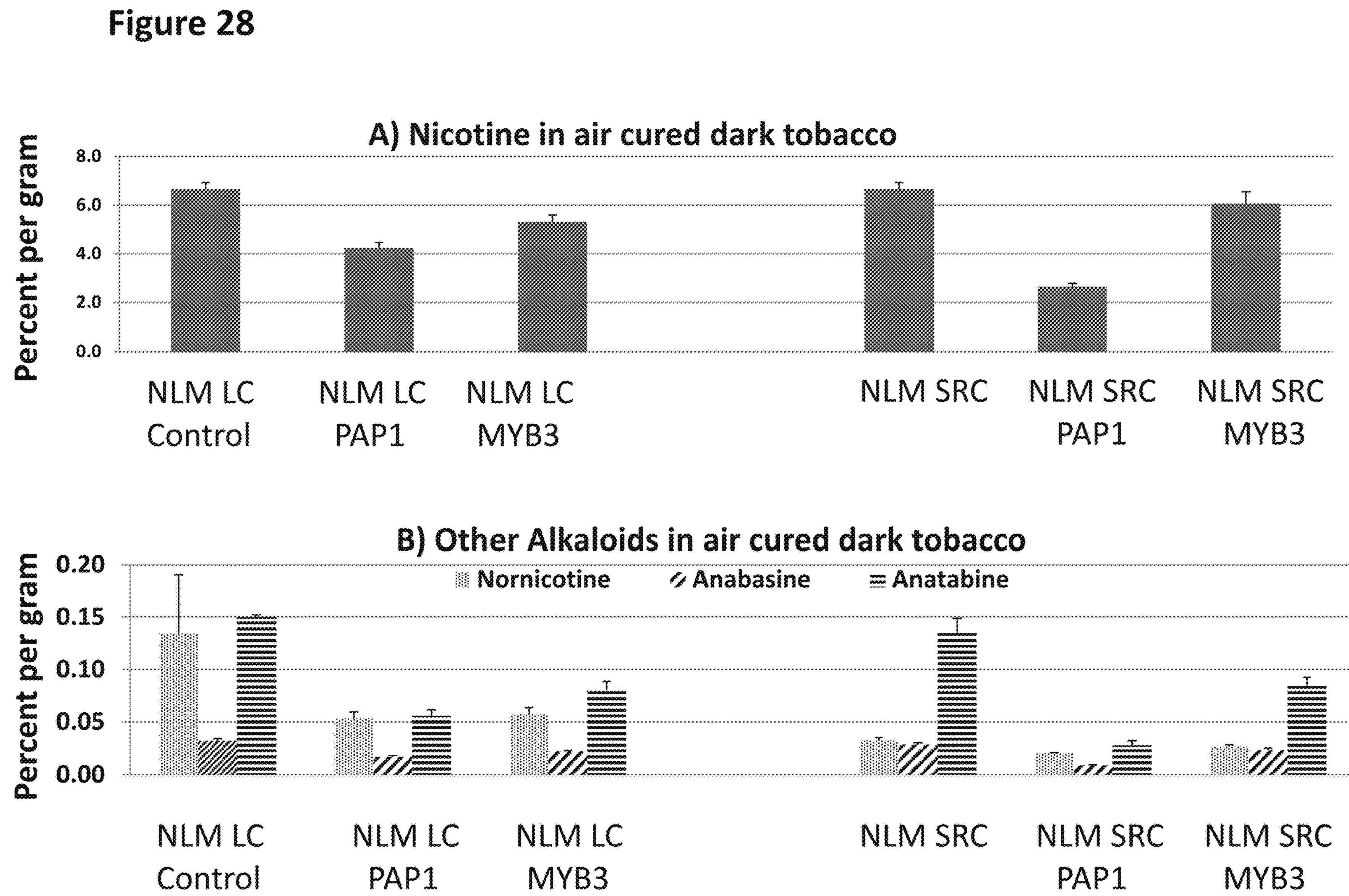
FIG. 28: Total alkaloid accumulation measured as percent per gram in dark tobacco leaves that are air cured. PAP1 and MYB2 are expressed in both NLM dark tobacco and NLM SRC dark tobacco. Plants are grown in the field and harvested using normal techniques before being air cured. A) The amounts of nicotine measured as percent per gram. B) The amounts of anatabine, anabasine, and nornicotine measured as percent per gram. Error bars represent standard error.

Overexpression of AtPAP1 or NtMYB3 significantly reduces both total alkaloids and total TSNAs in dark tobacco. The reductions are seen in dark tobacco leaves from plants that are grown in the field under both fire and air curing. See FIGS. 22, 27, and 28. The total reduction in TSNAs in these plants is the result of significant reductions in NNN, NNK, NAT, and NAB. Reductions in the individual TSNAs are in seen in both fire cured leaves (See FIGS. 23 and 24) and air cured leaves (See FIGS. 25 and 26).

TABLE 9

| Secondary metabolite accumulation in CsVMV:NtMYB3 overexpressing Narrow Leaf Madole tobacco plants. | | | | |
|---|---|---|---|---|
| Metabolism | Biochemical Name | MYB3 | NLM Control | MYB3/ NLM Control |
| Benzenoids | benzoate | 0.9089 | 0.2659 | 3.42 |
| | 4-hydroxybenzoate | 0.7365 | 0.4679 | 1.57 |
| Phenylpropanoids | chlorogenate | 5.9168 | 1.8605 | 3.18 |
| | aesculetin | 1.5639 | 0.6389 | 2.45 |
| | sinapoyl aldehyde | 2.1063 | 0.8820 | 2.39 |
| | 4-hydroxy cinnamate | 0.4746 | 0.2061 | 2.3 |
| | lariciresinol | 1.0498 | 0.5342 | 1.97 |
| | cryptochlorogenic acid | 2.6443 | 1.4087 | 1.88 |
| Terpenoids | beta-cryptoxanthin | 2.2629 | 1.0407 | 2.17 |
| Aromatic amino acid metabolism (PEP derived) | tyrosine | 2.2223 | 0.8026 | 2.77 |
| | tryptophan | 1.6922 | 0.6446 | 2.63 |
| | N-acetyltyrosine | 0.6238 | 0.3467 | 1.8 |
| | 3-dehydroshikimate | 1.3611 | 0.7780 | 1.75 |
| | phenylalanine | 1.0571 | 0.6024 | 1.75 |
| | O-sulfo-L-tyrosine | 0.4245 | 0.2499 | 1.7 |
| Glutathione metabolism | gamma-glutamyltryptophan | 0.7981 | 0.3127 | 2.55 |
| | gamma-glutamylserine | 1.5538 | 0.7072 | 2.2 |
| | gamma-glutamylglutamine | 0.2714 | 0.1436 | 1.89 |
| | glutathione, oxidized (GSSG) | 1.0281 | 0.5567 | 1.85 |
| | cysteine-glutathione disulfide | 0.6539 | 0.3686 | 1.77 |
| | gamma-glutamylisoleucine* | 0.5800 | 0.3423 | 1.69 |
| | gamma-glutamylglycine | 1.4032 | 0.9418 | 1.49 |

TABLE 10

| A list of plant-origin antioxidants that can be used to reduce TSNAs. | | |
|---|---|---|
| Chemical Classes | Compounds | Source of the Species |
| Anthocyanidin | Delphnidin | Tobacco, *Arabidopsis*. Cabbage, potato or *petunia* |
| | Cyanidin | Tobacco, *Arabidopsis*. Cabbage, potato or *petunia* |
| | Procyanidin | Tobacco, *Arabidopsis*. Cabbage, potato or *petunia* |
| | Prodelphinidin | Tobacco, Arabidopsis. Cabbage, potato or *petunia* |

TABLE 10-continued

A list of plant-origin antioxidants that can be used to reduce TSNAs.

| Chemical Classes | Compounds | Source of the Species |
|---|---|---|
| | Perlargonidin | Tobacco, *Arabidopsis*. Cabbage, potato or *petunia* |
| | Peonidin | Tobacco, *Arabidopsis*. Cabbage, potato or *petunia* |
| | Petunidin | Tobacco, *Arabidopsis*. Cabbage, potato or *petunia* |
| Flavanone | Hesperetin | Citrus or related species |
| | Naringenin | Citrus or related species |
| Flavanol | Catechin | Tobacco or other related species |
| | Epicatechin | Tobacco or other related species |
| Flavone | Apigenin | Parsley, tobacco or other related species |
| | Luteonin | Parsley, tobacco or other related species |
| Flavonol | Quercetin | Red kidney bean or other related species |
| | Myricetin | Red kidney bean or other related species |
| | Rutin | Tobacco, Red kidney bean or other related species |
| Isoflavone | Genistein | Soybean or other related species |
| | Daidzein | Soybean or other related species |
| Hydroxybenzoic Acid | Gallic acid | Tobacco, oak or other related species |
| | Vanillic acid | Tobacco, Acai or other related species |
| | Protocatechuic acid | Tobacco, Hibiscus or other related species |
| Hydroxycinnamic acid | Ferunic acid | Tobacco or other related species |
| | Cinnamic acid | Tobacco or other related species |
| | Coumeric acid | Tobacco or other related species |
| | Chlorogenic acid | Tobacco or other related species |
| | Coffeic acid | Tobacco or other related species |
| | Ferulic acid | Tobacco or other related species |
| Ellagitannin | Sanguiin | Raspberry or other related species |
| Stibene | Resveratrol | Grape or other related species |
| Lignan | Sesamin | Sesame or other related species |
| carotenoids | Caretonoids | Tobacco or carrots |
| | Vitamin C | Tobacco or carrots |
| Glycyrrhzin | | Licorice |

Example 12: Creation of Cisgenic Constructs to Modulate TSNA Levels

Cisgenic constructs are created to constitutively express AtPAP1, NtAN2, and NtAN1a. Tobacco native Ubiquitin (Ubi-4) or Tubulin (Tub) promoters are used in conjunction with a tobacco native heat shock protein (HSP) terminator. Sequences are incorporated into a p45-2-7 transformation vector, and modified tobacco plants are generated, according to Example 1. Constructs encoding Ubi4-P:PAP1-HSP-T (SEQ ID NO: 59), Ubi4-P:NtAN2-HSP-T (SEQ ID NO: 60), Tub-P:NtAN2-HSP-T (SEQ ID NO: 61), Ubi4-P:NtAN2-HSP-T:Tub-P:NtAN2-HSP-T (SEQ ID NO: 62), and Ubi4-P:NtAN1a-HSP-T:Tub-P:NtAN2-HSP-T (SEQ ID NO: 63) are transformed into tobacco plants. The presence of the cisgenic construct in a transformed plant is confirmed using amplicon sequencing. Modified tobacco plants (To and $T_1$ generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 7.

Figure 21:
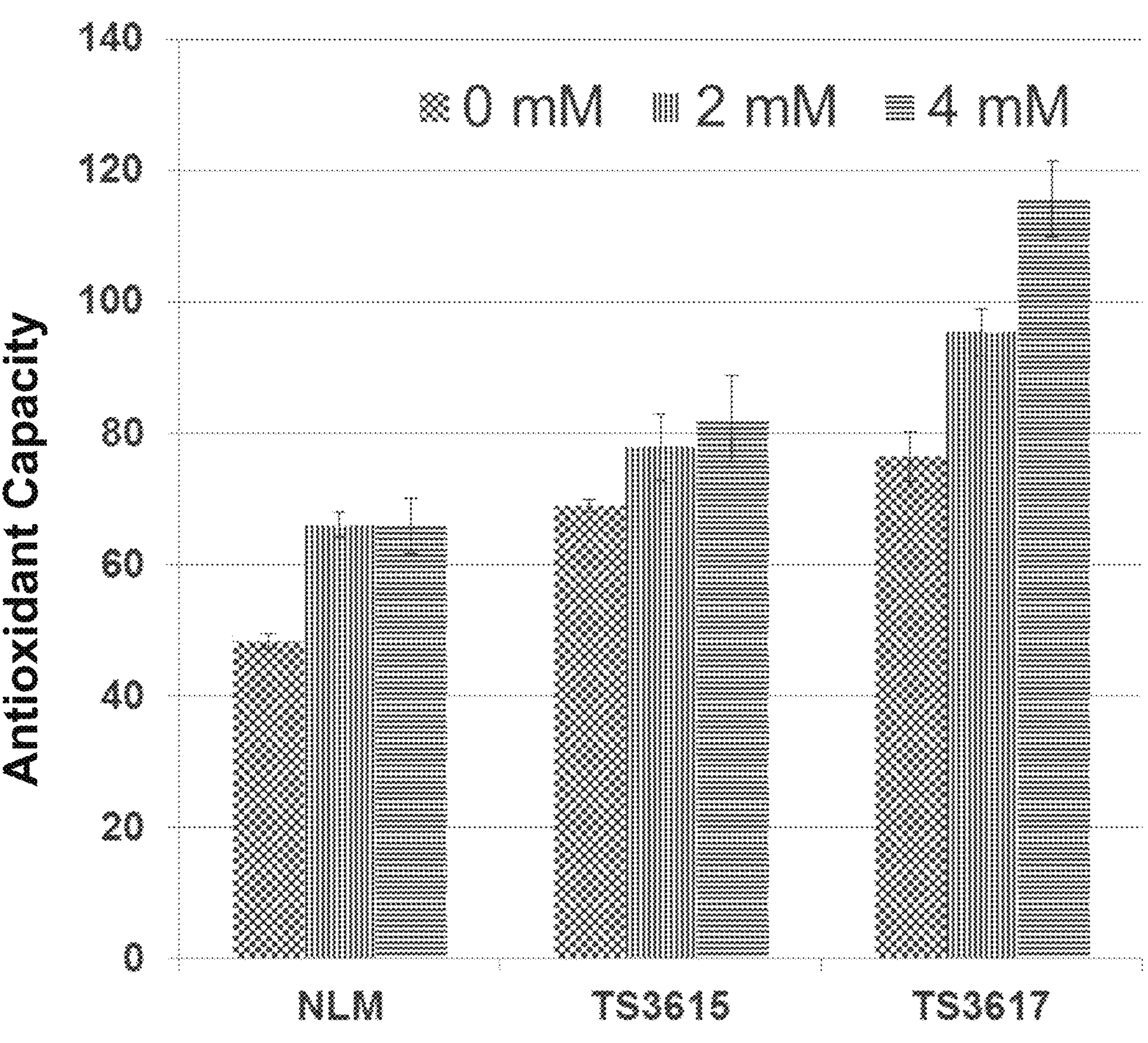
FIG. 21: Phenylalanine feeding of AtPAP1 overexpressing plants increases antioxidant capacity as determined by FRAP analysis. NLM and plants from two independent $T_2$ AtPAP1 overexpressing lines are treated with 0 mM, 2 mM, or 4 mM phenylalanine. Leaves are harvested and antioxidant capacity is determined using a FRAP analysis. In the control and both AtPAP1 overexpressing lines, antioxidant capacity increases with phenylalanine feeding.

Example 13: Antioxidant capacity of Phenylalanine fed AtPAP1 Overexpressing Plants Plants overexpressing AtPAP1 are grown in a greenhouse to test the effects of adding exogenous phenylalanine on antioxidant capacity. $T_2$ AtPAP1 overexpression lines TS3615 and TS3617 along with control NLM are sterilized and grown on MS medium agar plates containing 0 mM (control), 2 mM, and 4 mM phenylalanine. 25 plants per plate and 4 plates (replicates) per treatment are grown for 4 weeks under normal tissue culture conditions. After four weeks, all pooled leaf samples from a plate are harvested and tested for antioxidant capacity using a FRAP analysis as described in Example 7. Leaves from plants treated with both 2 mM and 4 mM phenylalanine showed increased FRAP activity compared to plants treated with the 0 mM control medium. Increase in FRAP activity is seen in both NLM as well as AtPAP1 overexpression lines TS3615 and TS3617 (See FIG. 21).

Example 14: Overexpression of Chorismate Mutase Increases Phenylalanine

Chorismate Mutase-like1, 2a, and 2b, having sequences of SEQ ID NOs: 68 to 70 respectively, are incorporated into a p45-2-7 transformation vector, and modified tobacco plants are generated, according to Example 1. Modified NLM tobacco plants (To and $T_1$ generation) and control tobacco plants are grown for 4-6 weeks after transplantation to soil, harvested, and cured in PGC chambers. Cured leaf samples are prepared for evaluation of TSNAs, oxidative degradation potential, alkaloids, and nitrites/nitrates as described in Examples 2 to 7. A FRAP assay is used to determine antioxidant capacity in $T_0$ plants as described in Example 7. Increased antioxidant capacity is detected in individual greenhouse grown $T_0$ plants compared to the average antioxidant capacity determined for at least five unmodified Narrow leaf Madole plants. $T_0$ plants overexpressing NtCM-like1, 2a, and 2b and having increased antioxidant capacity are identified and seed is collected from these plants. $T_1$ seed is grown in a greenhouse to measure phenylalanine content after confirming Chorismate Mutase overexpression. Compared to control NLM plants, plants overexpressing NtCM-like1, 2a, and 2b have increased amounts of phenylalanine.

Example 15: Overexpression of Chorismate Mutase Increases Antioxidant Capacity Plants overexpressing NtCM-like1, 2a, and 2b are created as described in Examples 1 and 9. The presence of overexpression constructs in a transformed plant is confirmed using amplicon sequencing. Plants overexpressing NtCM-like1, 2a, or 2b are grown in a greenhouse. Leave samples are collected to measure antioxidant capacity using the FRAP assay as described in Example 7. Compared to control NLM plants, plants overexpressing NtCM-like1, 2a, and 2b have an increased antioxidant capacity as measured using the FRAP assay.

Example 16: Overexpression of Chorismate Mutase Reduces TSNAs

Plants overexpressing NtCM-like1, 2a, and 2b are created as described in Examples 1 and 9 and grown in a greenhouse. The presence of overexpression constructs in a transformed plant is confirmed using amplicon sequencing. Plants overexpressing NtCM-like1, 2a, or 2b are grown in a greenhouse. Modified and control NLM tobacco is topped and leaves are harvested two weeks after topping. Leaves are cured using either air curing or fire curing methods as described in Example 2. Air and fire cured leaves are tested for TSNAs as described in Example 2. Plants overexpressing NtCM-like1, 2a, or 2b demonstrate reduced amounts of TSNAs compared to the unmodified NLM control plants.

Example 17: A Combination Approach for Further Reduction of TSNAs

A combination strategy is taken to combine Chorismate Mutase overexpression and the approach provided in Examples 2 to 7 to achieve a further TSNA reduction. Plants are transformed with one or more constructs described in Example 9 and one or more of the constructs described in Example 12 to achieve a further TSNA reduction. Antioxidant capacity is measured as described in Example 9 and TSNAs levels are measured as described in Example 2. The modified plants having two transgenes have TSNA amounts reduced more than modified tobacco plants having any one of the transgenes. Alternatively, a plant harboring one or more transgenes described in Example 9 are crossed with a plant harboring one or more transgenes described in Example 13. $F_1$ plants are tested to insure the presence of each desired transgenes. $F_1$ plants comprising one or more transgenes described in Example 9 and one or more transgenes described in Example 13 have TSNA amounts reduced more than either of the parent plants.

Three nicotine demethylase genes, known as CYP82E4, CYP82E5, and CYP82E10, mediate nornicotine biosynthesis in *Nicotiana tabacum*. Triple knockout mutants (cyp82e4, cyp82e5, cyp82e10) exhibit a dramatic reduction of nornicotine and consequently a reduction of NNN. A combination strategy is taken to combine nicotine demethylase mutants and the approach provided in Examples 2 to 7 to achieve a further TSNA reduction. A cyp82e4, cyp82e5, cyp82e10 triple mutant is transformed with one or more constructs described in Example 9 to increase antioxidant levels. Alternatively, cyp82e4, cyp82e5, cyp82e10 triple mutants are crossed with mutant or transgenic tobacco having elevated antioxidant levels described in Example 2.

What is claimed is:

1. A cured tobacco leaf of a modified tobacco plant, wherein said cured tobacco leaf comprises a decreased amount of one or more tobacco specific nitrosamines (TSNAs), a recombinant nucleic acid molecule comprising a promoter operably linked to a first polynucleotide encoding a Chorismate Mutase-like polypeptide having at least 95% sequence identity to a sequence selected from the group consisting of SEQ ID NOs: 68 to 70, and a recombinant nucleic acid molecule comprising a promoter operably linked to a second polynucleotide encoding a bHLH-like transcription factor polypeptide having at least 95% sequence identity to a sequence selected from the group consisting of SEQ ID NOs: 5 and 6, wherein said decreased amount is compared to an unmodified control tobacco plant.

2. The cured tobacco leaf of claim 1, wherein said Chorismate Mutase-like polypeptide has at least 99% sequence identity to a sequence selected from the group consisting of SEQ ID NOs: 68 to 70.

3. The cured tobacco leaf of claim 2, wherein said bHLH-like transcription factor polypeptide has at least 99% sequence identity to a sequence selected from the group consisting of SEQ ID NOs: 5 and 6.

4. The cured tobacco leaf of claim 1, wherein the amount of said one or more TSNAs is reduced by at least 50% compared to a cured tobacco leaf or a tobacco product from an unmodified control tobacco plant.

5. The cured tobacco leaf of claim 1, wherein said cured tobacco leaf comprises less than 0.08 ppm 4-methylnitrosoamino-1-(3-pyridyl)-1-butanone (NNK), wherein the level of NNK is measured based on a freeze-dried cured leaf sample using liquid chromatograph with tandem mass spectrometry (LC/MS/MS).

6. A tobacco product comprising the cured tobacco leaf of claim 1.

7. The tobacco product of claim 6, wherein said tobacco product is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, cut tobacco, loose leaf chewing tobacco, plug chewing tobacco, moist snuff, and nasal snuff.

8. The cured tobacco leaf of claim 1, further comprising a reduced amount of total alkaloids that is a least 10% less than the total amount of alkaloids in an unmodified control tobacco plant.

9. The cured tobacco leaf of claim 1, wherein said cured tobacco leaf comprises less than 2 ppm total TSNAs.

10. The cured tobacco leaf of claim 1, wherein said one or more tobacco-specific nitrosamines (TSNAs) are selected from the group consisting of N'-nitrosonornicotine (NNN), 4-methylnitrosoamino-1-(3-pyridyl)-1-butanone (NNK), N'-nitrosoanatabine (NAT) N'-nitrosoanabasine (NAB), and any combination thereof.

* * * * *